United States Patent
Bergman et al.

(10) Patent No.: US 10,005,792 B2
(45) Date of Patent: Jun. 26, 2018

(54) AMINOINDANE-, AMINOTETRAHYDRONAPHTHALENE- AND AMINOBENZOCYCLOBUTANE-DERIVED PRMT5-INHIBITORS

(71) Applicant: CTXT PTY LTD, Victoria (AU)

(72) Inventors: Ylva Elisabet Bergman, Victoria (AU); Romina Lessene, Victoria (AU); Danny Ganame, Victoria (AU); Richard Charles Foitzik, Victoria (AU); Benjamin Joseph Morrow, Victoria (AU); Michelle Ang Camerino, Victoria (AU); Scott Raymond Walker, Victoria (AU); H. Rachel Lagiakos, Victoria (AU); John Feutrill, Victoria (AU); Paul Anthony Stupple, Victoria (AU)

(73) Assignee: CTXT PTY. LTD., Victoria (AU)

( * ) Notice: Subject to any disclaimer, the term of this patent is extended or adjusted under 35 U.S.C. 154(b) by 0 days. days.

(21) Appl. No.: 15/508,074

(22) PCT Filed: Sep. 3, 2015

(86) PCT No.: PCT/EP2015/070146
§ 371 (c)(1),
(2) Date: Mar. 1, 2017

(87) PCT Pub. No.: WO2016/034671
PCT Pub. Date: Mar. 10, 2016

(65) Prior Publication Data
US 2017/0313713 A1    Nov. 2, 2017

(30) Foreign Application Priority Data
Sep. 3, 2014  (GB) .................................. 1415570.9
May 16, 2015 (GB) .................................. 1508453.6

(51) Int. Cl.
*C07D 207/12* (2006.01)
*C07D 209/44* (2006.01)
(Continued)

(52) U.S. Cl.
CPC ........ *C07D 491/107* (2013.01); *C07C 233/78* (2013.01); *C07C 235/42* (2013.01);
(Continued)

(58) Field of Classification Search
None
See application file for complete search history.

(56) References Cited

U.S. PATENT DOCUMENTS

| | | | |
|---|---|---|---|
| 6,008,219 A | 12/1999 | Stemp et al. | |
| 6,046,210 A | 4/2000 | Stemp et al. | |

(Continued)

FOREIGN PATENT DOCUMENTS

| | | |
|---|---|---|
| CN | 102417483 A | 4/2012 |
| DE | 261153 A1 | 10/1988 |

(Continued)

OTHER PUBLICATIONS

Secci, Daniela et al: "Conventional and microwave-assisted synthesis of benzimidazole derivatives and their in vitro inhibition of human cyclooxygenase", Journal of Heterocyclic Chemistry, 49(5), 1187-1195.

(Continued)

*Primary Examiner* — Alicia L Otton
(74) *Attorney, Agent, or Firm* — Stites & Harbison PLLC; Richard S. Myers, Jr.

(57) ABSTRACT

A compound of formula (1a), (1b) or (1c) wherein: n is 1 or 2; $R^N$ is H or Me; $R^1$ is optionally one or more halo or methyl groups; $R^{2a}$ and $R^{2b}$ are independently selected from the group consisting of: (i) F; (ii) H; (iii) Me; and (iv) $CH_2OH$; $R^{2c}$ and $R^{2d}$ (if present) are independently selected from the group consisting of: (i) F; (ii) H; (iii) Me; and (iv) $CH_2OH$; $R^{3a}$ and $R^{3b}$ are independently selected from H and Me; $R^{4a}$ is selected from OH, $-NH_2$, $-C(=O)NH_2$, and $-CH_2OH$; $R^{4b}$ is either H or Me; $R^5$ is either H or Me; A is either (i) optionally substituted phenyl; (ii) optionally substituted naphthyl; or (iii) optionally substituted $C_{5-12}$ heteroaryl.

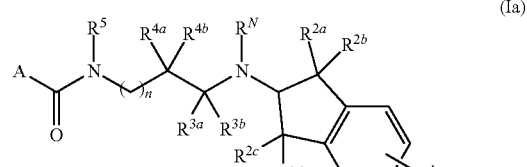

(Ia)

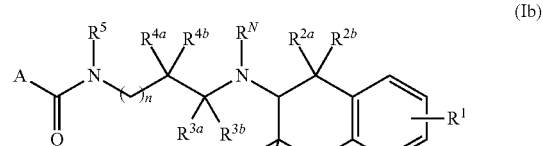

(Ib)

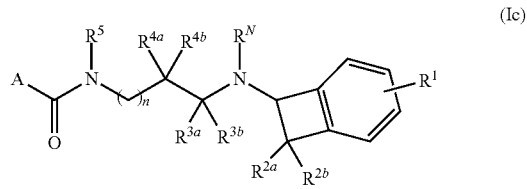

(Ic)

20 Claims, No Drawings

(51) Int. Cl.
| | |
|---|---|
| C07D 211/22 | (2006.01) |
| C07D 211/46 | (2006.01) |
| C07D 211/58 | (2006.01) |
| C07D 211/76 | (2006.01) |
| C07D 213/81 | (2006.01) |
| C07D 213/82 | (2006.01) |
| C07D 217/06 | (2006.01) |
| C07D 217/12 | (2006.01) |
| C07D 231/14 | (2006.01) |
| C07D 231/20 | (2006.01) |
| C07D 231/56 | (2006.01) |
| C07D 235/08 | (2006.01) |
| C07D 271/08 | (2006.01) |
| C07D 271/10 | (2006.01) |
| C07D 261/18 | (2006.01) |
| C07D 277/56 | (2006.01) |
| C07D 277/68 | (2006.01) |
| C07D 265/30 | (2006.01) |
| C07D 265/34 | (2006.01) |
| C07D 401/04 | (2006.01) |
| C07D 401/12 | (2006.01) |
| C07D 413/04 | (2006.01) |
| C07D 451/02 | (2006.01) |
| C07D 451/14 | (2006.01) |
| C07D 491/08 | (2006.01) |
| C07D 491/107 | (2006.01) |
| C07C 233/78 | (2006.01) |
| C07C 235/42 | (2006.01) |
| C07C 235/60 | (2006.01) |
| C07D 295/192 | (2006.01) |

(52) U.S. Cl.
CPC .......... C07C 235/60 (2013.01); C07D 207/12 (2013.01); C07D 209/44 (2013.01); C07D 211/22 (2013.01); C07D 211/46 (2013.01); C07D 211/58 (2013.01); C07D 211/76 (2013.01); C07D 213/81 (2013.01); C07D 213/82 (2013.01); C07D 217/06 (2013.01); C07D 231/14 (2013.01); C07D 231/20 (2013.01); C07D 231/56 (2013.01); C07D 235/08 (2013.01); C07D 261/18 (2013.01); C07D 265/30 (2013.01); C07D 265/34 (2013.01); C07D 271/08 (2013.01); C07D 271/10 (2013.01); C07D 277/56 (2013.01); C07D 277/68 (2013.01); C07D 295/192 (2013.01); C07D 401/04 (2013.01); C07D 401/12 (2013.01); C07D 413/04 (2013.01); C07D 451/02 (2013.01); C07D 451/14 (2013.01); C07D 491/08 (2013.01)

(56) References Cited

U.S. PATENT DOCUMENTS

| | | | |
|---|---|---|---|
| 6,274,593 | B1 | 8/2001 | Johns et al. |
| 6,579,892 | B1 | 6/2003 | Starck et al. |
| 2005/0101647 | A1 | 5/2005 | Oda et al. |
| 2005/0107398 | A1 | 5/2005 | Mach et al. |
| 2006/0235037 | A1 | 10/2006 | Purandare |
| 2010/0069431 | A1 | 3/2010 | Iwata et al. |
| 2016/0222005 | A1 | 8/2016 | Stupple et al. |

FOREIGN PATENT DOCUMENTS

| | | |
|---|---|---|
| GB | 2286395 A | 8/1995 |
| WO | WO96/30333 | 10/1996 |
| WO | WO97/43262 A1 | 11/1997 |
| WO | WO98/49145 | 11/1998 |
| WO | WO2003035065 A1 | 5/2003 |
| WO | WO2003082186 A2 | 10/2003 |
| WO | WO2004016611 A1 | 2/2004 |
| WO | WO2004024897 A2 | 3/2004 |
| WO | WO2005030206 A1 | 4/2005 |
| WO | WO2005042495 A1 | 5/2005 |
| WO | WO2006/008133 A2 | 1/2006 |
| WO | WO2006080821 A1 | 8/2006 |
| WO | WO2008061303 A1 | 5/2008 |
| WO | WO2009005551 A2 | 1/2009 |
| WO | WO2009113085 A1 | 9/2009 |
| WO | WO2009139076 A1 | 11/2009 |
| WO | WO2010025295 A2 | 3/2010 |
| WO | WO2012108689 A2 | 8/2012 |
| WO | WO2014100695 A1 | 6/2014 |
| WO | WO2014100716 A1 | 6/2014 |
| WO | WO2014100719 A2 | 6/2014 |
| WO | WO2014100730 A1 | 6/2014 |
| WO | WO2014100734 A1 | 6/2014 |

OTHER PUBLICATIONS

Rostamizadeh, Shahnaz et al: "Aqueous 1 M Glucose Solution as a Novel and Fully Green Reaction Medium and Catalyst for the Oxidant-Free Synthesis of 2-Arylbenzimidazoles", Synthetic Communications, 41(12), 1794-1884.

Chen, Yong-Fei et al: "Design and synthesis of new heterocyclic Bcr-Abl inhibitors", Heterocyclic Communications, 16(2-3), 123-135.

Goeker, Hakan et al: "Synthesis and potent antifungal activity against Candida species of some novel 1H-benzimidazoles", Journal of Heterocyclic Chemistry, 46(5), 936-948.

Kaynak, F. Betul et al: 11 Synthesis and crystal structure of 1-benzyl-2-(4-benzyloxyphenyl)-5,6-dichloro-1H-benzimidazole, Structural Chemistry, 19(3), 477-488.

Kus, Canan et al: 11 Antimicrobial activity studies on some morpholinobenzimidazole derivatives 11, Ankara Universitesi Eczacilik Fakultesidergisi , 35(4), 237-244.

K Vijayakumar et al: "Available on line www Synthesis, Anti-Tumor, Anti-Diabetic, and Anti-Asthmatic Activitives of Some Novel Benzimidazole Derivatives", Pharm. Res, vol. 2, No. 4 Jan. 1, 2010 (Jan. 1, 2010), 2010, pp. 215-224.

Richards M L et al: "Substituted 2-phenyl-benzimidazole derivatives: novel compounds that suppress key markers of allergy", European Journal of Medicinal Chemistry, Editions Scientifique Elsevier, Paris, FR, vol. 41, No. 8, Aug. 1, 2006 (Aug. 1, 2006), pp. 950-969.

Zhang, Zeyuan et al: Synthesis and antifungal activity of novel 2,5-disubstituted-1,3,4-oxadiazoles containing benzimidazole moiety, Journal of Pesticide Science (Tokyo, Japan) 37(4), 338-341.

Aggarwal, et al., Nuclear Cyclin D1/CDK4 Kinase Regulates CUL4 Expression and Triggers Neoplastic Growth via Activation of the PRMT5 Methyltransferase; Cancer Cell, 2010, 18, 329-340.

Berger, Shelley L., Out of the jaws of death: PRMT5 steers p53, nature cell biology vol. 10 | No. 12 | Dec. 2008, pp. 1389-1390.

Gu, et al., Protein arginine methyltransferase 5 is essential for growth of lung cancer cells, Biochemical Journal Immediate Publication. Published on Jun. 18, 2012 as manuscript BJ20120768, pp. 1-20.

Chen, et al., Epigenetic changes during disease progression in a murine model of human chronic lymphocytic leukemia, PNAS, Aug. 11, 2009, vol. 106, No. 32, pp. 13433-13438.

Cho, et al., Arginine methylation controls growth regulation by E2F-1, The EMBO Journal vol. 31 | No. 7 | 2012, pp. 1785-1797.

Durant, et al., p53 methylation, Cell Cycle 8:6, Mar. 15, 2009, pp. 801-802.

He, et al., Induction of human fetal hemoglobin expression by adenosine-2',3'-dialdehyde, Journal of Translational Medicine 2013, 11:14, pp. 1-7.

Jansson, et al., Arginine methylation regulates the p53 response, nature cell biology vol. 10 | No. 12 | Dec. 2008, pp. 1431-1439.

Kanduri, et al., Differential genome-wide array-based methylation profiles in prognostic subsets of chronic lymphocytic leukemia, Blood, Jan. 14, 2010 vol. 115, No. 2, pp. 296-305.

(56) References Cited

OTHER PUBLICATIONS

Karkhanis, et al., Versatility of PRMT5-induced methylation in growth control and development, Cell Press, 2011, pp. 1-9.
Kim, et al., Identification of Gastric Cancer—Related Genes Using a cDNA Microarray Containing Novel Expressed Sequence Tags Expressed in Gastric Cancer Cells, Clinical Cancer Research, Jan. 15, 2005, vol. 11, 473-482.
Krause, et al., Protein arginine methyltransferases: Evolution and assessment of their pharmacological and therapeutic potential, Pharmacology & Therapeutics 113 (2007) 50-87.
Le Guezennec, et al., MBD2/NuRD and MBD3/NuRD, Two Distinct Complexes with Different Biochemical and Functional Properties, Molecular and Cellular Biology, Feb. 2006, p. 843-851.
Nicholas, et al., Abstract LB-254: PRMT5 is upregulated in malignant and metastatic melanoma, and regulates expression of the MITF transcription factor, Cancer Res Apr. 15, 2012 72; LB-254.
Pal, et al., mSin3A/Histone Deacetylase 2- and PRMT5-Containing Brg1 Complex Is Involved in Transcriptional Repression of the Myc Target Gene cad, Molecular and Cellular Biology, Nov. 2003, p. 7475-7487.
Pollack, et al., The Human Homologue of the Yeast Proteins Skb1 and Hsl7p Interacts with Jak Kinases and Contains Protein Methyltransferase Activity, J. Biol. Chem. 1999, 274:31531-31542.
Powers, et al., Protein Arginine Methyltransferase 5 Accelerates Tumor Growth by Arginine Methylation of the Tumor Suppressor Programmed Cell Death 4, Cancer Res Published OnlineFirst Jun. 23, 2011, pp. OF1-OF9.
Rank, et al., Identification of a PRMT5-dependent repressor complex linked to silencing of human fetal globin gene expression, Blood, Sep. 2, 2010 vol. 116, No. 9, pp. 1585-1592.
Scoumanne, et al., PRMT5 is required for cell-cycle progression and p53 tumor suppressor function, Nucleic Acids Research, 2009, vol. 37, No. 15 4965-4976.
Pal, et al., Low levels of miR-92b/96 induce PRMT5 translation and H3R8/H4R3 methylation in mantle cell lymphoma, The EMBO Journal (2007) 26, 3558-3569.
Wang, et al., Protein Arginine Methyltransferase 5 Suppresses the Transcription of the RB Family of Tumor Suppressors in Leukemia and Lymphoma Cells, Molecular and Cellular Biology, Oct. 2008, p. 6262-6277.
Gu, et al., Protein Arginine Methyltransferase 5 Functions in Opposite Ways in the Cytoplasm and Nucleus of Prostate Cancer Cells, PLOS ONE, Aug. 2012 | vol. 7 | Issue 8, pp. e44033, pp. 1-13.
Mach, et al., Development of Novel 1,2,3,4-Tetrahydroisoquinoline Derivatives and Closely Related Compounds as Potent and Selective Dopamine D3 Receptor Ligands; Chembiochem; 2004; 5; pp. 508-518.
Braun, et al., Ber Dtsch Chem Ges; 1926; pp. 2416-2425.
Zajdel et al., Solid-Phase Synthesis of Aryl-Alkylamine Derivatives Using Protected Aminoalcohol Building Blocks on SynPhaseTM Lanterns; QSAR Comb. Sci. 26, 2007, No. 2, 215-219.

AMINOINDANE-, AMINOTETRAHYDRONAPHTHALENE- AND AMINOBENZOCYCLOBUTANE-DERIVED PRMT5-INHIBITORS

CROSS REFERENCE TO RELATED APPLICATIONS

This application is a § 371 National State Application of PCT/EP2015/070146 filed Sep. 3, 2015 which claims priority to GB 1415570.9 filed Sep. 3, 2014 and GB 1508453.6 filed May 16, 2015.

The present invention relates to amino-bicyclic compounds and their use as pharmaceuticals, and in particular, in treating cancer and hemoglobinopathies.

BACKGROUND TO THE INVENTION

Post-translational modification of proteins is a hallmark of signal transduction where cells are able to react quickly to changes or events in the cellular environment. Post-translational modification of proteins expands the structural and functional diversity of the proteome. The role of acetylation and phosphorylation of proteins has been extensively studied as highly reversible reactions for fine-tuning responses to external stimuli or changes in the environmental conditions. Recently, the importance of other types of protein modifications, including ubiquitination and methylation has begun to be recognized.

The methylation of proteins and the enzymes that carry out these reactions has increased the dimensions of gene regulation by marking genes that are transcriptionally active or silenced. Protein methylation can occur on amino acids such as lysine, arginine, histidine, or proline, and on carboxy groups.

Arginine methylation of mainly nuclear proteins is an important post-translational modification process involved in structural remodelling of chromatin, signal transduction, cellular proliferation, nucleocytoplasmic shuttling, translation, gene transcription, DNA repair, RNA processing, or mRNA splicing.

Methylation of proteins at arginine residues is catalysed by Protein Arginine Methyltransferase enzymes. The Protein Arginine Methyl Transferase (PRMT) family of enzymes are evolutionarily conserved between organisms but differ in the number of members in different organisms.

There are eleven members of the human PRMT family, eight of which have known enzymatic activity and target substrates. With the exception of PRMT2 and two recently identified putative PRMT genes (PRMT10 and PRMT11), all remaining proteins of the family possess enzymatic arginine methylation activity.

PRMTs are subdivided into two types based on the methylation that they catalyse at the guanidinium group of arginine residues of substrate proteins. There are three nitrogens in the guanidinium group, potentially all of which could be methylated; the two ψ-guanidino nitrogen atoms and the internal δ-guanidino nitrogen atom. Mono-methylation and dimethylation of arginine (MMA and DMA) is found in mammalian cells at one or both of the two ψ-guanidino nitrogen atoms; dimethylation may be either symmetric or asymmetric. The third methylated arginine is generated by monomethylation of the internal δ-guanidino nitrogen atom of arginine and has so far been documented only in yeast proteins. Type I PRMT enzymes catalyse the formation of MMA and asymmetric dimethylarginine by di-methylating the same nitrogen atom of the guanidinium group, whereas Type II PRMT enzymes catalyse the formation of MMA and symmetric di-methylarginine by mono-methylating each of the terminal nitrogen atoms. Type III enzymes methylate the internal δ-guanidino nitrogen atom. Of the eight well characterised human PRMTs, PRMT1, 3, 4, 6 and 8 are Type I enzymes, and PRMT5, 7 and 9 are Type II enzymes.

PRMTs catalyse the methylation of the guanidino nitrogen atoms of arginine residues through the transfer of a methyl group from S-adenosyl methionine (SAM). A by-product of the enzymatic methylation step is S-adenosyl-L-homocysteine (AdoHcy), which is hydrolyzed to adenosine and homocysteine by AdoHcy hydrolase (Krause et al., 2007).

PRMT5

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999).

PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

In addition to direct repressive histone marks induced by PRMT5, the enzyme's role in gene silencing is also mediated through the formation of multiprotein repressor complexes that include NuRD components, HDACs, MDB proteins and DNA methyltransferases, (Rank et al., 2010; Le Guezennec et al., 2006; Pal et al., 2003).

PRMT5 is involved in the methylation and functional modulation of the tumour suppressor protein p53. See (Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumour suppression.

p53 target genes have two alternative downstream effects: either they pause the cell cycle, allowing the DNA to be repaired, or, if repair is not possible, they activate processes leading to apoptosis (programmed cell death). How p53 'chooses' between these distinct outcomes is a central question in the field of tumour biology.

p53 is replete with post-translational modifications. Phosphorylation was one of the first post-translational modifications to be clearly defined on p53. In the last decade it has become additionally clear that p53 is modified not only by phosphorylation, but that it is extensively modified by lysine acetylation and methylation, among other modifications. Indeed, besides histone proteins p53 is the most common protein substrate known for these post-translational modifications. However, despite the plethora of post-translational modifications, p53 has not been identified, until recently, as a substrate for arginine methylation.

Jansson et al (Jansson et al., 2008) discovered that PRMT5 is physically associated with a p53 cofactor called Strap. A co-factor complex that contains Strap et al binds to p53 in response to DNA damage. Jansson et al demonstrated that PRMT5 methylates p53 in vitro, and mapped the sites of methylation (R333, R335 and R337). They developed an antibody that specifically detects p53 methylated on these sites and confirmed that p53 is methylated in vivo. Jansson et al went on to show that p53 methylation requires PRMT5 and is increased in response to etoposide, a DNA damaging agent.

The role of PRMT5 and p53 arginine methylation on cell cycle regulation and DNA damage response have been explored by both Jansson et al and Scoumanne et al (Jansson et al., 2008; Scoumanne et al., 2009). Although some differences are evident between the results from the two groups in respect of cell cycle regulation in unperturbed cells (which may be ascribed to cell type specific effects and/or the actual nature of the experimental arrangements), both groups report similar results with respect to the DNA damage response.

In response to DNA damage, caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilisation, decreased basal p53 levels, and decreased p53 oligomerisation, and also decreased expression of eIF4E a major component of translational machinery involved in ribosome binding to mRNA. Indeed, eIF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al showed that a p53 mutant in which each of the three critical arginine residues were substituted with lysine (p53KKK) retained the ability to induce apoptosis but its cell cycle arrest activity was significantly compromised.

Moreover, pS3KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

Taken together, it would seem that PRMT5 is a pro-survival factor, which regulates cell proliferation in unstressed conditions and modulates the p53 response during DNA damage. In particular, knockdown of PRMT5, leading to a reduction in the levels of arginine methylated p53, appears to bias the p53 DNA damage response to proapoptotic as opposed to cell cycle arrest.

PRMT5 is further linked to cancers in that it is aberrantly expressed in around half of human cancer cases. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including CLL are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al., 2007; Wang et al., 2008). Intriguingly, despite elevated levels of PRMT5 protein in these tumour cells, the levels of PRMT5 mRNA are reduced (by a factor of 2-5). Translation of PRMT5 mRNA is however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumour suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

PRMT5 Function and Hemoglobinopathies

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by subunits as the infant grows. The developmental switch in human β-like globin gene subtype from foetal (γ) to adult (β) that begins at birth heralds the onset of the hemoglobinopathies β-thalassemia and sickle cell disease (SCD). In β-thalassemia the adult chains are not produced. In SCD a point mutation in the coding sequence in the β globin gene leads to the production of a protein with altered polymerisation properties. The observation that increased adult γ-globin gene expression (in the setting of hereditary persistence of foetal hemoglobin (HPFH) mutations) significantly ameliorates the clinical severity of β-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as β-thalassemia and Sickle Cell Disease (SCD).

The present inventors have developed particular substituted β-hydroxy amides inhibit the activity of PRMT5 and therefore may be of use in treating conditions ameliorated by the inhibition of the activity of PRMT5.

SUMMARY OF THE INVENTION

A first aspect of the present invention provides a compound of formula Ia, Ib or Ic:

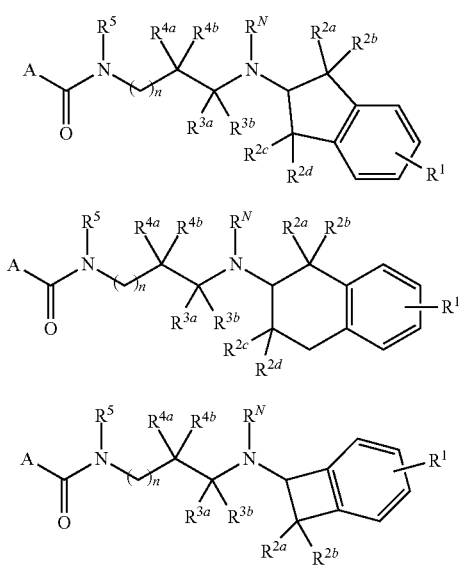

wherein:
n is 1 or 2;
$R^N$ is H or Me;
$R^1$ is optionally one or more halo or methyl groups;
$R^{2a}$ and $R^{2b}$ are independently selected from the group consisting of:
  (i) F;
  (ii) H;
  (iii) Me; and
  (iv) $CH_2OH$;
$R^{2c}$ and $R^{2d}$ (if present) are independently selected from the group consisting of:
  (i) F;
  (ii) H;
  (iii) Me; and
  (iv) $CH_2OH$;
$R^{3a}$ and $R^{3b}$ are independently selected from H and Me;
$R^{4a}$ is selected from OH, —$NH_2$, —C(=O)$NH_2$, and —$CH_2OH$;
$R^{4b}$ is either H or Me;
$R^5$ is either H or Me;
A is either
  (i) optionally substituted phenyl;
  (ii) optionally substituted naphthyl; or
  (iii) optionally substituted $C_{5-12}$ heteroaryl.

A second aspect of the present invention provides a compound of the first aspect for use in a method of therapy. The second aspect also provides a pharmaceutical composition comprising a compound of the first aspect and a pharmaceutically acceptable excipient.

A third aspect of the present invention provides a method of treatment of cancer, comprising administering to a patient in need of treatment, a compound of the first aspect of the invention or a pharmaceutical composition of the first aspect of the invention. The third aspect of the present invention also provides the use of a compound of the first aspect of the invention in the manufacture of a medicament for treating cancer, and a compound of the first aspect of the invention or pharmaceutical composition thereof for use in the treatment of cancer.

As described below, the compound of the first aspect may be administered simultaneously or sequentially with radiotherapy and/or chemotherapy in the treatment of cancer.

A fourth aspect of the present invention provides a method of treatment of hemoglobinopathies, comprising administering to a patient in need of treatment, a compound of the first aspect of the invention or a pharmaceutical composition of the first aspect of the invention. The fourth aspect of the present invention also provides the use of a compound of the first aspect of the invention in the manufacture of a medicament for treating hemoglobinopathies, and a compound of the first aspect of the invention or pharmaceutical composition of the first aspect of the invention for use in the treatment of hemoglobinopathies.

Definitions $C_{5-12}$ heteroaryl: The term "$C_{5-12}$ heteroaryl" as used herein, pertains to a monovalent moiety obtained by removing a hydrogen atom from an aromatic structure having from 5 to 12 rings atoms, of which from 1 to 3 are ring heteroatoms. The term 'aromatic structure' is used to denote a single ring or fused ring systems having aromatic properties, and the term 'ring heteroatom' refers to a nitrogen, oxygen or sulphur atom.

In this context, the prefixes (e.g. $C_{5-12}$, $C_{5-6}$, etc.) denote the number of atoms making up the aromatic structure, or range of number of atoms making up the aromatic structure, whether carbon atoms or heteroatoms.

Examples of $C_{5-12}$ heteroaryl structures include, but are not limited to, those derived from:
$N_1$: pyrrole (azole) ($C_5$), pyridine (azine) ($C_6$); pyridone ($C_6$); indole ($C_9$); quinoline ($C_{10}$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_1S_1$: thiazole ($C_5$), isothiazole ($C_5$);
$N_2S_1$: thiadiazole ($C_5$)
$N_2$: imidazole (1,3-diazole) ($C_5$), pyrazole (1,2-diazole) ($C_5$), pyridazine (1,2-diazine) ($C_6$), pyrimidine (1,3-diazine)

($C_6$) (e.g., cytosine, thymine, uracil), pyrazine (1,4-diazine) ($C_6$); benzimidazole ($C_9$)

$N_3$: triazole ($C_5$), triazine ($C_6$).

Optional Substituents

The optional substituents for the phenyl, naphthyl and $C_{5-12}$ heteroaryl groups in A may be selected from the following groups.

$C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

$C_{1-4}$ fluoroalkyl: The term "$C_{1-4}$ fluoroalkyl" refers to a $C_{1-4}$ alkyl group as defined above where one of more of the hydrogen atoms is replaced by a fluoro. Examples of $C_{1-4}$ fluoroalkyl include, but are not limited to, —$CF_3$, $CF_2H$, —$C_2F_5$, and —$C_2F_4H$.

$C_{3-6}$ cycloalkyl: the term '$C_{3-6}$ cycloalkyl' as used herein, pertains to a monovalent moiety obtained by removing a hydrogen atom from a carbon atom of a saturated cyclic core having 3, 4, 5 or 6 atom in the cyclic core all of which are carbon atoms. Examples of $C_{3-6}$ cycloalkyl include, but are not limited to, cyclopropyl, cyclohexyl and cyclopentyl.

$C_{5-6}$ heteroaryl: the term $C_{5-6}$ heteroaryl as used herein, pertains to a monovalent moiety obtained by removing a hydrogen atom from a ring atom of an aromatic structure having between one and three atoms that are not carbon forming part of said ring. Wherein, those atoms that are not carbon can be chosen independently from the list nitrogen, oxygen and sulphur. The group may be substituted by one or more $C_{1-4}$ alkyl groups.

Examples of $C_{5-6}$ heteroaryl groups include, but are not limited to, groups derived from:

$N_1$: pyridine ($C_6$);

$N_1O_1$: oxazole ($C_5$), isoxazole ($C_5$);

$N_2O_1$: oxadiazole (furazan) ($C_5$);

$N_2S_1$: thiadiazole ($C_5$)

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$).

$C_{5-6}$ heteroaryl methyl: —$CH_2$—($C_{5-6}$ heteroaryl), wherein $C_{5-6}$ heteroaryl is as defined above.

$C_{4-6}$ heterocyclyl: The term "$C_{4-6}$ heterocyclyl" as used herein, pertains to a monovalent moiety obtained by removing a hydrogen atom from a ring atom of a monocyclic heterocyclic compound, which moiety has from 4 to 6 ring atoms; of which from 1 to 2 atoms are heteroatoms, chosen from oxygen or nitrogen.

In this context, the prefixes (e.g. $C_{4-6}$) denote the number of ring atoms, or range of number of ring atoms, whether carbon atoms or heteroatoms.

Examples of $C_{4-6}$ heterocyclyl groups include, but are not limited to, those derived from:

$N_1$: azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$N_2$: diazetidine ($C_4$), imidazolidine ($C_5$), pyrazolidine (diazolidine) ($C_5$), imidazoline ($C_5$), pyrazoline (dihydropyrazole) ($C_5$), piperazine ($C_6$);

$O_1$: oxetane ($C_4$), tetrahydrofuran ($C_5$); oxane ($C_6$);

$O_2$: dioxetane ($C_4$), dioxolane ($C_5$); dioxane ($C_5$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$).

Those $C_{4-6}$ heterocyclyl groups which include a N atom may be substituted on this atom by an acyl group, and in particular, by —C(=O)Me.

The $C_{4-6}$ heterocyclyl groups may also bear a single oxo substituent, as for example in the following group:

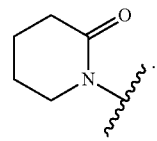

$C_{4-6}$ heterocyclyl methyl: —$CH_2$—($C_{4-6}$ heterocyclyl), wherein $C_{4-6}$ heterocyclyl is as defined above.

Phenyl: —$C_6H_5$, wherein the phenyl may itself be optionally substituted by one or more $C_{1-4}$ alkyl groups, one or more $C_{1-4}$ fluoroalkyl groups, one or more $C_{1-4}$ alkoxy groups, one or more halo substituents and one or more cyano substituents.

Benzyl: —$CH_2$-Phenyl, wherein phenyl is as defined above.

Halo: The term "halo" as used herein, refers to a group selected from fluoro, chloro, bromo and iodo.

Amido: —(C=O)NRR' wherein R and R' are independently selected from H, $C_{1-4}$ alkyl and $C_{4-6}$ heterocyclyl as defined above, or together form a group selected from (—$CH_2$—)$_n$ and —($CH_2$)$_m$—X—($CH_2$)$_p$—, where n=3-6, m and p=0-4, and X=O or NH. X may also be N—S(=O)$_2$, S or S(=O)$_2$. The cyclic amido groups may also be bridged by a further group selected from (—$CH_2$—)$_{n1}$ and —($CH_2$)$_{m1}$—X—($CH_2$)$_{p1}$—, where n1 is 1-3 and m1 and p1 are 1-3. The cyclic amido groups may also be further substituted by one, two or more hydroxy, oxo, $C_{1-2}$ alkyl, $C_{1-2}$ alkoxy, hydroxy-$C_{1-2}$ alkyl, $C_{1-2}$ alkoxy-$C_{1-2}$ alkyl groups or one spiro $C_{4-6}$ heteroaryl or spiro $C_{4-6}$ cycloalkyl group or be fused to an $C_{5-7}$ aromatic ring. Examples of amido groups include, but are not limited to, —C(=O)NH$_2$, —C(=O)NMe$_2$, —C(=O)NHMe, —C(=O)NHCH(CH$_3$)$_2$,

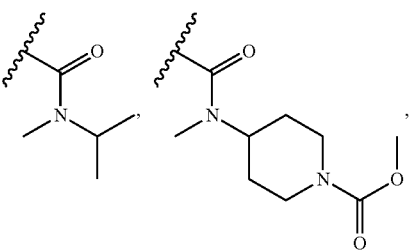

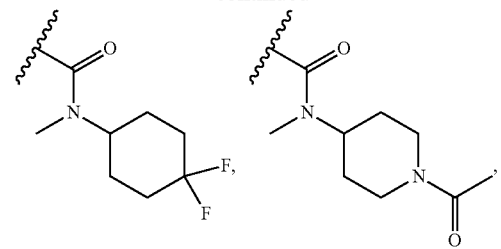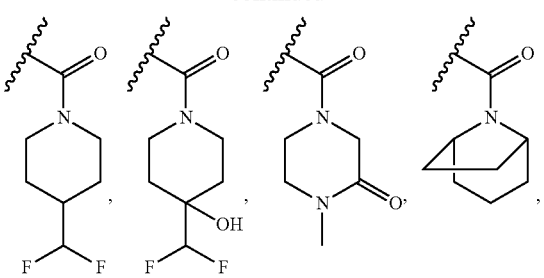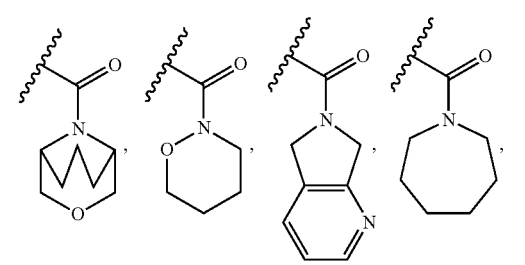

-continued

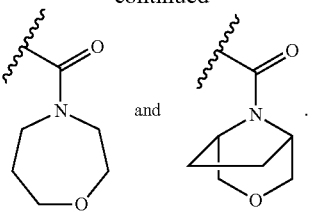 and

Amidomethyl: —CH₂-amido, where amido is as defined above, Examples of amidomethyl groups include, but are not limited to, —CH₂—C(=O)NH₂, —CH₂—C(=O)NMe₂, —CH₂—C(=O)NHMe,

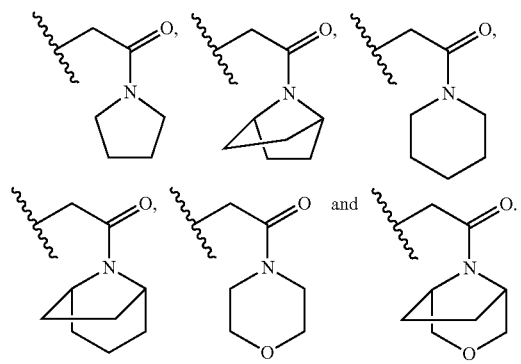

Acylamido: —NR(C=O)R' wherein R and R' are independently selected from H, $C_{1-4}$ alkyl and $C_{1-4}$ fluoro alkyl as defined above. R' may also be —(CH₂)ₙ—, where n is 3 or 4. Examples of an acylamido group include, but are not limited to, —N(H)C(=O)CF₃, —N(H)C(=O)Me, and:

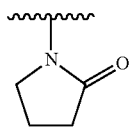 [SMILES: *N1CCCC1=O]

Acylamidomethyl: —CH₂-acylamido, where acylamido is as defined above, Examples of acylamidomethyl groups include, but are not limited to —CH₂—N(H)C(=O)Me and —CH₂—N(H)C(=O)CF₃.

$C_{1-4}$ alkyl ester: —C(=O)OR, wherein R is a $C_{1-4}$ alkyl group. Examples of $C_{1-4}$ alkyl ester groups include, but are not limited to, —C(=O)OCH₃, —C(=O)OCH₂CH₃, and —C(=O)OC(CH₃)₃.

$C_{1-4}$ alkyl ester methyl: —CH₂—($C_{1-4}$ alkyl ester), where $C_{1-4}$ alkyl ester is as defined above. Examples of $C_{1-4}$ alkyl ester methyl groups include, but are not limited to, —CH₂—C(=O)OCH₃, —CH₂—C(=O)OCH₂CH₃, and —CH₂—C(=O)OC(CH₃)₃.

$C_{1-4}$ alkyl carbamoyl: —NHC(=O)OR wherein R is a $C_{1-4}$ alkyl group as defined above. Examples of $C_{1-4}$ alkyl carbamoyl include, but are not limited to, —N(H)C(=O)OCH₃, —N(H)C(=O)OCH₂CH₃, and —N(H)C(=O)OC(CH₃)₃.

$C_{1-4}$ alkyl carbamoyl methyl: —CH₂—($C_{1-4}$ alkyl carbamoyl), where $C_{1-4}$ alkyl carbamoyl is as defined above. Examples of $C_{1-4}$ alkyl carbamoyl methyl include, but are not limited to, —CH₂—N(H)C(=O)OCH₃, —CH₂—N(H)C(=O)OCH₂CH₃, and —CH₂—N(H)C(=O)OC(CH₃)₃.

$C_{1-4}$ alkylacyl: —C(=O)R, wherein R is a $C_{1-4}$ alkyl group as defined above. Examples of $C_{1-4}$ alkylacyl groups include, but are not limited to, —C(=O)CH₃ (acetyl), —C(=O)CH₂CH₃ (propionyl) and —C(=O)C(CH₃)₃ (t-butyryl).

$C_{1-4}$ alkylacyl methyl: —CH₂—($C_{1-4}$ alkylacyl), where $C_{1-4}$ alkylacyl is as defined above. Examples of $C_{1-4}$ alkylacylmethyl groups include, but are not limited to, —CH₂—C(=O)CH₃, —CH₂—C(=O)CH₂CH₃, and —CH₂—C(=O)C(CH₃)₃.

Phenylcarbonyl: —C(=O)-phenyl, where phenyl is as defined above.

Carboxy (carboxylic acid): —C(=O)OH

Carboxymethyl: —CH₂—C(=O)OH.

Ether: —OP, wherein P is chosen from one of the following substituents: $C_{1-4}$ alkyl, benzyl, phenyl, $C_{1-4}$ fluoroalkyl, $C_{5-6}$ heteroaryl, —CH₂—$C_{5-6}$ heteroaryl, $C_{4-6}$ heterocyclyl, and —CH₂—$C_{4-6}$ heterocyclyl as defined above. Examples of an ether include, but are not limited to, —OPh, —OBn, —OCF₃, —OCH₂CF₃, —OCH(CH₃)₂, —OCH₂-cyclopropyl, —O-(N-acetyl)azetidinyl, e.g.     —O-(N-acetyl)piperidinyl, e.g.

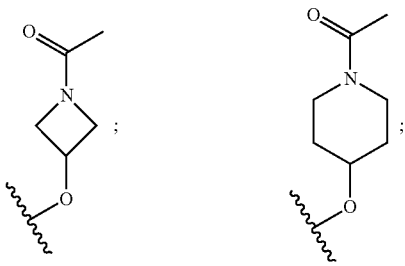

—O-oxentanyl, e.g.;     Piperidyloxy, e.g.

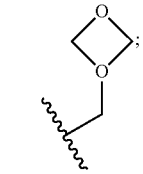 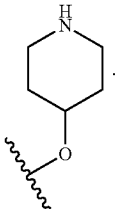

—O-(N-carboxylate)piperidinyl, e.g.

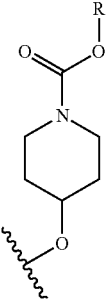     —O-tetrahydropyranyl, e.g.;

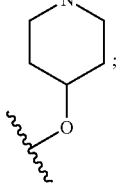

where R is
methyl, isopryl, isobutyl;

—O-tetrahydrofuranyl, e.g.; 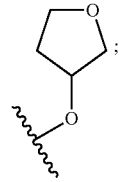

(8-methoxycarbonyl-8-azabicyclo[3.2.1]octan-3-yl)oxy: 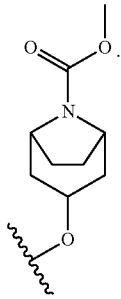

Amino: —NPP', wherein P and P' are independently chosen from H, $C_{1-4}$ alkyl, $C_{4-6}$ heterocyclyl, phenyl and $C_{5-6}$ heteroaryl as defined above. Examples of an amine include, but are not limited to, —$NH_2$, —N(H)pyridazinyl,

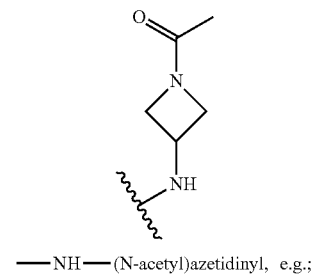

—NH—(N-acetyl)azetidinyl, e.g.;

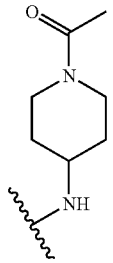

—NH—(N-acetyl)piperidinyl, e.g.;

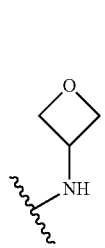 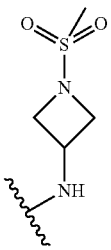

—NH-oxetanyl, e.g.;. (1-methylsulfonylazetidin-3-yl)amino;;

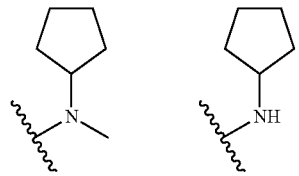

cyclopentyl(methyl)amino;; cyclopentylamino;

Aminomethyl: —$CH_2$-Amino, where amino is as defined above. Examples of aminomethyl include, but are not limited to, —$CH_2$—$NH_2$ and —$CH_2$—N(H)pyridazinyl.

Sulfonamido: —$SO_2NRR'$ wherein R and R' are independently selected from H, $C_{1-4}$ alkyl, phenyl and $C_{5-6}$ heteroaryl as defined above. Examples of sulfonamido groups include, but are not limited to, —$SO_2N(Me)_2$ and —$SO_2NPhMe$.

Sulfonamino: —$NHSO_2R$ wherein R is selected from $C_{1-4}$ alkyl, phenyl and $C_{5-6}$ heteroaryl as defined above. Examples of sulfonamino groups include, but are not limited to, —$NHSO_2Me$ and —$NHSO_2Ph$ Sulfone: —$SO_2R$, wherein R is selected from $C_{1-4}$ alkyl and $C_{1-4}$ fluoroalkyl as defined above. Example of sulfone groups includes but is not limited to $SO_2CF_3$.

Sulfoxide: —SOR, wherein R is selected from $C_{1-4}$ alkyl and $C_{1-4}$ fluoroalkyl as defined above.

Example of sulfoxide groups includes but is not limited to $SOCF_3$.

Nitrile: —CN.

Nitrilemethyl: —$CH_2$—CN

Fused N-heterocyclic ring: where A is phenyl, it may have a $C_{5-6}$ $N_1$-containing heterocyclic ring fused to it as a substituent group. The $C_{5-6}$ $N_1$-containing heterocyclic ring may in particular be selected from:

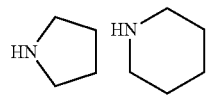

Which may be fused in any orientation, and wherein the N ring atom may be optionally substituted, for example by a $C_{1-4}$ alkylacyl group.

Includes Other Forms

Unless otherwise specified, included in the above are the well known ionic, salt, solvate, and protected forms of these substituents. For example, a reference to carboxylic acid (—COOH) also includes the anionic (carboxylate) form (—$COO^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—$O^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —$COO^-$), then a salt may be formed with a suitable cation. Examples of suitable inorganic cations include, but are not limited to, alkali metal ions such as $Na^+$ and $K^+$, alkaline earth cations such as $C^{2+}$ and $Mg^{2+}$, and other cations such as $Al^{+3}$. Examples of suitable organic cations include, but are not limited to, ammonium ion (i.e. $NH_4+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric.

Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, $—OCH_3$, is not to be construed as a reference to its structural isomer, a hydroxymethyl group, $—CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

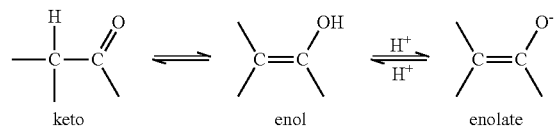

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3$H (T); C may be in any isotopic form, including $^{12}$C, $^{13}$O, and $^{14}$O; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of cancers and hemoglobinopathies.

Cancer

Modulators of PRMT5 mediated post-translational arginine methylation of p53 may regulate a pro-apoptotic p53 response, and may therefore be useful as therapeutic agents, for example in the treatment of cancer. Such agents may also be useful as therapeutic agents for the treatment of cancers which exhibit overexpression of PRMT5.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor. Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chrondrosarcoma, osteosarcoma).

The cancer may be a PRMT5 overexpressing cancer. The cancer may over express PRMT5 protein relative to non-cancerous tissue. In some cases, the cancer overproduces PRMT5 mRNA relative to non-cancerous tissue.

Alternatively or additionally, the cancer may be a p53 overexpressing cancer. The cell may overexpress p53 protein relative to non-cancerous tissue. It may overproduce p53 mRNA as compared to non-cancerous tissue. In some cases, the level of p53 protein and/or mRNA in the cell is at a level approximately equivalent to that of a non-cancerous cell.

The agents described herein may be useful in combination with other anti-cancer therapies. They may act synergistically with chemo- or radiotherapy, and/or with p53 targeted drugs.

An inhibitor of PRMT5 would in all likelihood augment the effects of drugs (such as the nutlins) that restore p53. Inhibition of PRMT5, resulting in decreased arginine-methylated p53, may sensitize tumour cells to chemo- and radiotherapy by switching, or at least biasing, the cellular outcome to apoptosis.

Combination Therapies p53 is activated by DNA damage. PRMT5 is part of the complex of proteins that activate and modulate p53 activity in response to DNA damage. It is likely that inhibition of PRMT5, resulting in decreased arginine-methylated p53, would sensitize tumour cells to chemo- and radiotherapy by switching or at least biasing the cellular outcome to apoptosis. PRMT5 inhibition is likely to synergize well with low dose chemo- or radiotherapy, by stabilizing p53, and biasing the cellular outcome to apoptosis.

Biasing the p53 response towards apoptosis would in all likelihood be of benefit, and an agent that so biases the response would be expected to augment the effect of a p53 resurrecting drug. Thus, in some cases, a PRMT5 modulator disclosed herein may be administered in conjunction with a radiotherapeutic or chemotherapeutic regime. It may be administered in conjunction with a drug that resurrects cellular p53 activity, for example, a p53 agonist. The PRMT5 modulator may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

Hemoglobinopathies

The compounds disclosed herein may be useful in the treatment or prevention of conditions that may benefit from the increased expression of γ-globin genes, for example, due to the release of repressive methylation of these genes. The compounds disclosed herein may be useful in the treatment or prevention of hemoglobinopathies. A hemoglobinopathy is a condition associated with the presence of abnormal hemoglobin in the blood of a subject. Such conditions include β-thalassemia and Sickle Cell Disease, α-thalassemia and δ-thalassemia.

Hemoglobinopathies treatable by the compounds disclosed herein may be ameliorated by the re-activation of the subjects γ-globin genes (γ genes). In such cases, the subject is not a fetal mammal.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesis the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula I (Ia, Ib and Ic), as described above, can be prepared by synthetic strategies outlined below, wherein the definitions above apply. The synthetic strategies could be applied to the use of racemic or single enantiomer starting materials.

General Synthesis Method 1

Scheme 1A illustrates the formation of the amide bond by coupling a relevant carboxylic acid to a primary amine or a secondary amine G1. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester.

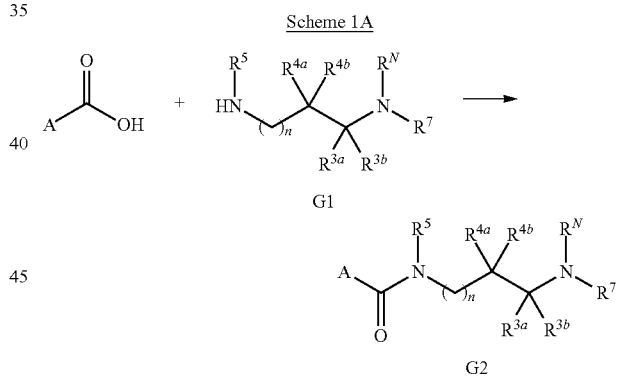

Scheme 1A $R^7$ represents the fused cyclic system.

Optionally, where $R^N$=H, a protecting group (PG) may be used such as but not limited to Boc, allyl, benzyl, 2,4-dimethoxybenzyl. As illustrated in Scheme 1B, coupling between a relevant carboxylic acid or activated acid, e.g. acyl halide to a primary amine or a secondary amine G3 bearing a protecting group (PG) is performed as described previously. Conditions for the removal of the protecting group are dependent on the type of protecting group employed, and may include but is not limited to such methods as acid hydrolysis, transition metal catalysed cleavage and hydrogenation over transition metal catalysts. Other suitable protecting groups and removal methods will be known to those skilled in the art (for example *Greene's Protective Groups in Organic Synthesis, 4th Edition*). The use of such a protecting group could be relevant in the other Schemes described.

Scheme 1B

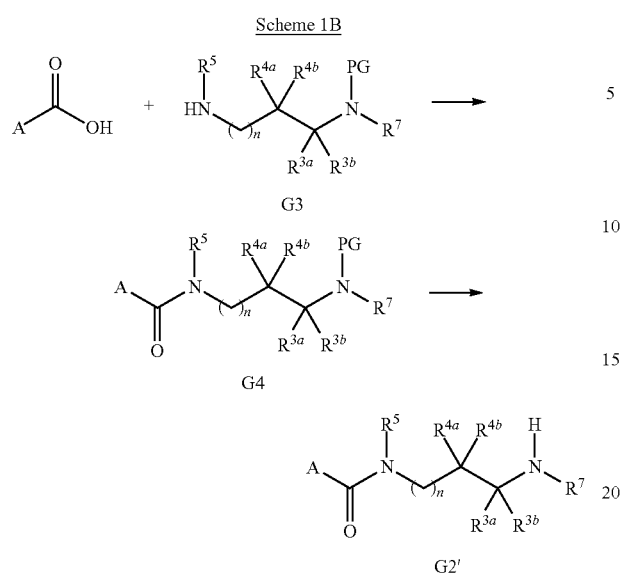

Where A contains a direct carboxylic acid substitution or a further substitution that also has a carboxylic acid substitution G5, another amide formation can be conducted to provide compounds of G6, scheme 1C. Coupling is possible with a primary or secondary amine or cyclised secondary amine including, but not limited to, azetidine, pyrrolidine, piperidine, piperazine and morpholine or substituted analogues thereof.

Scheme 1C

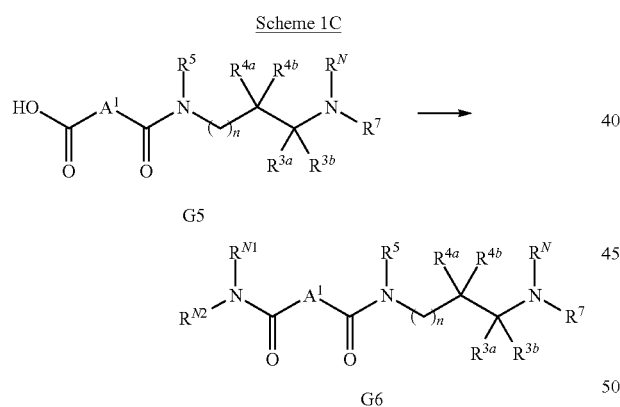

General Synthesis Method 2

Scheme 2A illustrates the synthesis of the substituted amine alcohol G9. This is achieved by opening the epoxide with a desired amine (HNR$^N$R$^7$) to form the intermediate G7. The phthalimide protecting group can then be removed by heating with hydrazine hydrate to form G8. Other suitable protecting groups and removal methods will be known to those skilled in the art (for example *Greene's Protective Groups in Organic Synthesis, 4th Edition*). Commercially available enantiomerically pure epoxides could be used to give single enantiomer products G9.

Scheme 2A

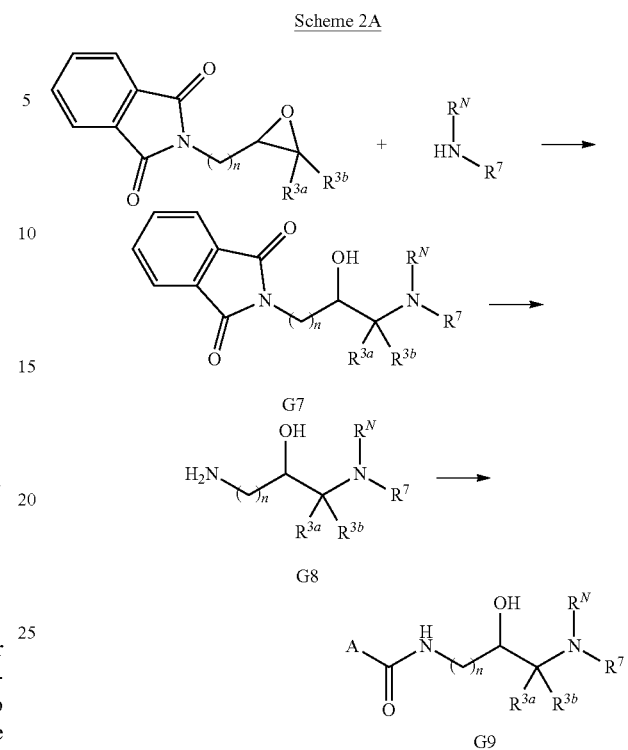

The amide formation to form G9 can be achieved by the methods outline in Scheme 1A. The synthesis of either enantiomer and the racemate can be achieved by the same method.

General Synthesis Method 3

Scheme 3A

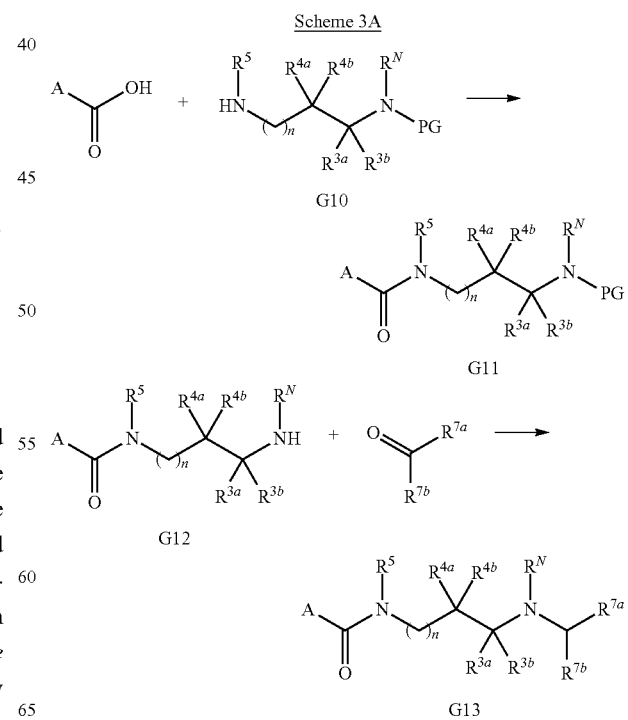

Where $R^{7a}$ and $R^{7b}$ together with the atom to which they are bound form $R^7$.

Scheme 3A illustrates the synthesis of compounds with the formula G13, beginning with an amide bond formation by coupling a relevant carboxylic acid to a primary amine or a secondary amine G10. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester.

Suitably protected amino groups and methods for the removal of said protecting groups will be known to those skilled in the art (for example *Greene's Protective Groups in Organic Synthesis, 4th Edition*). Suitable protecting groups might include Boc, CBz, or phthalimide. Upon removal of the protecting group to provide compounds of the general formula G12, these intermediates can be converted to the desired compound, G13. Methods to form such an intermediate will be apparent to those skilled in the art, but include for example reductive amination by the use of reagents such as, but not limited to sodium triacetoxyborohydride or sodium cyanoborohydride with acetic acid, and sodium triacetoxyborohydride triacetoxyborohydride or sodium borohydride with Ti(O$^i$Pr)$_4$.

General Synthesis Method 4

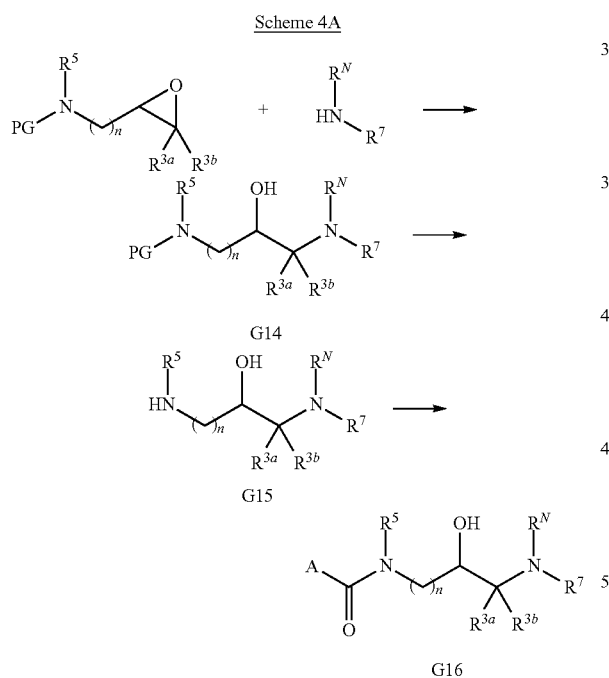

Scheme 4A illustrates an approach to the synthesis of compounds with the formula of G16, beginning with the reaction of the desired amine (HNR$^N$R$^7$) with an epoxide bearing a suitable protected amino group such as for example tert-butyl N-(oxiran-2-yl methyl) carbamate. Opening of the epoxide under suitable conditions furnishes the intermediate compound G14. Suitably protected amino groups and methods for the removal of said protecting groups will be known to those skilled in the art (for example *Greene's Protective Groups in Organic Synthesis, 4th Edition*). Upon removal of the protecting group to provide compounds of the general formula G15, these intermediates can be converted to the desired compound, G16, by the procedure outlined in Scheme 1A.

General Synthesis Method 5

Scheme 5A illustrates how to form amine substitutions such as shown in G17. An amide is reacted with a halo-epoxide or similar and the resultant mixture reacted on with a desired amine (HNR$^6$R$^7$) resulting in a product within the scope of G17. The group denoted (X) can be but is not limited to halogen, tosylate, nosylate or similar.

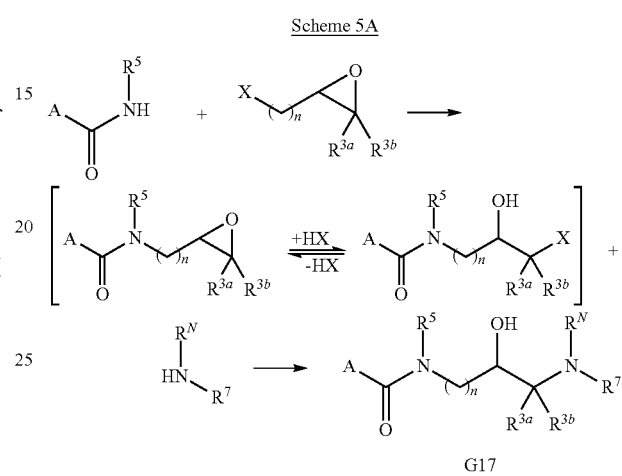

Alternatively enantiomerically pure forms of for example epichlorohydrin can be used to obtain the products G17 in enantiomerically pure form.

General Synthesis Method 6

Scheme 6A illustrates how to form amine substitutions such as shown in G19. Suitable amide protecting groups and methods for the removal of said protecting groups will be known to those skilled in the art (for example *Greene's Protective Groups in Organic Synthesis, 4th Edition*). An amide is reacted with a halo-epoxide or similar and the resultant mixture reacted on with a desired amine (HNR$^N$R$^7$) resulting in an intermediate G18. The group denoted (X) can be but is not limited to halogen, tosylate, nosylate or similar. Removal of the protecting group provides compounds of the general formula G19

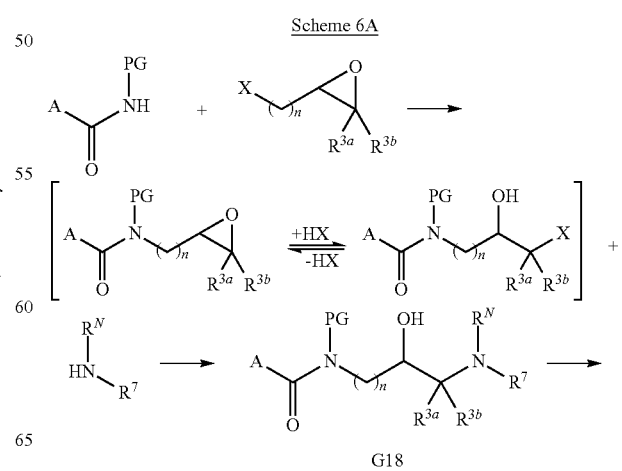

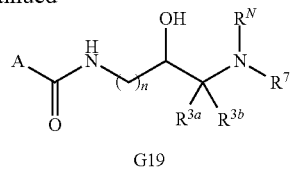

G19

Alternatively enantiomerically pure forms of the epoxide for example include but are not limited to epichlorohydrin, can be used to obtain the products G14 in enantiomerically pure form.

General Synthesis Method 7

Scheme 7A illustrates an approach to the synthesis of compounds with the formula of G23, beginning with the reaction of the desired amine (HNR$^N$R$^7$) with an epoxide bearing a leaving group (LG). The group represented by (LG) includes but not limited to halide, mesylate, tosylate, nosylate. Depending on the conditions and the nature of the leaving group, the reaction can proceed through two different pathways to give either epoxide with structure G20 or alcohol with structure G21. Treatment of either compound with primary amine (R$^5$—NH$_2$) furnishes intermediates with structure G22. These intermediates can be converted to the desired compound, G23, by the procedure outlined in Scheme 1A.

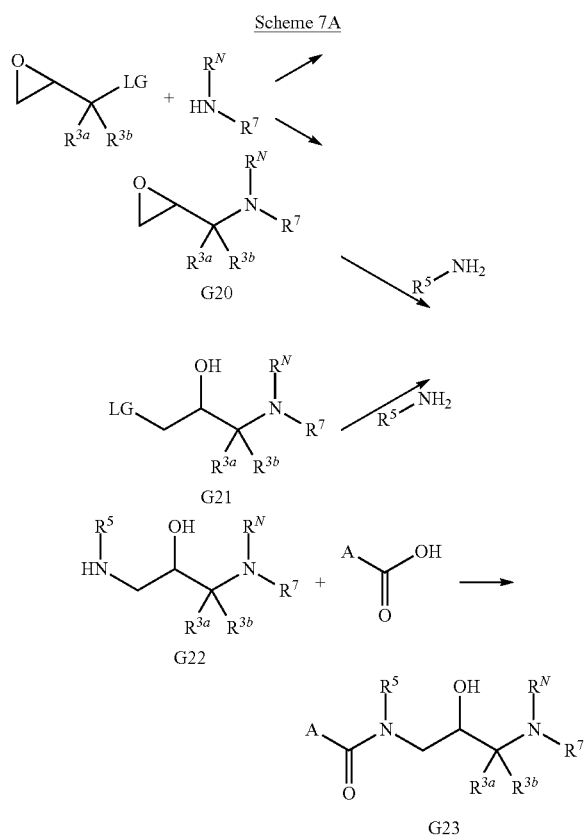

(LG) includes but is not limited to halide, mesylate, tosylate, nosylate. The group represented by (PG) is a suitable amine protecting group which includes but is not limited to Boc, phthalimide, benzyl, PMB, allyl. Suitable amine protecting groups and methods for the removal of said protecting groups will be known to those skilled in the art (for example *Greene's Protective Groups in Organic Synthesis, 4th Edition*). Upon removal of the protecting group, coupling with a suitable carboxylic acid can be performed by methods illustrated in Scheme 1A.

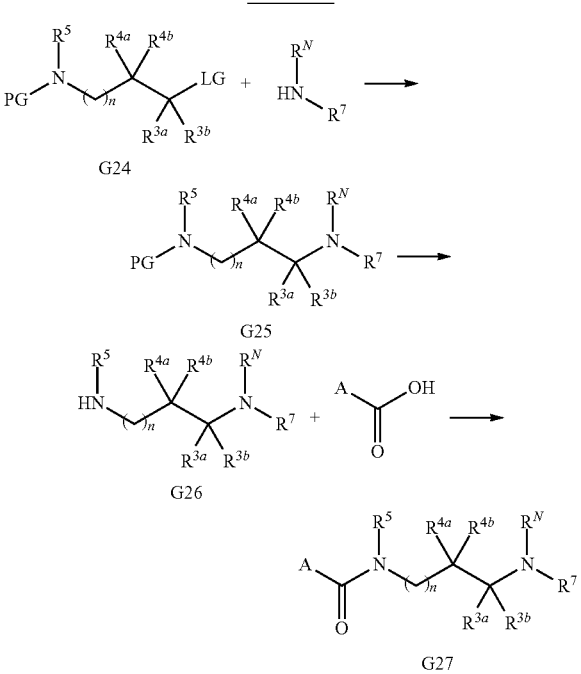

Alternatively, as shown in Scheme 8B, compounds with structure G28 can be coupled with the desired amine (HN-R$^N$R$^7$) to give compounds G27.

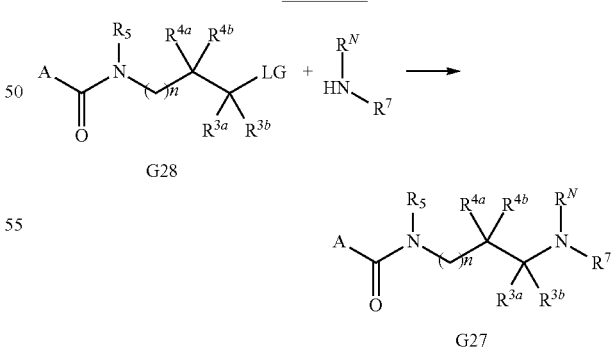

General Synthesis Method 8

Scheme 8A illustrates the synthesis of compounds G27 which begins with a coupling of a compound G24 with a desired amine (HNR$^N$R$^7$) by substitution of a leaving group (LG) to give intermediates G25. The group represented by General Synthesis Method 9

Scheme 9A illustrates the synthesis of compounds G32 where R$^{3a}$ and R$^{3b}$ are hydrogen. Amide bond formation of compounds with structure G28 with the desired amine (HNR$^N$R$^7$) give compounds with structure G29. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. Reduction of the amide to the corresponding amine G30 will be apparent to those skilled in the art but such methods include but are not limited to the use of a reducing agent such as $LiAlH_4$. Suitable amine protecting groups and methods for the removal of said protecting groups will be known to those skilled in the art (for example *Greene's Protective Groups in Organic Synthesis, 4th Edition*). Upon deprotection, intermediates G31 can be converted to the desired compound, G32, by the procedure outlined in Scheme 1A.

Alternatively where X=H in G28, a reductive amination could be performed, for example using sodium triacetoxy borohydride and acetic acid to form G30 directly, rather than proceeding via intermediate G29.

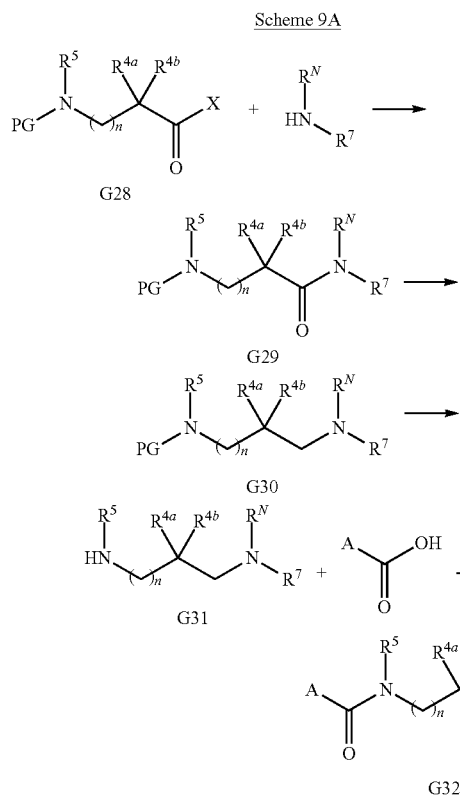

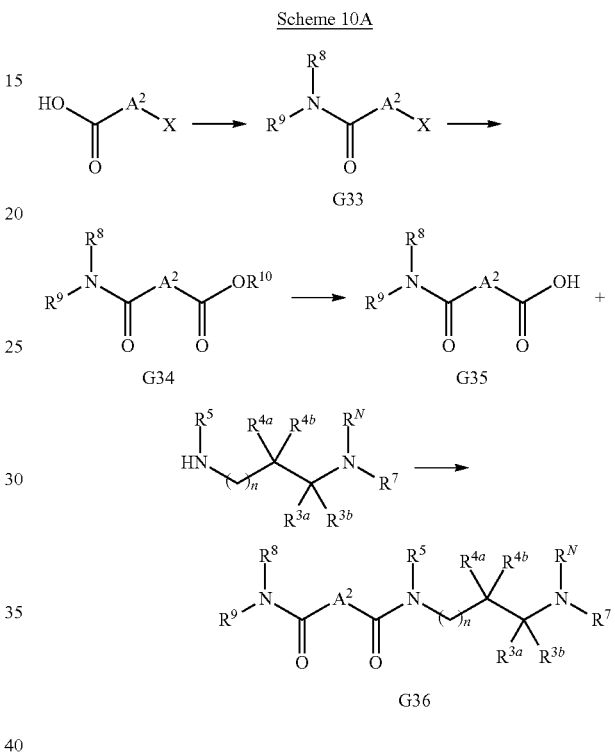

General Synthesis Method 10

Scheme 10A illustrates the addition of an amine ($HNR^8R^9$) as a substituent which is a part of A. This can be achieved by coupling a relevant carboxylic acid to a primary amine or a secondary amine, $NHR^8R^9$. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. The group denoted by (X) may be but not limited to halogen, tosylate or other suitable group. Conversion of (X) in G33 into an ester in G34 will be apparent to those skilled in the art, but include for example a carbonylation reaction which can be achieve by the use of carbon monoxide in the presence of an transition metal catalyst such as but not limited to $PdCl_2dppf.DCM$; and an alcoholic solvent such as but not limited to methanol, ethanol, isopropanol or tert-butyl alcohol. Formation of the carboxylic acid can be achieved by for example hydrolysis with a base such as an alkali metal hydroxide or an acid for example aqueous hydrochloric acid to form G35. The amide formation to form G36 can be achieved by the methods outline in Scheme 1A.

Alternatively, for the synthesis of ester G34 the order of steps can be reversed as described in Scheme 10B.

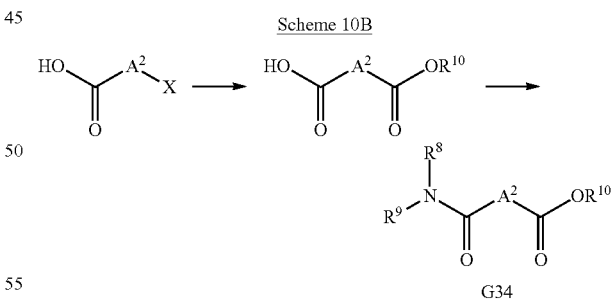

Alternatively for the synthesis of amide G36 the steps may be reordered such that the formation of the $R^8R^9N$ amide on the A substituent occurs after the coupling of A to the amine G26. This may be achieved by coupling a suitable amine with an intermediate where A bears a suitable functional group for coupling, for example but not limited to a carboxylic acid or alkali metal carboxylate salt, as shown in Scheme 10C Scheme 10C

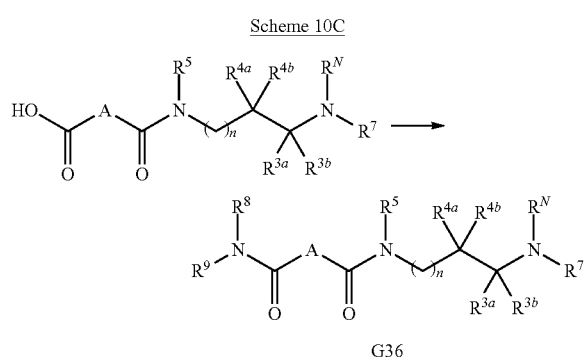

G36

General Synthesis Method 11

Scheme 11A illustrates the addition of an $R^{11}$ group, as a substituent which is part of A. This can be achieved using any suitable coupling reaction known to the person skilled in the art, for example by Suzuki coupling, Negishi coupling, $S_NAr$ reaction, Ullman coupling, Chan Lam coupling, an alkylation reaction e.g. $S_N2$ or $S_N1$, a Mitsonobu reaction, a C—H activation reaction, a Kumada coupling, a Buchwald reaction etc. The groups denoted by $R^{11}X$ and $B^1$ are chosen to be suitable for the coupling reaction employed. For example, in the case of a Suzuki coupling reaction (X) may be a halogen, tosylate or other suitable group and $B^1$ represents a suitable boron compound including, but not limited to, a boronic acid or boronic ester.

Scheme 11A

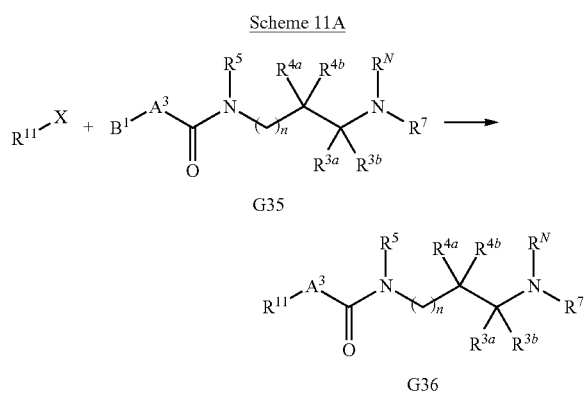

G36

Examples of $B^1$ that can be used in the Suzuki coupling include, but are not limited to, those shown below.

$B^1$=

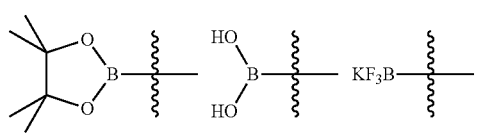

The types of $R^{11}X$ compounds that can be used in the Suzuki coupling include, but are not limited to, those shown in Table 1.

TABLE 1

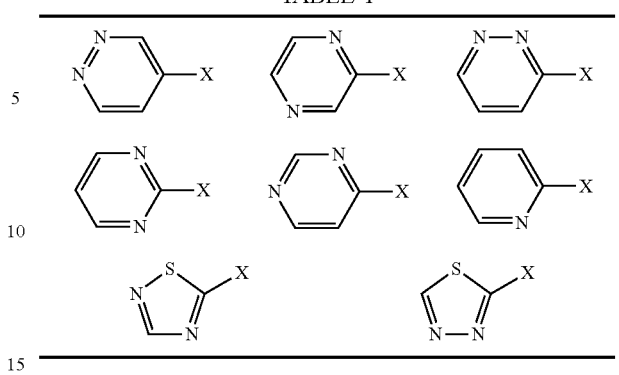

In addition to scheme 11A, the position of the (X) and ($B^1$) can be reversed as shown below in scheme 11B, to give the same final compound G36. Similarly to Scheme 11A, the groups denoted by $R^{11}B^1$ and (X) are chosen to be suitable for the coupling reaction employed. For example, in the case of a Suzuki coupling reaction (X) may be a halogen, tosylate or other suitable group and $R^{11}B^1$ represents a suitable boron compound including, but not limited to, a boronic acid of boronic ester.

Scheme 11B

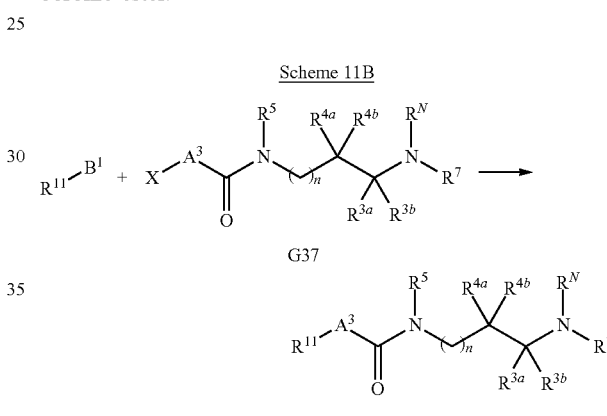

G36

The types of $R^{11}B^1$ compounds that can be used in the Suzuki coupling include, but are not limited to, those shown in Table 2.

TABLE 2

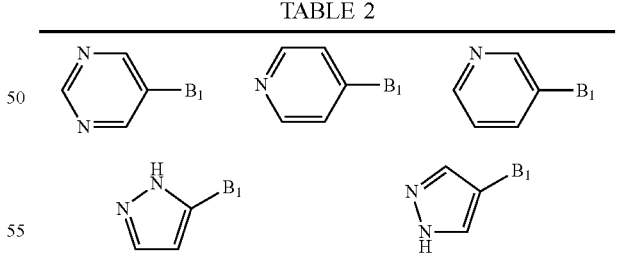

A variety of coupling reactions may be used to introduce the $R^{11}$ group other than Suzuki coupling, such as for example transition metal catalysed coupling reactions of for example tin (Stille type reaction) and zinc (Negishi type reaction) compounds. Substitution of the halogen by suitable nucleophiles in the presence or absence of other reagents such as for example transition metal compounds is also suitable.

Coupling reactions can also be used to prepare the carboxylic acids used above for amide formations, scheme 11C.

In the starting material G39 and G41, A as described herein, consists of -$A^3X$ and -$A^3B^1$ respectively. In the product G42, A as described herein, consists of -$A^3R^{11}$. The groups denoted by (X) and $B^1$ are chosen to be suitable for the coupling reaction employed. Potentially applicable reactions include, but are not limited to: Suzuki coupling, Negishi coupling, $S_NAr$ reaction, Ullman coupling, Chan Lam coupling, an alkylation reaction e.g. $S_N2$ or $S_N1$, a Mitsonobu reaction, a C—H activation reaction, a Kumada coupling, a Buchwald reaction etc. For example, in the case of a Suzuki coupling reaction (X) may be a halogen, tosylate or other suitable group and $B^1$ represents a suitable boron compound including, but not limited to, a boronic acid of boronic ester.

Scheme 11C

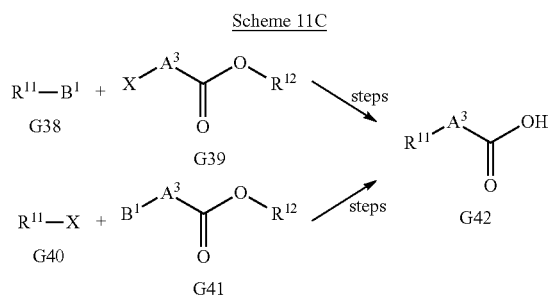

In G39 and G41 $R^{12}$ can be a H or a carbon group for example but not limited to Me, Et, Pr, iPr, Bu, t-Bu. It may be necessary to form the carboxylic acid before use in the amide coupling (Scheme 1A), generally this can be achieved by for example hydrolysis with a base such as an alkali metal hydroxide or an acid for example aqueous hydrochloric acid to form G42. The same method for converting an ester to a carboxylic acid is used in other general schemes.

General Synthesis Method 12

Scheme 12A illustrates the addition of an $R^{13}$ group, as a substituent which is part of A. This can be achieved using any suitable coupling reaction known to the person skilled in the art, for example, by a $S_NAr$ displacement or Buchwald coupling. The group denoted by (X) may be but not limited to halogen and is chosen to be suitable for the coupling reaction employed.

Scheme 12A

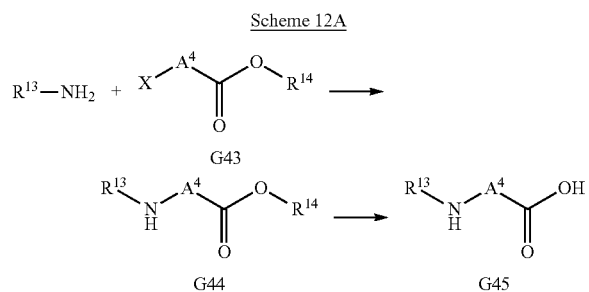

In G43 and G44 $R^{14}$ can be a H or a carbon group for example but not limited to Me, Et, Pr, iPr, Bu, t-Bu. In these instances in may be necessary to form the carboxylic acid before use in an amide coupling (Scheme 1A), generally this can be achieved by, for example, hydrolysis with a base such as an alkali metal hydroxide or an acid, for example, aqueous hydrochloric acid to form G45. The same method for converting an ester to a carboxylic acid is used in other general schemes.

Alternatively, to synthesise ether linked compounds, a similar strategy can be employed as shown in Scheme 12B. This can be achieved using any suitable coupling reaction known to a person skilled in the art, for example, by a $S_NAr$ displacement, an Ullman-type coupling or a Chan Lam coupling to give compounds with structure G46. Upon hydrolysis using methods previously described, compounds with structure G47 may be obtained and used in an amide bond formation as shown in scheme 1A.

Scheme 12B

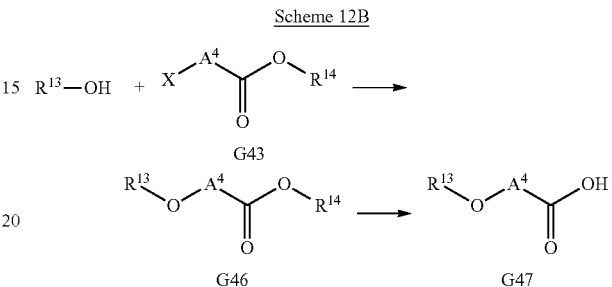

Throughout the above Scheme suitable protecting groups may be required on $R^{4a}$ or $R^{4b}$. In the case of either substituent being an alcohol, a silyl protecting group could be used, e.g. TBS. In the case of an amino substituent, suitable protecting groups could include Boc, phthalimide or dimethoxybenzyl, If $R^{4a}$ is OH in G36 it can be transformed through a range of functional group interconversions that are known to those skilled in the art. For example $R^{4a}$=NH2 can be introduced using a reagents such as DPPA and DBU to give the azide, which can then be reduced using triphenylphosphine. $R^{4a}$=CN can be introduced via activation of the alcohol to a suitable leaving group, e.g. $R^{4a}$=mesylate, tosylate or halogen and then treatment with a suitable source of cyanide, e.g. sodium cyanide. The resulting cyano compound can be hydrolysed to the primary amide $R^{4a}$=CONH$_2$ using acidic or basic conditions. Under more forcing acid or basic conditions, the carboxylic acid could be formed, i.e. $R^{4a}$=CO$_2$H. The carboxylic acid could be reduced to the corresponding primary alcohol, $R^{4a}$=CH$_2$OH using a suitable reducing agent, e.g. BH$_3$, or alternatively through activation of the acid to a mixed anhydride, $R^{4a}$=CO$_2$COR, where R=alkyl, and then treatment with a suitable reducing agent, e.g. sodium borohydride.

FURTHER EMBODIMENTS n

In some embodiments, n is 1. In some embodiments, n is 2.

$R^N$

In some embodiment, $R^N$ is H. In other embodiments, $R^N$ is Me.

$R^1$

In some embodiments, there may be no $R^1$ substituents. In some embodiments, $R^1$ represents one to four Me or halo groups, preferably one to three Me or halo groups and more preferably one or two Me or halo groups. In some of these embodiments, $R^1$ may represent F. In others of these embodiments, R' may represent Me groups.

$R^2$ $R^{2a}$, $R^{2b}$, $R^{2c}$ and $R^{2d}$ (if present) are independently selected from H, F, CH$_2$OH and Me. In some of these embodiments, $R^{2a}$, $R^{2b}$, $R^{2c}$ and $R^{2d}$ (if present) are independently selected from H, Me and CH$_2$OH. In further of these embodiments, $R^{2a}$, $R^{2b}$, $R^{2c}$ and $R^{2d}$ (if present) are independently selected from H and Me.

In some embodiments $R^{2a}$, $R^{2b}$, $R^{2c}$ and $R^{2d}$ (if present) are all H.

In some of those embodiments where $R^{2a}$, $R^{2b}$, $R^{2c}$ and $R^{2d}$ are all present (i.e. formulae Ia and Ib), they may be comprised of three H and one Me or CH$_2$OH group. It may be preferred in these embodiments that $R^{2a}$ is Me and $R^{2b}$, $R^{2c}$ and $R^{2d}$ are H. It may be preferred in these embodiments that $R^{2c}$ is Me or CH$_2$OH and $R^{2a}$, $R^{2b}$ and $R^{2d}$ are H.

In some of those embodiments where $R^{2a}$, $R^{2b}$, $R^{2c}$ and $R^{2d}$ are all present (i.e. formulae Ia and Ib), they may be comprised of two H and two Me groups. It may be preferred in these embodiments that $R^{2a}$ and $R^{2c}$ are Me and $R^{2b}$ and $R^{2d}$ are H. It may be preferred in these embodiments that $R^{2a}$ and $R^{2b}$ are Me and $R^{2c}$ and $R^{2d}$ are H. It may also be preferred in these embodiments that $R^{2c}$ and $R^{2d}$ are Me and $R^{2a}$ and $R^{2b}$ are H.

In some of those embodiment where only $R^{2a}$ and $R^{2b}$ are present (i.e. formula Ic), they may be comprised of one H and one Me or CH$_2$OH group.

In some of those embodiment where only $R^{2a}$ and $R^{2b}$ are present (i.e. formula Ic), they may both be a Me or CH$_2$OH group.

$R^3$ $R^{3a}$ and $R^{3b}$ are independently selected from H and Me. In some embodiments $R^{3a}$ is H and $R^{3b}$ is Me. In some embodiments $R^{3a}$ and $R^{3b}$ are both H. In some embodiments $R^{3a}$ and $R^{3b}$ are both Me.

$R^{4a}$

In some embodiments $R^{4a}$ is OH.

In other embodiments, $R^{4a}$ is —NH$_2$. In other embodiments $R^{4a}$ is —C(=O)NH$_2$. In other embodiments $R^{4a}$ is —CH$_2$OH.

It may be preferred that $R^{4a}$ is OH.

$R^{4b}$

In some embodiments $R^{4b}$ is H. In some embodiments $R^{4b}$ is Me.

$R^5$

In some embodiments $R^5$ is H. In some embodiments $R^5$ is Me.

Enantiomers

The carbon to which $R^{4a}$ and $R^{4b}$ are attached is a chiral centre.

When the compound contains this chiral centre, in some embodiments, the compound is a racemate.

When the compound contains this chiral centre, in some embodiments, the compound is a single enantiomer. In some of these embodiments, the compound is the (R)-enantiomer. In others of these embodiments, the compound is the (S)-enantiomer.

The compound may also include further chiral centres, for example, in compounds of formula Ia, in tetrahydronaphthalenyl group. In some embodiments, the compound is a racemate. In other embodiments, the compound is a single enantiomer. In some of these embodiments, the compound is the (R)-enantiomer. In others of these embodiments, the compound is the (S)-enantiomer.

$R^1$-$R^5$ & n

In some embodiments, $R^N$, $R^1$, $R^{2a}$, $R^{2b}$, $R^{2c}$, $R^{2d}$, $R^{3a}$, $R^{3b}$, $R^{4b}$ and $R^5$ are all H, $R^{4a}$ is OH and n is 1, and thus the compound of formula Ia is of formula Ia1, the compound of formula Ib is of formula Ib1, and the compound of formula Ic is of formula Ic1:

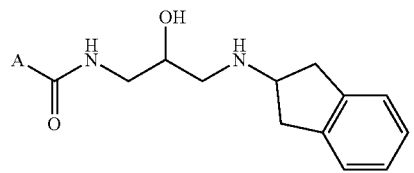

(Ia1)

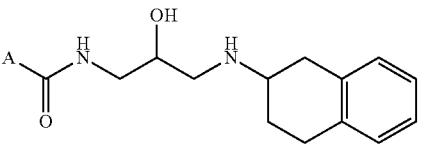

(Ib1)

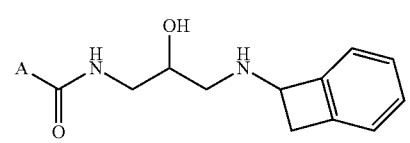

(Ic1)

In some embodiments, $R^1$, $R^{2a}$, $R^{2b}$, $R^{2c}$, $R^{2d}$, $R^{3a}$, $R^{3b}$, $R^{4b}$ and $R^5$ are all H, $R^{4a}$ is OH and n is 2, and thus the compound of formula Ia is of formula Ia2, the compound of formula Ib is of formula Ib2, and the compound of formula Ic is of formula Ic2:

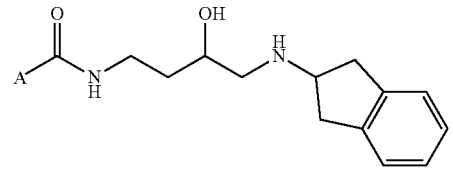

(Ia2)

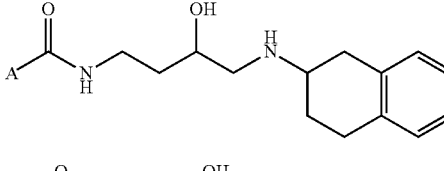

(Ib2)

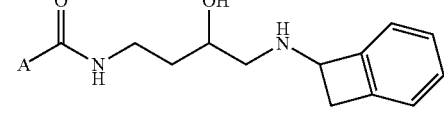

(Ic2)

A

Optional Substituents

When the optional substituent on A is C$_{1-4}$ alkyl, it may be preferably selected from methyl, ethyl, i-Pr, t-Bu.

When the optional substituent on A is C$_{1-4}$ fluoroalkyl, it may preferably be selected from —CF$_3$ and —CF$_2$H.

When the optional substituent on A is C$_{5-6}$ heteroaryl, it may be substituted by one or more C$_{1-4}$ alkyl groups. These groups may preferably be on one or more of the nitrogen ring atoms (if present). These groups may also preferably be methyl.

When the optional substituent on A is C$_{5-6}$ heteroaryl, it may preferably be selected from pyridizinyl, pyrimidinyl, pyridinyl, pyrazolyl, pyrazinyl, oxadiazolyl, isoxazolyl, triazolyl, imidazolyl, benzimidazolyl and thiadiazolyl.

When the optional substituent on A is C$_{5-6}$ heteroaryl methyl, it may preferably be selected from —CH$_2$-imidazolyl and —CH$_2$-triazolyl.

When the optional substituent on A is C$_{5-6}$ heterocyclyl, it may preferably be morpholino.

When the optional substituent on A is C$_{5-6}$ heterocyclyl methyl, it may preferably be selected from —CH$_2$-morpholino and —CH$_2$-piperazinyl.

When the optional substituent on A is phenyl, it may be substituted by one or more C$_{1-4}$ alkyl groups. These groups may preferably be methyl.

When the optional substituent on A is phenyl, it may be substituted by one or more C$_{1-4}$ fluoroalkyl groups. These groups may preferably be trifluoromethyl.

When the optional substituent on A is phenyl, it may be substituted by one or more C$_{1-4}$ alkoxy groups. These groups may preferably be methoxy.

When the optional substituent on A is phenyl, it may be substituted by one or more halo substituents. These groups may preferably be fluoro or chloro, more preferably fluoro.

When the optional substituent on A is phenyl, it may be substituted by one or more cyano groups. It may be preferred that there is a single cyano substituent.

When the optional substituent on A is halo, it may preferably be selected from F, Cl and Br.

When the optional substituent on A is amido, the amido substituent groups R and R' may preferably form a ring, which ring may also be bridged or substituted. If the amido group is not cyclic, it may preferably be selected from —C(=O)NH$_2$, —C(=O)NMeH, —C(=O)NMe$_2$ and —C(=O)N$^i$PrH. If the amido group is cyclic, it may preferably be selected from —C(=O)-piperidinyl, —C(=O)-hydroxypiperidinyl, —C(=O)-methoxypiperidinyl, —C(=O)-pyrrolidinyl, —C(=O)-morpholino, —C(=O)-methylmorpholino, —C(=O)-dimethylmorpholino and —C(=O)-azetidinyl. Further cyclic amido groups include:

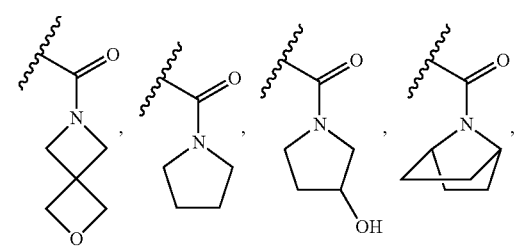

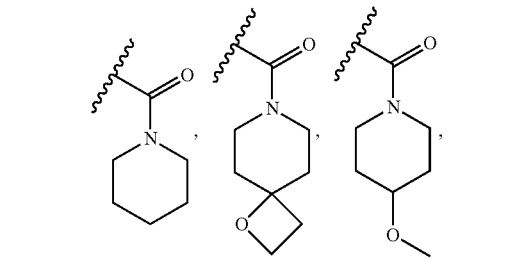

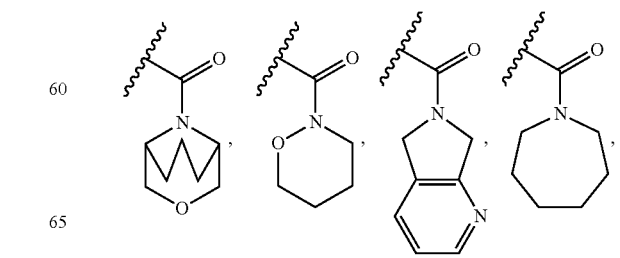

-continued

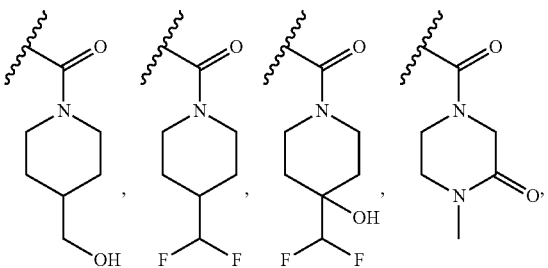

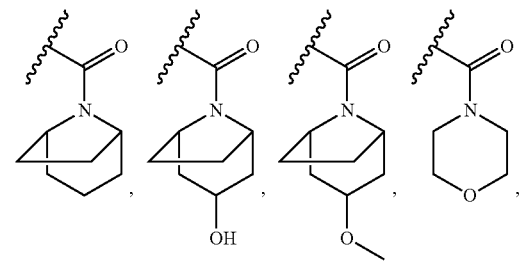

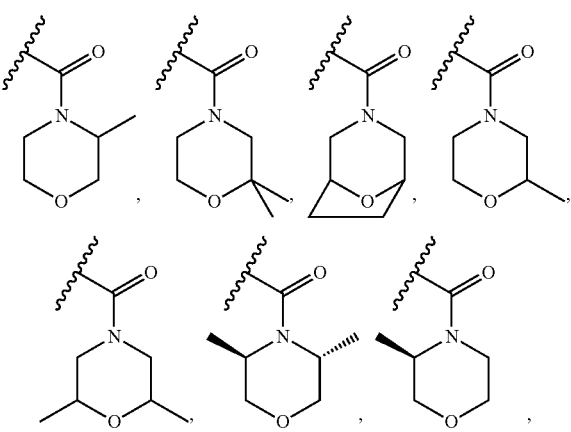

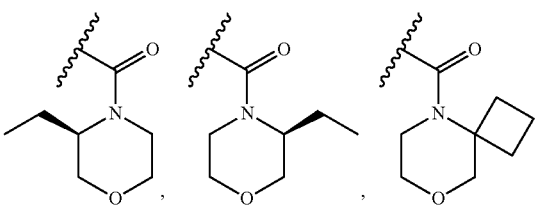

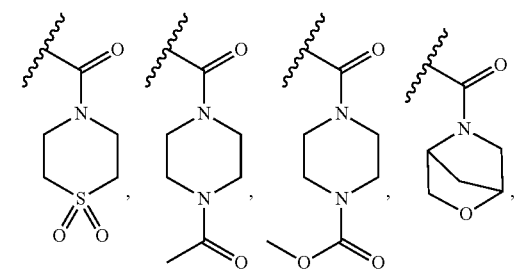

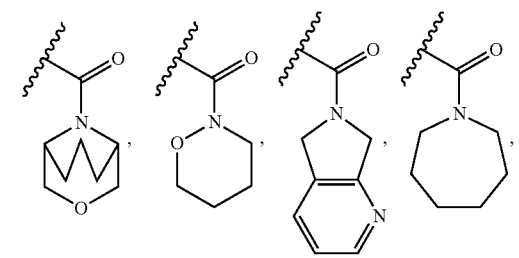

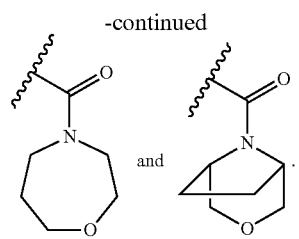 and .

When the optional substituent on A is amidomethyl, the amido substituent groups R and R' may preferably form a ring, which ring may also be bridged or substituted. If the amido group is not cyclic, the amidomethyl group may preferably be selected from —CH$_2$C(=O)NH$_2$, —CH$_2$C(=O)NMeH and —CH$_2$C(=O)N$^i$PrH. If the amido group is cyclic, the amidomethyl group may preferably be selected from —CH$_2$C(=O)-pyrrolidinyl, —CH$_2$C(=O)-morpholino, —C(=O)-hydroxypiperidinyl, —C(=O)-methoxypiperidinyl, —C(=O)-methylmorpholino and CH$_2$C(=O)-azetidinyl. Further cyclic amidomethyl groups include:

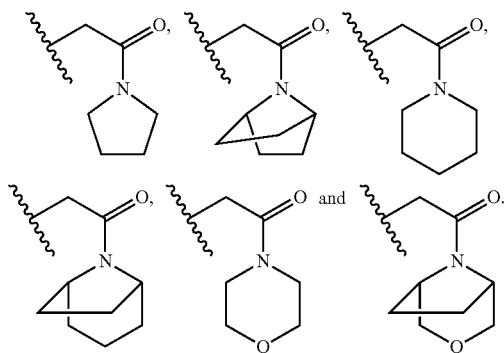

When the optional substituent on A is acylamido, it may preferably be γ-lactam.

When the optional substituent on A is acylamidomethyl, it may preferably be selected from —CH$_2$NHC(=O)Me, —CH$_2$NHC(=O)CF$_3$.

When the optional substituent on A is C$_{1-4}$ alkyl ester, it may preferably be —C(=O)—OMe.

When the optional substituent on A is C$_{1-4}$ alkyl ester methyl, it may preferably be —CH$_2$—C(=O)—OMe.

When the optional substituent on A is C$_{1-4}$ alkyl carbamoyl methyl, it may preferably be —CH$_2$NHC(=O)OMe.

When the optional substituent on A is C$_{1-4}$ alkylacyl, it may preferably be selected from —C(=O)Me and —C(=O)Et.

When the optional substituent on A is C$_{1-4}$ alkylacylmethyl, it may preferably be —CH$_2$C(=O)Me.

When the optional substituent on A is phenylcarbonyl, it may preferably be —C(=O)-Ph.

When the optional substituent on A is ether, it may preferably be selected from methoxy, ethoxy, —OBn, —OPh, —OCF$_3$, —OCF$_2$H, —O—(C$_6$H$_4$)—CN, —O-oxanyl, —OCH$_2$pyridinyl, —OCH$_2$-oxadiazolyl, —OCH$_2$-isoxazole, When the optional substituent on A is amino, the amino substituent may be a C$_{5-6}$ heteroaryl group, in which case the amino group may preferably be selected from —NH-pyrazinyl, —NH-pyrimidine. In other embodiments, the amino substituent may be a C$_{4-6}$ heterocyclyl group, such as optionally N-substituted azetidinyl, optionally N-substituted piperidinyl and oxetanyl. A further amino group may be:

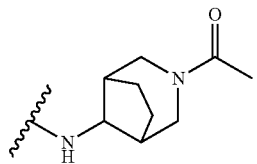 [SMILES: *NC1C2CCC1CN(C(C)=O)C2]

When the optional substituent on A is aminomethyl, it may preferably be —CH$_2$NH$_2$. Alternatively, the amino substituent may be as defined above When the optional substituent on A is sulfonamido it may preferably be selected from —SO$_2$NMePh, —SO$_2$NMe$_2$, and —SO$_2$NHEt.

When the optional substituent on A is sulfonamino, it may preferably be selected from —NHSO$_2$Ph and —NHSO$_2$Me.

When the optional substituent on A is sulfone, it may preferably be —SO$_2$CF$_3$.

Optionally Substituted Phenyl

In some embodiments A may be an optionally substituted phenyl.

In some of these embodiments, A is unsubstituted phenyl.

In some of these embodiments, the phenyl of A has 1, 2, 3, 4 or 5 substituents.

In some of these embodiments, the phenyl of A has 1 or 2 substituents.

It may be preferred that in some of these embodiments R$^1$, R$^{2a}$, R$^{2b}$, R$^{2c}$, R$^{2d}$, R$^{3a}$, R$^{3b}$, R$^{4b}$ and R$^5$ are all hydrogen and that R$^{4a}$ is OH and n is 1.

It may be preferred in some of these embodiments that at least one of R$^1$, R$^{2a}$, R$^{2b}$, R$^{2c}$, R$^{2d}$, R$^{3a}$, R$^{3b}$, R$^{4b}$ and R$^5$ is not hydrogen.

It may be preferred in some of these some of these embodiments that R$^{1-5}$ and n is such that the compound is of formula Ia1, Ia2, Ib1, Ib2, Ic1 or Ic2.

It may be preferred in these embodiments that the optional substituents are independently selected from the following: C$_{1-4}$ alkyl; C$_{1-4}$ fluoroalkyl; C$_{3-6}$ cycloalkyl; C$_{5-6}$ heteroaryl; C$_{5-6}$ heteroaryl methyl; C$_{4-6}$ heterocyclyl; C$_{4-6}$ heterocyclyl methyl; phenyl; benzyl; halo; amido; amidomethyl; acylamido; acylamidomethyl; C$_{1-4}$ alkyl ester; C$_{1-4}$ alkyl ester methyl; C$_{1-4}$ alkyl carbamoyl; C$_{1-4}$ alkyl carbamoyl methyl; C$_{1-4}$ alkylacyl; C$_{1-4}$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: C$_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—ON, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted by one, two or three methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetraydropyanyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$ CF₃, -γ-lactam, —CH₂NHC(=O)Me, —CH₂NHC(=O)OMe, —CH₂NHC(=O)CF₃, morpholino, —CH₂NH₂, —C(=O)Ph, —OCH₂-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

It may be preferred in these embodiments that, when the optional substituent is a $C_{5-6}$ heteroaryl group, the heteroaryl ring itself is substituted with one or more $C_{1-4}$ alkyl groups. It may be preferred in the above embodiments that 1 substituent is present. In may be preferred in the above embodiments that 2 substituents are present.

Halo and methoxy (including CF₃O) substituents may be preferred in the ortho position of the phenyl group. Ethoxy and alkyl (e.g. methyl, CF₂H and CF₃) substituents may also be preferred in the ortho position of the phenyl group. Alkyl and $C_{5-6}$ heteroaryl may be preferred in the meta position of the phenyl group. Amido and amidomethyl substituents may be preferred in the para position of the phenyl group. Particular favoured groups in the ortho position are ethoxy, methoxy, Cl, F and CF₂H.

A combination of substitutents that may be preferred is an ethoxy group in the ortho position of the phenyl group and an amido or amidomethyl group in the para position of the phenyl group.

In some embodiments, the phenyl group bears a halo or methoxy substituent in the ortho position, and an amido or amidomethyl substituent in the para position of the phenyl group.

In some embodiments, the phenyl group bears an amino substituent in the meta position.

Where the substituent on phenyl is a fused $C_{5-6}$ Ni-containing heterocyclic ring, A may have a core structure selected from:

Particular A groups of interest include:

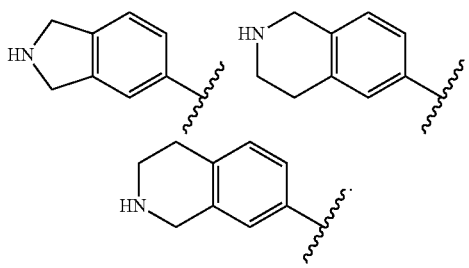

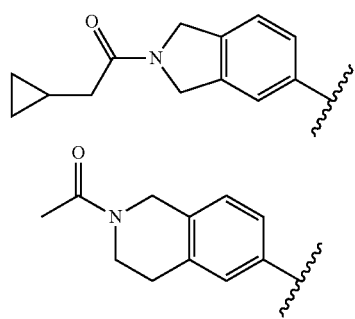

Optionally Substituted Naphthyl

When A is naphthyl, it may be in any orientation, e.g. naphth-1-yl, naphth-2-yl.

In some embodiments A may be optionally substituted naphthyl.

In some of these embodiments, A is unsubstituted naphthyl.

In some of these embodiments, the naphthyl ring of A has 1, 2, 3, 4 or 5 substituents.

In some of these embodiments, the naphthyl ring of A has 1 or 2 substituents.

It may be preferred that in some of these embodiments $R^1$, $R^{2a}$, $R^{2b}$, $R^{2c}$, $R^{2d}$, $R^{3a}$, $R^{3b}$, $R^{4b}$ and $R^5$ are all hydrogen and that $R^{4a}$ is OH and n is 1.

It may be preferred in some of these embodiments that at least one of $R^1$, $R^{2a}$, $R^{2b}$, $R^{2c}$, $R^{2d}$, $R^{3a}$, $R^{3b}$, $R^{4b}$ and $R^5$ is not hydrogen.

It may be preferred in some of these some of these embodiments that $R^{1-5}$ and n is such that the compound is of formula Ia1, Ia2, Ia3, Ia2, Ib2 or Ic2.

It may be preferred in these embodiments that the optional substituents refers to 0-2 substituents independently selected from the following: $C_{1-4}$ alkyl; $C_{1-4}$ fluoroalkyl; $C_{3-6}$ cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that 1 substituent is present. In may be preferred in these embodiments that 2 substituents are present.

Optionally Substituted $C_{5-12}$ Heteroaryl

In some embodiments A may be an optionally substituted $C_{5-12}$ heteroaryl group.

In some of these embodiments, A is unsubstituted $C_{5-12}$ heteroaryl group.

In some of these embodiments, the $C_{5-12}$ heteroaryl of A has 1, 2, 3, 4 or 5 substituents.

In some of these embodiments, the $C_{5-12}$ heteroaryl of A has 1 or 2 substituents.

It may be preferred in these embodiments that the $C_{5-12}$ heteroaryl ring is selected from one of the following: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl. The heteroatoms may be in any location in the ring, which may be joined to the remainder of the molecule via a ring carbon atom. It may be further preferred that the $C_{5-12}$ heteroaryl ring is either pyridinyl or pyrimidinyl. It may also be further preferred that the $C_{5-12}$ heteroaryl is selected from pyridyl, pyrimidinyl, oxazolyl, oxadiazolyl, pyrazolyl and thiazolyl and in particular:

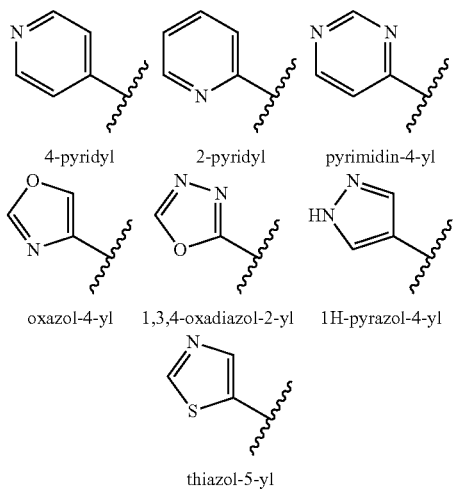

Further preferred groups may include benzothiazolyl and benzimidazolyol and in particular:

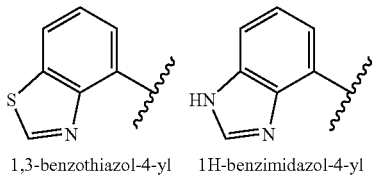

It may be preferred that in some of these embodiments $R^1$, $R^{2a}$, $R^{2b}$, $R^{2c}$, $R^{2d}$, $R^{3a}$, $R^{3b}$, $R^{4b}$ and $R^5$ are all hydrogen and that $R^{4a}$ is OH and n is 1.

It may be preferred in some of these embodiments that at least one of $R^1$, $R^{2a}$, $R^{2b}$, $R^{2c}$, $R^{2d}$, $R^{3a}$, $R^{3b}$, $R^{4b}$ and $R^5$ is not hydrogen.

It may be preferred in some of these some of these embodiments that $R^{1-5}$ and n is such that the compound is of formula Ia1, Ia2, Ib1, Ib2, Ic1 or Ic2.

It may be preferred in these embodiments that the optional substituents are independently selected from the following: $C_{1-4}$ alkyl; $C_{1-4}$ fluoroalkyl; $C_{3-6}$cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: $C_{1-4}$ alkyl; $C_{1-4}$ fluoroalkyl; $C_{5-6}$ heteroaryl, $C_{4-6}$ heterocyclyl; phenyl; halo; and ether.

It may be preferred in these embodiments that the optional substituent are selected from: methyl, ethyl, butyl, chloro, bromo, fluoro, morpholino, pyrrolidinyl, —OBn, —OPh, phenyl, para-bromophenyl, pyrazolyl, pyrimidinyl, imidazolyl and —$CF_3$.

In may be preferred in these embodiments that 1 substituent is present. In may be preferred in these embodiments that 2 substituents are present.

Halo and methoxy substituents may be preferred in the ortho position of a $C_6$ heteroayl group, or α-position of $C_5$ and $C_{7-12}$ heteroaryl group. Amido and amidomethyl substituents may be preferred in the para position of a $C_6$ heteroayl group, or γ-position of $C_5$ and $C_{7-12}$ heteroaryl group.

In some embodiments, a $C_6$ heteroayl group bears a halo or methoxy substituent in the ortho position, and an amido or amidomethyl substituent in the para position.

In some embodiments, a $C_6$ heteroayl group bears an amino substituent in the meta position. In some embodiment, a $C_5$ or $C_{7-12}$ heteroaryl group bears an amino substituent in the β-position.

Where the $C_6$ heteroayl group is 4-pyridyl, it may bear an ether substituent, for example in the 3-position. In some of these embodiments, the ether substituent may be —O—$C_{4-6}$ heterocyclyl, wherein the $C_{4-6}$ heterocyclyl may itself bear an ester group (e.g. methoxy ester).

Where the $C_6$ heteroayl group is 2-pyridyl, it may bear an amido substituent, for example in the 4-position.

Where the C6 heteroayl group is 4-pyrimidinyl, it may bear an amino substituent, for example in the 3-position. In some of these embodiments, the amino substituent may be —NH—$C_{4-6}$ heterocyclyl, wherein the $C_{4-6}$ heterocyclyl may itself bear an acyl group (e.g. —C(=O)Me).

Where A is a $C_5$ heteroaryl group (e.g. oxazolyl, oxadiazolyl, pyrazolyl and thiazolyl), it may bear an amino, phenyl or $C_6$ heteroaryl substituent in the β-position.

In some embodiments A is selected from one of the following groups:

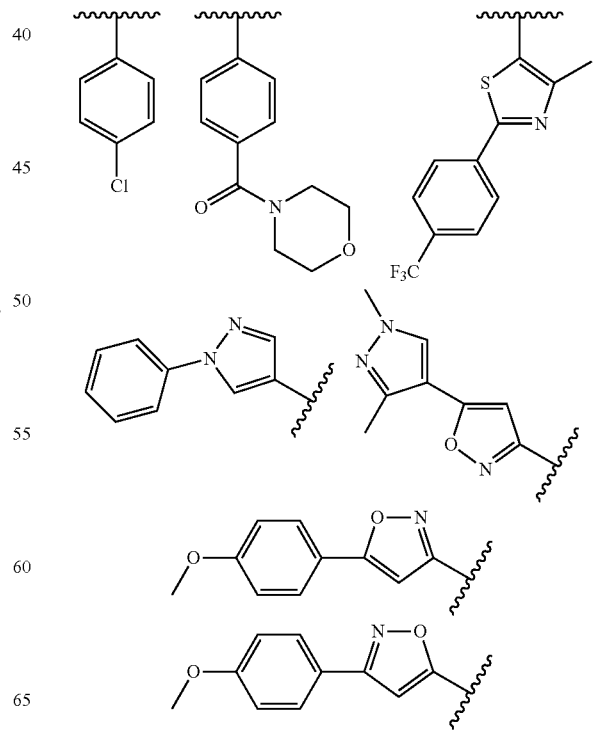

49
-continued
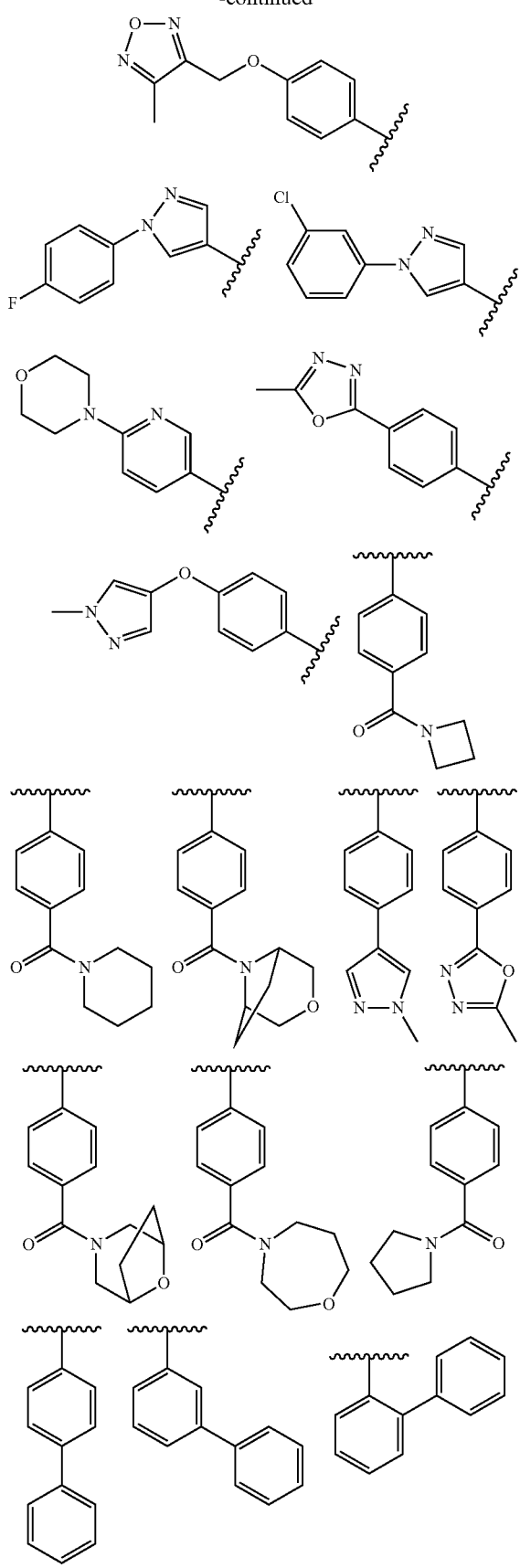
50
-continued
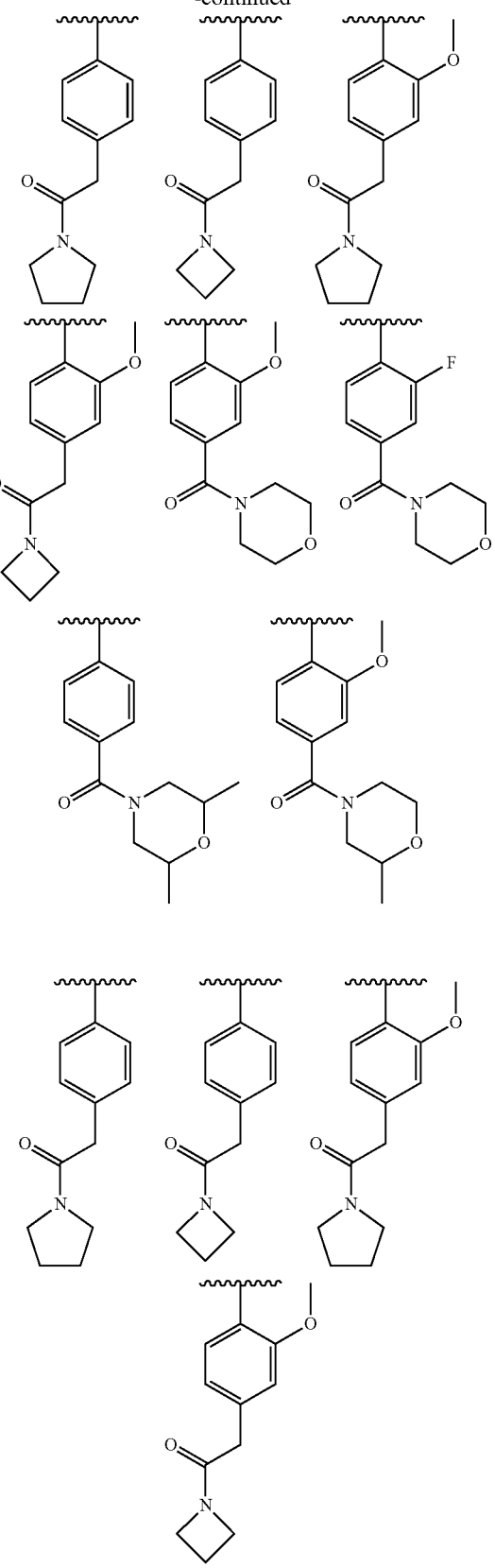
In some embodiments A may be selected from one of the following groups:

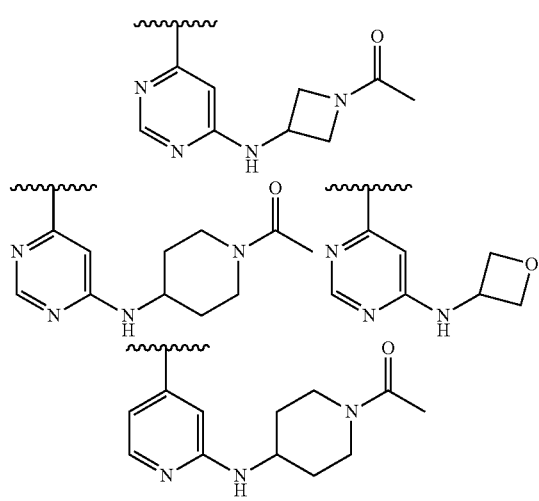

In some embodiments A may be selected from one of the following groups:

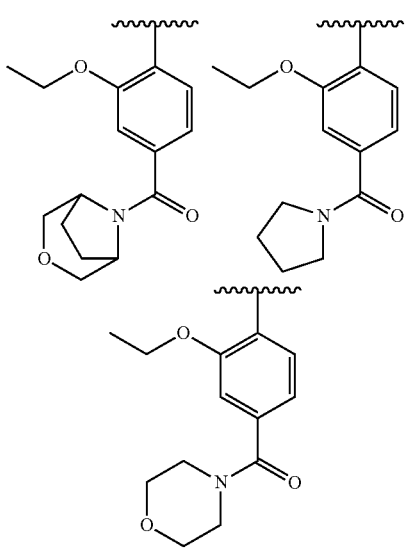

In some embodiments, A may be selected from: phenyl, with a para-amido substituent and an optional ortho-ethoxy substituent; phenyl, with a para-ether substituent; 6-amino-3-pyridyl; 5-amino-3-pyridyl; and 2-amino-4-pyridyl.

It may be preferred that in some of these embodiments $R^N$, $R^1$, $R^{2a}$, $R^{2b}$, $R^{2c}$, $R^{2d}$, $R^{3a}$, $R^{3b}$, $R^{4b}$ and $R^5$ are all hydrogen and that $R^{4a}$ is OH and n is 1.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol ($d_4$-MeOD) ethanol (EtOH), isopropanol (i-PrOH), ether or diethyl ether ($Et_2O$), ethyl acetate (EtOAc), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), deuterated chloroform ($CDCl_3$), diethylamine (DEA), deuterated dimethylsulfoxide ($d_6$-DMSO), N-ethyl-N'-(3-dimethylaminopropyl)carbodiimide hydrochloride (EDCl.HCl, EDCl), meta-chloroperoxybenzoic acid (mCPBA), 1,1'-bis(diphenylphosphino)ferrocene (dppf), tert-butyloxycarbonyl (Boc, BOC), 2-(trimethylsilyl) ethoxymethyl (SEM), triethylamine ($Et_3N$ or TEA), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA or DIEA), 1,1'-bis(diphenylphosphino)ferrocene dichloropalladium (II) ($PdCl_2(dppf)$), trans-dichlorobis(triphenylphosphine)palladium(II) ($PdCl_2(PPh_3)_2$), tris(dibenzylideneacetone)dipalladium(0) ($Pd_2(dba)_3$), tetrakis(triphenylphosphine)palladium(0) ($Pd(PPh_3)_4$), propylphosphonic anhydride (T3P), hexamethylphosphoramide (HMPA), 1,2-dichloroethane (DCE), benzyl (Bn) and 1-hydroxybenzotriazole (HOBt).

In addition, TLC refers to thin layer chromatography.

General Experimental Details

Unless otherwise stated the following generalisations apply. $^1$H NMR spectra were recorded on a Bruker Ultrashield Plus (400 MHz), a Bruker AVANCE (400 MHz) or a Bruker Avance DRX300 (300 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

LCMS data was generated using either an Agilent 6100 Series Single Quad LCMS (LCMS-A), an Agilent 1260 Infinity Series UPLC/MS (LCMS-B), a Agilent 1200 Series G6110A Quadrupole LCMS (LCMS-C), a Waters 2695 alliance (LCMS-D) or a Finnigan instrument (LCMS-E). Chlorine isotopes are reported as $^{35}$Cl, Bromine isotopes are reported as either $^{79}$Br or $^{81}$Br or both $^{79}$Br/$^{81}$Br.

LCMS Method A (LCMS-A):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC conditions:
Reverse Phase HPLC analysis
Column: Luna C8 (2) 5 μm 50×4.6 mm 100 Å
Column temperature: 30° C.
Injection Volume: 5 μL
Solvent A: Water 0.1% Formic Acid
Solvent B: MeCN 0.1% Formic Acid
Gradient: 5-100% solvent B over 10 min
Detection: 254 nm or 214 nm
MS conditions:
Ion Source: Quadrupole
Ion Mode: Multimode-ES
Drying gas temp: 300° C.
Vaporizer temperature: 200° C.
Capillary voltage (V): 2000 (positive)

Capillary voltage (V): 4000 (negative)
Scan Range: 100-1000
Step size: 0.1 sec
Acquisition time: 10 min
LCMS Method B (LCMS-B):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC conditions:
Reverse Phase HPLC analysis
Column: Poroshell 120 EC-C18 2.7 μm 50×3.0 mm
Column temperature: 35° C.
Injection Volume: 1 μL
Solvent A: Water 0.1% Formic Acid
Solvent B: MeCN 0.1% Formic Acid
Gradient: 5-100% solvent B over 3.8 min
Detection: monitored at 254 nm and 214 nm
MS conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
LCMS Method C (LCMS-C):
Instrument: Agilent 1200 Series G6110A Quadrupole
Pump: Binary pump
Detector: DAD
LC conditions:
Reverse Phase HPLC analysis
Column: Xbridge-C18, 2.5 μm, 2.1×30 mm
Column temperature: 30° C.
Injection Volume: 1-10 μL
Solvent A: Water 0.07% Formic acid
Solvent B: Methanol
Gradient: 30-95% solvent B over 3.5 min (for medium polarity samples) or 10-95% solvent B over 3.7 min (for large polarity samples)
Detection: monitored at 254 nm and 214 nm
MS conditions:
Ion Source: Quadrupole
Ion Mode: ES+
Drying gas temp: 350° C.
Drying gas flow: 10 L/min
Nebulizer pressure: 35 psi
Capillary voltage (V): 3500 (positive)
Scan Range: 50-900
LCMS Method D (LCMS-D)
Instrument: Waters ZQ 3100 Mass Detector
Waters 2545-Pump
Waters SFO System Fluidics Organizer
Waters 2996 Diode Array Detector
Waters 2767 Sample Manager
LC conditions:
Reverse Phase HPLC analysis
Column: XBridge™ C18 5 μm 4.6×100 mm
Injection Volume: 10 μL
Solvent A: Water 0.1% Formic Acid
Solvent B: MeCN 0.1% Formic Acid
Gradient: 10-100% B over 10 min
Flow rate: 1.5 mL/min
Detection: 100-600 nm
MS conditions
Ion Source: Single-quadrupole
Ion Mode: ES positive
Source Temp: 150° C.
Desolvation Temp: 350° C.
Detection: Ion counting
Capillary (KV): 3.00
Cone (V): 30
Extractor (V): 3
RF Lens (V): 0.1
Scan Range: 100-1000 Amu
Scan Time: 0.5 sec
Acquisition time: 10 min
Gas Flow: 100 L/h
Desolvation: 650 L/h
LCMS Method E (LCMS-E)
Instrument: Finnigan LCG Advantage Max
Finnigan Surveyor LC Pump
Finnigan Surveyor Autosampler
Finnigan Surveyor PDA Detector
LC conditions:
Reverse Phase HPLC analysis
Column: Gemini 3 μm C18 20×4.0 mm 110 Å
Injection Volume: 10 μL
Solvent A: Water 0.1% Formic Acid
Solvent B: MeCN 0.1% Formic Acid
Gradient: 10-100% B over 10 min
Detection: 100-600 nm
MS conditions
Ion Source: Ion trap
Ion Mode: ES positive
Temp: 300° C.
Detection: Ion counting
Scan Range: 80-1000 Amu
Scan Time: 0.2 sec
Acquisition time: 10 min
Preparative Mass-Directed LC
Instrument:
Waters ZQ 3100-Mass Detector
Waters 2545-Pump
Waters SFO System Fluidics Organizer
Waters 2996 Diode Array Detector
Waters 2767 Sample Manager
LC conditions:
Reverse Phase HPLC analysis
Column: XBridge™ C18 5 μm 19×50 mm
Injection Volume 500 μL
Solvent A: Water 0.1% Formic Acid
Solvent B: MeCN 0.1% Formic Acid
Gradient: 25-100% B over 10 min
Flow rate: 19 mL/min
Detection: 100-600 nm
MS conditions:
Ion Source: Single-quadrupole
Ion Mode: ES positive
Source Temp: 150° C.
Desolvation Temp: 350° C.
Detection: Ion counting
Capillary (KV)-3.00
Cone (V): 30
Extractor (V): 3
RF Lens (V): 0.1
Scan Range: 100-1000 Amu
Scan Time: 0.5 sec
Acquisition time: 10 min Gas Flow
Desolvation L/hour-650
Cone L/hour-100
Preparative RP-HPLC:
Agilent 1260 Infinity HPLC system
UV detection at 210 nm and 254 nm
Gradient or isocratic elution through a Phenomenex Luna C8 (2) column 100 Å Axia (250×21.2 mm; particle size 5 μm)
Flow rate: 10 mL/min
Gradients are as specified in the individual examples.

Analytical thin-layer chromatography was performed on Merck silica gel 60 F254 aluminium-backed plates which were visualised using fluorescence quenching under UV light or a basic KMnO$_4$ dip or Ninhydrin dip.

Preparative thin-layer chromatography (prep TLC) was performed using Tklst (China), grand grade: (HPTLC): 8±2 μm>80%; (TLC): 10-40 μm. Type: GF254. Compounds were visualised by UV (254 nm).

Flash chromatography was performed using a Biotage Isolera purification system using either Grace or RediSep® silica cartridges.

Column chromatography was performed using Tklst (China), grand grade, 100-200 meshes silica gel.

Microwave irradiation was achieved using a CEM Explorer SP Microwave Reactor.

Where necessary, anhydrous solvents were purchased from Sigma-Aldrich or dried using conventional methods.

Additional Cartridges used are as follows:
Phase Separator:
Manufacturer: Biotage
Product: ISOLUTE Phase Separator (3 mL unless otherwise stated)
SCX and SCX-2 cartridges:
Manufacturer: Biotage
Product: ISOLUTE SCX 1 g, (6 mL SPE Column unless otherwise stated)
Manufacturer: Biotage
Product: ISOLUTE® SCX-2 1 g (6 mL Column)
Manufacturer: Silicycle
Product: SCX-2 500 mg or 5 g
Manufacturer: Agilent
Product: Bond Elut® SCX 10 g
Sample Extraction Cartridge:
Manufacturer: Waters Product: Oasis® HLB 35 cc (6 g) LP extraction cartridge Intermediate Preparations (i) 1-Amino-3-((2,3-dihydro-1H-inden-2-yl)amino)propan-2-ol (I2)

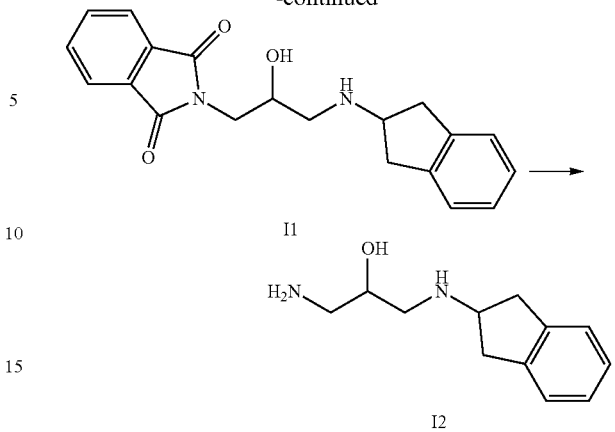

(a) 2-(3-((2,3-Dihydro-1H-inden-2-yl)amino)-2-hydroxypropyl)isoindoline-1,3-dione (I1)

A mixture of N-glycidylphthalimide (2.00 g, 9.84 mmol) and 2-aminoindane (1.57 g, 11.8 mmol) in ethanol (50 mL) was stirred at 80° C. for 24 hours. The volatiles were removed in vacuo and the residue was purified by column chromatography (2×40 g SiO$_2$ cartridges, 0-20% MeOH (containing 1% v/v 2 M NH$_3$ in MeOH) in DCM) then (40 g SiO$_2$ cartridge, 0-10% MeOH (containing 1% v/v 2 M NH$_3$ in MeOH) in DCM) to give the desired compound as a brown solid (1.69 g, 51%). $^1$H NMR (400 MHz, CDCl$_3$) δ 7.87-7.81 (m, 2H), 7.74-7.69 (m, 2H), 7.20-7.15 (m, 2H), 7.15-7.11 (m, 2H), 3.99-3.92 (m, 1H), 3.84-3.70 (m, 2H), 3.64-3.55 (m, 1H), 3.18-3.10 (m, 2H), 2.82 (dd, J=12.2, 3.8 Hz, 1H), 2.75 (dd, J=15.6, 6.1 Hz, 2H), 2.65 (dd, J=12.2, 7.3 Hz, 1H).

(b) 1-Amino-3-((2,3-dihydro-1H-inden-2-yl)amino)propan-2-ol (I2)

A solution of 2-(3-((2,3-dihydro-1H-inden-2-yl)amino)-2-hydroxypropyl)isoindoline-1,3-dione I1 (1.69 g, 5.02 mmol) in EtOH (35 mL) and DCM (35 mL) was treated with hydrazine hydrate (50-60%, 0.94 mL, 15.0 mmol) and the mixture was stirred for 96 hours at room temperature under nitrogen. The suspension was filtered through Celite and the filtrate solvent was concentrated in vacuo. The residue was dissolved in MeOH and loaded onto an SCX cartridge (Agilent HF Bond Elut-SCX, 10 g cartridge). The cartridge was washed with methanol (5 column volumes) and the product was eluted with 2 M NH$_3$ in MeOH (5 column volumes). The solvent was removed in vacuo to give the desired product as a brown oil (1.00 g, 97%). $^1$H NMR (400 MHz, CDCl$_3$) δ 7.23-7.17 (m, 2H), 7.16-7.11 (m, 2H), 3.69-3.57 (m, 2H), 3.21-3.11 (m, 2H), 2.85-2.72 (m, 4H), 2.68-2.54 (m, 2H).

(ii) (S)-1-Amino-3-((2,3-dihydro-1H-inden-2-yl)amino)propan-2-ol (I4)

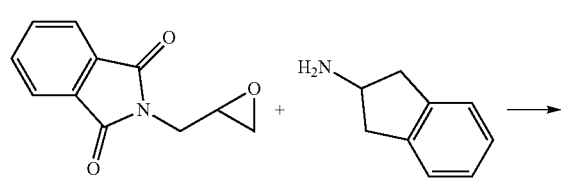

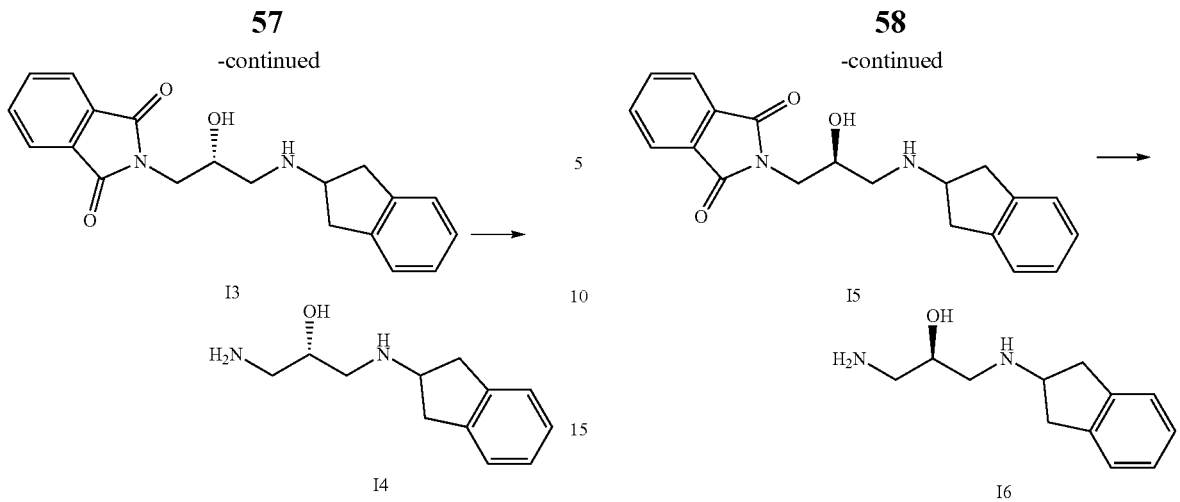

(a) (R)-2-(3-((2,3-Dihydro-1H-inden-2-yl)amino)-2-hydroxypropyl)isoindoline-1,3-dione (I3)

(S)—N-glycidylphthalimide (2.20 g, 10.8 mmol) and 2-aminoindane (1.70 g, 13.0 mmol) were dissolved in ethanol (45 mL) and the reaction was heated under nitrogen at 80° C. for 22 hours. The volatiles were removed under reduced pressure and the resulting dark residue was purified by column chromatography (40 g SiO$_2$, 0-20% methanol/DCM) to give the desired compound (1.80 g, 51%); $^1$H NMR (300 MHz, CDCl$_3$) 7.84-7.77 (m, 2H), 7.71-7.64 (m, 2H), 7.20-7.06 (m, 4H), 4.01 (m, 1H), 3.84-3.68 (m, 2H), 3.64-3.55 (m, 1H), 3.18-3.10 (m, 2H), 2.85-2.77 (m, 2H), 2.74-2.61 (m, 2H).

(b) (S)-1-Amino-3-((2,3-dihydro-1H-inden-2-yl)amino)propan-2-ol (I4)

A mixture of (R)-2-(3-((2,3-dihydro-1H-inden-2-yl)amino)-2-hydroxypropyl)isoindoline-1,3-dione I3 (1.84 g, 5.47 mmol) and hydrazine monohydrate (380 µL, 7.67 mmol) in ethanol (16 mL) and DCM (16 mL) was stirred at room temperature for 20 hours. The resulting solid was filtered off through Celite, washed with DCM (20 mL) and concentrated under reduced pressure. The residue was dissolved in methanol (15 mL) and the solution applied evenly to SCX cartridges (3×5 g). The cartridges were washed with methanol (20 mL for each cartridge) and eluted with a 2 M solution of ammonia in methanol (20 mL for each cartridge). After concentration of the combined ammonia eluates, the resulting compound was subjected to another round of purification by SCX cartridge, as described, to give the desired compound (950 mg, 84%); $^1$H NMR (300 MHz, CDCl$_3$) 7.18-7.09 (m, 4H), 3.62 (m, 2H), 3.15-3.09 (m, 2H), 2.76-2.66 (m, 4H), 2.62-2.51 (m, 2H).

(iii) (R)-1-Amino-3-((2,3-dihydro-1H-inden-2-yl)amino)propan-2-ol (I6)

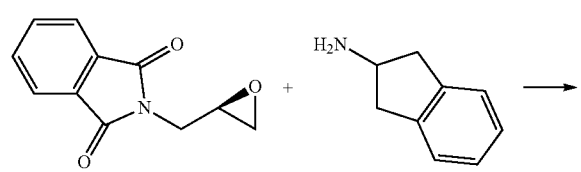

(a) (S)-2-(3-((2,3-Dihydro-1H-inden-2-yl)amino)-2-hydroxypropyl)isoindoline-1,3-dione (I5)

(R)—N-Glycidylphthalimide (2.50 g, 12.30 mmol) and 2-aminoindane (1.97 g, 14.7 mmol) were dissolved in ethanol (50 mL) and the reaction was heated under nitrogen at 80° C. for 72 hours. The ethanol was removed under reduced pressure and the dark residue was purified by column chromatography (40 g SiO$_2$, 0-10% methanol/DCM) to give the desired compound (1.22 g, 29%).

(b) (R)-1-Amino-3-((2,3-dihydro-1H-inden-2-yl)amino)propan-2-ol (I6)

A mixture of (S)-2-(3-((2,3-dihydro-1H-inden-2-yl)amino)-2-hydroxypropyl)isoindoline-1,3-dione I5 (1.22 g, 3.63 mmol) and hydrazine monohydrate (252 µL, 5.09 mmol) in ethanol (13 mL) and DCM (13 mL) was stirred at room temperature for 20 hours. The resulting solid was filtered through Celite and washed with ethanol (20 mL). The volatiles were removed under reduced pressure. The residue was dissolved in methanol (15 mL) and the solution applied evenly to SCX cartridges (3×5 g). The cartridges were washed with methanol (20 mL) and eluted with a 2 M solution of ammonia in methanol (20 mL). The combined ammonia eluates were concentrated in vacuo to give the desired compound (740 mg, 99%).

(iv) 4-((1-Methyl-1H-pyrazol-4-yl)oxy)benzoic acid (I7)

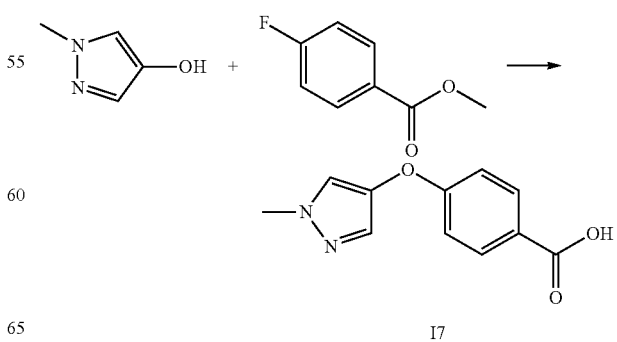

5-Hydroxy-1-methylpyrazole (0.250 g, 2.55 mmol) was added portion-wise to a stirring suspension of methyl 4-fluorobenzoate (0.35 mL, 2.7 mmol) and potassium carbonate (0.70 g, 5.1 mmol) in DMSO (10 mL) at room temperature. The resulting suspension was heated at 150° C. overnight. Water (50 mL) was added and the resulting solution was stirred for 4 hours. The reaction was cooled to room temperature, water (50 mL) was added and extracted with EtOAc (3×30 mL). The organic layers were discarded. The aqueous layer was acidified with 6 M HCl (2 mL) and extracted with EtOAc (3×30 mL). The combined organic extracts were washed with brine (3×30 mL), dried ($Na_2SO_4$), filtered and concentrated in vacuo to give a pale yellow oil. The oil was purified by column chromatography (24 g $SiO_2$ cartridge, 50-100% EtOAc (with 1% v/v AcOH) in petroleum benzine 40-60° C.) to give the desired compound as a colourless solid (327 mg, 59%). $^1$H NMR (400 MHz, $d_6$-DMSO) δ 7.95-7.86 (m, 2H), 7.81 (s, 1H), 7.42 (s, 1H), 7.09-7.00 (m, 2H), 3.82 (s, 3H), LCMS-B RT 2.98 min; m/z 219.1 [M+H]$^+$; 217.1 [M−H]$^-$.

(v) (R)-1-Amino-3-((2,3-dihydro-1H-inden-2-yl)(2,4-dimethoxybenzyl)amino)propan-2-ol (I10)

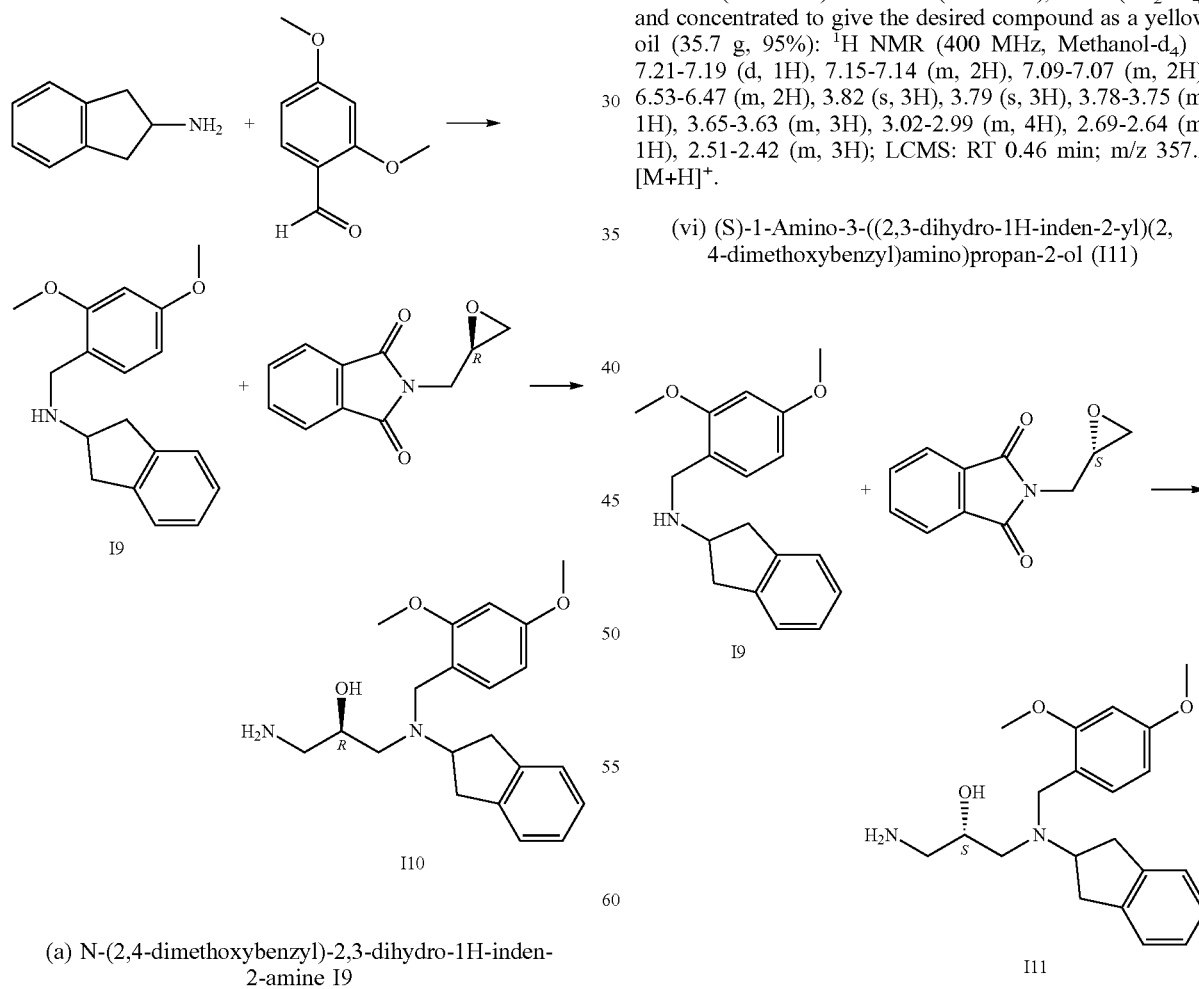

(a) N-(2,4-dimethoxybenzyl)-2,3-dihydro-1H-inden-2-amine I9

To a solution of 2,3-dihydro-1H-inden-2-amine (20.0 g, 150.2 mmol) in ethanol (300 mL) was added 2,4-dimethoxybenzaldehyde (25.0 g, 150.2 mmol). The reaction mixture was stirred at 70° C. for 2 h, then the reaction cooled to 0° C. and $NaBH_4$ (11.4 g, 300.3 mmol) was added. The resulting mixture was stirred at 0° C. for 30 min and poured into water (150 mL), $CH_2Cl_2$ (150 mL) was added and the resulting mixture filtered. The filtrate was concentrated under reduced pressure and the aqueous mixture extracted with EtOAc (50 mL×3). The organic layer was washed with brine (80 mL×2), dried ($Na_2SO_4$) and concentrated to give the desired compound as a yellow oil (41 g, 96%): LCMS: RT 1.45 min; m/z 284.2 [M+H]$^+$.

(b) (R)-1-Amino-3-((2,3-dihydro-1H-inden-2-yl)(2,4-dimethoxybenzyl)amino)propan-2-ol I10

To a solution of N-(2,4-dimethoxybenzyl)-2,3-dihydro-1H-inden-2-amine I9 (30.0 g, 105.9 mmol) in ethanol (400 mL) was added (R)-2-(oxiran-2-ylmethyl)isoindoline-1,3-dione (22.6 g, 111.1 mmol). The resulting mixture was heated at reflux overnight then $N_2H_4.H_2O$ (15.9 g, 317.6 mmol) was added. The resulting mixture was heated at reflux a further 4 h, then the reaction cooled and the precipitate removed by filtration. The filter cake was rinsed with ethanol (100 mL×2) and the filtrate concentrated under reduced pressure. The residue obtained was dissolved in $CH_2Cl_2$ (200 mL), washed with saturated aqueous $NaHCO_3$ solution (80 mL×3) and brine (80 mL×3), dried ($Na_2SO_4$) and concentrated to give the desired compound as a yellow oil (35.7 g, 95%): $^1$H NMR (400 MHz, Methanol-$d_4$) δ 7.21-7.19 (d, 1H), 7.15-7.14 (m, 2H), 7.09-7.07 (m, 2H), 6.53-6.47 (m, 2H), 3.82 (s, 3H), 3.79 (s, 3H), 3.78-3.75 (m, 1H), 3.65-3.63 (m, 3H), 3.02-2.99 (m, 4H), 2.69-2.64 (m, 1H), 2.51-2.42 (m, 3H); LCMS: RT 0.46 min; m/z 357.2 [M+H]$^+$.

(vi) (S)-1-Amino-3-((2,3-dihydro-1H-inden-2-yl)(2,4-dimethoxybenzyl)amino)propan-2-ol (I11)

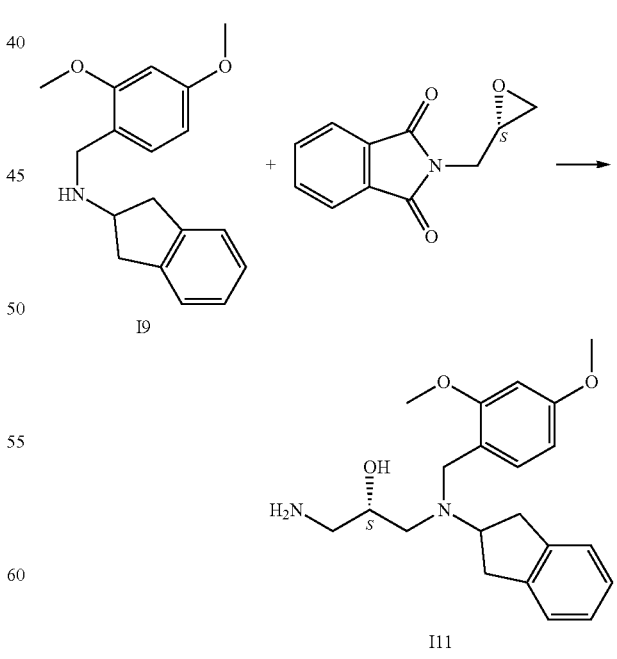

To a solution of N-(2,4-dimethoxybenzyl)-2,3-dihydro-1H-inden-2-amine I9 (10.0 g, 35.2 mmol) in ethanol (150 mL) was added (S)-2-(oxiran-2-ylmethyl)isoindoline-1,3- dione (7.5 g, 36.9 mmol). The resulting mixture was heated at reflux overnight then the reaction cooled and N₂H₄.H₂O (4.9 g, 97.4 mmol) added. The resulting mixture was heated at reflux for a further 4 h, then filtered and the filter cake rinsed with ethanol (20 mL). The filtrate was concentrated and the residue obtained dissolved in CH₂Cl₂ (200 mL), washed with saturated aqueous solution of NaHCO₃ (80 mL×3) and brine (20 mL×2), dried (Na₂SO₄) and concentrated to give the desired compound as a yellow oil (11.4 g, 87%): ¹H NMR (400 MHz, Methanol-d₄) δ 7.21-7.15 (m, 3H), 7.10-7.07 (m, 2H), 6.55-6.54 (m, 1H), 6.50-6.48 (m, 1H), 3.83 (s, 3H), 3.78 (s, 3H), 3.80-3.70 (m, 2H), 3.63-3.61 (m, 2H), 3.03-2.95 (m, 4H), 2.83-2.60 (m, 1H), 2.58-2.51 (m, 3H); LCMS: RT 0.52 min; m/z 357.2 [M+H]⁺.

(vii) 1-Amino-3-((2,3-dihydro-1H-inden-2-yl)(2,4-dimethoxybenzyl)amino)propan-2-ol (I12)

(viii) (R)-4-((3-((2,3-Dihydro-1H-inden-2-yl)(2,4-dimethoxybenzyl)amino)-2-hydroxypropyl)carbamoyl)benzoic acid (I4)

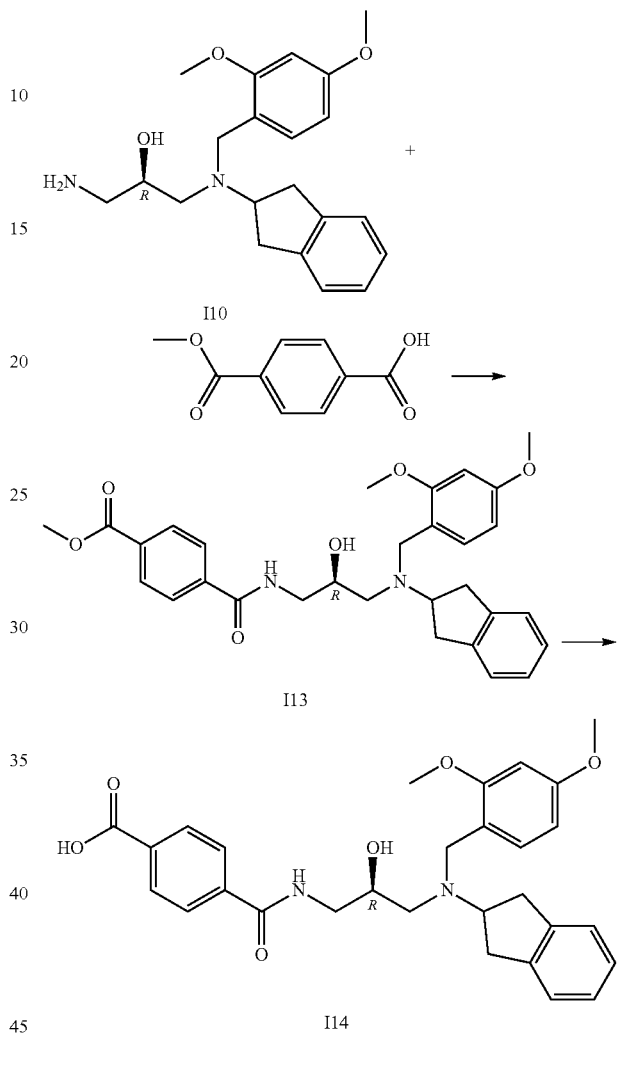

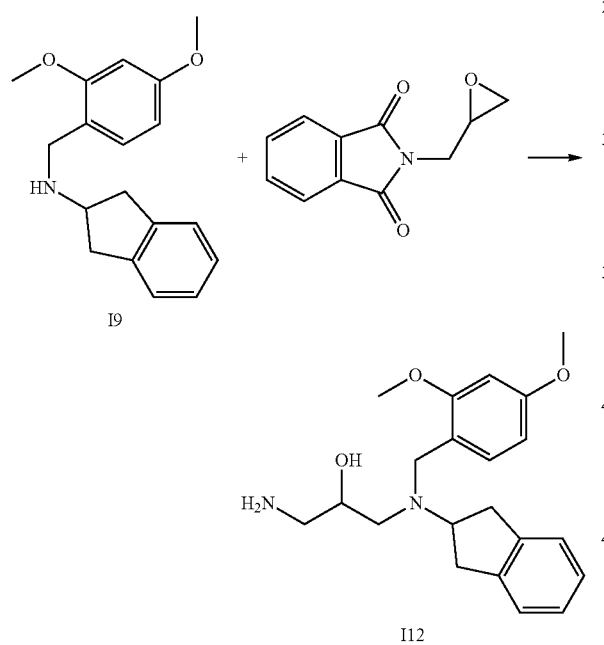

To a solution of N-(2,4-dimethoxybenzyl)-2,3-dihydro-1H-inden-2-amine I9 (10.0 g, 35.2 mmol) in ethanol (150 mL) was added 2-(oxiran-2-ylmethyl)isoindoline-1,3-dione (7.5 g, 37.1 mmol). The resulting mixture was heated at reflux overnight, then cooled to room temperature and N₂H₄.H₂O (4.9 g, 97.4 mmol) added. The resulting mixture was heated at reflux for a further 3 h. The reaction was cooled to RT, filtered and the filter cake rinsed with ethanol (50 mL). The filtrate was concentrated then dissolved in CH₂Cl₂, washed with a saturated aqueous solution of NaHCO₃ (80 mL×3) and brine (20 mL×2), dried (Na₂SO₄) and concentrated to give the desired compound as yellow oil (10.5 g, 83%): LCMS: RT 0.53 min; m/z 357.2 [M+H]⁺.

(a) (R)-Methyl 4-((3-((2,3-dihydro-1H-inden-2-yl)(2,4-dimethoxybenzyl)amino)-2-hydroxypropyl)carbamoyl)benzoate I13

To a solution of (R)-1-amino-3-((2,3-dihydro-1H-inden-2-yl)(2,4-dimethoxybenzyl)amino) propan-2-ol I10 (25.0 g, 70.2 mmol) in CH₂Cl₂ (500 mL) was added 4-(methoxycarbonyl)benzoic acid (13.9 g, 77.2 mmol), DIPEA (18.1 g, 140.4 mmol), HOBt (0.95 g, 7.0 mmol) and EDCl (16.2 g, 84.2 mmol). The resulting mixture was stirred at room temperature overnight. The reaction was partitioned with a saturated solution of NaHCO₃ and extracted with CH₂Cl₂ (100 mL×2). The combined organic layers were washed with brine (100 mL×2), dried (Na₂SO₄) and concentrated. The residue was purified by column chromatography (100% CH₂Cl₂ to 1% methanol in CH₂Cl₂) to give the desired compound as a yellow oil (19.8 g, 55%): LCMS: RT 2.30 min; m/z 519.3 [M+H]⁺.

(b) (R)-4-((3-((2,3-dihydro-1H-inden-2-yl)(2,4-dimethoxybenzyl)amino)-2-hydroxypropyl)carbamoyl)benzoic acid I14

To a solution of (R)-methyl 4-((3-((2,3-dihydro-1H-inden-2-yl)(2,4-dimethoxybenzyl)amino)-2-hydroxypropyl)carbamoyl)benzoate I13 (17.4 g, 33.7 mmol) in a mixture of THF (250 mL) methanol (12 mL) and water (12 mL) was added LiOH.H$_2$O (7.0 g, 168.3 mmol). The reaction was stirred at room temperature for 48 h. The solvent was removed and the residue diluted with water (200 mL). The pH of the mixture was adjusted to pH 6 by addition of 3 M aqueous HCl. The mixture was extracted with CH$_2$Cl$_2$ (150 mL×3). The combined organic layers were washed with brine (100 mL×2), dried (Na$_2$SO$_4$) and concentrated to give the desired compound as a white solid (9.4 g, 56%): LCMS: RT 2.34 min; m/z 505.3 [M+H]$^+$.

(ix) 4-((3-((2,3-Dihydro-1H-inden-2-yl)(2,4-dimethoxybenzyl)amino)-2-hydroxypropyl)carbamoyl)benzoic acid (I16)

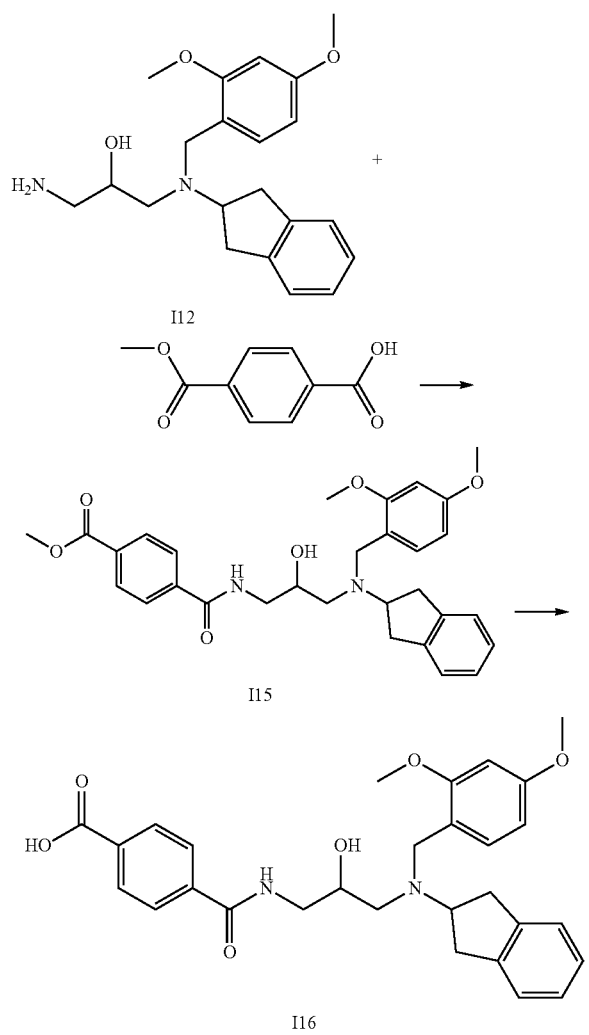

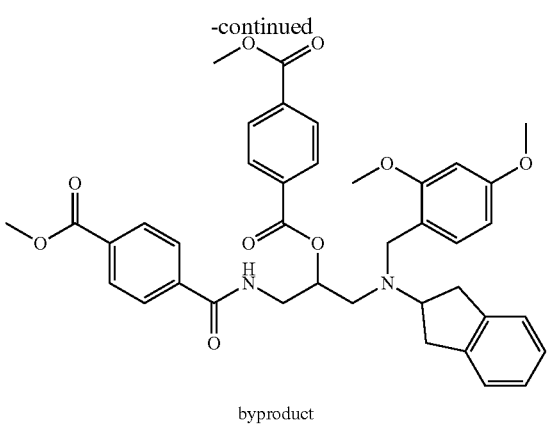

byproduct

(a) Methyl 4-((3-((2,3-dihydro-1H-inden-2-yl)(2,4-dimethoxybenzyl)amino)-2-hydroxypropyl)carbamoyl)benzoate I15

To a solution of 4-(methoxycarbonyl)benzoic acid (1.6 g, 9.0 mmol) in CH$_2$Cl$_2$ (100 mL) was added HATU (4.7 g, 12.3 mmol) and DIPEA (2.2 g, 16.8 mmol). The mixture was stirred at room temperature for 1 h then 1-amino-3-((2,3-dihydro-1H-inden-2-yl)(2,4-dimethoxybenzyl)amino)propan-2-ol I12 (4.0 g, 11.2 mmol) was added. The resulting mixture was stirred at room temperature overnight. Water (100 mL) was added and the phases were separated. The organic layer was washed with a saturated aqueous solution of NaHCO$_3$ (100 mL) and brine (100 mL), dried (Na$_2$SO$_4$) and concentrated. The residue was purified by column chromatography (0.7% methanol in CH$_2$Cl$_2$) to give the byproduct as a yellow oil (1.4 g) further elution (4% methanol in CH$_2$Cl$_2$) gave the desired compound as a yellow oil (2.8 g, 48%). LCMS: RT 2.33 min; m/z 519.3 [M+H]$^+$.

(b) 4-((3-((2,3-Dihydro-1H-inden-2-yl)(2,4-dimethoxybenzyl)amino)-2-hydroxypropyl) carbamoylbenzoic acid I16

To a solution of (R)-methyl 4-((3-((2,3-dihydro-1H-inden-2-yl)(2,4-dimethoxybenzyl)amino)-2-hydroxypropyl)carbamoyl)benzoate I15 (2.6 g, 5.0 mmol) in a mixture of THF (40 mL), methanol (2 mL) and water (2 mL) was added LiOH.H$_2$O (1.1 g, 25.1 mmol). The resulting mixture was stirred at room temperature overnight. The solvent was removed and the residue obtained diluted with water (50 mL). The pH of the aqueous mixture was adjusted to 6 by addition of 4 M aqueous HCl solution, then extracted with CH$_2$Cl$_2$ (100 mL×3). The combined organic layers were washed with brine (50 mL), dried (Na$_2$SO$_4$) and concentrated to give the desired compound as a white solid (1.6 g, 64%). LCMS: RT 2.19 min; m/z 505.3 [M+H]$^+$.

65

(x) 2-(4-((3-((2,3-Dihydro-1H-inden-2-yl)(2,4-dimethoxybenzyl)amino)-2-hydroxypropyl)carbamoyl)phenyl)acetic acid (I18)

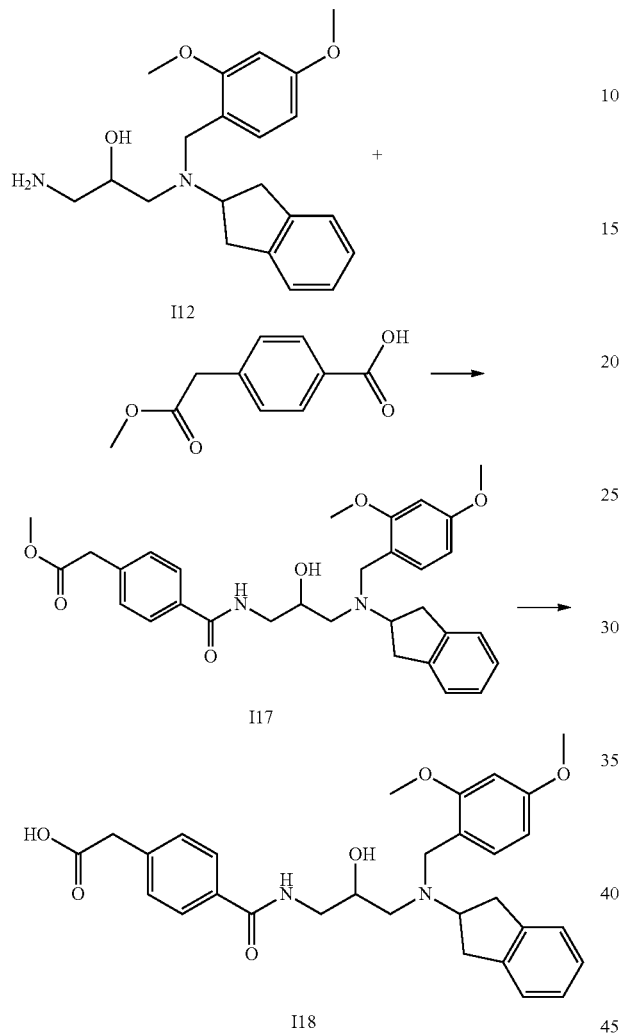

(a) Methyl 2-(4-((3-((2,3-dihydro-1H-inden-2-yl)(2,4-dimethoxybenzyl)amino)-2-hydroxypropyl) carbamoyl)phenyl)acetate I17

To a solution of 4-(2-methoxy-2-oxoethyl)benzoic acid (1.0 g, 5.1 mmol) in CH$_2$Cl$_2$ (50 mL) was added HATU (2.7 g, 7.1 mmol) and DIPEA (1.2 g, 9.7 mmol). The mixture was stirred at room temperature for 1 h, then 1-amino-3-((2,3-dihydro-1H-inden-2-yl)(2,4-dimethoxybenzyl)amino)propan-2-ol I12 (2.3 g, 6.4 mmol) was added. The resulting mixture was stirred at room temperature overnight, then diluted with water (80 mL). The organic layer was separated, washed with a saturated aqueous NaHCO$_3$ solution (100 mL), brine (100 mL), dried (Na$_2$SO$_4$) and concentrated. The residue was purified by column chromatography (0.5% methanol in CH$_2$Cl$_2$) to give the desired compound as a yellow oil (0.92 g, 27%): LCMS: RT 2.24 min; m/z 533.4 [M+H]$^+$.

66

(b) 2-(4-((3-((2,3-Dihydro-1H-inden-2-yl)(2,4-dimethoxybenzyl)amino)-2-hydroxypropyl)carbamoyl)phenyl)acetic acid I18

To a solution of methyl 2-(4-((3-((2,3-dihydro-1H-inden-2-yl)(2,4-dimethoxybenzyl)amino)-2-hydroxypropyl)carbamoyl)phenyl)acetate I17 (1.5 g, 2.8 mmol) in a mixture of THF (20 mL), methanol (2 mL) and water (2 mL) was added LiOH.H$_2$O (0.6 g, 1.4 mmol). The resulting mixture was stirred at room temperature overnight. The solvent was removed, and the residue diluted with water (50 mL). The pH of the aqueous solution was adjusted to 6 by addition of 4 M aqueous HCl solution. The aqueous mixture was extracted with CH$_2$Cl$_2$ (10 mL×3) and the combined organic layers dried (Na$_2$SO$_4$) and concentrated to give the desired compound as a yellow oil (0.63 g, 42%): LCMS: RT 2.16 min; m/z 519.3 [M+H]$^+$.

(xi) (R)-4-((3-((2,3-Dihydro-1H-inden-2-yl)(2,4-dimethoxybenzyl)amino)-2-hydroxypropyl)carbamoyl)-3-ethoxybenzoic acid (I25)

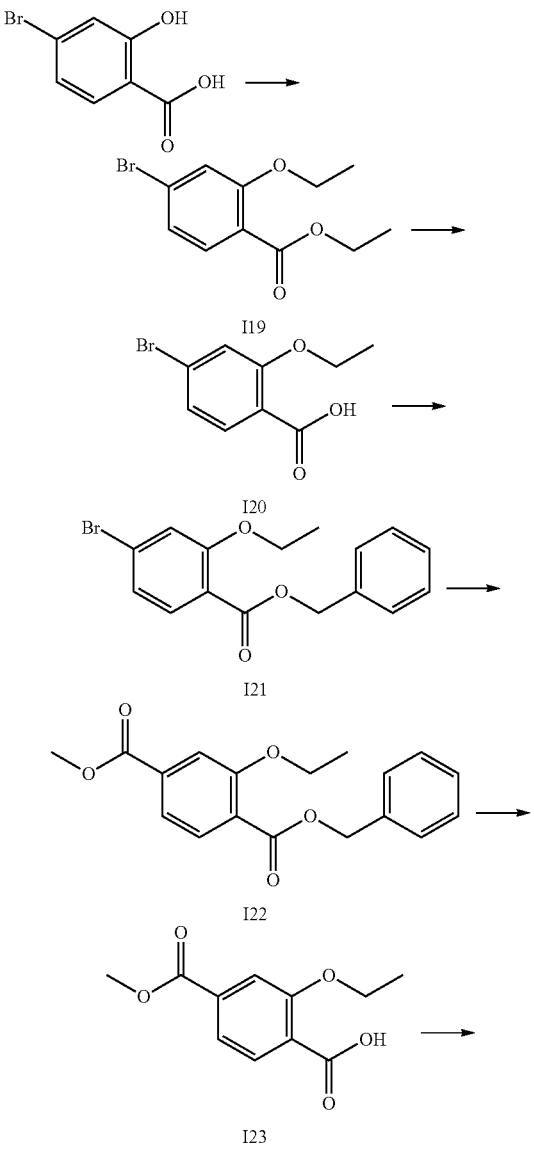

-continued

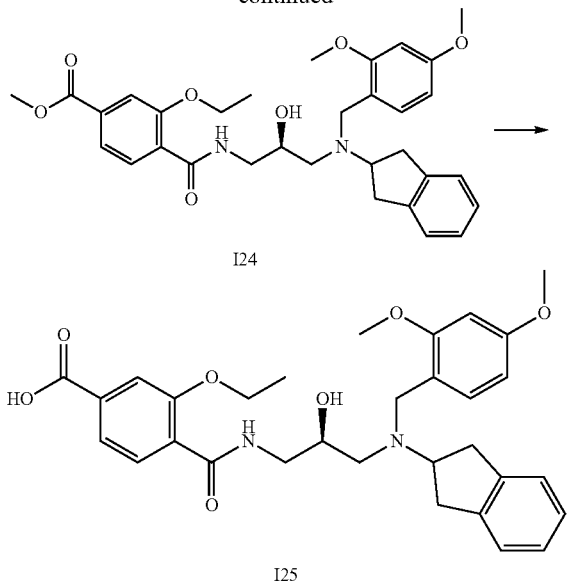

(a) Ethyl-4-bromo-2-ethoxybenzoate I19

To a mixture of 4-bromo-2-hydroxybenzoic acid (20.0 g, 92.6 mmol) and $K_2CO_3$ (38.4 g, 277.9 mmol) in dimethylsulfoxide (50 mL) at 40° C. was added ethyl bromide (15.2 g, 138.9 mmol) dropwise over 30 min. The reaction was stirred for 2 h then further ethyl bromide (15.2 g, 138.9 mmol) was added over 30 min. The reaction was stirred a further 8 h then diluted with $CH_2Cl_2$ (150 mL) and filtered. The filtrate was washed with water (200 mL×10) and brine (200 mL×3), dried over $Na_2SO_4$ and concentrated to give the desired compound as a brown solid (24.3 g, 96%): LCMS: RT 2.93 min; m/z 273.0 [M+H]$^+$.

(b) 4-Bromo-2-ethoxybenzoic acid I20

To a solution of ethyl 4-bromo-2-ethoxybenzoate I19 (24.1 g, 88.6 mmol) in a mixture of THF (150 mL), methanol (15 mL) and water (15 mL) was added LiOH.$H_2O$ (18.6 g, 44.3 mmol). The resulting mixture was stirred at room temperature for 24 h. The solvent was removed, and the residue was diluted with water (200 mL). The pH of the aqueous mixture was adjusted to 6 by addition of 2 M aqueous HCl solution. The aqueous mixture was extracted with $CH_2Cl_2$ (150 mL×3) and the combined organic layers washed with brine (100 mL×3), dried ($Na_2SO_4$) and concentrated to give the desired compound as a yellow solid (19.8 g, 92%): LCMS: RT 2.47 min; m/z 246.9 [M+H]$^+$ for $^{81}$Br.

(c) Benzyl-4-bromo-2-ethoxybenzoate I21

To a solution of 4-bromo-2-ethoxybenzoic acid I20 (16.4 g, 67.2 mmol) in acetonitrile (75 mL) was added benzyl bromide (13.8 g, 80.7 mmol) and $K_2CO_3$ (18.6 g, 134.4 mmol). The resulting mixture was stirred at 40° C. overnight. The reaction mixture was filtered and concentrated. The residue obtained was diluted with $CH_2Cl_2$ (50 mL) and washed with water (100 mL×2). The organic layer was washed with brine (70 mL×3), dried ($Na_2SO_4$) and concentrated. The residue was purified by column chromatography (1% EtOAc in petroleum ether) to give the desired compound as a light yellow oil (20.9 g, 93%): LCMS: RT 3.31 min; m/z 334.9 [M+H]$^+$.

(d) 1-Benzyl 4-methyl 2-ethoxyterephthalate I22

To a solution of benzyl 4-bromo-2-ethoxybenzoate I21 (20.0 g, 59.9 mmol) in methanol (100 mL) was added Pd(dppf)Cl$_2$ (2.2 g, 3 mmol) and TEA (13.3 g, 131.7 mmol). The resulting mixture was heated at reflux overnight under an atmosphere of carbon monoxide. The reaction mixture was concentrated and the residue obtained diluted with water and extracted with $CH_2Cl_2$ (50 mL×3). The combined organic layers were washed with brine (60 mL×2), dried ($Na_2SO_4$) and concentrated. The residue was purified by column chromatography (2% EtOAc in petroleum ether) to give the desired compound as a white solid (15.1 g, 81%): LCMS: RT 3.03 min; m/z 315.1 [M+H]$^+$.

(e) 2-Ethoxy-4-(methoxycarbonyl)benzoic acid I23

To a solution of 1-benzyl 4-methyl 2-ethoxyterephthalate I22 (14.9 g, 47.4 mmol) in THF (100 mL) was added 10% Pd/C (1.5 g). The resulting mixture was stirred at room temperature overnight under $H_2$ atmosphere. The reaction mixture was filtered through celite, and the filter cake washed with THF (50 mL). The filtrate was concentrated and the residue diluted with water. The pH of the aqueous solution was adjusted to 6 by addition of a 2 M aqueous HCl solution. The resultant mixture was extracted with $CH_2Cl_2$ (50 mL×3) and the combined organic layers washed with brine (50 mL×2), dried ($Na_2SO_4$) and concentrated to give the desired compound as a white solid (10.2 g, 96%): LCMS: RT 2.13 min; m/z 225.0 [M+H]$^+$.

(f) Methyl (R)-4-((3-((2,3-dihydro-1H-inden-2-yl)(2,4-dimethoxybenzyl)amino)-2-hydroxypropyl)carbamoyl)-3-ethoxybenzoate I24

To a solution of 2-ethoxy-4-(methoxycarbonyl)benzoic acid I23 (3.8 g, 17.0 mmol) in $CH_2Cl_2$ (40 mL) was added (R)-1-amino-3-((2,3-dihydro-1H-inden-2-yl)(2,4-dimethoxybenzyl)amino)propan-2-ol I10 (5.5 g, 15.1 mmol), HOBt (208.6 mg, 1.5 mmol), DIPEA (4.0 g, 30.9 mmol) and EDCI (3.7 g, 18.5 mmol). The resulting mixture was stirred at room temperature overnight. The mixture was partitioned with saturated aqueous NaHCO$_3$ solution and extracted with $CH_2Cl_2$ (30 mL×2). The combined organic layers were washed with brine (20 mL×2), dried ($Na_2SO_4$) and concentrated. The residue obtained was purified by column chromatography (1% methanol in $CH_2Cl_2$) to give the desired compound as a yellow oil (6.6 g, 76%): LCMS: RT 2.41 min; m/z 563.2 [M+H]$^+$.

(g) (R)-4-((3-((2,3-Dihydro-1H-inden-2-yl)(2,4-dimethoxybenzyl)amino)-2-hydroxypropyl)carbamoyl)-3-ethoxybenzoic acid I25

To a solution of methyl (R)-4-((3-((2,3-dihydro-1H-inden-2-yl)(2,4-dimethoxybenzyl)amino)-2-hydroxypropyl)carbamoyl)-3-ethoxybenzoate I24 (6.5 g, 11.6 mmol) in a mixture of THF (40 mL), methanol (4 mL) and water (4 mL) was added LiOH.$H_2O$ (2.4 g, 57.8 mmol). The resulting mixture was stirred at room temperature overnight. The mixture was concentrated, and the residue diluted with water (20 mL). The pH of the aqueous mixture was adjusted to 6 by addition of a 2 M aqueous HCl solution. The aqueous was then extracted with CH$_2$Cl$_2$ (10 mL×3) and the combined organic layers washed with brine (20 mL×2), dried (Na$_2$SO$_4$) and concentrated to give the desired compound as a white solid (6.3 g, 98%): LCMS: RT 2.26 min; m/z 549.3 [M+H]$^+$.

(xii) 4-(Morpholine-4-carbonyl)benzoic acid (I27)

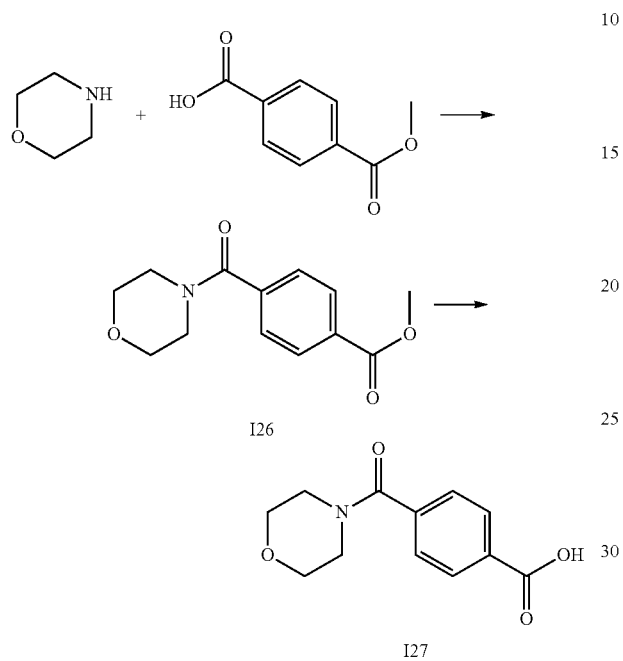

(a) Methyl 4-(morpholine-4-carbonyl)benzoate I26

To a solution of mono-methyl terephthalate (10.0 g, 55.9 mmol) in dichloromethane (500 mL) at 0° C. was added oxalyl chloride (8.5 g, 66.6 mmol) and a catalytic amount of DMF (0.5 mL). The mixture was stirred at 0° C. for 3 h. Morpholine (9.7 g, 111.0 mmol) was added followed by triethylamine (7.9 g, 77.7 mmol), the reaction was allowed to warm to room temperature and stirred for 16 h. The reaction was diluted with a saturated aqueous solution of NaHCO$_3$ (250 mL). The aqueous layer was extracted with dichloromethane (3×250 mL) and the combined organic layers washed with 0.5 M aqueous HCl solution (100 mL), water (200 mL) and brine (100 mL). The organic layer was dried (Na$_2$SO$_4$), filtered and concentrated in vacuo to give a solid which was crystallized (petroleum ether: ethyl acetate=20:1) to give the desired compound (11.3 g, 82%) as a yellow solid. LCMS: RT 1.11 min; m/z 250.1 [M+H]$^+$ (b) 4-(Morpholine-4-carbonyl)benzoic acid I27

To a solution of methyl 4-(morpholine-4-carbonyl)benzoate I26 (10.5 g, 42.1 mmol) in a mixture of THF (200 mL), MeOH (20 mL) and water (2 mL) was added LiOH.H$_2$O (1.9 g, 46.3 mmol) and the reaction stirred at room temperature for 24 h. The solvents were removed under reduced pressure and the resulting gum suspended in a 0.5 M aqueous citric acid solution (250 mL). The aqueous layer extracted with dichloromethane (3×250 mL) and the combined organic fractions dried (MgSO$_4$) and concentrated in vacuo to yield the product as a tan solid (8.8 g, 88%). LCMS: RT 0.48 min; m/z 236.1 [M+H]$^+$. $^1$H NMR (400 MHz, Methanol-d$_4$) δ=8.23-8.04 (d, 2H), 7.67-7.48 (d, 2H), 3.79 (br s, 2H), 3.75-3.68 (m, 2H), 3.68-3.61 (m, 2H), 3.49-3.40 (m, 2H).

(xiii) 3-(Morpholine-4-carbonyl)benzoic acid I29

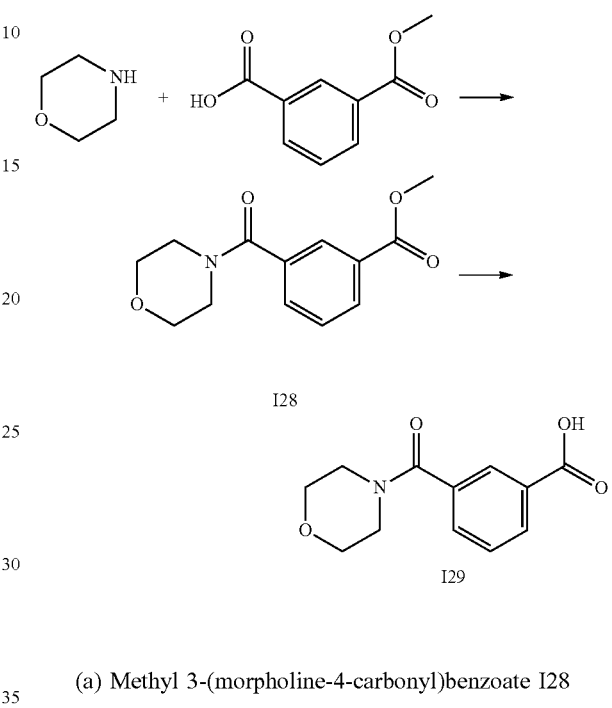

(a) Methyl 3-(morpholine-4-carbonyl)benzoate I28

Morpholine (958 μL, 11.1 mmol, 1 equiv), mono-methyl isopthalate (2.00 g, 11.1 mmol, 1 equiv), MeCN (50 mL), DIPEA (5.80 mL, 33.3 mmol, 3 equiv) and HATU (4.64 g, 12.2 mmol, 1.1 equiv) were stirred at room temperature. After two hours the mixture was quenched with 5% w/v aqueous sodium carbonate solution (50 mL) and the organic solvents removed in vacuo. The aqueous residue was extracted with ethyl acetate (3×50 mL), and the pooled organic extracts washed with water (2×50 mL), dried over sodium sulfate and concentrated. Chromatography (40 g silica cartridge, 0-50% ethyl acetate in petroleum benzine) and collection of the suspected product fractions gave the desired compound (2.72 g, 98% yield) as a pale brown oil. LCMS-B: RT=3.32 min, m/z=250 [M+H]$^+$.

(b) 3-(morpholine-4-carbonyl)benzoic acid I29

LiOH.H$_2$O (1.37 g, 32.7 mmol, 3 equiv) was added to a solution of I28 (2.72 g, 10.9 mmol) in MeOH (20 mL) and water (10 mL), the resulting suspension was stirred for 16 hours at room temperature. The volatiles were removed in vacuo to give a white solid. Water was added followed by a 0.5 M aqueous solution of citric acid until the solution was at pH 4. The mixture was stirred for 30 minutes before it was extracted with EtOAc (3×70 mL). The combined organic layers were washed with brine (100 mL), dried (MgSO$_4$) and concentrated in vacuo to give the desired compound (1.74 g, 68% yield) as a white solid. LCMS-B: RT=3.19 min, m/z=236 [M+H]$^+$, 234 [M−H]$^−$.

(xiv) 2-(2-Cyclopropylacetyl)isoindoline-5-carboxylic acid I32

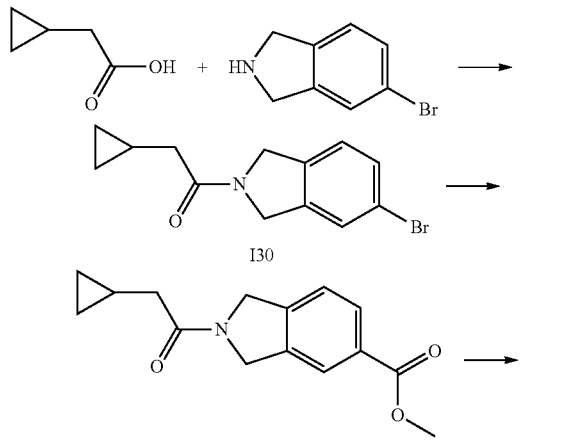

(a) 1-(5-Bromoisoindolin-2-yl)-2-cyclopropylethanone I30

To a solution of 2-cyclopropylacetic acid (96 mg, 0.96 mmol) in dichloromethane (10 mL) was added HOBt (212.8 mg, 1.39 mmol), DIPEA (421.2 mg, 3.26 mmol) and EDCl (266.4 mg, 1.39 mmol). The mixture was stirred at 0° C. for 20 min then a solution of 5-bromoisoindoline (190 mg, 0.96 mmol) in dichloromethane (5 mL) was added. The resulting mixture was stirred at room temperature overnight. Water (20 mL) was added and the mixture extracted with dichloromethane (20 mL×3). The combined organic layers were dried ($Na_2SO_4$), filtered and concentrated in vacuo to give the crude product. The crude product was purified by column chromatography (Petroleum ether: ethyl acetate=10:1) to give the desired product (145 mg, 68%) as a yellow oil. LCMS: RT 2.69 min; m/z 280.2 $[M+H]^+$.

(b) Methyl 2-(2-cyclopropylacetyl)isoindoline-5-carboxylate I31

To a solution of 1-(5-bromoisoindolin-2-yl)-2-cyclopropylethanone I30 (140 mg, 0.5 mmol) in methanol (10 mL) was added triethylamine (111.1 mg, 1.1 mmol) and Pd(dppf)Cl$_2$ (18.3 mg, 0.025 mmol,). The mixture was heated at reflux under a carbon monoxide atmosphere overnight. The mixture was concentrated to give the crude product which was purified by column chromatography (Petroleum ether: ethyl acetate=10:1) to give the desired product (103 mg, 79%) as a yellow oil. LCMS: RT 2.38 min; m/z 260.3 $[M+H]^+$ (c) 2-(2-Cyclopropylacetyl)isoindoline-5-carboxylic acid I32

To a solution of 2-(2-cyclopropylacetyl)isoindoline-5-carboxylic acid I31 (97 mg, 0.37 mmol) in mixture of THF (8 mL), methanol (0.8 mL), and water (0.08 mL) was added LiOH.H$_2$O (77.7 mg, 1.85 mmol). The resulting mixture was stirred at room temperature for 3 days. The mixture was concentrated to give the crude product which was dissolved in water and washed with dichloromethane (10 mL). The aqueous layer was neutralized by addition of a 0.5 M aqueous HCl solution (10 mL) and the solution extracted with dichloromethane (20 mL×3). The combined organic layers were dried ($Na_2SO_4$) and concentrated to give the desired product (50 mg, 55%) as a pale solid. LCMS: RT 2.11 min; m/z 246.3 $[M+H]^+$ (xv) 2-(2-Cyclopropylacetyl)-1,2,3,4-tetrahydroisoquinoline-7-carboxylic acid I35

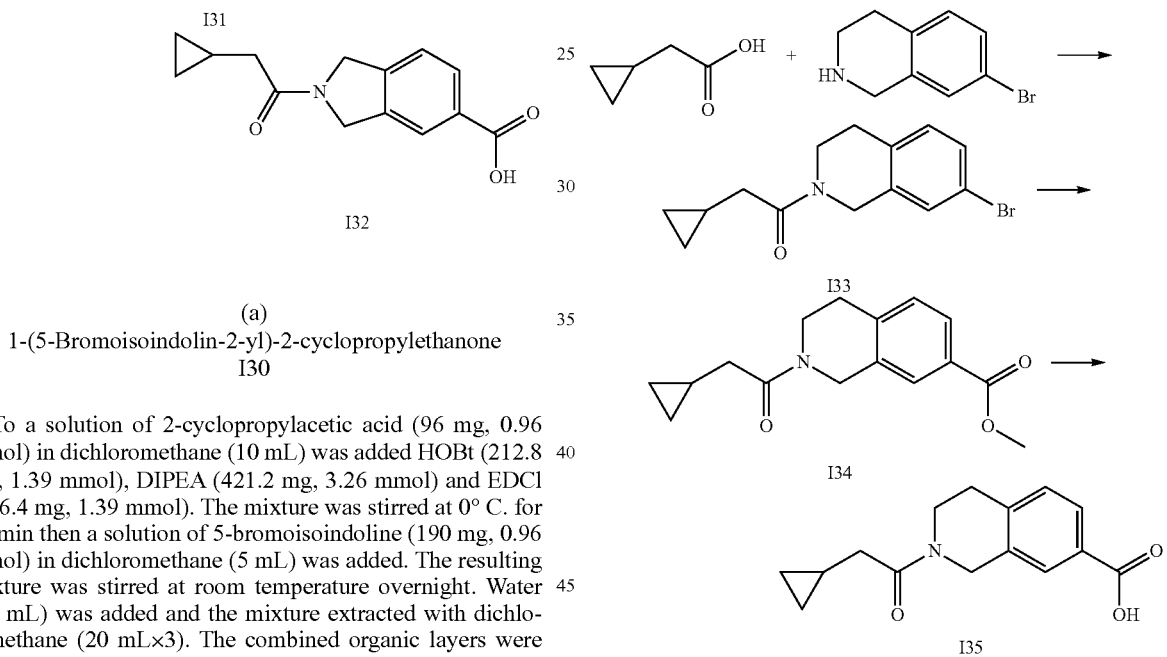

(a) 1-(7-Bromo-3,4-dihydroisoquinolin-2(1H)-yl)-2-cyclopropylethanone I33

To a solution of 2-cyclopropylacetic acid (201.2 mg, 2.01 mmol) in DCM (30 mL) was added DIPEA (1.4 g, 8.8 mmol), HOBt (445.5 mg, 2.91 mmol) and EDCl (557.8 mg, 2.91 mmol). The mixture was stirred at 0° C. for 20 min then 7-bromo-1,2,3,4-tetrahydroisoquinoline hydrochloride (500 mg, 2.01 mmol) was added. The resulting mixture was stirred at room temperature overnight. The reaction was diluted with water (20 mL) and the solution extracted with DCM (30 mL×3). The combined organic layers were dried ($Na_2SO_4$) and concentrated to give the crude product which was purified by column chromatography (petroleum ether: ethyl acetate=10:1) to give the desired product (420 mg, 71%) as a yellow oil. LCMS: RT 2.59 min; m/z 294.0 $[M+H]^+$.

(b) Methyl 2-(2-cyclopropylacetyl)-1,2,3,4-tetrahydroisoquinoline-7-carboxylate I34

To a solution of 1-(7-bromo-3,4-dihydroisoquinolin-2(1H)-yl)-2-cyclopropylethanone I33 (400 mg, 1.36 mmol) in MeOH (10 mL) was added triethylamine (303.0 mg, 3.0 mmol), and Pd(dppf)Cl$_2$ (49.9 mg, 0.068 mmol). The mixture was heated at reflux under a carbon monoxide atmosphere overnight. The solvent was removed under reduced pressure to give the crude product which was purified by column chromatography (Petroleum ether: ethyl acetate=5:1) to give the desired product (160 mg, 79%) as a yellow oil. LCMS: RT 2.47 min; m/z 274.3 [M+H]$^+$

(c) 2-(2-Cyclopropylacetyl)-1,2,3,4-tetrahydroisoquinoline-7-carboxylic acid I35

To a solution of methyl 2-(2-cyclopropylacetyl)-1,2,3,4-tetrahydroisoquinoline-7-carboxylate I34 (150 mg, 0.54 mmol) in a mixture of THF (8 mL), methanol (0.8 mL), and water (0.08 mL) was added LiOH.H$_2$O (69.3 mg, 1.65 mmol). The resulting mixture was stirred at room temperature for 2 days. The mixture was concentrated to give the crude product which was diluted with water and washed with dichloromethane (10 mL). The water layer was neutralized by addition of a 0.5 M aqueous HCl solution (10 mL) and extracted with dichloromethane (20 mL×3). The combined organic layers were dried (Na$_2$SO$_4$) and concentrated to give the desired product (70 mg, 50%) as a pale solid. LCMS: RT 2.20 min; m/z 260.1 [M+H]$^+$

(xvi) 2-(2-Cyclopropylacetyl)-1,2,3,4-tetrahydroisoquinoline-7-carboxylic acid I38

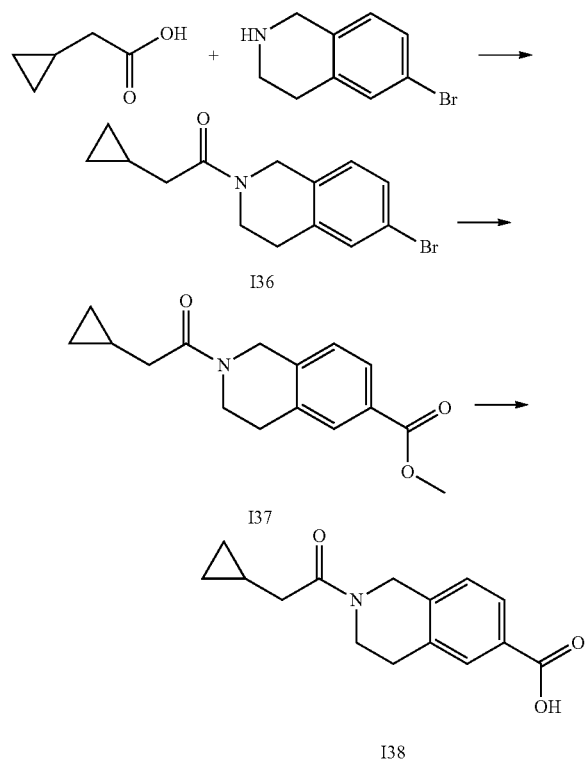

(a) 1-(6-Bromo-3,4-dihydroisoquinolin-2(1H)-yl)-2-cyclopropylethanone I36

To a solution of 2-cyclopropylacetic acid (236.2 mg, 2.36 mmol) in DCM (30 mL) was added DIPEA (1.03 g, 8.0 mmol), HOBt (523.6 mg, 3.42 mmol) and EDCl (655.6 mg, 3.42 mmol). The mixture was stirred at 0° C. for 20 min then 6-bromo-1,2,3,4-tetrahydroisoquinoline (500 mg, 2.01 mmol) was added. The resulting mixture was stirred at room temperature overnight. The reaction was diluted with water (20 mL) and the aqueous layer extracted with DCM (30 mL×3). The combined organic layers were dried (Na$_2$SO$_4$) and concentrated to give the crude product which was purified by column chromatography (petroleum ether: ethyl acetate=10:1) to give the desired product (580 mg, 83%) as a yellow oil. LCMS: RT 2.69 min; m/z 294.0 [M+H]$^+$

(b) Methyl 2-(2-cyclopropylacetyl)-1,2,3,4-tetrahydroisoquinoline-6-carboxylate I37

To a solution of 1-(6-bromo-3,4-dihydroisoquinolin-2(1H)-yl)-2-cyclopropylethanone I36 (560 mg, 1.90 mmol) in MeOH (30 mL) was added triethylamine (422.2 mg, 4.18 mmol), and Pd(dppf)Cl$_2$ (69.7 mg, 0.095 mmol). The mixture was heated at reflux under a carbon monoxide atmosphere overnight. The mixture was concentrated to give the crude product which was purified by column chromatography (Petroleum ether: ethyl acetate=5:1) to give the desired product (280 mg, 54%) as a pale oil. LCMS: RT 2.45 min; m/z 274.1 [M+H]$^+$

(c) 2-(2-Cyclopropylacetyl)-1,2,3,4-tetrahydroisoquinoline-7-carboxylic acid I38

To a solution of methyl 2-(2-cyclopropylacetyl)-1,2,3,4-tetrahydroisoquinoline-6-carboxylate I37 (200 mg, 0.73 mmol) in mixture of THF (10 mL), methanol (1 mL), and water (0.1 mL) was added LiOH.H$_2$O (94.0 mg, 2.26 mmol). The resulting mixture was stirred at room temperature for 2 days. The mixture was concentrated to give the crude product. Water was added and the aqueous layer washed with dichloromethane (10 mL). The aqueous layer was neutralized by addition of a 0.5 M aqueous HCl solution (10 mL) and the solution was extracted with dichloromethane (20 mL×3). The organic layer was dried (Na$_2$SO$_4$) and concentrated to give the desired product (170 mg, 89%) as a yellow solid. LCMS: RT 2.15 min; m/z 260.3 [M+H]$^+$

(xvii) 2-Acetyl-1,2,3,4-tetrahydroisoquinoline-6-carboxylic acid I41

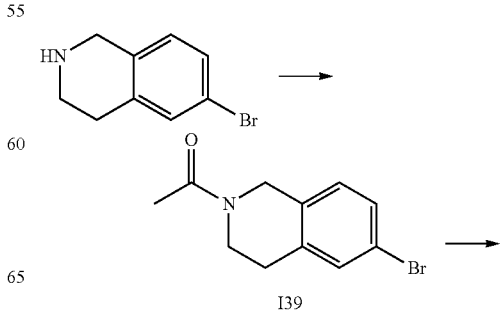

-continued

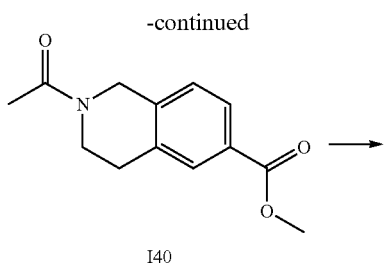

I40

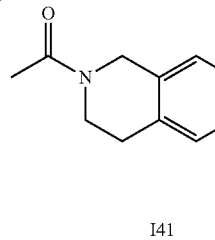

I41

(a) 1-(6-Bromo-3,4-dihydroisoquinolin-2(1H)-yl) ethanone I39

To a solution of 6-bromo-1,2,3,4-tetrahydroisoquinoline (456.0 mg, 2.15 mmol) in DCM (20 mL) was added triethylamine (326.0 mg, 3.22 mmol) and acetic anhydride (219.5 mg, 2.15 mmol) at 0° C. The resulting mixture was stirred at 0° C. for 3 h, then allowed to warm to room temperature and stirred overnight. The reaction mixture was washed with a saturated aqueous $NaHCO_3$ solution (20 mL×2), the organic layer separated, dried ($Na_2SO_4$) and concentrated to give the desired product (500 mg, 91%) as an orange oil. LCMS: RT 2.41 min; m/z 254.0 $[M+H]^+$ (b) Methyl 2-acetyl-1,2,3,4-tetrahydroisoquinoline-6-carboxylate I40

To a solution of 1-(6-bromo-3,4-dihydroisoquinolin-2 (1H)-yl)ethanone I39 (500 mg, 1.97 mmol) in MeOH (30 mL) was added triethylamine (437.0 mg, 4.33 mmol), and Pd(dppf)Cl$_2$ (71.9 mg, 0.098 mmol). The mixture was heated at reflux under a carbon monoxide atmosphere overnight. The mixture was concentrated to give the crude product which was purified by column chromatography (Petroleum ether: ethyl acetate=2:1) to give the desired product (360 mg, 78%) as an orange oil. LCMS: RT 2.07 min; m/z 234.1 $[M+H]^+$ (c) 2-Acetyl-1,2,3,4-tetrahydroisoquinoline-6-carboxylic acid I41

To a solution of methyl 2-acetyl-1,2,3,4-tetrahydroisoquinoline-6-carboxylate I40 (200 mg, 0.86 mmol) in a mixture of THF (10 mL), methanol (1 mL), and water (0.1 mL) was added LiOH.H$_2$O (108.3 mg, 2.58 mmol). The resulting mixture was stirred at room temperature for 2 days. The mixture was concentrated to give the crude product which was diluted with water and washed with dichloromethane (10 mL). The aqueous layer was neutralized by addition of a 0.5 M aqueous HCl solution (10 mL) and the solution extracted with dichloromethane (20 mL×3). The organic layer was dried (Na$_2$SO$_4$) and concentrated to give the desired product (100 mg, 53%) as a white solid. LCMS: RT 3.01 min; m/z 220.1 $[M+H]^+$ (xviii) 2-Acetyl-1,2,3,4-tetrahydroisoquinoline-7-carboxylic acid I44

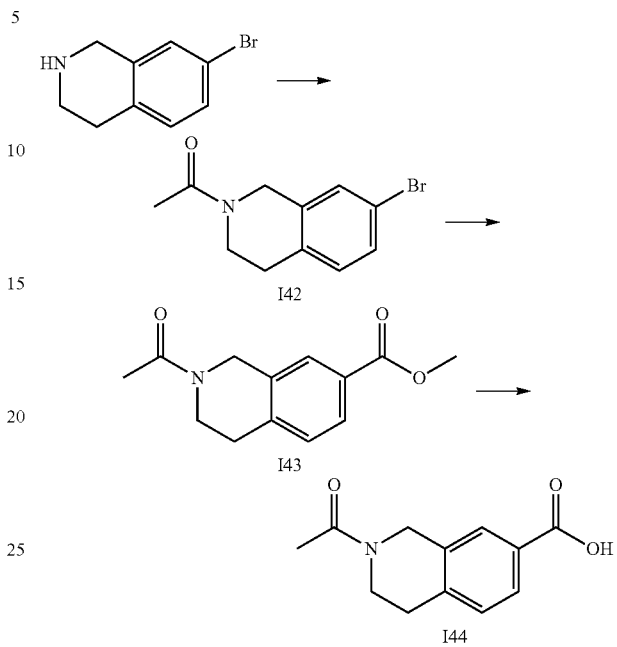

(a) 1-(7-Bromo-3,4-dihydroisoquinolin-2(1H)-yl) ethanone I42

To a solution of 7-bromo-1,2,3,4-tetrahydroisoquinoline (500 mg, 2.0 mmol), triethylamine (650 mg, 6.4 mmol) and DMAP (25 mg, 0.2 mmol) in DCM (20 mL) at 0° C. was added acetic anhydride (210 mg, 2.1 mmol). The resulting mixture was stirred at room temperature overnight. The reaction was washed with NaHCO$_3$ solution (20 mL×2) and the organic layer dried (Na$_2$SO$_4$) and concentrated to give the desired product (350 mg, 70%) as a clear oil. LCMS: RT 3.03 min; m/z 254.1 $[M+H]^+$ (b) Methyl 2-acetyl-1,2,3,4-tetrahydroisoquinoline-7-carboxylate I43

To a solution of 1-(7-bromo-3,4-dihydroisoquinolin-2 (1H)-yl)ethanone I42 (350 mg, 1.385 mmol) in MeOH (30 mL) was added triethylamine (307.1 mg, 2.25 mmol), and Pd(dppf)Cl$_2$ (50.6 mg, 0.069 mmol). The mixture was heated at reflux under a carbon monoxide atmosphere overnight. The mixture was concentrated to give the crude product which was purified by column chromatography (Petroleum ether: ethyl acetate=3:1) to give the desired product (150 mg, 46%) as an orange oil. LCMS: RT 2.35 min; m/z 234.3 $[M+H]^+$ (c) 2-Acetyl-1,2,3,4-tetrahydroisoquinoline-7-carboxylic acid I44

To a solution of methyl 2-acetyl-1,2,3,4-tetrahydroisoquinoline-7-carboxylate I43 (150 mg, 0.64 mmol) in a mixture of THF (10 mL), methanol (1 mL), and water (0.1 mL) was added LiOH.H$_2$O (80.6 mg, 1.92 mmol). The resulting mixture was stirred at room temperature for 1 day. The mixture was concentrated to give the crude product which was diluted with water and washed with dichloromethane (10 mL). The water layer was neutralized by addition of a 0.5 M aqueous HCl solution (10 mL) and the solution was extracted with dichloromethane (20 mL×3). The organic layer was dried ($Na_2SO_4$) and concentrated to give the desired product (80 mg, 57%) as a yellow oil. LCMS: RT 1.57 min; m/z 220.1 [M+H]+

(xix) 6-(Piperidine-1-carbonyl)nicotinic acid I47

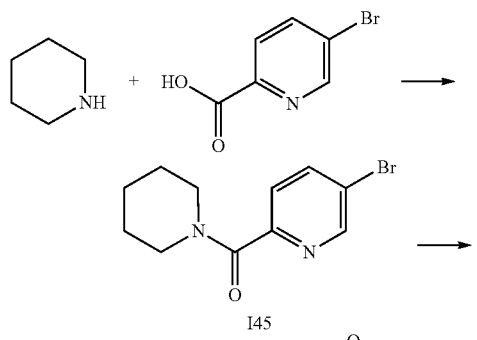

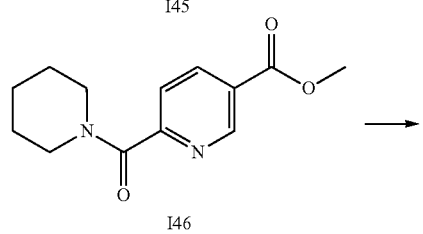

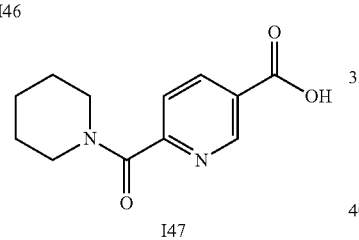

(a) (5-Bromopyridin-2-yl)(piperidin-1-yl)methanone I45

To a solution of 5-bromopicolinic acid (5.0 g, 25.0 mmol) in DCM (250 mL) was added HATU (11.4 g, 30.0 mmol) and $Et_3N$ (8.8 g, 88.0 mmol). The mixture was stirred at room temperature for 30 min then piperidine (2.6 g, 30.0 mmol) was added and the resulting mixture stirred at room temperature overnight. Water (200 mL) was added and the organic layer separated. The aqueous layer was extracted with DCM (2×200 mL) and the combined organic fractions washed with brine (200 mL), dried ($Na_2SO_4$) and concentrated. The residue was purified by column chromatography (0-30% EtOAc/petroleum ether) to give the desired compound as yellow oil (6.0 g, 90%): LCMS: RT 2.21 min, m/z 269.1; 271.1 [M+H]+ for $^{79}Br$ and $^{81}Br$ respectively (b) Methyl 6-(piperidine-1-carbonyl)nicotinate I46

To a solution of (5-bromopyridin-2-yl)(piperidin-1-yl) methanone I45 (4.0 g, 14.9 mmol) in MeOH (50 mL) was added $Et_3N$ (3.3 g, 32.8 mmol) and $PdCl_2(dppf)$ (410 mg, 0.75 mmol). The mixture was heated at reflux under a CO balloon overnight. The solvent was removed and the residue diluted with water (50 mL). The aqueous layer was extracted with DCM (3×50 mL) and the combined organic layers washed with brine (100 mL), dried ($Na_2SO_4$) and concentrated. The residue was purified by column chromatography (0-30% EtOAc/petroleum ether) to give the desired compound as a yellow solid (650 mg, 18%): LCMS: RT 1.86 min, m/z 249.1 [M+H]+.

(c) 6-(Piperidine-1-carbonyl)nicotinic acid I47

To a solution of methyl 6-(piperidine-1-carbonyl)nicotinate I46 (600 mg, 2.4 mmol) in MeOH (5 mL) was added a solution of NaOH (193 mg, 4.8 mmol) in water (0.5 mL). The resulting mixture was stirred at room temperature overnight. The solvent was removed and the residue resuspended in water. The pH of the aqueous solution was adjusted to pH 4 by addition of a 4 M aqueous HCl solution. The aqueous layer was extracted with DCM (5×50 mL) and the combined organic layers dried ($Na_2SO_4$) and concentrated to give the desired compound as a yellow solid (300 mg, 53%): LCMS: RT 0.96 min, m/z 235.1 [M+H]+

(xx) 2-Propoxybenzoic acid I49

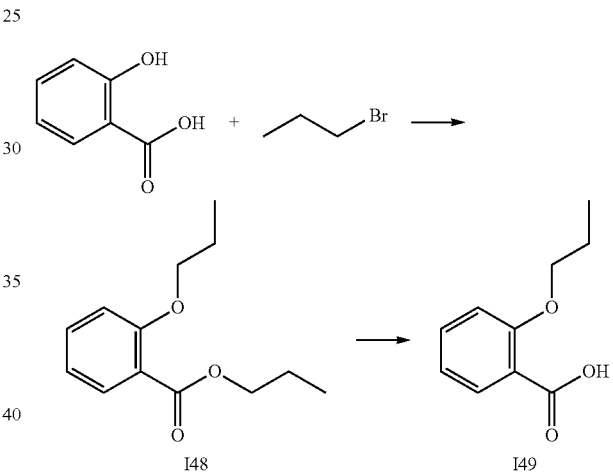

(a) Propyl 2-propoxybenzoate I48

To a mixture of 2-hydroxybenzoic acid (5.0 g, 36.2 mmol), NaI (0.5 g, 3.6 mmol) and $K_2CO_3$ (13.4 g, 0.11 mol) in DMSO (10 mL) at 36° C. was added 1-bromopropane (6.7 g, 54.3 mmol) dropwise over a period of 30 min. The reaction was stirred for 2 h, then further 1-bromopropane (6.7 g, 54.3 mmol) was added over a period of 30 min. The resulting mixture was stirred at 36° C. overnight then diluted with DCM (50 mL) and filtered. The solid was washed with DCM (2×50 mL) and the filtrate washed with water (5×100 mL) and brine (100 mL), dried ($Na_2SO_4$) and concentrated to give the desired compound as colorless oil (7.4 g, 93%): $^1H$ NMR (400 MHz, $CDCl_3$) δ 7.78-7.76 (m, 1H), 7.43-7.39 (m, 1H), 6.96-6.92 (m, 2H), 4.27-4.24 (m, 2H), 4.00-3.96 (m, 2H), 1.89-1.72 (m, 4H), 1.07-1.00 (m, 6H): LCMS: RT 2.26 min, m/z 223.1 [M+H]+

(b) 2-Propoxybenzoic acid I49

To a solution of propyl 2-propoxybenzoate I48 (1.0 g, 4.5 mmol) in a mixture of THF (10 mL), MeOH (2 mL) and water (2 mL) was added $LiOH.H_2O$ (0.95 g, 22.5 mmol).

The resulting mixture was stirred at room temperature overnight. The solvent was removed and the residue diluted with water (10 mL). The aqueous layer was washed with DCM (2×10 mL) and the pH adjusted to 2 by addition of a solution of concentrated HCl. The aqueous layer was extracted with DCM (3×10 mL) and the combined organic layers dried (Na$_2$SO$_4$) and concentrated to give the desired compound as yellow oil (300 mg, 53%): $^1$H NMR (400 MHz, CDCl$_3$) δ 10.98 (brs, 1H), 8.19-8.17 (m, 1H), 7.56-7.52 (m, 1H), 7.14-7.10 (m, 1H), 7.05-7.03 (m, 1H), 4.23-4.20 (m, 2H), 1.99-1.90 (m, 2H), 1.12-1.08 (m, 3H): LCMS: RT 2.15 min, m/z 181.1 [M+H]$^+$ (xxi) 2-Isopropoxybenzoic acid I51

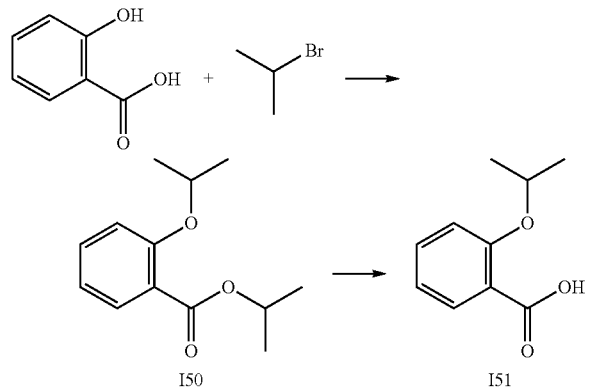

(a) Isopropyl 2-isopropoxybenzoate I50

To a mixture of 2-hydroxybenzoic acid (5.0 g, 36.2 mmol), K$_2$CO$_3$ (13.4 g, 0.11 mol) and NaI (0.5 g, 3.6 mmol) in DMSO (10 mL) at 36° C. was added 2-bromopropane (6.7 g, 54.3 mmol) dropwise over a period of 30 min. The reaction was stirred for 2 h, then further 2-bromopropane (6.7 g, 54.3 mmol) was added dropwise over 30 min. The resulting mixture was stirred at 36° C. overnight. The mixture was diluted with DCM (50 mL) and the solids removed by filtration. The filter cake was washed with DCM (2×50 mL) and the combined filtrates washed with water (5×100 mL) and brine (100 mL), dried (Na$_2$SO$_4$) and concentrated to give the desired compound as a colorless oil (2.3 g, 29%): $^1$H NMR (400 MHz, CDCl$_3$) δ 7.70-7.68 (m, 1H), 7.40-7.36 (m, 1H), 6.97-6.91 (m, 2H), 5.28-5.21 (m, 1H), 4.61-4.55 (m, 1H), 1.36-1.34 (m, 12H): LCMS: RT 2.19 min, m/z 223.1 [M+H]$^+$ (b) 2-Isopropoxybenzoic acid I51

To a solution of propyl 2-isopropoxybenzoate I50 (1.0 g, 4.5 mmol) in a mixture of THF (10 mL), i-PrOH (1 mL) and water (0.1 mL) was added LiOH.H$_2$O (0.95 g, 22.5 mmol). The resulting mixture was stirred at room temperature for 3 days. The solvent was removed and the residue diluted with water (20 mL). The aqueous layer was washed with DCM (20 mL) and the pH adjusted to 2 by addition of concentrated HCl. The aqueous layer was extracted with DCM (3×20 mL) and the combined organic layers dried (Na$_2$SO$_4$) and concentrated to give the desired compound as yellow oil: (600 mg, 75%): $^1$H NMR (400 MHz, d$_4$-MeOD) δ 7.85-7.82 (m, 1H), 7.47-7.43 (m, 1H), 7.07-7.05 (m, 1H), 6.99-6.96 (m, 1H), 4.72-4.65 (t, 1H), 1.33-1.31 (m, 6H): LCMS: RT 2.15 min, m/z 181.1 [M+H]$^+$ (xxii) 2-(2,2,2-Trifluoroethoxy)benzoic acid I52

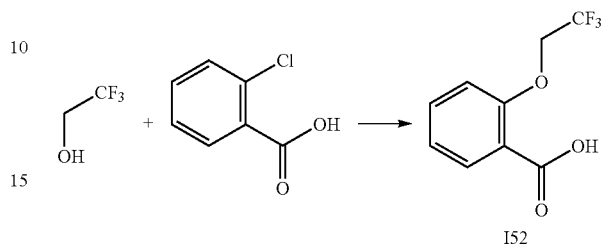

To a solution of 2,2,2-trifluoroethanol (4.8 g, 47.9 mmol) in DMF (30 mL) was added sodium tert-butoxide (2.8 g, 28.7 mmol) at 0° C. The solution was stirred at room temperature for 1 h then 2-chlorobenzoic acid (3.0 g, 19.2 mmol) and CuBr (247 mg, 1.7 mmol) were added. The reaction was heated at 120° C. for 5 hours under nitrogen, then 20% v/v aqueous HCl solution was added. The resulting mixture was extracted with CH$_2$Cl$_2$ (60 mL) and the combined organic layers dried (Na$_2$SO$_4$) and concentrated. The residue was purified by column chromatography (2% MeOH/in CH$_2$Cl$_2$) to give the crude product (1.8 g). 100 mg of this material was further purified by prep TLC (EtOAc: petroleum ether=1:1) to give the desired compound (67 mg, 29%) as a white solid: $^1$H NMR (400 MHz, CD$_3$OD) δ 7.65-7.63 (m, 1H), 7.51-7.47 (m, 1H), 7.18-7.16 (m, 1H), 7.10-7.06 (m, 1H), 4.77-4.70 (m, 2H); LCMS: RT 3.60 min; m/z 221.1[M+H]$^+$.

(xxiii) 4-((3R,5R)-3,5-Dimethylmorpholine-4-carbonyl)benzoic acid I54

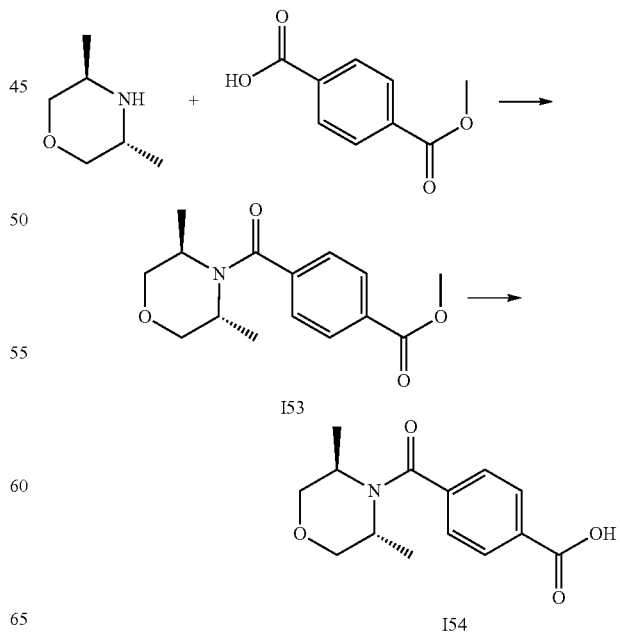

(a) Methyl 4-((3R,5R)-3,5-dimethylmorpholine-4-carbonyl)benzoate I53

To a solution of 4-(methoxycarbonyl)benzoic acid (285 mg, 1.6 mmol) in CH$_2$Cl$_2$ (10 mL) was added DIPEA (594 mg, 4.6 mmol) and HATU (608 mg, 1.6 mmol) and the mixture stirred for 1 h. (3R,5R)-3,5-dimethylmorpholine (200 mg, 1.3 mmol) was added and the reaction stirred at room temperature for 2 days. The mixture was diluted with water (50 mL) and extracted with CH$_2$Cl$_2$ (3×30 mL). The combined organic layers were washed with brine (50 mL), dried (Na$_2$SO$_4$) and concentrated. The residue was purified by column chromatography (20% EtOAc in petroleum ether) to give the desired compound as a white solid (200 mg, 55%): $^1$H NMR (400 MHz, CD$_3$OD) δ 8.11-8.10 (m, 2H), 7.61-7.59 (m, 2H), 3.93 (s, 3H), 3.92-3.89 (m, 4H), 3.53-3.49 (m, 2H), 1.29-1.27 (s, 6H); LCMS: RT 2.22 min; m/z 278.1[M+H]$^+$.

(b) 4-((3R,5R)-3,5-Dimethylmorpholine-4-carbonyl)benzoic acid I54

To a solution of methyl 4-((3R,5R)-3,5-dimethylmorpholine-4-carbonyl)benzoate I53 (180 mg, 0.65 mmol) in a mixture of THF (5 mL), MeOH (0.5 mL) and water (0.05 mL) was added LiOH.H$_2$O (100 mg, 2.34 mmol) and the resulting mixture stirred at room temperature overnight. The solvent was removed and the residue diluted with water (5 mL). The aqueous solution was acidified to pH 3 by addition of a 1M aqueous HCl solution and extracted with CH$_2$Cl$_2$ (3×50 mL). The combined organic extracts were dried (Na$_2$SO$_4$) and concentrated to give the desired compound as a white solid (150 mg, 88%): $^1$H NMR (400 MHz, CD$_3$OD) δ 8.12-8.10 (m, 2H), 7.60-7.58 (m, 2H), 3.93-3.89 (m, 4H), 3.53-3.49 (m, 2H), 1.29-1.28 (m, 6H); LCMS RT 1.67 min; m/z 264.1 [M+H]$^+$.

(xxiv) 2-Methoxy-4-(2-morpholino-2-oxoethyl)benzoic acid I59

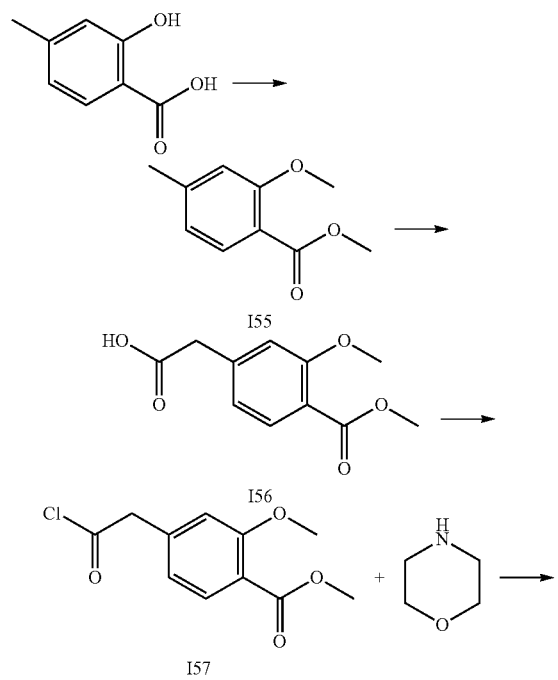

(a) Methyl 2-methoxy-4-methylbenzoate I55

To a solution of 2-hydroxy-4-methylbenzoic acid (10.0 g, 66 mmol) in acetone (500 mL) was added K$_2$CO$_3$ (18.0 g, 131 mmol). Me$_2$SO$_4$ (22 g, 178 mmol) was then added dropwise and the resulting mixture heated at reflux for 14 hours. The mixture was poured into cold water and extracted with EtOAc (70 mL×3). The combined organic layers were dried (Na$_2$SO$_4$), filtered and concentrated and the residue was purified by column chromatography (1% EtOAc in petroleum ether) to give the desired compound as a yellow liquid (7.6 g, 64%). LCMS: RT 2.31 min; m/z 181.1 [M+1]$^+$.

(b) 2-(3-Methoxy-4-(methoxycarbonyl)phenyl)acetic acid I56

To a solution of diisopropylamine (1.3 g, 13.3 mmol) in dry THF (50 mL) at −50° C. was added n-BuLi (2.5M in hexane, 5.4 mL, 13.3 mmol) dropwise under nitrogen atmosphere. The mixture was stirred at −50° C. for 30 min and then HMPA (2.4 g, 13.3 mmol) was added, followed by methyl 2-methoxy-4-methylbenzoate I55 (2.0 g, 11.1 mmol). The resultant mixture was stirred at −78° C. for 2 h then CO$_2$ gas was bubbled through the mixture. During the course of the addition, the reaction mixture became pale, the mixture was stirred for another 30 min then poured into a solution of 1M aqueous HCl (100 mL). The aqueous layer was extracted with dichloromethane and the combined organic layers washed with water and brine, dried (Na$_2$SO$_4$) and concentrated. The residue was purified by column chromatography (0-1% methanol in dichloromethane) to give the desired compound (270 mg, 11%) as colorless oil. LCMS RT 1.50 min; m/z 225.1 [M+H]$^+$.

(c) Methyl 4-(2-chloro-2-oxoethyl)-2-methoxybenzoate I57

To a solution of 2-(3-methoxy-4-(methoxycarbonyl)phenyl)acetic acid I56 (135 mg, 0.6 mmol) in dichloromethane (5 mL) with a catalytic amount of DMF (1 mL) was added oxalyl chloride (99 mg, 0.8 mmol). The mixture was stirred at room temperature overnight then the reaction mixture was concentrated to give the desired product which was used for the next step without further purification.

(d) Methyl 2-methoxy-4-(2-morpholino-2-oxoethyl)benzoate I58

To a solution of methyl 4-(2-chloro-2-oxoethyl)-2-methoxybenzoate I57 (146 mg, 0.6 mmol) in dichloromethane (5 mL) was added DIPEA (155 mg, 1.2 mmol) and morpholine (63 mg, 0.7 mmol). The reaction was stirred at room temperature overnight then the reaction mixture was partitioned with water, washed with water (2×20 mL) and brine and concentrated to afford the crude product. The residue was purified by column chromatography (0-10% EtOAc in petroleum ether) to give the desired compound (67 mg, 38%) as a colorless oil. LCMS: RT 1.16 min; m/z 294.1 [M+H]$^+$.

(e) 2-Methoxy-4-(2-morpholino-2-oxoethyl)benzoic acid I59

To a solution of Methyl 2-methoxy-4-(2-morpholino-2-oxoethyl)benzoate I58 (67 mg, 0.2 mmol) in a mixture of THF (3 mL), MeOH (0.3 mL) and water (0.3 mL) was added LiOH.H$_2$O (19 mg, 0.5 mmol). The mixture was stirred at room temperature overnight then concentrated under reduced pressure. The residue was dissolved in water and the pH adjusted to 2 by addition of a 1M aqueous HCl solution. The aqueous mixture was extracted with dichloromethane (3×5 mL) and the combined organic layers dried (Na$_2$SO$_4$) and concentrated to give the desired compound which was used for the next step without further purification. LCMS: RT 0.41 min; m/z 280.1 [M+H]$^+$.

(xxv) 1-Oxa-7-azaspiro[3.5]nonane I60

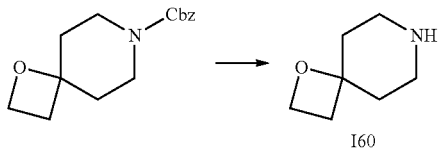 [SMILES: "I60" ; O=C(OCc1ccccc1)N1CCC2(CCO2)CC1 ; C1CC2(CCN1)CCO2]

I60

Benzyl 1-oxa-7-azaspiro[3.5]nonane-7-carboxylate (1 g, 3.8 mmol) and 10% Pd/C (100 mg) in methanol (10 mL) was stirred at room temperature under a hydrogen atmosphere overnight. The reaction mixture was filtered through celite and the filtrate concentrated. The residue was used for the next step without further purification. LCMS: RT 0.30 min; m/z 128.1 [M+H]$^+$.

(xxvi) 4-(2-Methoxy-2-oxoethyl)benzoic acid I61

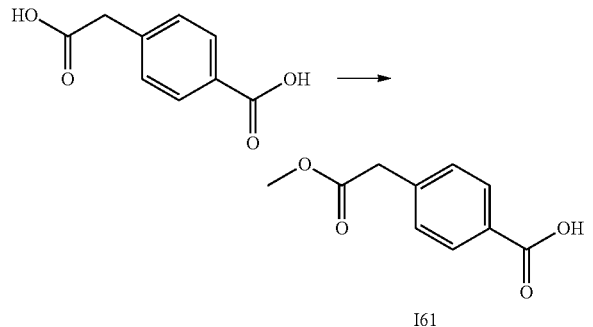

I61

To a solution of 4-(carboxymethyl)benzoic acid (5.0 g, 27.7 mmol) in methanol (60 mL) was added thionyl chloride (0.1 mL, 1.3 mmol). The reaction was stirred at room temperature overnight. The reaction mixture was concentrated and the residue was purified by chromatography (dichloromethane) to give the desired compound (3.0 g, 57%) as a white solid. LCMS: RT 2.00 min; m/z 195.1 [M+H]$^+$.

(xxvii) 4-(2-Oxo-2-(pyrrolidin-1-yl)ethyl)benzoic acid I64

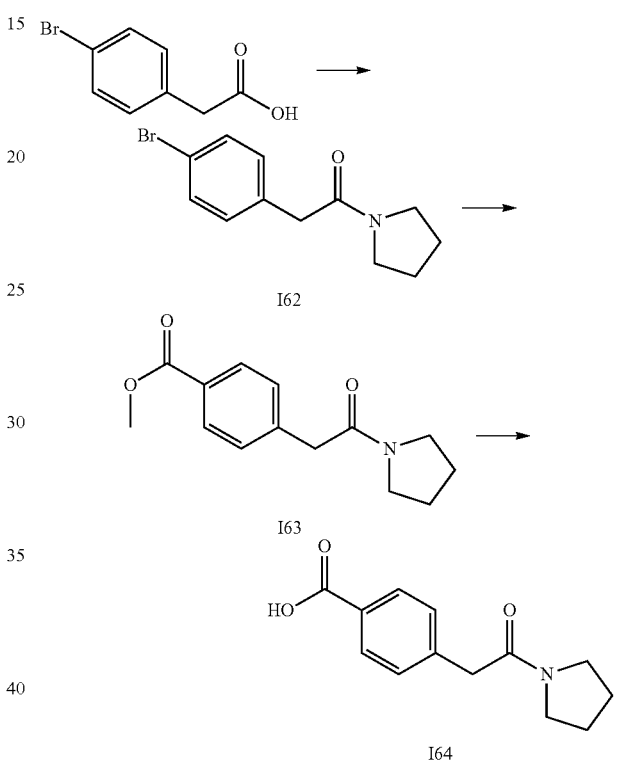

I64

(a) 2-(4-Bromophenyl)-1-(pyrrolidin-1-yl)ethanone I62

To a solution of 2-(4-bromophenyl)acetic acid (2.0 g, 4.3 mmol) in THF (10 mL) was added HATU (3.6 g, 4.7 mmol), DIPEA (2.2 g, 8.6 mmol) and pyrrolidine (0.64 g, 4.5 mmol). The solution was stirred at room temperature overnight then poured into a 1 M aqueous solution of HCl (20 mL). The aqueous layer was extracted with dichloromethane, washed with water and brine, dried (Na$_2$SO$_4$), concentrated and the residue obtained purified by column chromatography (0-2% methanol in dichloromethane) to give the desired compound (2.0 g, 84%) as a white solid.

(b) Methyl 4-(2-oxo-2-(pyrrolidin-1-yl)ethyl)benzoate I63

A solution of 2-(4-bromophenyl)-1-(pyrrolidin-1-yl)ethanone I62 (1.15 g, 4.3 mmol), Pd(dppf)Cl$_2$ (157 mg, 0.2 mmol) and triethylamine (953 mg, 9.4 mmol) in methanol (60 mL) under a CO (g) atmosphere was heated at reflux overnight. The reaction mixture was concentrated and the residue was purified by column chromatography (dichloromethane) to give the desired compound (130 mg, 13%) as an orange oil. LCMS: RT 2.11 min; m/z 248.1 [M+H]+.

(c) 4-(2-Oxo-2-(pyrrolidin-1-yl)ethyl)benzoic acid I64

To a solution of methyl 4-(2-oxo-2-(pyrrolidin-1-yl)ethyl) benzoate I63 (130 mg, 0.53 mmol) in a mixture of THF (2 mL), methanol (0.2 mL) and water (0.2 mL) was added LiOH.H$_2$O (27 mg, 0.63 mmol) and the mixture stirred at room temperature overnight. The reaction mixture was concentrated under reduced pressure, the residue was dissolved in water and then acidified to pH 4 by the addition of a 1 M aqueous HCl solution. The aqueous layer was extracted with dichloromethane (2×5 mL) and the combined organic fractions dried (Na$_2$SO$_4$) and concentrated to give the desired compound (67 mg, 54%) which was used for the next step without further purification. LCMS: RT 3.31 min; m/z 234.1 [M+H]+.

(xxviii) 4-(2-Morpholino-2-oxoethyl)benzoic acid I67

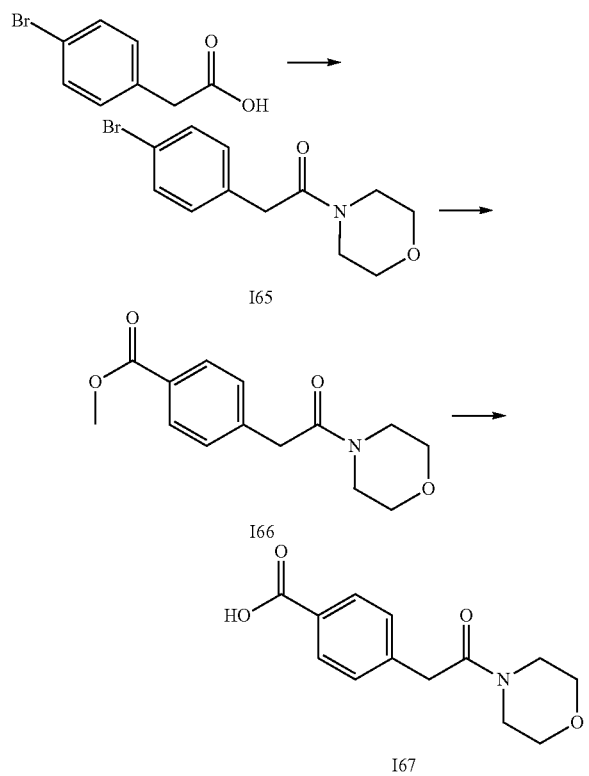

(a) 2-(4-Bromophenyl)-1-morpholinoethanone I65

To a solution of 2-(4-bromophenyl)acetic acid (500 mg, 2.3 mmol) in dichloromethane (50 mL) was added morpholine (243 mg, 2.8 mmol), HATU (1.06 g, 2.8 mmol) and Et$_3$N (810 mg, 8.0 mmol). The reaction was stirred at room temperature overnight. Water was added and the organic phase separated, washed with water (100 mL) and brine, dried (Na$_2$SO$_4$), concentrated and the residue purified by chromatography (0-50% EtOAc in petroleum ether) to give the desired compound (500 mg, 76%) as a yellow solid. LCMS: RT 2.21 min; m/z 284.0 [M+H]+.

(b) Methyl 4-(2-morpholino-2-oxoethyl)benzoate I66

A solution of 2-(4-bromophenyl)-1-morpholinoethanone I65 (446 mg, 1.6 mmol), Pd(dppf)Cl$_2$ (62 mg, 0.08 mmol) and triethylamine (377 mg, 3.7 mmol) in methanol (60 mL) under a CO (g) atmosphere was heated at reflux overnight. The reaction mixture was concentrated and the residue was purified by column chromatography (0-10% EtOAc in petroleum ether) to give the desired compound (329 mg, 80%) as an orange oil. LCMS: RT 1.43 min; m/z 264.1 [M+H]+.

(c) 4-(2-Morpholino-2-oxoethyl)benzoic acid I67

To a solution of methyl 4-(2-morpholino-2-oxoethyl)benzoate I66 (329 mg, 3.8 mmol) in a mixture of THF (10 mL), methanol (1 mL) and water (1 mL) was added LiOH.H$_2$O (319 mg, 7.6 mmol) and the mixture stirred at room temperature overnight. The reaction mixture was concentrated and the residue dissolved in water. The pH of the solution was adjusted to 4 by addition of a 1 M aqueous HCl solution and the aqueous mixture was extracted with dichloromethane (2×25 mL). The combined organic layers were dried (Na$_2$SO$_4$) and concentrated to give the desired compound (118 mg, 38%) as a yellow solid. LCMS: RT 2.67 min; m/z 250.1 [M+H]+.

(xxix) 1-Benzyl-2-oxo-1,2-dihydropyridine-4-carboxylic acid I68

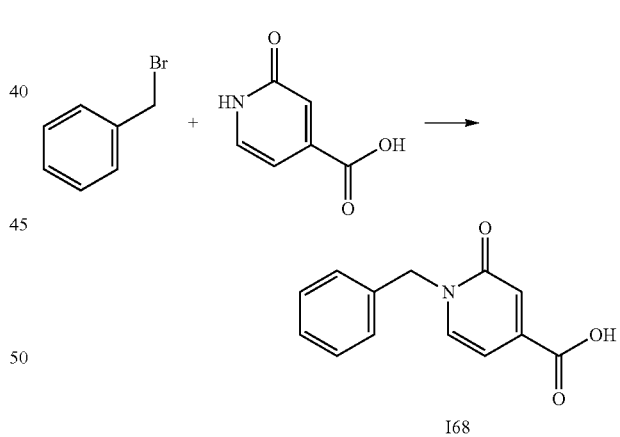

To a suspension of NaH (60% dispersion in mineral oil, 1.1 g, 25.3 mmol) in THF (16 mL) at 0° C. was added 2-oxo-1,2-dihydropyridine-4-carboxylic acid (0.78 g, 5.6 mmol). The reaction was stirred at 0° C. for 30 min then benzyl bromide (1.9 g, 11.2 mmol) and DMF (2 mL) were added. The resulting mixture was stirred at room temperature overnight, water (2 mL) was added and the pH of the aqueous layer adjusted to 4 by addition of a 3 M aqueous HCl solution. The aqueous layer was extracted with CH$_2$Cl$_2$ (10 mL×2) and the combined organic layers washed with brine (15 mL×2), dried (Na$_2$SO$_4$) and concentrated to give the desired compound as a yellow liquid (219.1 mg, 17%): LCMS: RT 1.81 min; m/z 230.1 [M+H]+.

(xxx) 4-(3-Oxa-8-azabicyclo[3.2.1]octane-8-carbonyl)-2-ethoxybenzoic acid I72

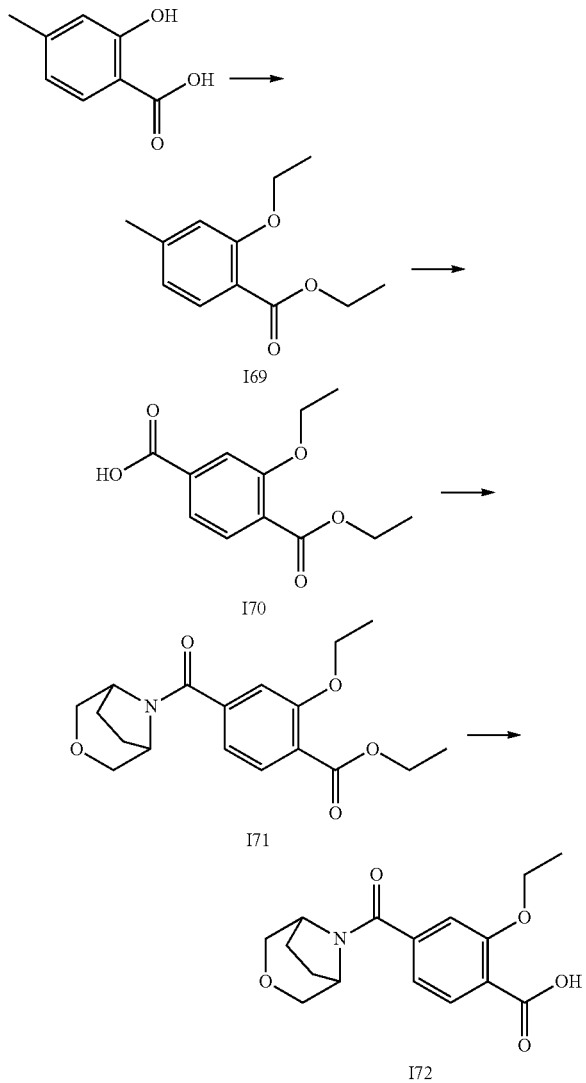

(a) Ethyl-2-ethoxy-4-methylbenzoate I69

To a mixture of 2-hydroxy-4-methylbenzoic acid (8.2 g, 53.9 mmol) and K$_2$CO$_3$ (22.4 g, 161.7 mmol) in dimethylsulfoxide (70 mL) at 40° C. was added and ethyl iodide (12.6 g, 80.8 mmol) dropwise over a period of 30 min. The reaction was stirred for 2 h then further ethyl iodide (12.6 g, 80.8 mmol) was added over 30 min. The resulting mixture was stirred a further 8 h at 40° C., then diluted with CH$_2$Cl$_2$ (150 mL) and filtered. The filtrate was washed with water (200 mL×10) and brine (200 mL×2), dried (Na$_2$SO$_4$) and concentrated to give the desired compound as a yellow liquid (10.1 g, 90%): LCMS: RT 2.70 min; m/z 209.1 [M+H]$^+$.

(b) 3-Ethoxy-4-(ethoxycarbonyl)-benzoic acid I70

To a solution of ethyl 2-ethoxy-4-methylbenzoate I69 (10.0 g, 48.1 mmol) in a mixture of pyridine (25 mL) and water (75 mL) was added KMnO$_4$ (22.8 g, 144.2 mmol). The resulting mixture was heated at 50° C. for 48 h, then cooled and allowed to stir at room temperature for 24 h. The mixture was filtered and the filter cake washed with hot water. The combined aqueous filtrates were washed with EtOAc (75 mL×3) and acidified with 2M aqueous HCl solution. The mixture was extracted with CH$_2$Cl$_2$ (150 mL×3). The combined organic layers were washed with brine, dried (Na$_2$SO$_4$) and concentrated to give the desired compound as a white solid (5.0 g, 44%): LCMS: RT 0.25 min; m/z 239.0 [M−H]$^+$.

(c) Ethyl 4-(3-oxa-8-azabicyclo[3.2.1]octane-8-carbonyl)-2-ethoxybenzoate I71

To a solution of 3-ethoxy-4-(ethoxycarbonyl)benzoic acid I70 (2.5 g, 10.4 mmol) in CH$_2$Cl$_2$ (20 mL) was added 3-oxa-8-azabicyclo[3.2.1]octane hydrochloride (1.42 g, 9.5 mmol), HOBt (135.1 mg, 1.0 mmol), DIPEA (2.5 g, 19.0 mmol) and EDCl (2.2 g, 11.4 mmol). The resulting mixture was stirred at room temperature overnight. The mixture was partitioned with saturated aqueous NaHCO$_3$, and extracted with CH$_2$Cl$_2$ (20 mL×2). The combined organic layers were washed with brine, dried (Na$_2$SO$_4$) and concentrated. The residue was purified by column chromatography (1% methanol in dichloromethane) to give the desired compound as a yellow oil (2.5 g, 80%): LCMS: RT 2.40 min; m/z 334.1 [M+H]$^+$.

(d) 4-(3-Oxa-8-azabicyclo[3.2.1]octane-8-carbonyl)-2-ethoxybenzoic acid I72

To a solution of ethyl-4-(3-oxa-8-azabicyclo-[3.2.1]-octane-8-carbonyl)-2-ethoxybenzoate I71 (2.4 g, 7.2 mmol) in a mixture of THF (20 mL), methanol (2 mL) and water (2 mL) was added LiOH.H$_2$O (1.5 g, 36 mmol). The resulting mixture was stirred at room temperature for 24 h. The solvent was removed, and the residue obtained diluted with water (20 mL). The pH of the aqueous mixture was adjusted to 6 by addition of a 2 M aqueous HCl solution. The mixture was extracted with CH$_2$Cl$_2$ (20 mL×3) and the combined organic layers washed with brine (10 mL×2), dried (Na$_2$SO$_4$) and concentrated to give the desired compound as a yellow oil (1.7 g, 79%): $^1$H NMR (400 MHz, d$_4$-MeOD) δ 7.83 (d, J=7.8 Hz, 1H), 7.19 (d, J=1.0 Hz, 1H), 7.10 (dd, J=7.8, 1.3 Hz, 1H), 4.65 (br s, 1H), 4.20 (q, J=7.0 Hz, 2H), 3.97 (br s, 1H), 3.82 (d, J=10.8 Hz, 1H), 3.72 (d, J=11.0 Hz, 2H), 3.59 (d, J=10.9 Hz, 1H), 2.13-1.94 (m, 4H), 1.45 (t, J=7.0 Hz, 3H). LCMS: RT 1.20 min; m/z 306.1 [M+H]$^+$.

(xxxi) 4-(3-Oxa-8-azabicyclo[3.2.1]octane-8-carbonyl)benzoic acid I74

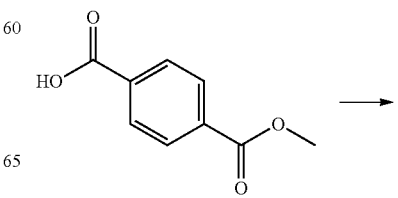

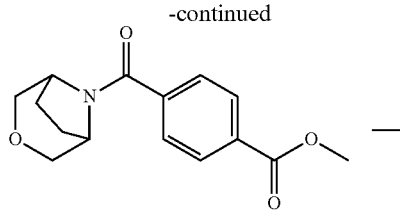

I73

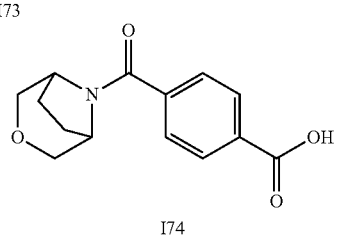

I74

(a) Methyl 4-(3-oxa-8-azabicyclo[3.2.1]octane-8-carbonyl)benzoate I73

To a solution of 4-(methoxycarbonyl)benzoic acid (664 mg, 3.7 mmol) in CH$_2$Cl$_2$ (20 mL) was added, 3-oxa-8-azabicyclo[3.2.1]octane hydrochloride (500 mg, 3.4 mmol), DIPEA (865.9 mg, 6.7 mmol), HOBt (45 mg, 0.3 mmol) and EDCl (771.4 mg, 4.0 mmol). The resulting mixture was stirred at room temperature overnight. The mixture was partitioned against with aqueous NaHCO$_3$ (20 mL×2) and the aqueous layer extracted with CH$_2$Cl$_2$ (5 mL×2). The combined organic layers were washed with brine (20 mL×2), dried (Na$_2$SO$_4$) and concentrated. The crude residue obtained was purified by column chromatography (1% methanol in CH$_2$Cl$_2$) to give the desired compound as a white solid (786.9 mg, 85%): LCMS: RT 0.61 min; m/z 276.1 [M+H]$^+$.

(b) 4-(3-Oxa-8-azabicyclo[3.2.1]octane-8-carbonyl)benzoic acid I74

To a solution of methyl 4-(3-oxa-8-azabicyclo[3.2.1]octane-8-carbonyl)benzoate I73 (770 mg, 2.8 mmol) in a mixture of THF (20 mL), methanol (2 mL) and water (2 mL) was added LiOH.H$_2$O (587.8 mg, 14.0 mmol). The resulting mixture was stirred at room temperature overnight, then the solvent removed and the residue obtained diluted with water (20 mL). The pH of the aqueous solution was adjusted to 6 by addition of a 2 M aqueous HCl solution. The aqueous layer was extracted with CH$_2$Cl$_2$ (20 mL×3) and the combined organic layers washed with brine (20 mL×2), dried (Na$_2$SO$_4$) and concentrated to give the desired compound (460 mg, 63%) as a white solid: LCMS: RT 0.83 min; m/z 262.1 [M+H]$^+$.

(xxxii)
2-Methoxy-4-(morpholine-4-carbonyl)benzoic acid I78

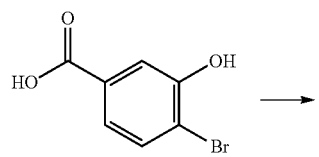

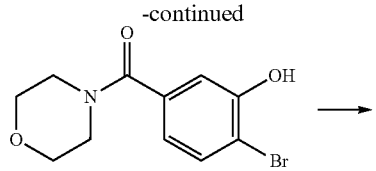

I75

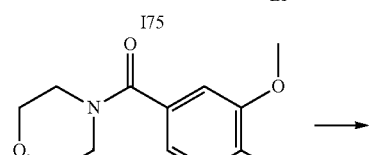

I76

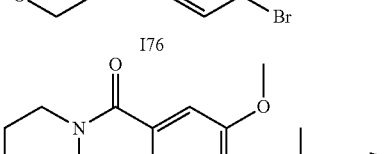

I77

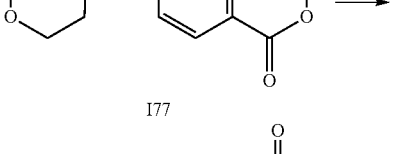

I78

(a) (4-Bromo-3-hydroxyphenyl)(morpholino)methanone I75

To a solution of 4-bromo-3-hydroxybenzoic acid (6.0 g, 27.6 mmol) in THF (300 mL) was added HATU (12.6 g, 33.2 mmol), DIPEA (4.3 g, 33.2 mmol) and morpholine (3.6 g, 44.2 mmol). The solution was stirred at room temperature overnight then poured into a solution of 1 M aqueous HCl (400 mL). The aqueous layer was extracted with dichloromethane, washed with water and brine, dried (Na$_2$SO$_4$), concentrated and the residue purified by column chromatography (0-5% methanol/dichloromethane) to give the desired compound (5.9 g, 75%) as a white solid.

(b) (4-Bromo-3-methoxyphenyl)(morpholino)methanone I76

To a solution of (4-bromo-3-hydroxyphenyl)(morpholino)methanone I75 (8.6 g, 30.0 mmol) in DMF (120 mL) was added iodomethane (5.1 g, 36.1 mmol) and K$_2$CO$_3$ (6.2 g, 45.1 mmol). The solution was stirred at room temperature overnight then poured into water (600 mL). The aqueous layer was extracted with dichloromethane, the combined organic layers were washed with water and brine, dried (Na$_2$SO$_4$), concentrated and the residue was purified by column chromatography (0-2% methanol in dichloromethane) to give the desired compound (7.5 g, 83%) as a white solid.

(c) Methyl 2-methoxy-4-(morpholine-4-carbonyl)benzoate I77

To a solution of (4-bromo-3-methoxyphenyl)(morpholino)methanone I76 (300 mg, 1.0 mmol) in methanol (10 mL) was added triethylamine (222 mg, 2.2 mmol) and Pd(dppf)Cl$_2$ (37 mg, 0.05 mmol). The mixture was heated at reflux under a CO atmosphere overnight. The reaction mixture was concentrated and the residue diluted with water (50 mL) and extracted with EtOAc (50 mL×2). The organic layer was washed with brine, dried (Na$_2$SO$_4$), concentrated and the residue was purified by column chromatography (0-5% methanol in dichloromethane) to give the desired compound (200 mg, 80%) as a red oil. LCMS: RT 0.97 min, m/z 280.1 [M+H]$^+$ (d) 2-Methoxy-4-(morpholine-4-carbonyl)benzoic acid I78

To a solution of methyl 2-methoxy-4-(morpholine-4-carbonyl)benzoate I77 (200 mg, 0.7 mmol) in a mixture of methanol (0.1 mL), THF (1 mL) and water (0.1 mL) was added LiOH.H$_2$O (33 mg, 0.8 mmol). The mixture was stirred at room temperature overnight then poured into water (20 mL) and acidified to pH 6 by addition of a 1 M aqueous HCl solution. The mixture was extracted with dichloromethane (10 mL×6) and the combined organic layers washed with brine, dried (Na$_2$SO$_4$) and concentrated. The residue obtained was purified by column chromatography (0-10% methanol in dichloromethane) to give the desired compound (152 mg, 80%) as a white solid. LCMS: RT 0.41 min, m/z 266.1 [M+H]$^+$ (xxxiii) 6-(3-Oxa-8-aza bicyclo[3.2.1]octane-8-carbonyl)-2-ethoxynicotinic acid I82

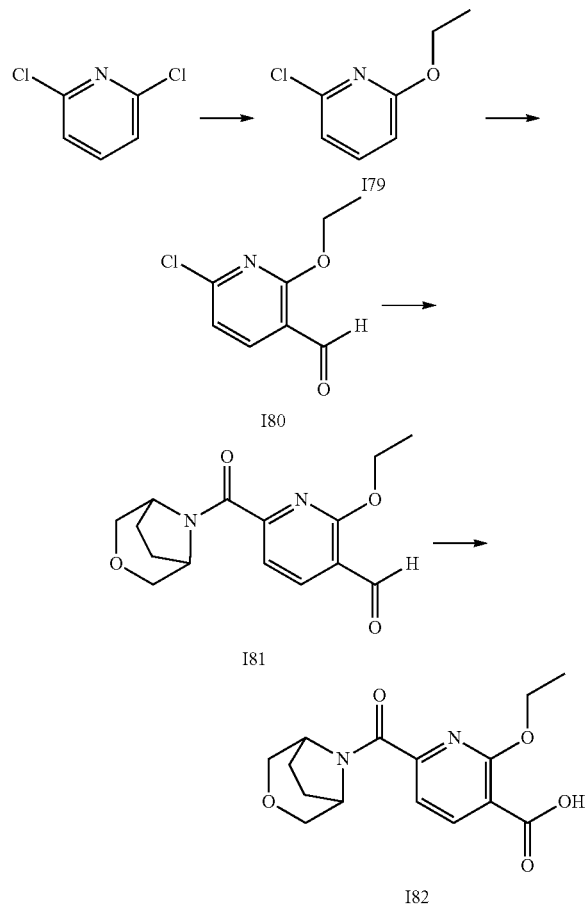

(a) 2-Chloro-6-ethoxypyridine I79

To a solution of 2,6-dichloropyridine (5.0 g, 33.8 mmol) in EtOH (50 mL) was added EtONa (9.2 g, 0.14 mol). The mixture was stirred at 60° C. for 24 h. The solvent was removed and the residue was dissolved in water (100 mL). The aqueous layer was acidified to pH 7 with 2 M aqueous HCl then extracted with DCM (100 mL×2). The combined organic layers were washed with water (100 mL) and brine (100 mL), dried (Na$_2$SO$_4$) and concentrated to give the title compound as yellow oil (4.2 g, 79%). LCMS: RT 2.64 min; m/z 158.1 [M+H]$^+$.

(b) 6-Chloro-2-ethoxynicotinaldehyde 180

To a solution of 2-chloro-6-ethoxypyridine 179 (2.0 g, 12.7 mmol) in THF (40 mL) at −78° C. was added t-BuLi (1.6 M in pentane, 8.8 mL, 14.0 mmol) dropwise under N$_2$. After stirring at the same temperature for 1 h, DMF (2.8 g, 38.1 mmol) was added dropwise and the reaction mixture was stirred at −78° C. for 30 min then warmed to room temperature and stirred for 30 min. The reaction mixture was quenched with 2M aqueous HCl (5 mL) and extracted with EtOAc (50 mL×2). The combined organic layers were washed with water (50 mL×3) and brine (50 mL), dried (Na$_2$SO$_4$) and concentrated to give the title compound as yellow oil (2.0 g, 87%): $^1$H NMR (400 MHz, DMSO-d$_6$) δ 10.17 (s, 1H), 8.09 (d, J=8.0 Hz, 1H), 7.23 (d, J=8.0 Hz, 1H), 4.44 (m, 2H), 1.38 (m, 3H). LCMS: RT 2.64 min; m/z 186 [M+H]$^+$; 218.1 [M+MeOH+H]$^+$.

(c) 6-(3-oxa-8-azabicyclo[3.2.1]octane-8-carbonyl)-2-ethoxynicotinaldehyde I81

To a solution of 3-oxa-8-azabicyclo[3.2.1]octane hydrochloride (1.5 g, 10.3 mmol) in toluene (80 mL) was added Et$_3$N (2.6 g, 25.8 mmol), Xantphos (0.2 g, 0.34 mmol) and Pd(OAc)$_2$ (40 mg, 0.17 mmol). The mixture was degassed three times under N$_2$ followed by addition of 6-chloro-2-ethoxynicotinaldehyde I80 (1.6 g, 8.6 mmol). The mixture was degassed three times under N$_2$ and then three times under CO. The mixture was stirred at 90° C. overnight. Water (80 mL) was added and the mixture was extracted with EtOAc (80 mL×2). The combined organic layers were washed with water (80 mL), brine (80 mL), dried (Na$_2$SO$_4$) and concentrated. The residue was purified by column chromatography (100% petroleum ether to 50% EtOAc in petroleum ether) to give the title compound as a yellow solid (1.1 g, 44%): LCMS: RT 2.22 min; m/z 291.1 [M+H]$^+$.

(d) 6-(3-Oxa-8-azabicyclo[3.2.1]octane-8-carbonyl)-2-ethoxynicotinic acid I82

To a mixture of 6-(3-oxa-8-azabicyclo[3.2.1]octane-8-carbonyl)-2-ethoxynicotinaldehyde I81 (100 mg, 0.34 mmol) in a mixture of t-BuOH (5 mL) and 2-methylbut-2-ene (2 mL) was added a solution of NaH$_2$PO$_4$.2H$_2$O (376 mg, 2.4 mmol) and NaClO$_2$ (300 mg, 3.3 mmol) in water (5 mL). The resulting mixture was stirred at room temperature for 2 h. The solvent was removed under reduced pressure. The residue obtained was dissolved in water and the aqueous layer was acidified to pH 5 with 2 M aqueous HCl and extracted with EtOAc (20 mL×4). The combined organic layers were dried (Na$_2$SO$_4$) and concentrated to give the title compound as a white solid (80 mg, 76%): LCMS: RT 1.74 min; m/z 307.1 [M+H]$^+$.

(xxxiv) 2-Ethoxy-4-(5-methyl-1,3,4-oxadiazol-2-yl)benzoic acid I85

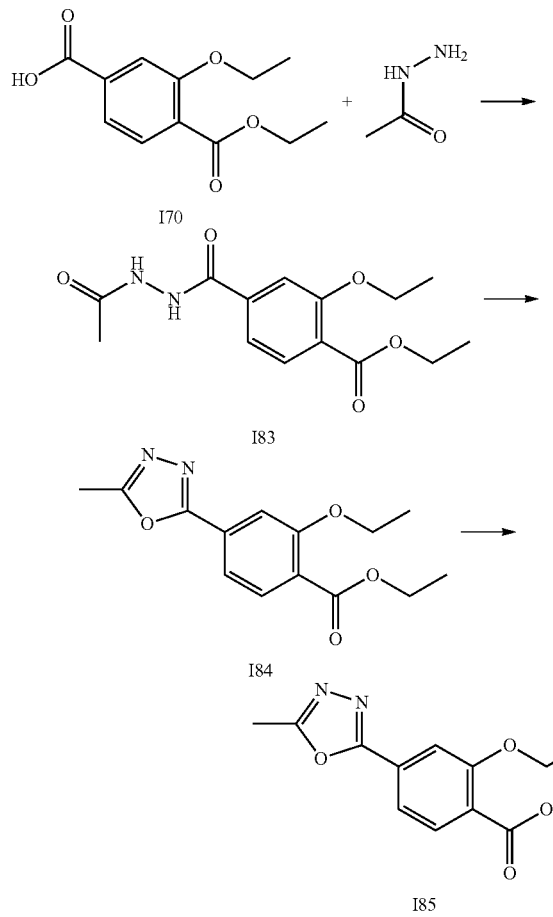

(a) Ethyl 4-(2-acetylhydrazinecarbonyl)-2-ethoxybenzoate I83

To a solution of 3-ethoxy-4-(ethoxycarbonyl)benzoic acid I70 (500 mg, 2.1 mmol) in CH$_2$Cl$_2$ (20 mL) was added DIPEA (960 mg, 7.4 mmol), HOBt (30 mg, 0.2 mmol), EDCl (800 mg, 4.2 mmol) and acetohydrazide (156 mg, 2.1 mmol). The mixture was stirred at room temperature overnight then diluted with CH$_2$Cl$_2$ (50 mL). The organic layer was washed with water (50 mL) and brine (50 mL), dried (Na$_2$SO$_4$) and concentrated. The residue was purified by column chromatography (0-4% v/v MeOH in CH$_2$Cl$_2$) to give the title compound as an off-white solid (350 mg, 57%). LCMS: RT 4.79 min; m/z 294.9 [M+H]$^+$.

(b) Ethyl 2-ethoxy-4-(5-methyl-1,3,4-oxadiazol-2-yl)benzoate I84

A mixture of ethyl 4-(2-acetylhydrazinecarbonyl)-2-ethoxybenzoate I83 (330 mg, 1.1 mmol) in POCl$_3$ (3 mL) was heated at reflux for 1.5 h. The mixture was poured into ice-water (20 mL) and the aqueous layer extracted with CH$_2$Cl$_2$ (20 mL×2). The combined organic layers were washed with a saturated aqueous NaHCO$_3$ solution (40 mL×3), brine (40 mL), dried (Na$_2$SO$_4$) and concentrated to give the crude product as a yellow solid (290 mg, 94%). The crude product was used for the next step without purification. $^1$H NMR (400 MHz, CDCl$_3$) δ 7.86 (d, J=8.4 Hz, 1H), 7.64 (d, J=1.2 Hz, 1H), 7.57 (m, 1H), 4.41-4.35 (m, 2H), 4.23-4.17 (m, 2H), 2.63 (s, 3H), 1.49 (m, 3H), 1.39 (m, 3H). LCMS: RT 5.40 min; m/z 277.0 [M+H]$^+$.

(c) 2-Ethoxy-4-(5-methyl-1,3,4-oxadiazol-2-yl)benzoic acid I85

To a solution of ethyl 2-ethoxy-4-(5-methyl-1,3,4-oxadiazol-2-yl)benzoate I84 (270 mg, 1.0 mmol) in MeOH (10 mL) was added a solution of NaOH (193 mg, 4.8 mmol) in water (2 mL). The resulting mixture was stirred at room temperature overnight. The solvent was removed and the residue was suspended in water (5 mL). The pH of the aqueous solution was adjusted to pH 4-5 by addition of 1 M aqueous HCl solution. The solid which precipitated was collected by filtration, washed with water (5 mL) and dried to give the title compound as a yellow solid (110 mg, 45%). LCMS: RT 4.77 min, m/z 249.0 [M+H]$^+$

(xxxv) 3-(Methylcarbamoyl)benzoic acid I87

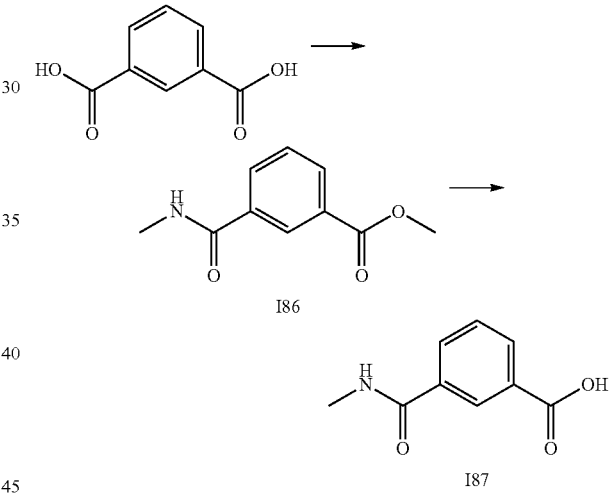

(a) Methyl 3-(methylcarbamoyl)benzoate I86

To a solution of isophthalic acid (2.0 g, 12 mmol) in DCM (40 mL) with a catalytic amount of DMF (5 drops) at 0° C. under N$_2$ atmosphere was added oxalyl chloride (3.81 g, 30 mmol) dropwise. The mixture was allowed to warm to room temperature and stirred for 2 h. The mixture was concentrated under vacuum and the residue was dissolved in DCM (20 mL). 2 M methylamine in tetrahydrofuran solution (9 mL, 18 mmol) was then added dropwise and the reaction stirred at room temperature overnight. The reaction was quenched with MeOH (20 mL), stirred for 30 min then the solvent removed under vacuum. The residue was dissolved in DCM (20 mL) and water (10 mL) and the aqueous layer extracted with DCM (3×5 mL). The combined organic extracts were washed with saturated aqueous NaHCO$_3$ (3×10 mL) and brine (3×10 mL), dried (Na$_2$SO$_4$) and concentrated. The crude product was purified by silica gel chromatography (ethyl acetate/petroleum ether=1/3 v/v) to give the title compound as a white solid (155 mg, 7%): $^1$H NMR (400 MHz, MeOD) δ 8.66 (s, 1H), 8.42 (s, 1H), 8.10-8.07 (m, 2H), 7.62 (m, 1H), 3.88 (s, 3H), 2.80 (m, 3H); LCMS RT 0.91 min; m/z 194.1 [M+H]+.

(b) 3-(Methylcarbamoyl)benzoic acid I87

To a solution of methyl 3-(methylcarbamoyl)benzoate I86 (150 mg, 0.78 mmol) in a mixture of THF (4 mL), MeOH (2 mL) and water (1 mL) was added lithium hydroxide monohydrate (163 mg, 3.88 mmol). The resulting mixture was stirred at room temperature overnight. The organic solvent was removed under vacuum and the aqueous acidified to a pH of 1-2 by addition of 3M aqueous HCl solution. The precipitate which formed was collected by filtration, and dried to give the title compound as a white solid (115 mg, 82%). LCMS RT 1.74 min; m/z 180.1 [M+H]+.

(xxxvi) 4-(3-Oxa-8-azabicyclo[3.2.1]octane-8-carbonyl)-2-chlorobenzoic acid I89

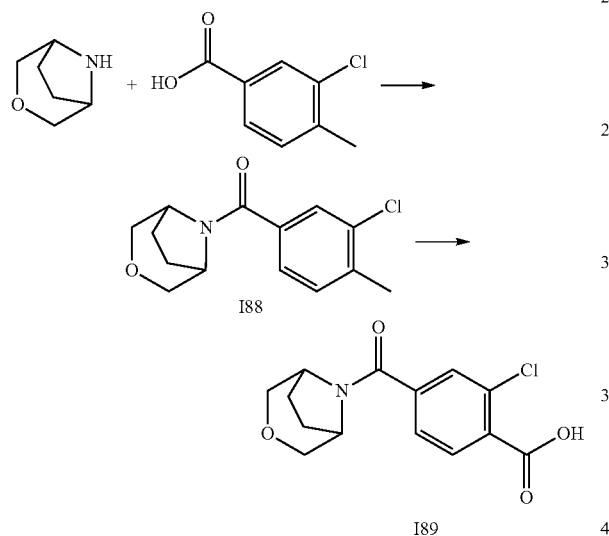

(a) 3-Oxa-8-azabicyclo[3.2.1]octan-8-yl(3-chloro-4-methylphenyl)methanone I88

To a solution of 3-chloro-4-methylbenzoic acid (2.26 g, 13.24 mmol) in DCM (20 mL) was added DIPEA (4.7 g, 36.10 mmol), EDCl (3.5 g, 18.05 mmol), HOBt (190 mg, 1.40 mmol) and 3-oxa-8-azabicyclo[3.2.1]octane hydrochloride (1.8 g, 12.03 mmol). The resulting mixture was stirred at room temperature overnight. The mixture was diluted with water (10 mL) and partitioned with DCM (10 mL). The aqueous layer was extracted with DCM (3×5 mL) and the combined organic extracts washed with saturated aqueous NaHCO₃ (3×5 mL) and brine (3×5 mL), dried (Na₂SO₄), filtered and concentrated. The crude product was purified by silica gel chromatography (ethyl acetate/petroleum ether=1/10) to give the title compound (3.0 g, 92%) as a white solid: ¹H NMR (400 MHz, MeOD) δ 7.50 (d, J=1.6 Hz, 1H), 7.40 (d, J=7.6 Hz, 1H), 7.33 (m, 1H), 4.61-4.56 (m, 1H), 3.99 (s, 1H), 3.78-3.59 (m, 4H), 2.41 (s, 3H), 2.00-1.99 (m, 4H); LCMS RT 2.51 min; m/z 266.1 [M+H]+

(b) 4-(3-Oxa-8-azabicyclo[3.2.1]octane-8-carbonyl)-2-chlorobenzoic acid I89

To a solution of 3-oxa-8-azabicyclo[3.2.1]octan-8-yl(3-chloro-4-methylphenyl)methanone I88 (500 mg, 1.88 mmol) in a mixture of pyridine (5 mL) and water (15 mL) was added KMnO₄ (1.78 g, 11.28 mmol) in portions. The resulting mixture was heated to 50° C. and stirred 48 h. The mixture was filtered and the filtrate was extracted with ethyl acetate (3×5 mL). The pH of the aqueous phase was adjusted pH 1-2 by addition of concentrated HCl, and then extracted with DCM (8×5 mL). The combined organic extracts were dried (Na₂SO₄), filtered and concentrated to give the title compound (340 mg, 61%) as a white solid. LCMS RT 0.88 min; m/z 296.1 [M+H]+.

(xxxvii) 2-Ethoxy-5-methyl-4-(morpholine-4-carbonyl)benzoic acid I96

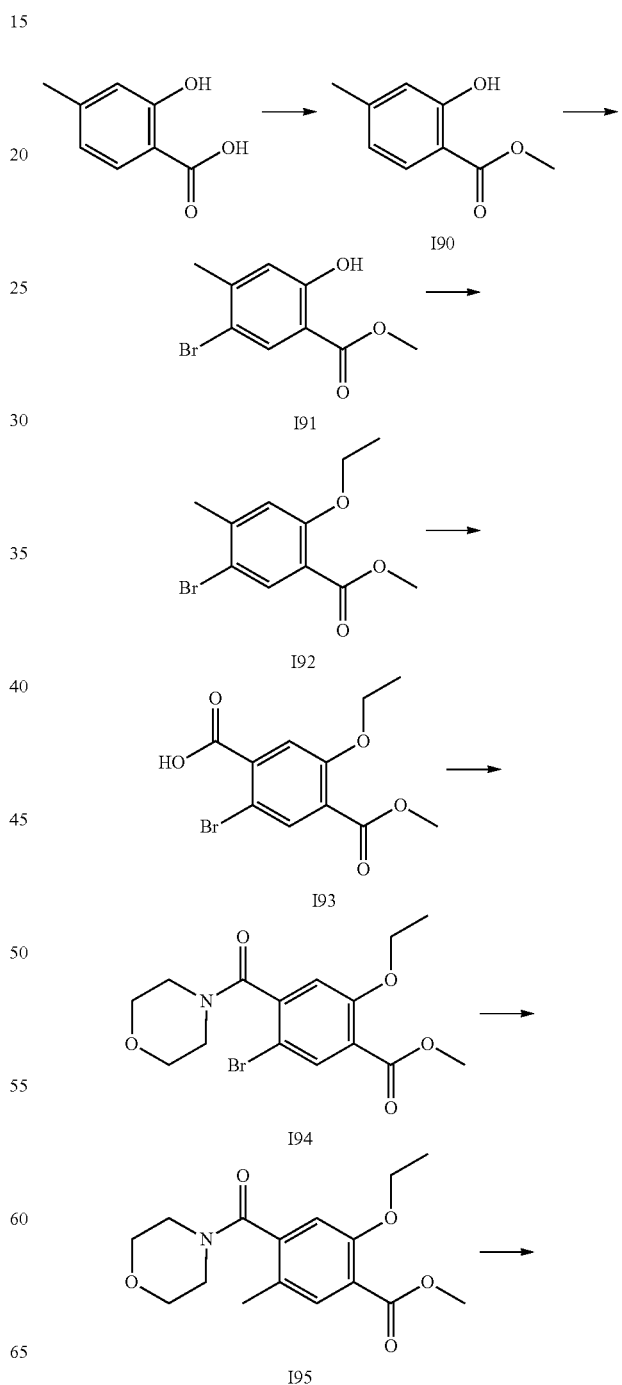

-continued

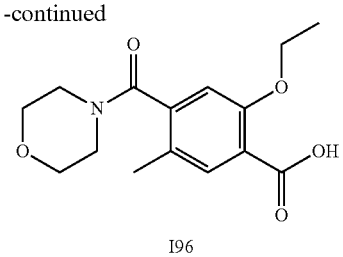

I96

(a) Methyl 2-hydroxy-4-methylbenzoate I90

To a solution of 2-hydroxy-4-methylbenzoic acid (4.0 g, 26.2 mmol) in methanol (40 mL) was added $SOCl_2$ (4.6 g, 39.4 mmol). The mixture was stirred at 50° C. for 1 d. The mixture was concentrated to give the crude product which was dissolved in $CH_2Cl_2$ (50 mL) and the mixture was washed with water (20 mL) and saturated aqueous $NaHCO_3$ solution (20 mL×3). The organic layer was dried ($Na_2SO_4$) and concentrated to give the title compound as a brown oil (4.2 g, 96%): LCMS: RT 2.74 min; m/z 167.1 $[M+H]^+$.

(b) Methyl 5-bromo-2-hydroxy-4-methylbenzoate I91

To a solution of methyl 2-hydroxy-4-methylbenzoate I90 (2.2 g, 13.24 mmol) in chloroform (20 mL) was added $Br_2$ (2.09 g, 13.24 mmol) dropwise. The mixture was stirred at 0° C. for 1 h. The reaction was quenched by addition of sodium sulfite (30 mL, 1 M aqueous solution) and the aqueous layer extracted with $CH_2Cl_2$ (30 mL×3). The organic layer was dried ($Na_2SO_4$) and concentrated to give the title compound as yellow oil (3.1 g, 96%): LCMS: RT 3.20 min; m/z 245.0 $[M+H]^+$.

(c) Methyl 5-bromo-2-ethoxy-4-methylbenzoate I92

To a solution of methyl 5-bromo-2-hydroxy-4-methylbenzoate I91 (3.1 g, 12.7 mmol) in DMSO (10 mL) at 40° C. was added $K_2CO_3$ (5.26 g, 38.1 mmol) and ethyl bromide (2.07 g, 14.05 mmol) dropwise. The mixture was stirred at 40° C. for 2 h. Further ethyl bromide (2.07 g, 14.05 mmol) was then added dropwise and the resulting mixture was stirred at 40° C. for 8 h. The reaction was quenched with water (20 mL) and extracted with $CH_2Cl_2$ (30 mL×3). The organic layer was washed with water (20 mL×10), dried ($Na_2SO_4$) and concentrated to give the title compound as brown oil (2.5 g, 73%): LCMS: RT 2.86 min; m/z 273.0 $[M+H]^+$.

(d) 2-Bromo-5-ethoxy-4-(methoxycarbonyl)benzoic acid I93

To a solution of methyl 5-bromo-2-ethoxy-4-methylbenzoate I92 (2.5 g, 9.19 mmol) in pyridine (5 mL) and water (15 mL) was added $KMnO_4$ (4.3 g, 27.57 mmol). The mixture was stirred at 50° C. for 24 hours, then at room temperature for 2 days. The mixture was filtered through celite, the precipitate was resuspended in 70° C. hot water and filtered again. The aqueous solution was washed with EtOAc (30 mL), then acidified with 2M aqueous HCl solution. The mixture was extracted with $CH_2Cl_2$ (50 mL×5) and the combined organic layers dried ($Na_2SO_4$) and concentrated to give the title compound as a white solid (610 mg, 23%). LCMS: RT 2.26 min; m/z 303.1 $[M+H]^+$.

(e) Methyl 5-bromo-2-ethoxy-4-(morpholine-4-carbonyl)benzoate I94

To a solution of 2-bromo-5-ethoxy-4-(methoxycarbonyl)benzoic acid I93 (600 mg, 1.98 mmol) in $CH_2Cl_2$ (10 mL) at 0° C. was added oxalyl chloride (377 mg, 2.97 mmol) and DMF (0.01 mL). The mixture was stirred at 0° C. for 3 h then morpholine (344.9 mg, 3.96 mmol) was added to the mixture, followed by triethylamine (280 mg, 2.77 mmol). The resulting mixture was stirred at room temperature overnight. The reaction was poured into water (30 mL) and the aqueous layer extracted with $CH_2Cl_2$ (50 mL×3). The organic layer was dried ($Na_2SO_4$) and concentrated and the residue was purified by column chromatography ($CH_2Cl_2$: methanol=100:1 v/v) to give the title compound as red oil (790 mg, 95%): LCMS: RT 2.30 min; m/z 372.0 $[M+H]^+$.

(f) Methyl 2-ethoxy-5-methyl-4-(morpholine-4-carbonyl)benzoate I95

To a solution of methyl 5-bromo-2-ethoxy-4-(morpholine-4-carbonyl)benzoate I94 (360 mg, 0.97 mmol) in DMF (10 mL) was added $K_2CO_3$ (268.1 mg, 1.94 mmol), methyl boronic acid (116 mg, 1.94 mmol) and $Pd(PPh_3)_4$ (56 mg, 0.05 mmol). The resulting mixture was heated at 100° C. under $N_2$ for 1 day. Water (20 mL) was added to the mixture, and the aqueous extracted with $CH_2Cl_2$ (20 mL×3). The organic layer was washed with brine (20 mL), dried ($Na_2SO_4$) and concentrated. The residue was purified by column chromatography ($CH_2Cl_2$: methanol=100:1 v/v) to give the title compound as yellow oil (100 mg, purity about 80%). LCMS: RT 2.08 min; m/z 308.1$[M+H]^+$.

(g) 2-Ethoxy-5-methyl-4-(morpholine-4-carbonyl)benzoic acid I96

To a solution of methyl 2-ethoxy-5-methyl-4-(morpholine-4-carbonyl)benzoate I95 (100 mg, 0.32 mmol) in a mixture of THF (10 mL), methanol (1 mL) and water (0.1 mL) was added $LiOH.H_2O$ (41 mg, 0.96 mmol). The resulting mixture was stirred at room temperature for 1 day. The reaction mixture was concentrated and the residue diluted with water (20 mL). The pH of the aqueous mixture was adjusted to 6 by addition of 1 M aqueous HCl solution and the aqueous layer extracted with $CH_2Cl_2$ (20 mL×3). The combined organic layers were dried ($Na_2SO_4$) and concentrated and the crude product purified by preparative TLC ($CH_2Cl_2$: methanol=10:1 v/v) to give the title compound as a white solid (20 mg, 45%). LCMS: RT 0.85 min; m/z 294.1 $[M+H]^+$.

(xxxviii) 6-(3-Oxa-8-azabicyclo[3.2.1]octane-8-carbonyl)-4-ethoxynicotinic acid I102

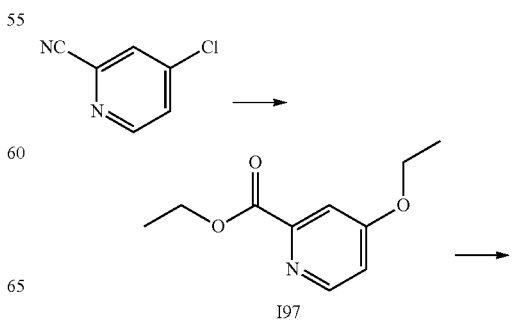

I97

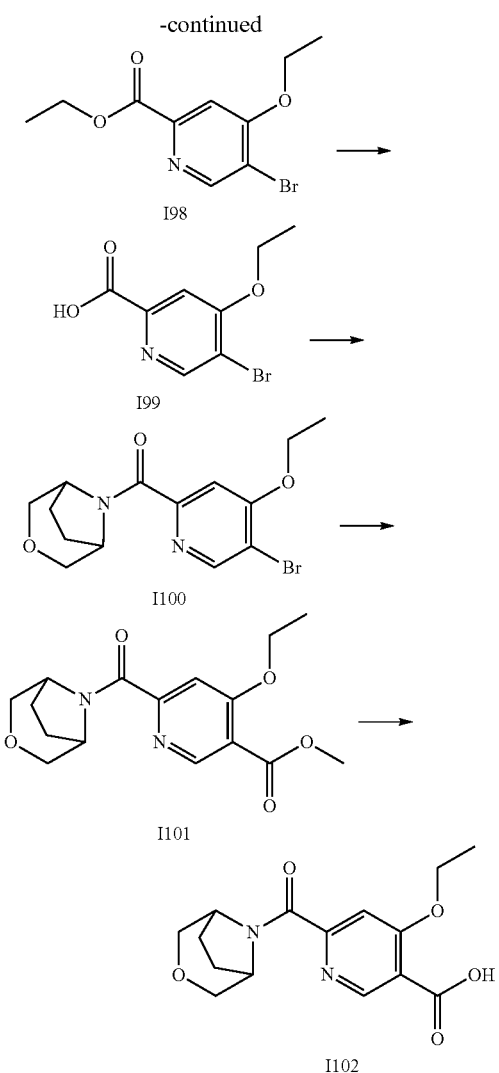

(a) Ethyl 4-ethoxypicolinate I97

A solution of 4-chloropicolinonitrile (5.5 g, 39.7 mmol) in a saturated solution of HCl in EtOAc (80 mL) was stirred at 80° C. for 2 days. The solvent was removed under reduced pressure. Saturated aqueous NaHCO$_3$ solution (200 mL) was added and the aqueous layer was extracted with CH$_2$Cl$_2$ (3×200 mL). The combined organic extracts were dried (Na$_2$SO$_4$) and concentrated to give the title compound as a white solid (2.6 g, 34%): $^1$H NMR (400 MHz, CDCl$_3$) δ 8.52 (d, J=5.6 Hz, 1H), 7.63 (d, J=2.4 Hz, 1H), 6.93-6.91 (m, 1H), 4.80-4.43 (m, 2H), 4.16-4.11 (m, 2H), 1.46-1.41 (m, 6H); LCMS: RT 1.35 min; m/z 196.1[M+H]$^+$.

(b) Ethyl 5-bromo-4-ethoxypicolinate 198

To a solution of ethyl 4-ethoxypicolinate 197 (1.6 g, 8.2 mmol) in concentrated H$_2$SO$_4$ (80 mL) was added N-bromosuccinimide (2.7 g, 14.8 mmol). The reaction was stirred at room temperature overnight and then quenched by addition of a saturated aqueous NaHCO$_3$ solution (150 mL). The aqueous layer was extracted with CH$_2$Cl$_2$ (3×130 mL) and the combined organic layers were dried (Na$_2$SO$_4$) and concentrated to give the title compound as a yellow solid (2.0 g, 91%): $^1$H NMR (400 MHz, CDCl$_3$) δ 8.67 (s, 1H), 7.63 (s, 1H), 4.94-4.40 (m, 2H), 4.29-4.23 (m, 2H), 1.54-1.51 (m, 3H), 1.46-1.42 (m, 3H). LCMS: RT 2.59 min; m/z 274.0 [M+H]$^+$ for $^{79}$Br, 276.0 [M+H]$^+$ for $^{81}$Br.

(c) 5-Bromo-4-ethoxypicolinic acid I99

To a solution of ethyl 5-bromo-4-ethoxypicolinate I98 (1.6 g, 6.0 mmol) in a mixture of THF (20 mL), CH$_3$OH (2 mL) and H$_2$O (0.2 mL) was added LiOH.H$_2$O (1.0 g, 24.0 mmol). The reaction was stirred at room temperature for 2 d. The solvent was removed under reduced pressure and the residue was dissolved in water (10 mL) and acidified to pH 3 with 1M aqueous HCl. The aqueous phase was extracted with CH$_2$Cl$_2$ (4×50 mL) and the combined organic extracts were dried (Na$_2$SO$_4$) and concentrated to give the title compound as a yellow solid (800 mg, 54%). LCMS: RT 0.86 min; m/z 246.0 [M+H]$^+$ for $^{79}$Br, 248.0 [M+H]$^+$ for $^{81}$Br.

(d) 3-Oxa-8-azabicyclo[3.2.1]octan-8-yl(5-bromo-4-ethoxypyridin-2yl)methanone I100

To a solution of 5-bromo-4-ethoxypicolinic acid I99 (300 mg, 1.2 mmol) and 3-oxa-8-azabicyclo[3.2.1]octane (153 mg, 1.0 mmol) hydrochloride salt in CH$_2$Cl$_2$ (5 mL) were added DIPEA (0.72 mL, 4.1 mmol), EDCl (393 mg, 2.0 mmol) and HOBt (15 mg, 0.1 mmol). The mixture was stirred at room temperature overnight. The reaction was quenched by addition of saturated aqueous NaHCO$_3$ solution (50 mL) and the mixture was extracted with CH$_2$Cl$_2$ (3×50 mL). The combined organic layers were dried (Na$_2$SO$_4$) and concentrated and the residue was purified by silica gel chromatography (20% EtOAc in petroleum ether v/v) to give the title compound as a yellow solid (262 mg, 75%). LCMS: RT 5.56 min; m/z 340.9 [M+H]$^+$ for $^{79}$Br, 342.9 [M+H]$^+$ for $^{81}$Br.

(e) Methyl 6-(3-oxa-8-azabicyclo[3.2.1]octane-8-carbonyl)-4-ethoxynicotinate I101

To a solution of 3-oxa-8-azabicyclo[3.2.1]octan-8-yl(5-bromo-4-ethoxypyridin-2-yl)methanone I100 (650 mg, 1.9 mmol) in MeOH (50 mL) was added Et$_3$N (577 mg, 5.7 mmol) and PdCl$_2$(dppf) (73 mg, 0.05 mmol). The reaction was stirred under a CO atmosphere and heated at reflux for 2 days. The solvent was removed under reduced pressure and the residue was taken up in water (100 mL) and extracted with CH$_2$Cl$_2$ (3×100 mL). The combined organic layers were dried over (Na$_2$SO$_4$) and concentrated. The residue was purified by silica gel chromatography (33% EtOAc in petroleum ether v/v) to give the title compound as a brown solid (400 mg, 66%). LCMS: RT 4.94 min; m/z 320.8 [M+H]$^+$.

(f) 6-(3-Oxa-8-azabicyclo[3.2.1]octane-8-carbonyl)-4-ethoxynicotinic acid I102

To a solution of methyl 6-(3-oxa-8-azabicyclo[3.2.1]octane-8-carbonyl)-4-ethoxynicotinate I101 (350 mg, 1.1 mmol) in CH$_3$OH (20 mL) was added NaOH (2.2 mL of a 1 M aqueous solution) and the mixture stirred at room temperature overnight. The solvent was removed under reduced pressure and the residue was taken up in water (15 mL). The aqueous was acidified to pH 4 by addition of 1M aqueous HCl. The aqueous phase was extracted with CH$_2$Cl$_2$ (4×60 mL) and the combined extracts were dried (Na$_2$SO$_4$)

and concentrated to give the title compound as a yellow solid I102 (320 mg, 95%). LCMS: RT 0.61 min; m/z 307.1 [M+H]⁺.

(xxxix) 2-Ethoxy-3-methyl-4-(morpholine-4-carbonyl)benzoic acid I109

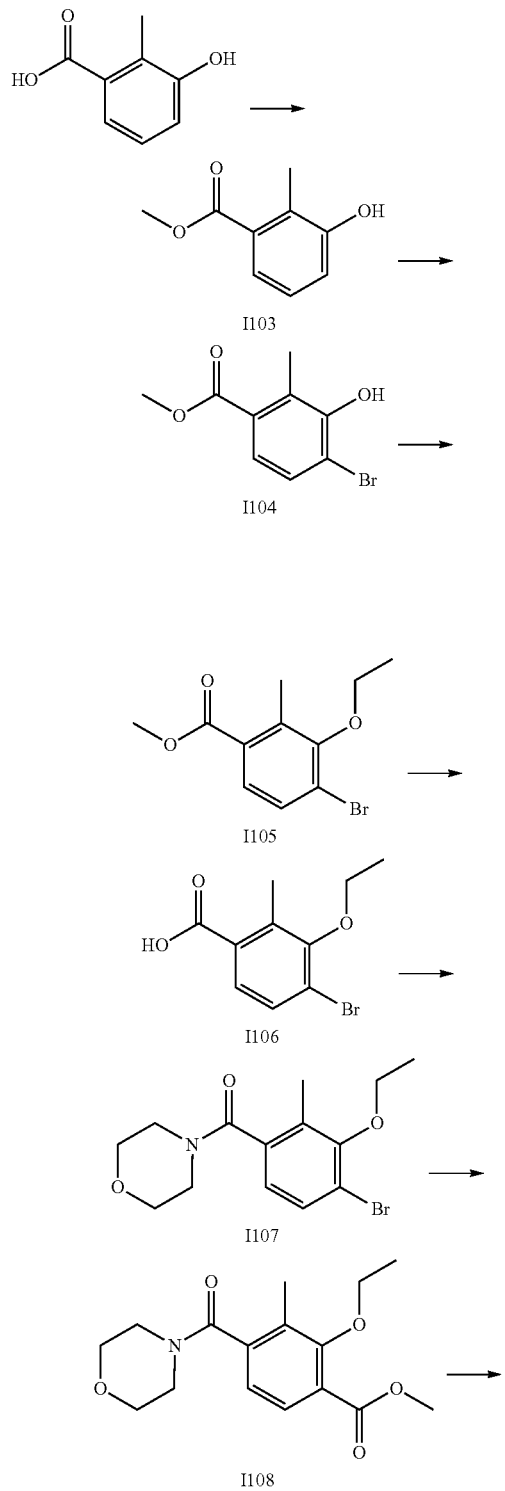

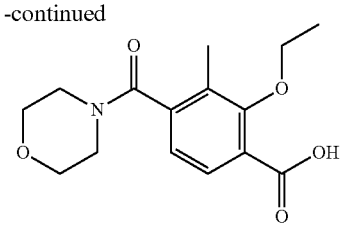

(a) Methyl 3-hydroxy-2-methylbenzoate I103

To a solution of 3-hydroxy-2-methylbenzoic acid (10.0 g, 65.7 mmol) in MeOH (100 mL) was added SOCl₂ (15.6 g, 131.5 mmol) slowly and the mixture was stirred at 50° C. overnight. The reaction mixture was concentrated and the residue dissolved in DCM (100 mL). The organic solution was washed with saturated aqueous NaHCO₃ solution, dried (Na₂SO₄) and concentrated to give the title product (10.7 g, 98%) as white solid. LCMS: RT 1.98 min; m/z 167.1 [M+H]⁺.

(b) Methyl 4-bromo-3-hydroxy-2-methylbenzoate I104

To a solution of tert-butylamine (2.0 g, 27.1 mmol) in DCM (180 mL) at –70° C. was added a solution of Br₂ (4.2 g, 27.1 mmol) in DCM (10 mL) dropwise and the mixture was stirred at –70° C. for 1 h. A solution of methyl 3-hydroxy-2-methylbenzoate I103 (4.5 g, 27.1 mmol) in DCM (10 mL) was then added dropwise and the resulting mixture allowed to warm to room temperature and stirred overnight. The reaction was quenched by addition of water (30 mL) and the aqueous layer extracted with DCM (3×50 mL). The combined organic layers were washed with brine, dried (Na₂SO₄) and concentrated. The crude residue obtained was purified by silica gel chromatography (2% EtOAc in petroleum ether v/v) to give the title product (2.2 g, 33%) as a white solid. LCMS: RT 2.46 min; m/z 245.0 [M+H]⁺ for ⁷⁹Br, 247.0 [M+H]⁺ for ⁸¹Br. ¹H NMR (400 MHz, d₆-DMSO) δ 9.38 (s, 1H), 7.46 (d, J=8.4 Hz, 1H), 7.17 (d, J=8.4 Hz, 1H), 3.80 (s, 3H), 2.38 (s, 3H).

(c) Methyl 4-bromo-3-ethoxy-2-methylbenzoate I105

To a solution of methyl 4-bromo-3-hydroxy-2-methylbenzoate I104 (2.1 g, 8.6 mmol) in DMSO (10 mL) was added K₂CO₃ (3.5 g, 25.8 mmol) and ethyl bromide (1.4 g, 12.9 mmol). The reaction was stirred at 40° C. overnight. Water (30 mL) was added and the aqueous extracted with DCM (3×20 mL). The organic layer was washed with water (10×30 mL), dried (Na₂SO₄), and concentrated to give the title product (2.2 g, 95%) as a yellow solid. LCMS: RT 3.08 min; m/z 273.0 [M+H]⁺ for ⁷⁹Br, 275.0 [M+H]⁺ for ⁸¹Br.

(d) 4-Bromo-3-ethoxy-2-methylbenzoic acid I106

To a solution of methyl 4-bromo-3-ethoxy-2-methylbenzoate I105 (2.1 g, 10.0 mmol) in a mixture of MeOH (10 mL) and water (0.2 mL) was added NaOH (0.4 g, 20.0 mmol). The reaction was stirred at room temperature overnight and then the solvent was removed under reduced pressure. The residue obtained was dissolved in water (20 mL) and acidified with 1 M aqueous HCl to pH 2. The aqueous layer was extracted with DCM (4×20 mL) and the combined organic layers dried (Na₂SO₄) and concentrated to give the title product (2.4 g, 92%) as a white solid. LCMS: RT 2.75 min; m/z 281.0 [M+Na]⁺ for ⁷⁹Br, 283.0 [M+Na]⁺ for ⁸¹Br.

(e) (4-Bromo-3-ethoxy-2-methylphenyl)(morpholino)methanone I107

To a solution of 4-bromo-3-ethoxy-2-methylbenzoic acid I106 (2.4 g, 9.3 mmol) in DCM (500 mL) at 0° C. was added oxalyl chloride (3.5 g, 27.9 mmol) and DMF (0.2 mL). The reaction was stirred for 3 h then morpholine (1.6 g, 18.6 mmol) and triethylamine (4.1 g, 40.9 mmol) were added and stirring was continued overnight at 0° C. Water (100 mL) was added and the mixture was extracted with DCM (2×100 mL). The combined organic layers were washed with brine, dried (Na₂SO₄) and concentrated. The residue was purified by silica gel chromatography (1% MeOH in DCM v/v) to give the title compound (720 mg, 24%) as a white solid which was used without further purification. LCMS: RT 2.48 min; m/z 328.1 [M+H]⁺ for ⁷⁹Br, 330.1 [M+H]⁺[M+H]⁺ for ⁸¹Br.

(f) Methyl 2-ethoxy-3-methyl-4-(morpholine-4-carbonyl)benzoate I108

To a solution of (4-bromo-3-ethoxy-2-methylphenyl)(morpholino)methanone I107 (720 mg, 2.2 mmol) in MeOH (10 mL) was added PdCl₂(dppf) (81 mg, 0.11 mmol) and triethylamine (489 mg, 4.8 mmol). The reaction was stirred under a CO atmosphere and heated at reflux overnight. The mixture was concentrated and the residue was dissolved in DCM (20 mL), washed with water and brine, dried (Na₂SO₄) and concentrated. The residue obtained was purified by silica gel chromatography (1% MeOH in DCM v/v) to give the title product (670 mg, 80% purity by HPLC) as yellow oil. LCMS: RT 2.02 min; m/z 308.2 [M+H]⁺.

(g) 2-Ethoxy-3-methyl-4-(morpholine-4-carbonyl)benzoic acid I109

To a solution of methyl 2-ethoxy-3-methyl-4-(morpholine-4-carbonyl)benzoate I108 (670 mg, 2.2 mmol) in a mixture of THF (1 mL), MeOH (10 mL) and water (0.1 mL) was added LiOH.H₂O (275 mg, 6.5 mmol) The reaction was stirred at room temperature overnight and then concentrated under reduced pressure. The residue was dissolved in water (20 mL) then acidified with 1 M aqueous HCl to pH 2. The aqueous mixture was extracted with DCM (10 mL×3) and the combined organic layers were dried (Na₂SO₄) and concentrated to give the title product (310 mg, 48%) as brown oil. LCMS: RT 0.89 min; m/z 294.1 [M+H]⁺.

(xl) 2-Fluoro-4-(3-oxa-8-aza-bicyclo[3.2.1]octane-8-carbonyl)-benzoic acid I111

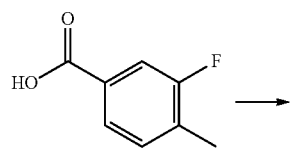

-continued

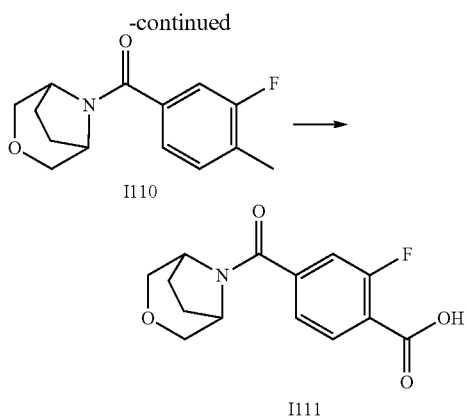

(a) (3-Fluoro-4-methyl-phenyl)-(3-oxa-8-aza-bicyclo[3.2.1]oct-8-yl)-methanone I110

To a solution of 3-fluoro-4-methylbenzoic acid (2.0 g, 13.0 mmol) and 3-oxa-8-azabicyclo[3.2.1]octane hydrochloride salt (1.8 g, 11.8 mmol) in CH₂Cl₂ (10 mL) were added DIPEA (6.3 mL, 35.4 mmol), EDCl (2.72 g, 14.2 mmol) and HOBt (162.1 mg, 1.2 mmol). The mixture was stirred at room temperature overnight. A saturated aqueous NaHCO₃ solution (50 mL) was added and the mixture was extracted with CH₂Cl₂ (3×50 mL). The combined organic extracts were dried (Na₂SO₄) and concentrated. The residue was purified by silica gel chromatography (5% EtOAc in petroleum ether v/v) to give the title compound as a yellow solid (1.7 g, 58%). LCMS: RT 2.30 min; m/z 250.1 [M+H]⁺.

(b) 2-Fluoro-4-(3-oxa-8-aza-bicyclo[3.2.1]octane-8-carbonyl)-benzoic acid I111

To a solution of (3-fluoro-4-methyl-phenyl)-(3-oxa-8-aza-bicyclo[3.2.1]oct-8-yl)-methanone I110 (800 mg, 3.2 mmol) in a mixture of pyridine (6 mL) and H₂O (12 mL) was added KMnO₄ (5.1 g, 32 mmol) and the mixture stirred at room temperature for 2 days. The resulting suspension was filtered through Celite and the filtrate washed with CH₂Cl₂ (3×50 mL). The remaining aqueous layer was acidified to pH 3 by addition of 2 M aqueous HCl, and extracted with CH₂Cl₂ (4×60 mL). The combined organic layers were dried (Na₂SO₄) and concentrated to give the title compound I111 as an off-white solid (500 mg, 56%). LCMS: RT 2.89 min; m/z 280.1 [M+H]⁺.

(xli) 4-(3-Oxa-8-azabicyclo[3.2.1]octane-8-carbonyl)-2-ethoxybenzoic acid I115

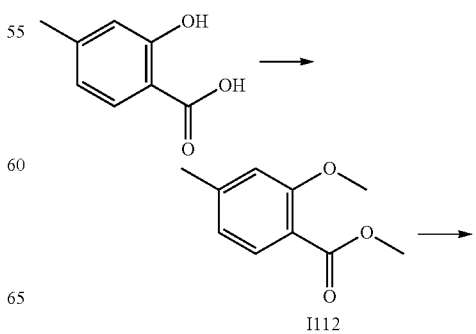

-continued

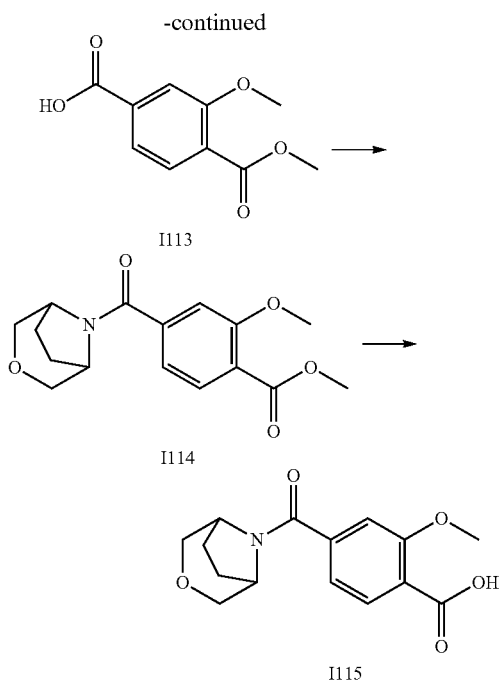

(a) Methyl 2-methoxy-4-methylbenzoate I112

To a mixture of 2-hydroxy-4-methylbenzoic acid (10.0 g, 65.7 mmol) and $K_2CO_3$ (22.7 g, 164.3 mmol) in DMF (200 mL) at room temperature was added methyl iodide (20.5 g, 144.5 mmol) over a period of 10 min. The resulting mixture was stirred at room temperature overnight, then diluted with $CH_2Cl_2$ (150 mL) and filtered. The filtrate was washed with water (200 mL×10) and brine (200 mL×2), dried ($Na_2SO_4$) and concentrated to give the title compound as a yellow liquid (11.0 g, 93%).

(b) 3-Methoxy-4-(methoxycarbonyl)benzoic acid I113

To a solution of methyl 2-methoxy-4-methylbenzoate I112 (10.0 g, 48.05 mmol) in a mixture of pyridine (30 mL) and water (90 mL) was added $KMnO_4$ (30.37 g, 192.2 mmol). The resulting mixture was heated at 50° C. for 48 h, then cooled and allowed to stir at room temperature for 24 h. The mixture was filtered and the filter cake washed with hot water. The combined aqueous filtrates were washed with EtOAc (75 mL×3) and acidified to pH 2 with a 2 M aqueous HCl solution. The mixture was extracted with $CH_2Cl_2$ (150 mL×3). The combined organic layers were washed with brine, dried ($Na_2SO_4$) and concentrated to give the title compound as a white solid (7.0 g, 61%). LCMS: RT 1.24 min; m/z 211.0 [M+H]$^+$.

(c) Methyl 4-(3-oxa-8-azabicyclo[3.2.1]octane-8-carbonyl)-2-methoxybenzoate I114

To a solution of 3-methoxy-4-(methoxycarbonyl)benzoic acid I113 (500 mg, 2.10 mmol) in $CH_2Cl_2$ (20 mL) was added 3-oxa-8-azabicyclo[3.2.1]octane hydrochloride (377 mg, 2.52 mmol), HOBt (426 mg, 3.15 mmol), triethylamine (850 mg, 8.4 mmol) and EDCl (602 mg, 3.15 mmol). The resulting mixture was stirred at room temperature overnight. Saturated aqueous $NaHCO_3$ solution was added. The organic layer was separated and the aqueous phase was extracted with $CH_2Cl_2$ (20 mL×2). The combined organic layers were washed with brine, dried ($Na_2SO_4$) and concentrated. The residue was purified by column chromatography (5% methanol in dichloromethane v/v) to give the title compound as a white solid (800 mg, 59%).

(d) 4-(3-Oxa-8-azabicyclo[3.2.1]octane-8-carbonyl)-2-methoxybenzoic acid I115

To a solution of methyl 4-(3-oxa-8-azabicyclo[3.2.1]octane-8-carbonyl)-2-methoxybenzoate I114 (0.9 g, 2.9 mmol) in a mixture of THF (4 mL) and methanol (4 mL) was added aqueous NaOH solution (2 M, 4 mL). The resulting mixture was stirred at room temperature for 14 h. The solvent was removed, and the residue was diluted with water (20 mL). The pH of the aqueous mixture was adjusted to 6 by addition of 2 M aqueous HCl solution. The mixture was extracted with $CH_2Cl_2$ (20 mL×3) and the combined organic layers washed with brine (10 mL×2), dried ($Na_2SO_4$) and concentrated to give the title compound as a white solid (0.7 g, 83%): LCMS: RT 0.55 min; m/z 292.1 [M+H]$^+$.

(xlii) (R)-tert-butyl(3-amino-2-hydroxypropyl)(2,3-dihydro-1H-inden-2-yl)carbamate I117

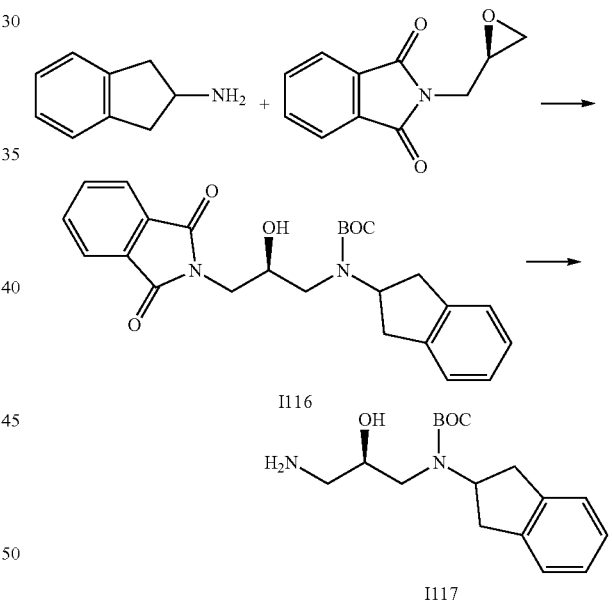

(a) (R)-tert-Butyl(2,3-dihydro-1H-inden-2-yl)(3-(1,3-dioxoisoindolin-2-yl)-2-hydroxypropyl)carbamate I116

A mixture of 2,3-dihydro-1H-inden-2-amine (5.0 g, 24.61 mmol) and (R)-2-(oxiran-2-ylmethyl)isoindoline-1,3-dione (4.91 g, 36.91 mmol) in EtOH (100 mL) was heated at reflux overnight. After cooling to room temperature, triethyamine (9.94 g, 98.44 mmol) and (Boc)$_2$O (10.74 g, 49.22 mmol) were added and the reaction mixture was stirred at room temperature overnight. The mixture was concentrated and purified by column (EtOAc/Pet. Ether=1/4, v/v) to give the title compound (5.4 g, 50%) as an oil.

(b) (R)-tert-butyl(3-amino-2-hydroxypropyl)(2,3-dihydro-1H-inden-2-yl)carbamate I117

A mixture of (R)-tert-butyl(2,3-dihydro-1H-inden-2-yl)(3-(1,3-dioxoisoindolin-2-yl)-2-hydroxypropyl)carbamate I116 (4.4 g, 10.08 mmol) and NH$_2$NH$_2$.H$_2$O (80%, 1.89 g, 30.24 mmol) in EtOH (100 mL) was heated at reflux for 4 h. After cooling to room temperature, the mixture was filtered and the filtercake was washed with EtOH (50 mL). The filtrate was concentrated and then dissolved in CH$_2$Cl$_2$, washed with saturated aqueous solution NaHCO$_3$ (80 mL×3) and brine (20 mL×2), dried (Na$_2$SO$_4$) and concentrated to give the title compound (3.1 g, crude) as a yellow oil, which was used for the next step without further purification. LCMS: RT 2.17 min; m/z 307.2 [M+H]$^+$.

(xliii) 4-(2-(3-oxa-8-azabicyclo[3.2.1]octan-8-yl)-2-oxoethyl)-2-ethoxybenzoic acid I121

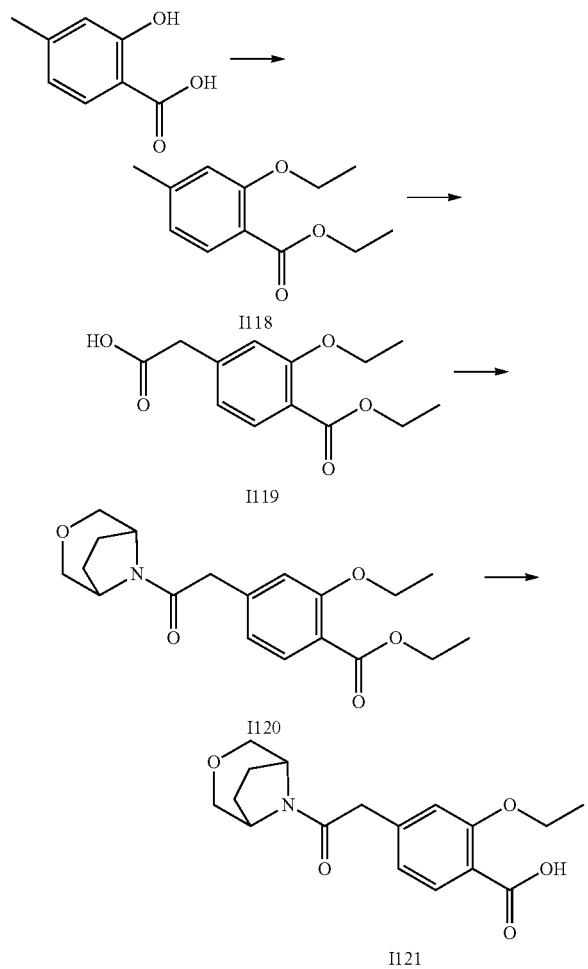

(a) Ethyl 2-ethoxy-4-methylbenzoate I118

To a mixture of 2-hydroxy-4-methylbenzoic acid (20.0 g, 131.5 mmol) and K$_2$CO$_3$ (54.5 g, 394.5 mmol) in DMSO (50 mL) at 40° C. was added bromoethane (21.5 g, 197.2 mmol) over 30 min. The reaction was stirred at 40° C. for 2 h. Further bromoethane (21.5 g, 197.2 mmol) was then added dropwise and the reaction stirred at 40° C. for 8 h. DCM (200 mL) was added and the mixture was filtered. The organic layer was separated washed with water (150 mL×4), dried (Na$_2$SO$_4$) and concentrated to give the title product (24.1 g, 88%) as clear oil. LCMS: RT 2.77 min; m/z 209.1[M+H]$^+$.

(b) 2-(3-ethoxy-4-(ethoxycarbonyl)phenyl)acetic acid I119

To a solution of diisopropylamine (1.46 g, 14.4 mmol) in dry THF (20 ml) at −30° C. was added n-BuLi (2.4 M in hexane, 5.8 mL, 14.4 mmol) slowly under nitrogen atmosphere. The mixture was stirred at −30° C. for 30 min then cooled to −78° C. and HMPA (4.0 g) added. A solution of ethyl 2-ethoxy-4-methylbenzoate I118 (2.0 g, 9.6 mmol) in dry THF (5 mL) was then added dropwise and the resultant mixture stirred at −78° C. for 2 h. CO$_2$ (g) was then bubbled through the mixture for a further 30 min until the colour disappeared. The reaction was allowed to warm to 10° C. then was diluted with water (20 mL) and extracted with ether (20 mL×2). The aqueous layer was acidified to pH 2 by addition of 10% aqueous H$_2$SO$_4$ and the mixture extracted with DCM (20 mL×2). The combined DCM layers were washed with water and brine, dried (Na$_2$SO$_4$) and concentrated to give the title compound (550 mg, 23%) as yellow oil. LCMS: RT 2.36 min; m/z 253.1[M+H]$^+$.

(c) Ethyl 4-(2-(3-oxa-8-azabicyclo[3.2.1]octan-8-yl)-2-oxoethyl)-2-ethoxybenzoate I120

A mixture of 2-(3-ethoxy-4-(ethoxycarbonyl)phenyl)acetic acid I119 (550 mg, 2.2 mmol), 3-oxa-8-azabicyclo[3.2.1]octane hydrochloride salt (320 mg, 2.1 mmol), EDCI (500 mg, 2.6 mmol), HOBt (30 mg, 0.22 mmol) and DIEA (710 mg, 5.5 mmol) in DCM (10 mL) was stirred at room temperature for overnight. Water (20 mL) was added and the reaction mixture extracted with DCM (10 mL×3), the organic layers were combined and washed with saturated aqueous NaHCO$_3$, water and brine, dried (Na$_2$SO$_4$) and concentrated to give the title product (710 mg, 93%) as yellow oil. LCMS: RT 2.38 min; m/z 348.2 [M+H]$^+$.

(d) 4-(2-(3-oxa-8-azabicyclo[3.2.1]octan-8-yl)-2-oxoethyl)-2-ethoxybenzoic acid I121

To a solution of ethyl 4-(2-(3-oxa-8-azabicyclo[3.2.1]octan-8-yl)-2-oxoethyl)-2-ethoxybenzoate I120 (710 mg, 2.0 mmol) in a mixture of THF (5 mL), MeOH (10 mL) and water (5 mL) was added LiOH.H$_2$O (429 mg, 10.2 mmol). The reaction was stirred at room temperature overnight then the solvent removed under vacuum. The residue obtained was dissolved in water (10 mL) then acidified to pH 2 by addition of 10% aqueous H$_2$SO$_4$ solution. The resulting mixture was extracted with DCM (10 mL×3) and the organic layers dried (Na$_2$SO$_4$) and concentrated to give the title product (540 mg, 85%) as yellow solid. LCMS: RT 1.20 min; m/z 320.2 [M+H]$^+$.

(xliv) (S)-tert-butyl(3-amino-2-hydroxypropyl)(2,3-dihydro-1H-inden-2-yl)carbamate I123

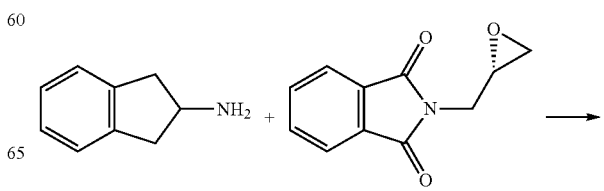

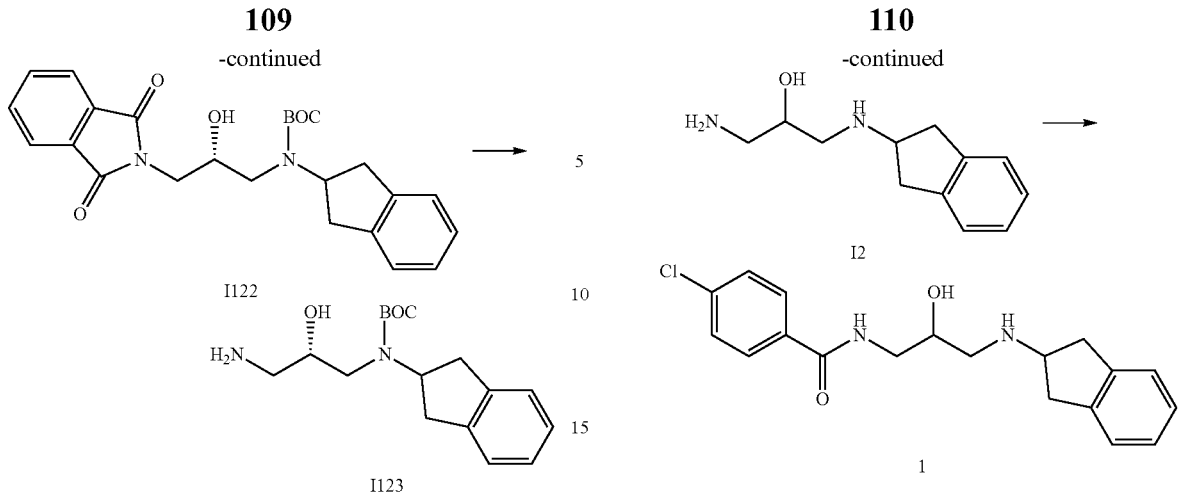

(a) (S)-tert-butyl(2,3-dihydro-1H-inden-2-yl)(3-(1,3-dioxoisoindolin-2-yl)-2-hydroxypropyl)carbamate I122

A mixture of 2,3-dihydro-1H-inden-2-amine (5.0 g, 24.61 mmol) and (S)-2-(oxiran-2-ylmethyl)isoindoline-1,3-dione (4.91 g, 36.91 mmol) in EtOH (100 mL) was heated at reflux overnight. After cooling to room temperature, triethylamine (9.94 g, 98.44 mmol) and (Boc)$_2$O (10.74 g, 49.22 mmol) were added and the reaction mixture was stirred at room temperature overnight. The mixture was concentrated and purified by silica gel column chromatography (EtOAc/petroleum ether=1/4 v/v) to give the title compound (5.4 g, 50%) as an oil. $^1$H NMR (400 MHz, DMSO-d$_6$) δ 7.88-7.82 (m, 4H), 7.16-7.09 (m, 4H), 6.28 (d, J=4.4 Hz, 1H), 4.51 (br s, 1H), 4.05-3.97 (m, 1H), 3.61-3.38 (m, 3H), 3.32-3.09 (m, 5H), 1.31 (s, 9H).

(b) (S)-tert-butyl(3-amino-2-hydroxypropyl)(2,3-dihydro-1H-inden-2-yl)carbamate I123

A mixture of (S)-tert-butyl(2,3-dihydro-1H-inden-2-yl)(3-(1,3-dioxoisoindolin-2-yl)-2-hydroxypropyl)carbamate I122 (5.0 g, 11.46 mmol) and NH$_2$NH$_2$.H$_2$O (80%, 2.2 g, 34.37 mmol) in EtOH (100 mL) was heated at reflux for 4 h. After cooling to room temperature, the mixture was filtered and the filter cake was washed with EtOH (50 mL). The filtrate was concentrated and then dissolved in CH$_2$Cl$_2$, washed with saturated aqueous solution NaHCO$_3$ (80 mL×3), brine (20 mL×2), dried (Na$_2$SO$_4$) and concentrated to give the title compound (3.4 g, crude) as a yellow oil, which was used for the next step without further purification. LCMS: RT 1.99 min; m/z 307.2 [M+H]$^+$.

Example 1: 4-Chloro-N-(3-((2,3-dihydro-1H-inden-2-yl)amino)-2-hydroxypropyl)benzamide (1)

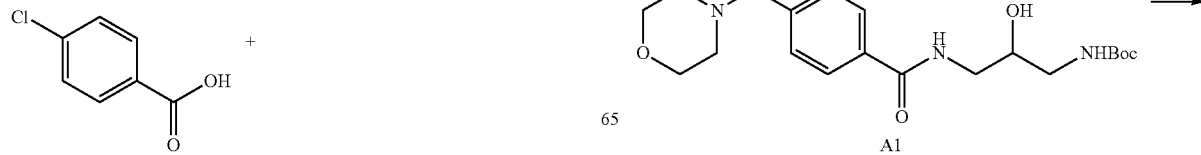

A solution of 4-chlorobenzoic acid (0.057 g, 0.36 mmol) in N,N-dimethylformamide (2 mL) containing N,N-diisopropylethylamine (0.230 mL, 1.31 mmol), N-ethyl-N'-(3-dimethylaminopropyl)carbodiimide hydrochloride (0.095 g, 0.49 mmol) and 1-hydroxybenzotriazole hydrate (wetted with not less than 20 wt. % water, 0.095 g, 0.49 mmol) was stirred at room temperature for 20 minutes. A solution of 1-amino-3-((2,3-dihydro-1H-inden-2-yl)amino)propan-2-ol I2 (0.068 g, 0.33 mmol) in DCM (1 mL) was added and stirred at room temperature for 20 hours under a nitrogen atmosphere. Water and ethyl acetate were added. The aqueous phase was extracted with ethyl acetate (2×20 mL) and the combined organic extracts were washed with water (2×20 mL), brine, dried (sodium sulfate), filtered and concentrated in vacuo. The resulting residue was suspended in diethyl ether, sonicated for 10 seconds, filtered and dried to give the desired compound as cream coloured solid (0.090 g, 79%). $^1$H NMR (300 MHz, d$_4$-methanol) δ 7.81 (d, J=8.55 Hz, 2H), 7.47 (d, J=8.55 Hz, 2H), 7.20-7.10 (m, 4H), 3.98-3.90 (m, 1H), 3.68-3.59 (m, 1H), 3.48 (d, J=5.37 Hz, 2H), 3.20 (ddd, J=15.7, 7.15, 4.0 Hz, 2H), 2.84-2.76 (m, 3H), 2.73-2.66 (m, 1H). LCMS-D: RT 4.85 min; m/z 345 [M+H]$^+$.

Example 2: N-(3-((2,3-Dihydro-1H-inden-2-yl)amino)-2-hydroxypropyl)-4-(morpholine-4-carbonyl)benzamide (2)

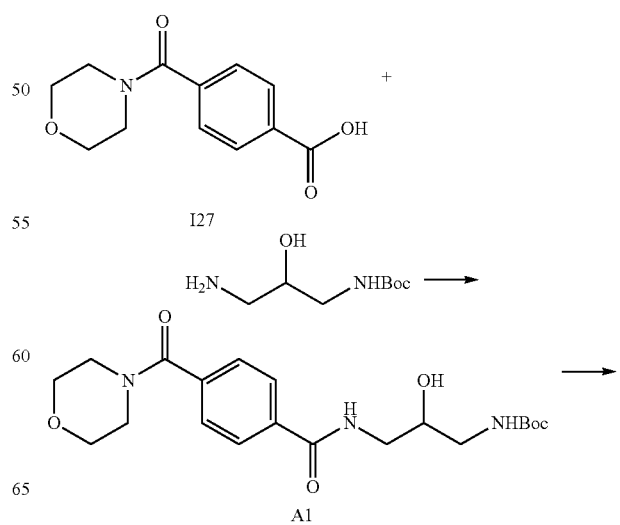

-continued

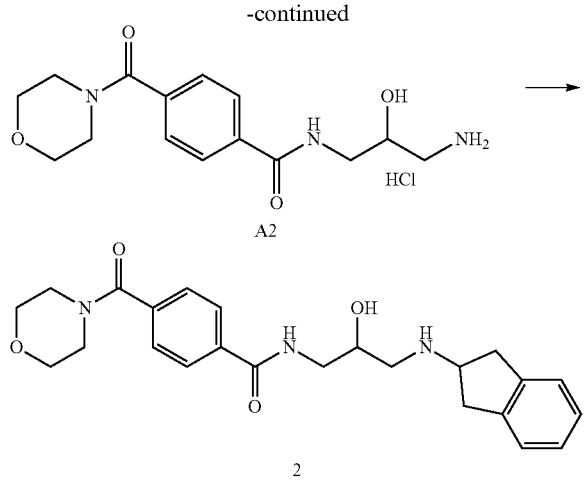

(a) tert-Butyl (2-hydroxy-3-(4-(morpholine-4-carbonyl)benzamido)propyl)carbamate (A1)

To a solution of 4-(4-morphlinylcarbonyl)benzoic acid I27 (400 mg, 1.70 mmol) in DCM (15 mL) was added N,N-diisopropylethylamine (1.19 mL, 6.80 mmol), N-ethyl-N'-(3-dimethylaminopropyl)carbodiimide hydrochloride (489 mg, 2.55 mmol) and 1-hydroxybenzotriazole hydrate (390 mg, 2.55 mmol) and the mixture was stirred at room temperature for 20 minutes. The solution was cooled to 0° C. and N-Boc-1,3-diamino-2-propanol (356 mg, 1.87 mmol) was added. After stirring at 0° C. for 10 minutes, the mixture was stirred at room temperature for 20 hours whilst under a nitrogen atmosphere. Water (15 mL) and DCM (20 mL) were added. The aqueous phase was extracted with DCM (2×30 mL) and the combined organic extracts were washed with brine (60 mL), dried (sodium sulfate), filtered and concentrated under reduced pressure to give the desired compound (450 mg, 65%). LCMS-D: RT 4.60 min; m/z 408 [M+H]$^+$.

(b) N-(3-Amino-2-hydroxypropyl)-4-(morpholine-4-carbonyl)benzamide hydrochloride (A2)

A solution of tert-butyl (2-hydroxy-3-(4-(morpholine-4-carbonyl)benzamido)propyl)carbamate A1 (450 mg, 1.10 mmol) in 4.0 M hydrochloric acid in 1,4-dioxane (1.38 mL, 5.52 mmol) and 1,4-dioxane (5 mL) was heated at 60° C. for 2 hours under a nitrogen atmosphere. The solvent was removed under reduced pressure to give the desired compound (271 mg, 72%).

(c) N-(3-((2,3-Dihydro-1H-inden-2-yl)amino)-2-hydroxypropyl)-4-(morpholine-4-carbonyl)benzamide (2)

N-(3-amino-2-hydroxypropyl)-4-(morpholine-4-carbonyl)benzamide hydrochloride A2 (about 200 mg) was dissolved in methanol (6 mL) and applied to an SCX cartridge (5 g). The cartridge was washed with methanol (40 mL) and eluted with 2 M ammonia in methanol (20 mL). The ammonia wash was concentrated to give the free base (163 mg, 0.53 mmol). The material was dissolved in 1,2-dichloroethane (10 mL) and THF (5 mL) and diisopropylethyl amine (92.4 μL, 0.53 mmol) was added. To the resulting solution, was added 2-indanone (76.5 mg, 0.18 mmol), sodium triacetoxyborohydride (592 g, 2.65 mmol, 95%) and glacial acetic acid (61 μL, 1.06 mmol). The mixture was stirred at room temperature for 20 hours under a nitrogen atmosphere. The solution was made basic using 10 M aqueous NaOH, then water (15 mL) and ethyl acetate (15 mL) were added. The aqueous phase was extracted with ethyl acetate (2×20 mL) and the combined organic extracts were washed with water (20 mL), brine (20 mL), dried (sodium sulfate), filtered and concentrated in vacuo. The material was purified by column chromatography (SiO$_2$, 0-20% methanol/DCM) to give the desired compound (77 mg, 34%); $^1$H NMR (300 MHz, CDCl$_3$) 7.83 (d, J=8.4 Hz, 2H), 7.64 (m, 1H), 7.40 (d, J=8.4 Hz, 2H), 7.17 (m, 4H), 3.92 (br m, 3H), 3.77 (m, 3H), 3.66 (m, 4H), 3.45-3.37 (m, 3H), 3.19 (dd, J=15.7, 7.2 Hz, 2H), 2.96-2.84 (m, 3H), 2.73 (dd, J=12.2, 7.6 Hz, 1H). LCMS-D: RT 4.15 min; m/z 424.3 [M+H]$^+$.

Example 3: (R)—N-(3-((2,3-Dihydro-1H-inden-2-yl)amino)-2-hydroxypropyl)-4-methyl-2-(4-(trifluoromethyl)phenyl)thiazole-5-carboxamide (3)

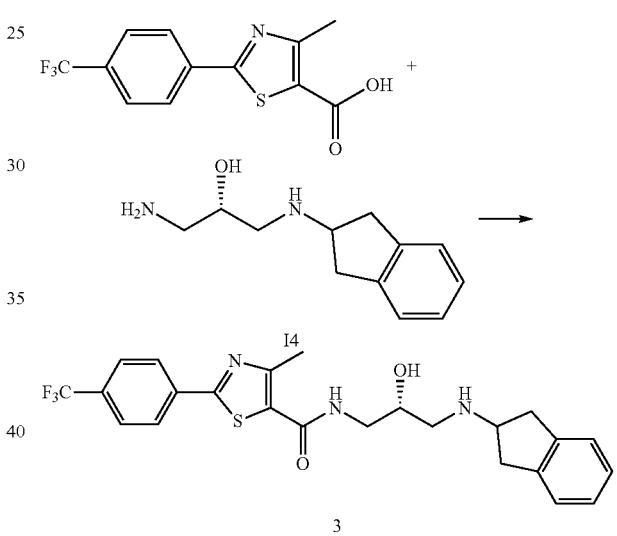

A solution of 4-methyl-2-(4-(trifluoromethyl)phenyl)-1,3-thiazole-5-carboxylic acid (101 mg, 0.352 mmol) in DCM (4.0 mL) containing N,N-diisopropylethylamine (0.184 mL, 1.06 mmol), N-ethyl-N'-(3-dimethylaminopropyl)carbodiimide hydrochloride (88 mg, 0.46 mmol) and 1-hydroxybenzotriazole hydrate (70 mg, 0.46 mmol) was stirred for 20 minutes. 1-Amino-3-((2,3-dihydro-1H-inden-2-yl)amino)propan-2-ol I4 (65 mg, 0.32 mmol) in DCM (1 mL) was added and the mixture was stirred at room temperature for 24 hours under a nitrogen atmosphere. Water (15 mL) and DCM (15 mL) were added. The aqueous phase was extracted with DCM (2×15 mL) and the combined organic extracts were washed with brine (20 mL), dried (sodium sulfate), filtered and concentrated in vacuo. The residue was dissolved in methanol and applied to an SCX cartridge (1 g). The cartridge was washed with methanol (10 mL) and eluted with 2M ammonia in ethanol (10 mL). The ammonia solution was concentrated under vacuum and the residue purified by preparative HPLC to afford the desired compound (67 mg, 40%); $^1$H NMR (300 MHz, d$_4$-methanol) δ 8.51 (br s, 1H), 8.12 (d, J=8.8 Hz, 2H), 7.77 (d, J=8.8 Hz, 2H), 7.26-7.16 (m, 4H), 4.11 (m, 2H), 3.57-3.47 (m, 2H), 3.44-

3.35 (m, 2H), 3.25-3.11 (m, 3H), 3.10-2.99 (m, 1H), 2.69 (s, 3H). LCMS Method-D: RT 5.42 min; m/z 476.19 [M+H]$^+$.

Example 4

General Procedure A

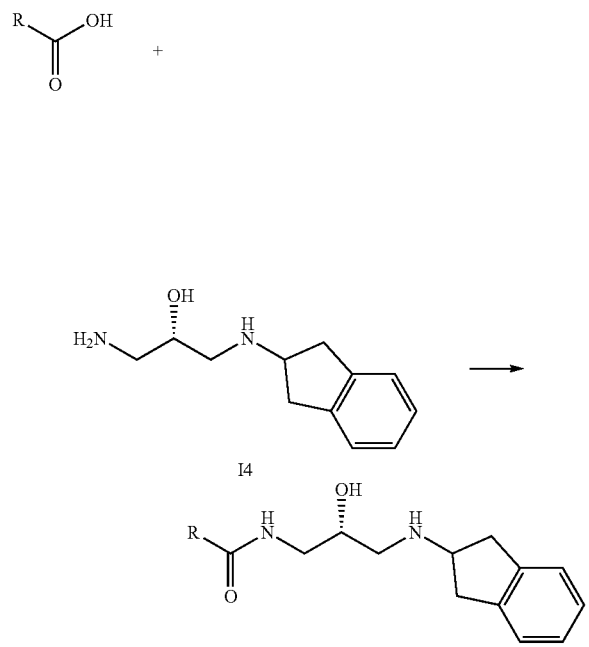

A solution of appropriate carboxylic acid (0.220 mmol-0.590 mmol, 1 equiv.) in DCM (2-10 mL) containing N,N-diisopropylethylamine (3 equiv.), N-ethyl-N'-(3-dimethylaminopropyl)carbodiimide hydrochloride (1.3 equiv.) and 1-hydroxybenzotriazole hydrate (1.3 equiv.) was stirred for 20 minutes. (S)-1-amino-3-((2,3-dihydro-1H-inden-2-yl)amino)propan-2-ol I4 (0.9 equiv.) in DCM (1 mL) was added and the mixture was stirred at room temperature for 24 hours under a nitrogen atmosphere. Water (15 mL) and DCM (15 mL) were added. The aqueous phase was extracted with DCM (2×15 mL) and the combined organic extracts were washed with brine (20 mL), dried (sodium sulfate), filtered and concentrated in vacuo. The residue was dissolved in methanol and applied to an SCX cartridge (1 g). The cartridge was washed with methanol (10 mL) and eluted with 2 M ammonia in ethanol (10 mL). The ammonia solution was concentrated under vacuum and the residue purified by preparative-HPLC (Waters) to afford the desired compound.

General Procedure B

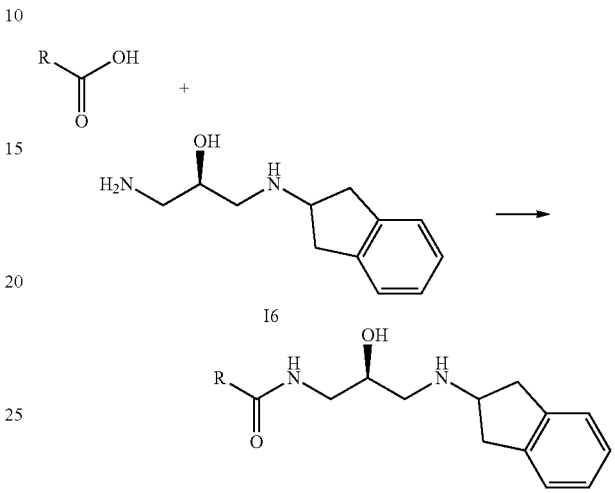

A solution of appropriate carboxylic acid (0.209-0.889 mmol, 1 equiv.) in DCM (2-10 mL) containing N,N-diisopropylethylamine (3 equiv.), N-ethyl-N'-(3-dimethylaminopropyl)carbodiimide hydrochloride (1.3 equiv.) and 1-hydroxybenzotriazole hydrate (1.3 equiv.) was stirred for 20 minutes. (S)-1-Amino-3-((2,3-dihydro-1H-inden-2-yl)amino)propan-2-ol I6 (0.9 equiv.) in DCM (1 mL) was added and the mixture was stirred at room temperature for 24 hours under a nitrogen atmosphere. Water (10 mL) and DCM (10 mL) were added. The aqueous phase was extracted with DCM (2×10 mL) and the combined organic extracts were washed with brine (15 mL), dried (sodium sulfate), filtered and concentrated in vacuo. The residue was dissolved in methanol and applied to an SCX cartridge (1 g). The cartridge was washed with methanol (10 mL) and eluted with 2 M ammonia in ethanol (10 mL). The ammonia solution was concentrated under vacuum and the residue purified by preparative-HPLC (Waters) to afford the desired compound.

| Starting Material | Structure | LCMS | Method |
|---|---|---|---|
| 4![pyrazole-COOH structure] 52.5 mg, 0.279 mmol | ![product structure] (R)-N-(3-((2,3-Dihydro-1H-inden-2-yl)amino)-2-hydroxypropyl)-1-phenyl-1H-pyrazole-4-carboxamide | LCMS Method-D: RT 4.77 min; m/z 377.3 [M + H]$^+$ | A Reaction solvent: DCM (2.0 mL) |

| Starting Material | Structure | LCMS | Method |
|---|---|---|---|
| 5 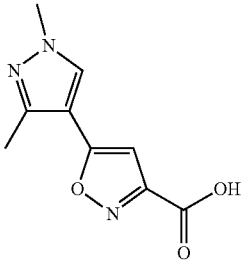<br>101 mg, 0.487 mmol | 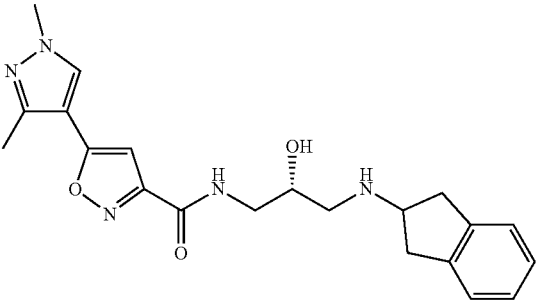 [SMILES: Cc1nn(C)cc1-c1cc(C(=O)NC[C@H](O)CNC2Cc3ccccc3C2)no1]<br>(R)-N-(3-((2,3-Dihydro-1H-inden-2-yl)amino)-2-hydroxypropyl)-5-(1,3-dimethyl-1H-pyrazol-4-yl)isoxazole-3-carboxamide | LCMS Method-D: RT 4.40 min; m/z 396.30 [M + H]⁺. | A Reaction solvent: DCM (4.0 mL) |
| 6 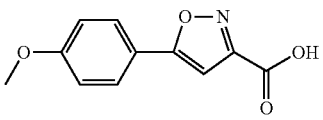<br>103 mg, 0.470 mmol | 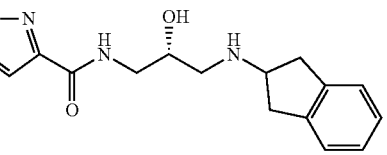<br>(R)-N-(3-((2,3-Dihydro-1H-inden-2-yl)amino)-2-hydroxypropyl)-5-(4-methoxyphenyl)isoxazole-3-carboxamide | LCMS Method-D: RT 4.98 min; m/z 408.34 [M + H]⁺. | A Reaction solvent: DCM (4.0 mL) |
| 7 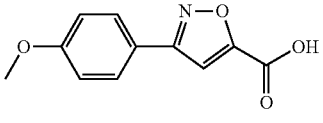<br>134 mg, 0.611 mmol | 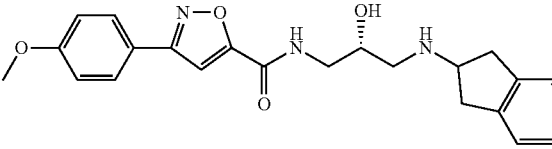<br>(R)-N-(3-((2,3-Dihydro-1H-inden-2-yl)amino)-2-hydroxypropyl)-3-(4-methoxyphenyl)isoxazole-5-carboxamide | LCMS Method-D: RT 4.95 min; m/z 407.34 [M + H]⁺. | A Reaction solvent: DCM (5.0 mL) |
| 8 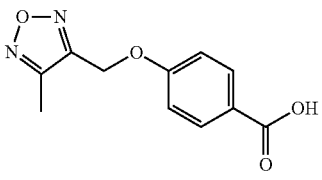<br>52.0 mg, 0.222 mmol | 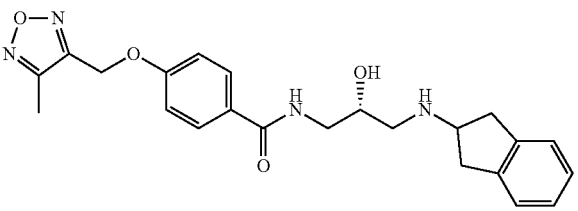 [SMILES: Cc1nonc1COc1ccc(C(=O)NC[C@H](O)CNC2Cc3ccccc3C2)cc1]<br>(R)-N-(3-((2,3-Dihydro-1H-inden-2-yl)amino)-2-hydroxypropyl)-4-((4-methyl-1,2,5-oxadiazol-3-yl)methoxy)benzamide | LCMS Method-D: RT 4.68 min; m/z 423.33 [M + H]⁺. | A Reaction solvent: DCM (2.0 mL) |
| 9 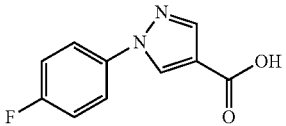 [SMILES: O=C(O)c1cnn(-c2ccc(F)cc2)c1]<br>105 mg, 0.509 mmol | 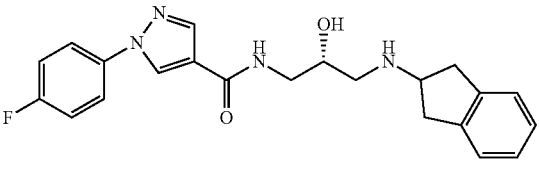 [SMILES: O=C(NC[C@H](O)CNC1Cc2ccccc2C1)c1cnn(-c2ccc(F)cc2)c1]<br>(R)-N-(3-((2,3-Dihydro-1H-inden-2-yl)amino)-2-hydroxypropyl)-1-(4-fluorophenyl)-1H-pyrazole-4-carboxamide | LCMS Method-D: RT 4.90 min; m/z 395.4 [M + H]⁺. | A Reaction solvent: DCM (4.0 mL) |

| Starting Material | Structure | LCMS | Method |
|---|---|---|---|
| 10 (3-chlorophenyl pyrazole-4-carboxylic acid)<br>51.0 mg, 0.229 mmol | (R)-1-(3-Chlorophenyl)-N-(3-((2,3-dihydro-1H-inden-2-yl)amino)-2-hydroxypropyl)-1H-pyrazole-4-carboxamide | LCMS Method-D: RT 5.12 min; m/z 411.3 [M + H]$^+$. | A Reaction solvent: DCM (2.0 mL) |
| 11 (6-morpholinonicotinic acid)<br>100 mg, 0.480 mmol | (R)-N-(3-((2,3-Dihydro-1H-inden-2-yl)amino)-2-hydroxypropyl)-6-morpholinonicotinamide | LCMS Method-D: RT 4.03 min; m/z 397.2 [M + H]$^+$. | A Reaction solvent: DCM (4.0 mL) |
| 12 (4-(5-methyl-1,3,4-oxadiazol-2-yl)benzoic acid)<br>58.0 mg, 0.284 mmol | (R)-N-(3-((2,3-Dihydro-1H-inden-2-yl)amino)-2-hydroxypropyl)-4-(5-methyl-1,3,4-oxadiazol-2-yl)benzamide | LCMS Method-D: RT 4.33 min; m/z 393.3 [M + H]$^+$. | A Reaction solvent: DCM (4.0 mL) |
| 13 (4-((1-methyl-1H-pyrazol-4-yl)oxy)benzoic acid)<br>100 mg, 0.458 mmol | (R)-N-(3-((2,3-Dihydro-1H-inden-2-yl)amino)-2-hydroxypropyl)-4-((1-methyl-1H-pyrazol-4-yl)oxy)benzamide | LCMS Method-D: RT 4.55 min; m/z 407.3 [M + H]$^+$. | A Reaction solvent: DCM (4.0 mL) |
| 14 (4-chlorobenzoic acid)<br>108 mg, 0.690 mmol | (S)-4-Chloro-N-(3-((2,3-dihydro-1H-inden-2-yl)amino)-2-hydroxypropyl)benzamide | LCMS Method-D: RT 4.83 min; m/z 345.3 [M + H]$^+$. | B Reaction solvent: DCM (10 mL) |

-continued

| Starting Material | Structure | LCMS | Method |
|---|---|---|---|
| 15 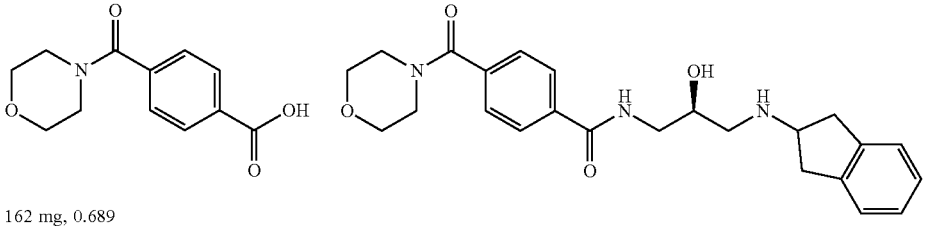<br>162 mg, 0.689 mmol | 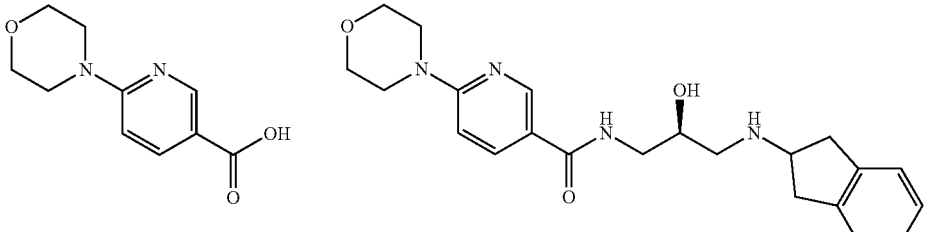<br>(S)-N-(3-((2,3-Dihydro-1H-inden-2-yl)amino)-2-hydroxypropyl)-4-(morpholine-4-carbonyl)benzamide | LCMS Method-D: RT 4.17 min; m/z 424.3 [M + H]+. | B Reaction solvent: DCM (7 mL) |
| 16 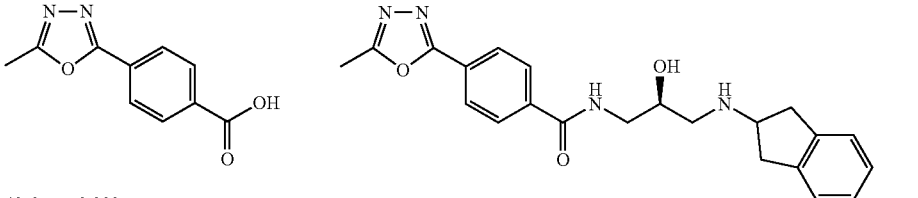<br>185 mg, 0.889 mmol | 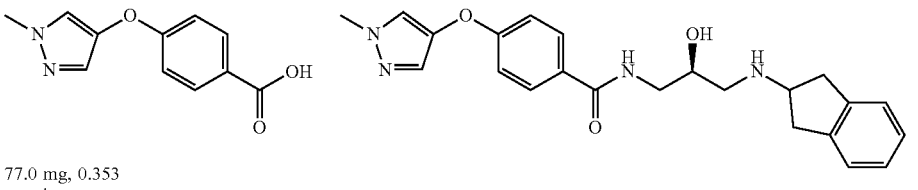<br>(S)-N-(3-((2,3-Dihydro-1H-inden-2-yl)amino)-2-hydroxypropyl)-6-morpholinonicotinamide | LCMS Method-D: RT 4.13 min; m/z 397.4 [M + H]+. | B Reaction solvent: DCM (7.0 mL) |
| 17 <br>42.6 mg, 0.209 mmol | (S)-N-(3-((2,3-Dihydro-1H-inden-2-yl)amino)-2-hydroxypropyl)-4-(5-methyl-1,3,4-oxadiazol-2-yl)benzamide | LCMS Method-D: RT 4.33 min; m/z 393.3 [M + H]+. | B Reaction solvent: DCM (5.0 mL) |
| 18 <br>77.0 mg, 0.353 mmol | (S)-N-(3-((2,3-dihydro-1H-inden-2-yl)amino)-2-hydroxypropyl)-4-((1-methyl-1H-pyrazol-4-yl)oxy)benzamide | LCMS Method-D: RT 4.57 min; m/z 407.4 [M + H]+. | B Reaction solvent: DCM (7.0 mL) |

Example 5: 4-((3-((2,3-Dihydro-1H-inden-2-yl)amino)-2-hydroxypropyl)carbamoyl)benzoic acid (19)

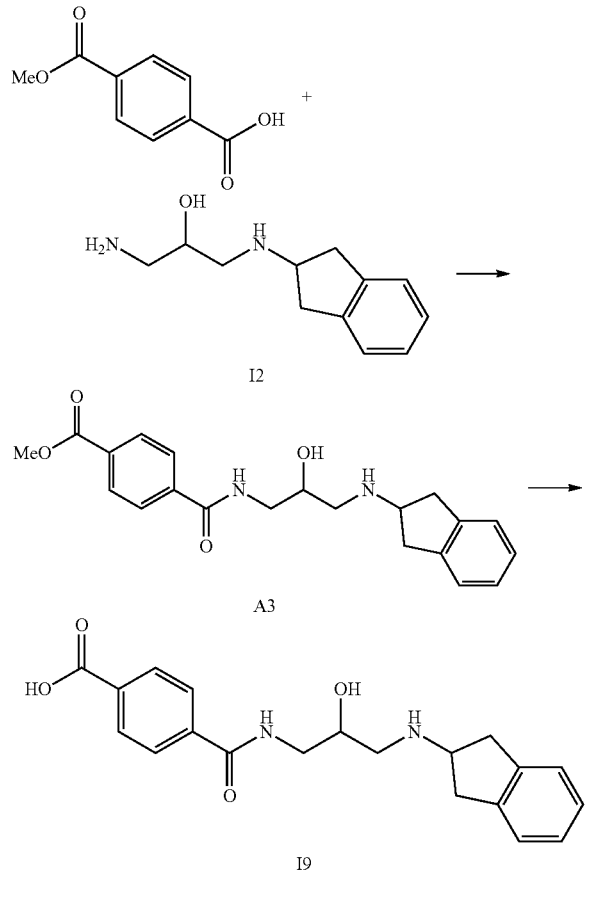

(a) Methyl 4-((3-((2,3-dihydro-1H-inden-2-yl)amino)-2-hydroxypropyl)carbamoyl)benzoate (A3)

A solution of 4-(methoxycarbonyl)benzoic acid (1.95 g, 10.8 mmol) in DCM (15 mL) containing N,N-diisopropylethylamine (11.5 mL, 66.2 mmol), N-ethyl-N'-(3-dimethylaminopropyl)carbodiimide hydrochloride (5.50 g, 28.7 mmol) and 1-hydroxybenzotriazole hydrate (4.39 g, 28.7 mmol) was stirred for 20 minutes. 1-Amino-3-((2,3-dihydro-1H-inden-2-yl)amino)propan-2-ol (I2) (2.10 g, 10.2 mmol) in DCM (1 mL) was added and the mixture was stirred at room temperature for 24 hours under a nitrogen atmosphere. Water (10 mL) and DCM (10 mL) were added. The aqueous phase was extracted with DCM (2×10 mL) and the combined organic extracts were washed with brine (15 mL), dried (sodium sulfate), filtered and concentrated in vacuo. The residue was dissolved in methanol (7 mL) and loaded on to an SCX cartridge. The cartridge was washed with methanol (30 mL) and eluted with 2 M ammonia in ethanol (20 mL). The ammonia solution was concentrated under vacuum and the residue was purified by column chromatography (SiO$_2$, 0-30% ethyl methanol/DCM) to give desired compound (644 mg, 16%): LCMS Method-D: RT 4.57 min; m/z 369.3 [M+H]$^+$.

(b) 4-((3-((2,3-Dihydro-1H-inden-2-yl)amino)-2-hydroxypropyl)carbamoyl)benzoic acid (19)

To a solution of methyl 4-((3-((2,3-dihydro-1H-inden-2-yl)amino)-2-hydroxypropyl)carbamoyl) benzoate A3 (481 mg, 1.31 mmol) in THF (15 mL) and water (6 mL) was added LiOH (47 mg, 1.96 mmol) in water (1 mL). The reaction was stirred at room temperature overnight. The reaction mixture was concentrated under reduced pressure and dissolved in water (2 mL). The material was applied to a desalting column (10 g, Phenomenex, Strata-XL Polymeric reversed phase). The column was washed with water (20 mL) and eluted with methanol (20 mL). The methanol eluate was concentrated to give the desired compound (395 mg, 85%). LCMS Method-D: RT 4.17 min; m/z 355.4 [M+H]$^+$.

Example 6: 4-(Azetidine-1-carbonyl)-N-(3-((2,3-dihydro-1H-inden-2-yl)amino)-2-hydroxypropyl)benzamide (20)

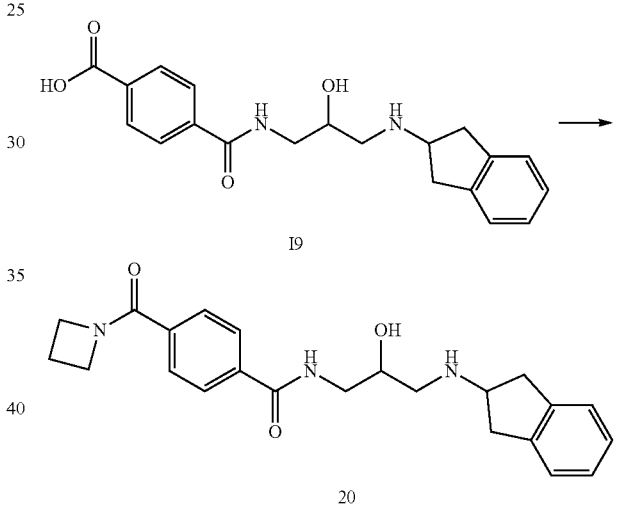

A solution of 4-((3-((2,3-dihydro-1H-inden-2-yl)amino)-2-hydroxypropyl)carbamoyl)benzoic acid 19 (95 mg, 0.27 mmol) in DCM (7 mL) containing N,N-diisopropylethylamine (201 µL, 1.15 mmol), N-ethyl-N'-(3-dimethylaminopropyl)carbodiimide hydrochloride (67 mg, 0.35 mmol) and 1-hydroxybenzotriazole hydrate (54 mg, 0.35 mmol) was stirred for 20 minutes. Azetidine (18 µL, 0.27 mmol) was added and the mixture was stirred at room temperature for 24 hours under a nitrogen atmosphere. Water (10 mL) and DCM (10 mL) were added. The aqueous phase was extracted with DCM (2×10 mL) and the combined organic extracts were washed with brine (15 mL), dried (sodium sulfate), filtered and concentrated in vacuo. The residue was purified by preparative HPLC to give the desired compound (32 mg, 30%); $^1$H NMR (300 MHz, d$_4$-methanol) δ 8.43 (br s, 1H), 7.95 (m, 2H), 7.73 (m, 2H), 7.29-7.19 (m, 4H), 4.38 (t, J=7.7 Hz, 2H), 4.24-4.08 (m, 4H), 3.61-3.50 (m, 2H), 3.47-3.38 (m, 2H), 3.29-3.13 (m, partially obscured by solvent), 3.10-3.03 (m, 1H). LCMS Method-D: RT 4.22 min; m/z 394.4 [M+H]$^+$.

Example 7: N-(3-((2,3-Dihydro-1H-inden-2-yl)amino)-2-hydroxypropyl)-4-(pyrrolidine-1-carbonyl)benzamide (21)

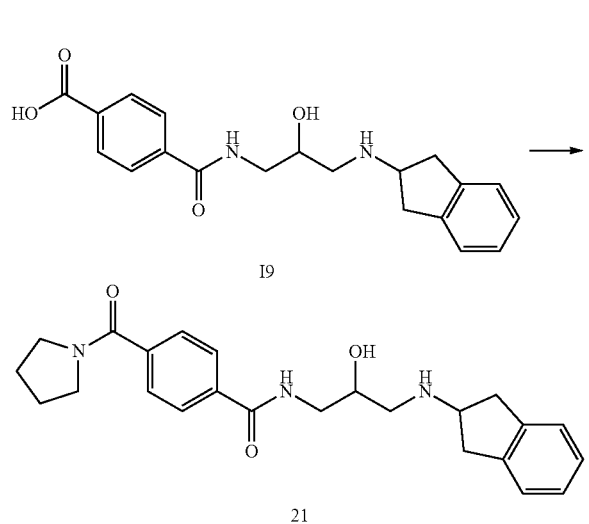

A solution of 4-((3-((2,3-dihydro-1H-inden-2-yl)amino)-2-hydroxypropyl)carbamoyl)benzoic acid I9 (102 mg, 0.29 mmol) in DCM (7 mL) containing N,N-diisopropylethylamine (201 µL, 1.15 mmol), N-ethyl-N'-(3-dimethylaminopropyl)carbodiimide hydrochloride (72 mg, 0.37 mmol) and 1-hydroxybenzotriazole hydrate (57 mg, 0.37 mmol) was stirred for 20 minutes. Pyrrolidine (24 µL, 0.29 mmol) was added and the mixture was stirred at room temperature for 24 hours under a nitrogen atmosphere. Water (10 mL) and DCM (10 mL) were added. The aqueous phase was extracted with DCM (2×10 mL) and the combined organic extracts were washed with brine (15 mL), dried (sodium sulfate), filtered and concentrated in vacuo. The material was dissolved in DCM (7 mL) containing N,N-diisopropylethylamine (201 µL, 1.15 mmol), N-ethyl-N'-(3-dimethylaminopropyl)carbodiimide hydrochloride (72 mg, 0.37 mmol) and 1-hydroxybenzotriazole hydrate (57 mg, 0.37 mmol). The mixture was stirred for 20 minutes. Pyrrolidine (119 µL, 1.44 mmol) was added and the mixture was stirred at room temperature for 24 hours under a nitrogen atmosphere. Water (10 mL) and DCM (10 mL) were added. The aqueous phase was extracted with DCM (2×10 mL) and the combined organic extracts were washed with brine (15 mL), dried (sodium sulfate), filtered and concentrated in vacuo. The residue was purified by preparative HPLC to give the desired compound (7 mg, 6%); $^1$H NMR (300 MHz, d$_4$-methanol) δ 8.54 (br s, 1H), 7.94 (d, J=8.1 Hz, 2H), 7.63 (d, J=8.0 Hz, 2H), 7.29-7.19 (m, 4H), 4.11 (m, 2H), 3.64 (m, 2H), 3.53 (m, 2H), 3.47-3.38 (m, 4H), 3.28-3.00 (m, 4H), 2.09-1.89 (m, 4H). LCMS Method-D: RT 4.37 min; m/z 408.4 [M+H]$^+$.

Example 8: N-(3-((2,3-Dihydro-1H-inden-2-yl)amino)-2-hydroxypropyl)-4-(piperidine-1-carbonyl)benzamide (22)

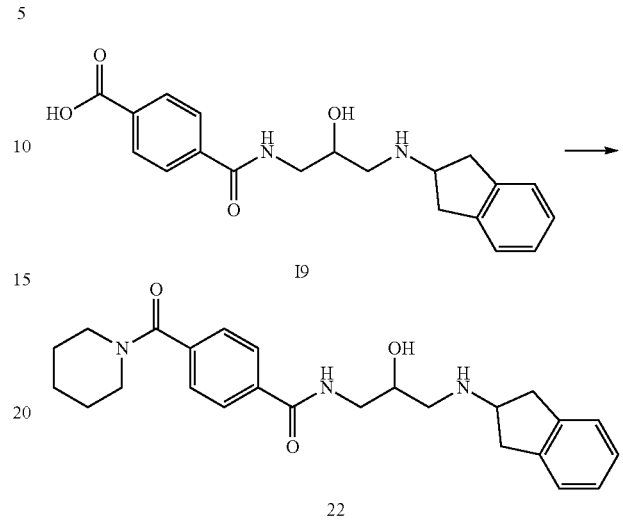

A solution of 4-((3-((2,3-dihydro-1H-inden-2-yl)amino)-2-hydroxypropyl)carbamoyl)benzoic acid 19 (105 mg, 0.296 mmol) in DCM (7 mL) containing N,N-diisopropylethylamine (206 µL, 1.19 mmol), N-ethyl-N'-(3-dimethylaminopropyl)carbodiimide hydrochloride (74 mg, 0.39 mmol) and 1-hydroxybenzotriazole hydrate (59 mg, 0.39 mmol) was stirred for 20 minutes. Piperidine (29 µL, 0.30 mmol) was added and the mixture was stirred at room temperature for 24 hours under a nitrogen atmosphere. Water (10 mL) and DCM (10 mL) were added. The aqueous phase was extracted with DCM (2×10 mL) and the combined organic extracts were washed with brine (15 mL), dried (sodium sulfate), filtered and concentrated in vacuo. The residue was purified by preparative HPLC to give the desired compound (76 mg, 61%). $^1$H NMR (300 MHz, d$_4$-methanol) δ 8.39 (br s, 1H), 7.95 (m, 2H), 7.51 (m, 2H), 7.29-7.19 (m, 4H), 4.14 (m, 2H), 3.74 (m, 2H), 3.62-3.51 (m, 2H), 3.49-3.42 (m, 2H), 3.40-3.37 (m, 2H), 3.29-3.13 (m, 3H), 3.10-3.03 (m, 1H), 1.72 (br m, 4H), 1.56 (br m, 2H); LCMS Method-D: RT 4.58 min; m/z 422.3 [M+H]$^+$.

Example 9: N-(3-((2,3-Dihydro-1H-inden-2-yl)amino)-2-hydroxypropyl)-[1,1'-biphenyl]-4-carboxamide (24)

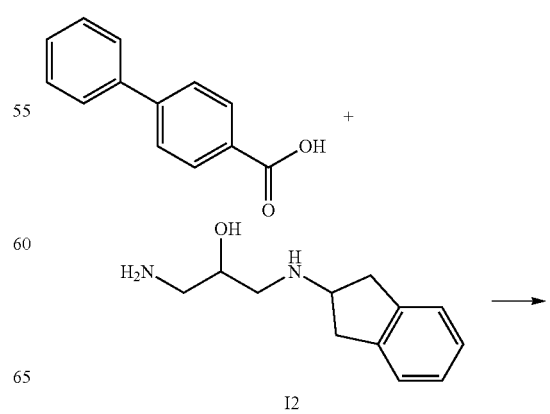

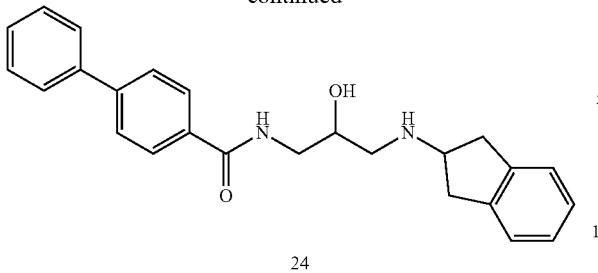

24

A solution of 4-biphenylcarboxylic acid (0.074 g, 0.37 mmol) in DCM (4 mL) containing N,N-diisopropylethylamine (0.132 mL, 1.01 mmol), N-ethyl-N'-(3-dimethylaminopropyl)carbodiimide hydrochloride (0.098 g, 0.51 mmol) and 1-hydroxybenzotriazole hydrate (wetted with not less than 20 wt. % water, 0.098 g, 0.509 mmol) was stirred at room temperature for 20 minutes. A solution of 1-amino-3-((2,3-dihydro-1H-inden-2-yl)amino)propan-2-ol I2 (0.070 g, 0.339 mmol) in DCM (2 mL) was added. The mixture was then stirred at room temperature for 20 hours whilst under a nitrogen atmosphere. Water was added and the resulting mixture formed a white precipitate which was filtered and dried. The white solid was washed with diethyl ether and collected by filtration to give the desired compound as an amorphous white solid (0.105 g, 80%). LCMS Method-D: RT 5.28 min; m/z 387.4 [M+H]$^+$.

Example 10: N-(3-((2,3-Dihydro-1H-inden-2-yl)amino)-2-hydroxypropyl)[1,1'-biphenyl]-3-carboxamide (25)

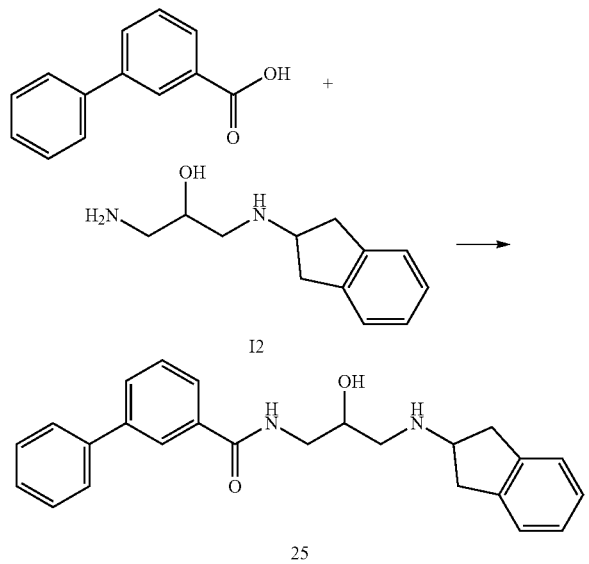

25

A solution of 3-biphenylcarboxylic acid (0.074 g, 0.37 mmol) in DCM (4 mL) containing N,N-diisopropylethylamine (0.132 mL, 1.01 mmol), N-ethyl-N'-(3-dimethylaminopropyl)carbodiimide hydrochloride (0.098 g, 0.51 mmol) and 1-hydroxybenzotriazole hydrate (wetted with not less than 20 wt. % water, 0.098 g, 0.51 mmol) was stirred at room temperature for 20 minutes. A solution of 1-amino-3-((2,3-dihydro-1H-inden-2-yl)amino)propan-2-ol I2 (0.070 g, 0.34 mmol) in DCM (2 mL) was added. The mixture was stirred at room temperature for 20 hours under a nitrogen atmosphere. Water and DCM were added. The aqueous phase was extracted with DCM (2×15 mL) and the combined organic extracts were washed with brine, dried (magnesium sulfate), filtered and concentrated under reduced pressure. The product was purified by column chromatography (12 g SiO$_2$ cartridge, 0-10% methanol in DCM) to give the desired product as an amorphous white solid (0.026 g, 19%). LCMS Method-D: RT 5.28 min; m/z 387.4 [M+H]$^+$.

Example 11: N-(3-((2,3-Dihydro-1H-inden-2-yl)amino)-2-hydroxypropyl)-[1,1'-biphenyl]-2-carboxamide (26)

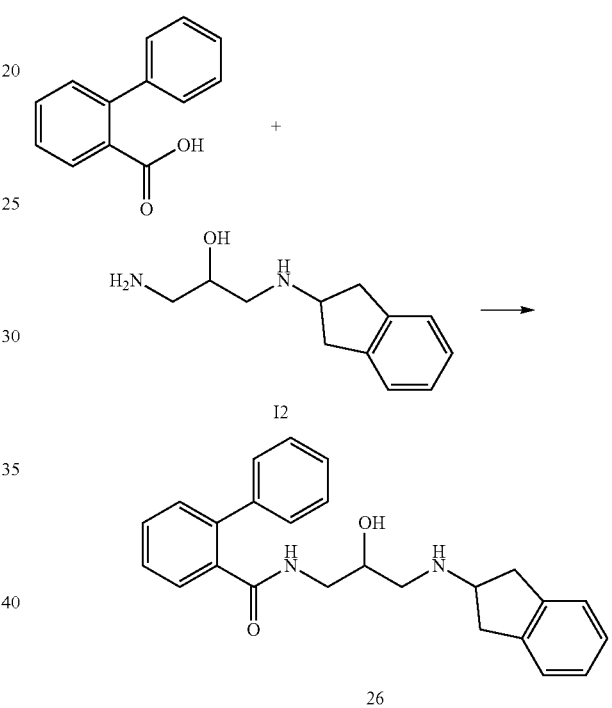

26

A solution of 2-biphenylcarboxylic acid (0.074 g, 0.373 mmol) in DCM (4 mL) containing N,N-diisopropylethylamine (0.132 mL, 1.01 mmol, 3 equiv.), N-ethyl-N'-(3-dimethylaminopropyl)carbodiimide hydrochloride (0.098 g, 0.509 mmol, 1.5 equiv) and 1-hydroxybenzotriazole hydrate (wetted with not less than 20 wt. % water, 0.098 g, 0.509 mmol) was stirred at room temperature for 20 minutes. After this time, a solution of 1-amino-3-((2,3-dihydro-1H-inden-2-yl)amino)propan-2-ol I2 (0.070 g, 0.339 mmol) in DCM (2 mL) was added. The mixture was then stirred at room temperature for 20 hours whilst under a nitrogen atmosphere. Water and DCM were added. The aqueous phase was extracted with DCM (2×15 mL) and the combined organic extracts were washed with brine, dried (magnesium sulfate), filtered and concentrated under reduced pressure. The product was purified by column chromatography (12 g SiO$_2$ Cartridge, 0-10% methanol in DCM) to give the desired product as an amorphous solid (0.060, 45%). LCMS Method-D: RT 4.92 min; m/z 387.3 [M+H]$^+$.

Example 12: N-(3-((2,3-Dihydro-1H-inden-2-yl)amino)-2-hydroxypropyl)-2-fluoro-4-(morpholine-4-carbonyl)benzamide (27)

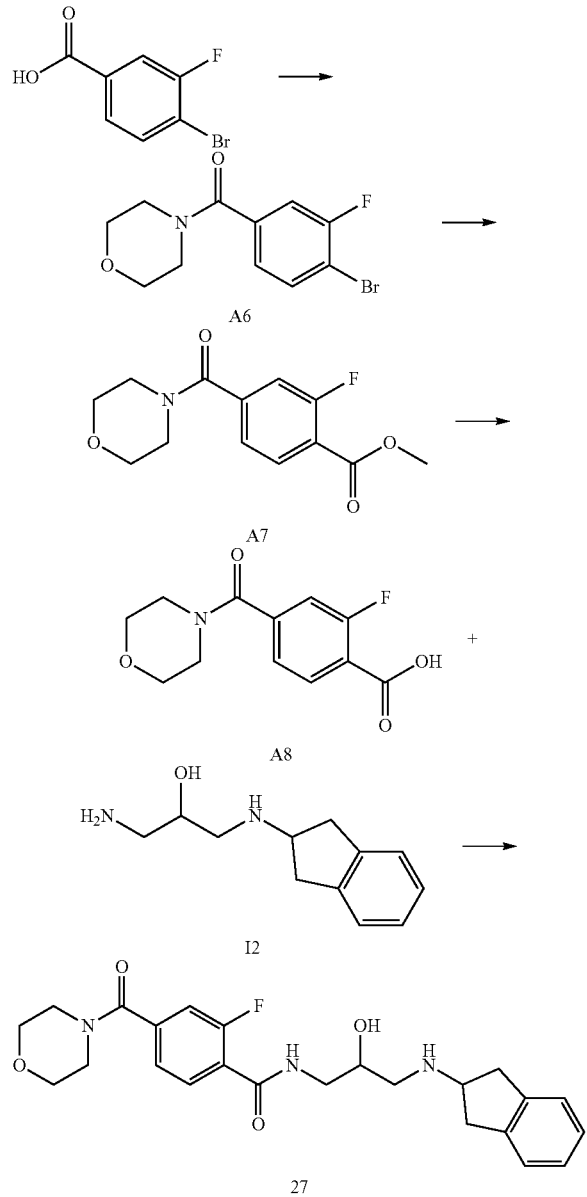

(a) (4-Bromo-3-fluorophenyl)(morpholino)methanone (A6)

4-Bromo-3-fluorobenzoic acid (2.19 g, 10.0 mmol), morpholine (2.59 mL, 30.0 mmol), DMAP (122 mg, 10 mol %) and EDCl.HCl (2.88 g, 15.0 mmol) in DCM (100 mL), were stirred at room temperature. After 17 hours, the mixture was added to 2% w/v aqueous sodium hydroxide (100 mL) and the separated aqueous phase was extracted with DCM (2×50 mL). The combined organic extracts were washed with 1 M HCl (75 mL), brine (50 mL), dried over sodium sulfate and concentrated. Chromatography (40 g silica cartridge, 0-60% ethyl acetate/petroleum benzine 40-60° C.) gave the desired compound as a colourless syrup (2.63 g, 91%): $^1$H NMR (400 MHz, CDCl$_3$) δ 7.61 (dd, J=8.1, 6.8 Hz, 1H), 7.19 (dd, J=8.5, 1.9 Hz, 1H), 7.08 (ddd, J=8.1, 1.9, 0.7 Hz, 1H), 3.70 (br s, 6H), 3.45 (br s, 2H); LCMS-B: RT 3.49 min; m/z 290.0, 288.1 [M+H]$^+$.

(b) Methyl 2-fluoro-4-(morpholine-4-carbonyl)benzoate (A7)

(4-Bromo-3-fluorophenyl)(morpholino)methanone A6 (2.62 g, 9.09 mmol), dry methanol (20 mL), PdCl$_2$(dppf).DCM (376 mg, 5 mol %) and triethylamine (2.54 mL, 18.2 mmol) were loaded into a Schlenk tube and flushed with nitrogen. The tube was flushed with carbon monoxide and the mixture brought to reflux under carbon monoxide (balloon). After 18 hours, the mixture was cooled to room temperature, filtered through Celite and the Celite washed with methanol (40 mL). The combined filtrates were concentrated and chromatography (40 g silica cartridge, 20-60% ethyl acetate/petroleum benzine 40-60° C.) gave the desired compound as a pale orange solid (2.25 g, 93%). $^1$H NMR (400 MHz, CDCl$_3$) δ 7.99 (t, J=7.3 Hz, 1H), 7.25-7.17 (m, 2H), 3.94 (s, 3H), 3.78 (br s, 4H), 3.63 (br s, 2H), 3.40 (br s, 2H); LCMS-A: RT 5.30 min; m/z 268.1 [M+H]$^+$.

(c) 2-Fluoro-4-(morpholine-4-carbonyl)benzoic acid (A8)

Methyl 2-fluoro-4-(morpholine-4-carbonyl)benzoate A7 (1.00 g, 3.74 mmol) was dissolved in THF (20 mL) and a solution of lithium hydroxide monohydrate (188 mg, 4.49 mmol) in water (10 mL) was added. The mixture was stirred vigorously at room temperature. After two hours, the volatile solvents were removed in vacuo. The aqueous residue was cooled to 4° C. and 3.0 aqueous HCl (5 mL) cooled to 4° C. was added. The resulting slurry was diluted with water (5 mL) and filtered. The collected solids were washed with water (5 mL) and air dried to give the desired compound as a white solid (817 mg, 86%). $^1$H NMR (400 MHz, d$_4$-methanol) δ 8.05-7.99 (m, 1H), 7.32 (s, 1H), 7.30 (dd, J=3.7, 1.4 Hz, 1H), 3.76 (br s, 4H), 3.63 (br s, 2H), 3.42 (br s, 2H); LCMS-B: RT 3.20 min; m/z 254.2 [M+H]$^+$; 276.2 [M+Na]$^+$.

(d) N-(3-((2,3-Dihydro-1H-inden-2-yl)amino)-2-hydroxypropyl)-2-fluoro-4-(morpholine-4-carbonyl)benzamide (27)

A mixture of 2-fluoro-4-(morpholine-4-carbonyl)benzoic acid A8 (0.057 g, 0.23 mmol) and triethylamine (0.14 mL, 0.97 mmol) in DCM (5 mL) was cooled to 0° C. under a nitrogen atmosphere and isobutyl chloroformate (32 µL, 0.24 mmol) was added dropwise. The mixture was stirred for 45 minutes at 0° C. and allowed to settle. The liquid phase was transferred via syringe to a solution of 1-amino-3-((2,3-dihydro-1H-inden-2-yl)amino)propan-2-ol I2 (0.050 g, 0.24 mmol) in DCM (10 mL) at 0° C. After 1.25 hours, the mixture was diluted with DCM (10 mL) and aqueous sodium hydroxide (2 M, 25 mL) and the separated aqueous phase was extracted with DCM (2×25 mL). The combined organic extracts were washed with brine (25 mL), dried (MgSO$_4$) and concentrated in vacuo. The residue was purified by column chromatography (24 g SiO$_2$ cartridge, 0-10% MeOH (containing 1% v/v 2 M NH$_3$ in MeOH) in DCM) to give a white solid. The solid was dissolved in a minimal amount of DCM and the product was precipitated by the addition of cyclohexane. The precipitate was vacuum filtered and air dried to give the desired compound as a white solid (0.020 g, 20%). $^1$H NMR (400 MHz, $d_6$-DMSO) δ 8.46 (t, J=5.7 Hz, 1H), 7.69 (t, J=7.5 Hz, 1H), 7.42-7.35 (m, 1H), 7.35-7.29 (m, 1H), 7.25-7.19 (m, 2H), 7.18-7.12 (m, 2H), 5.38 (s, 1H), 3.95-3.74 (m, 2H), 3.71-3.48 (m, 6H), 3.23-3.10 (m, 2H), 3.00-2.82 (m, 3H), 2.81-2.69 (m, 1H), residual $H_2O$ obscured peaks in the alkyl region; LCMS-B: RT 3.20 min; m/z 442.3 [M+H]$^+$.

Example 13: N-(3-((5-Bromo-2,3-dihydro-1H-inden-2-yl)amino)-2-hydroxypropyl)-4-chlorobenzamide (28)

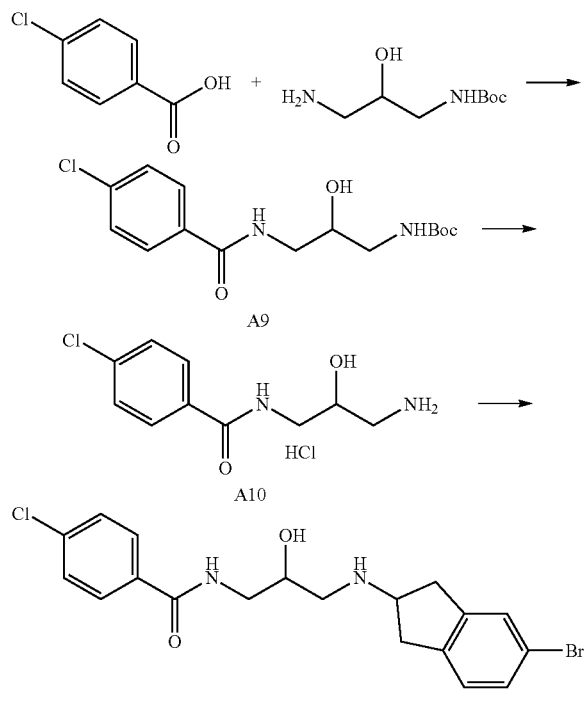

(a) tert-Butyl (3-(4-chlorobenzamido)-2-hydroxypropyl)carbamate (A9)

A solution of 4-chlorobenzoic acid (3.00 g, 19.2 mmol) in DCM (40 mL) containing N,N-diisopropylethylamine (10.01 mL, 57.5 mmol), N-ethyl-N'-(3-dimethylaminopropyl)carbodiimide hydrochloride (4.77 g, 25.0 mmol) and 1-hydroxybenzotriazole hydrate (wetted with not less than 20 wt. % water, 4.76 g, 25.0 mmol) was stirred at room temperature for 20 minutes. N-Boc-1,3-diamino-2-propanol (4.01 g, 21.1 mmol) was added and the mixture was stirred at room temperature for 20 hours under a nitrogen atmosphere. Water was added and the aqueous phase was extracted with DCM (2×20 mL). The combined organic extracts were washed with brine, dried (sodium sulfate), filtered and concentrated under reduced pressure. The material was purified using column chromatography (120 g $SiO_2$ Cartridge, 0-30% methanol in DCM) to give of the desired compound as a white foam (3.44 g, 54%). $^1$H NMR (300 MHz, $d_6$-DMSO) δ 8.47 (t, J=5.50 Hz, 1H), 7.88 (d, J=8.58 Hz, 2H), 7.54 (d, J=8.58 Hz, 2H), 6.70 (t, J=5.58 Hz, 1H), 4.93 (d, J=5.06 Hz, 1H), 3.66-3.61 (m, 1H), 3.30-3.26 (m, 1H), 3.26-3.11 (m, 1H), 3.04-2.50 (m, 2H), 1.38 (s, 9H).

(b) N-(3-Amino-2-hydroxypropyl)-4-chlorobenzamide hydrochloride (A10)

A solution of tert-butyl (3-(4-chlorobenzamido)-2-hydroxypropyl)carbamate A9 (3.44 g, 10.5 mmol) in 4.0 M hydrochloric acid in 1,4-dioxane (10.4 mL, 41.9 mmol) and 1,4-dioxane (15 mL) was heated at 50° C. for 2.5 hours. The solvent was evaporated under reduced pressure to give the desired compound product as a white foam (2.77 g, 99%). $^1$H NMR (300 MHz, $d_6$-DMSO) δ 8.80 (t, J=5.61 Hz, 1H), 7.91 (d, J=6.78 Hz, 2H), 7.55 (d, J=8.55 Hz, 2H), 3.95-3.82 (m, 1H), 3.57-3.23 (m, 5H), 3.02-2.85 (m, 1H), 2.77-2.60 (m, 1H).

(c) N-(3-((5-Bromo-2,3-dihydro-1H-inden-2-yl)amino)-2-hydroxypropyl)-4-chlorobenzamide (28)

To a solution of N-(3-amino-2-hydroxypropyl)-4-chlorobenzamide hydrochloride A10 (0.070 g, 0.26 mmol) in 1,2-dichloroethane (1 mL) and methanol (1 mL) was added N,N-diisopropylethylamine (0.046 mL, 0.26 mmol), 5-bromo-1H-inden-2 (3H)-one (0.067 g, 0.32 mmol), acetic acid (0.024 mL, 0.40 mmol), and sodium triacetoxyborohydride (0.224 g, 1.05 mmol). The reaction mixture was stirred at room temperature for 20 hours under a nitrogen atmosphere. The reaction mixture was diluted with 2.5 M aqueous sodium hydroxide and DCM. The aqueous phase was extracted with DCM (2×15 mL) and the combined organic extracts were washed with brine, dried (sodium sulfate), filtered and concentrated under reduced pressure. The material was purified by silica column chromatography (12 g $SiO_2$ Cartridge, 0-15% methanol in DCM) to give the desired compound as a light brown solid (0.040 g, 35%): LCMS RT 4.41 min; m/z 424.7 [M+H]$^+$.

Example 14: 4-Chloro-N-(4-((2,3-dihydro-1H-inden-2-yl)amino)-3-hydroxybutyl)benzamide (29)

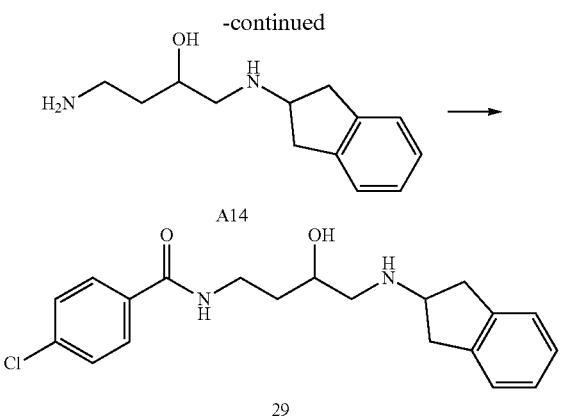

(a) 2-(But-3-en-1-yl)isoindoline-1,3-dione (A11)

A mixture of potassium phthalimide (500 mg, 2.70 mmol), acetonitrile (5 mL) and 4-bromobut-1-ene (0.548 mL, 5.40 mmol) was stirred at 90° C. After 18 hours, the mixture was cooled to room temperature, filtered and the collected solids were washed with ethyl acetate (5 mL). The combined filtrates were concentrated and column chromatography (12 g silica cartridge, 0-100% ethyl acetate/hexanes) gave the desired compound as a white solid (431 mg, 79%). $^1$H NMR (400 MHz, CDCl$_3$) δ 7.87-7.80 (m, 2H), 7.73-7.67 (m, 2H), 5.86-5.72 (m, 1H), 5.11-4.99 (m, 2H), 3.77 (t, J=7.1 Hz, 2H), 2.49-2.40 (m, 2H). LCMS-B: RT 3.71 min; m/z 202.1 [M+H]$^+$.

(b) 2-(2-(Oxiran-2-yl)ethyl)isoindoline-1,3-dione (A12)

A mixture of 2-(but-3-en-1-yl)isoindoline-1,3-dione A11 (428 mg, 2.13 mmol), chloroform (5 mL) and 70-75% mCPBA (629 mg, 2.55 mmol) was stirred at room temperature. After 18 hours, the mixture was quenched with 10% w/v aqueous sodium thiosulfate (2.5 mL) and was stirred vigorously for 5 minutes. The mixture was diluted with a saturated aqueous solution of sodium bicarbonate (5 mL), water (20 mL) and chloroform (10 mL). The separated aqueous phase was extracted with chloroform (2×10 mL). The combined organic extracts were dried over sodium sulfate and concentrated in vacuo to give the desired compound as a white solid (451 mg, 98%). The material was carried forward without further purification. $^1$H NMR (400 MHz, CDCl$_3$) δ 7.88-7.82 (m, 2H), 7.74-7.69 (m, 2H), 3.97-3.80 (m, 2H), 3.03-2.94 (m, 1H), 2.74-2.68 (m, 1H), 2.47-2.41 (m, 1H), 2.04-1.93 (m, 1H), 1.90-1.79 (m, 1H). LCMS-B: RT 3.43 min; m/z 218.1 [M+H]$^+$

(c) 2-(4-((2,3-Dihydro-1H-inden-2-yl)amino)-3-hydroxybutyl)isoindoline-1,3-dione (A13)

A mixture of 2-(2-(oxiran-2-yl)ethyl)isoindoline-1,3-dione A12 (100 mg, 0.460 mmol), dry acetonitrile (2 mL), 2-aminoindane (64 mg, 0.48 mmol) and calcium triflate (78 mg, 50 mol %) was stirred at room temperature. After two hours, the mixture was concentrated in vacuo and purified by column chromatography (12 g SiO$_2$ cartridge, 0-20% methanol/DCM) to give the desired compound as a colourless solid (139 mg, 86%). $^1$H NMR (400 MHz, DMSO) δ 7.92-7.77 (m, 2H), 7.32-7.11 (m, 6H), 4.04-3.96 (m, 1H), 3.28 (dd, J=16.6, 7.7 Hz, overlaps with solvent), 2.92 (dd, J=16.6, 5.1 Hz, 2H); LCMS-B: m/z 351.2 [M+H]$^+$.

(d) 4-Amino-1-((2,3-dihydro-1H-inden-2-yl)amino)butan-2-ol (A14)

A mixture of 2-(4-((2,3-dihydro-1H-inden-2-yl)amino)-3-hydroxybutyl)isoindoline-1,3-dione A13 (137 mg, 0.391 mmol), ethanol (2 mL) and hydrazine hydrate (0.2 mL) was stirred at 80° C. After three hours, the mixture was cooled to room temperature, the resulting slurry filtered and the collected solids washed with cold ethanol (2 mL). The combined filtrates were concentrated to give the title compound as a white solid (101 mg, >100% yield). The material was carried forward without further purification.

(e) 4-Chloro-N-(4-((2,3-dihydro-1H-inden-2-yl)amino)-3-hydroxybutyl)benzamide (29)

A mixture of 4-amino-1-((2,3-dihydro-1H-inden-2-yl)amino)butan-2-ol A14 (44 mg, 0.20 mmol), MeCN (2 mL), DIPEA (0.070 mL, 0.40 mmol) and 4-chlorobenzoyl chloride (0.026 mL, 0.20 mmol) was stirred at room temperature. After 18 hours, methanol (0.1 mL) was added and the mixture loaded onto a 5 g SCX cartridge. The cartridge was washed with methanol (40 mL) then eluted with 3.5 M ammonia in methanol (40 mL). The basic eluate was concentrated in vacuo, and preparative TLC (5% methanol/DCM) gave the desired compound as a colourless syrup (7 mg, 9% yield). $^1$H NMR (400 MHz, d$_4$-methanol) δ 7.83-7.78 (m, 2H), 7.49-7.45 (m, 2H), 7.21-7.10 (m, 4H), 3.86-3.76 (m, 1H), 3.75-3.64 (m, 1H), 3.61-3.44 (m, 2H), 3.26-3.16 (m, 2H), 2.88-2.79 (m, 3H), 2.76-2.67 (m, 1H), 1.87-1.77 (m, 1H), 1.75-1.64 (m, 1H).

Example 15: 4-Chloro-N-(2-hydroxy-3-((1,2,3,4-tetrahydronaphthalen-2-yl)amino)propyl)benzamide (30)

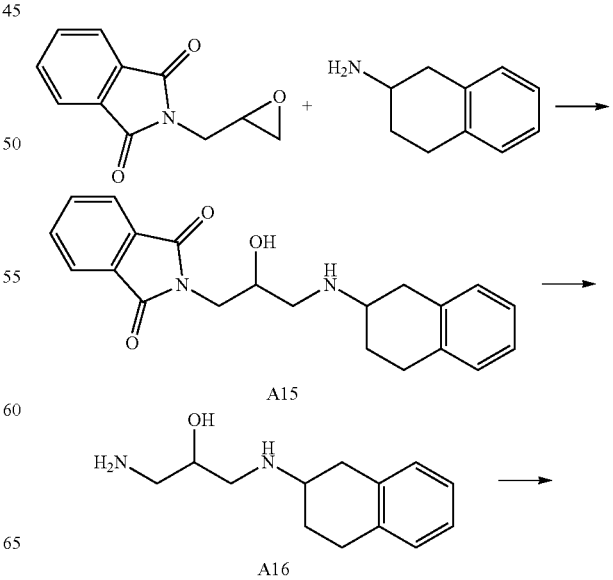

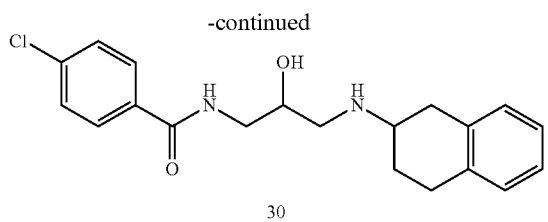

30

(a) 2-(2-Hydroxy-3-((1,2,3,4-tetrahydronaphthalen-2-yl)amino)propyl)isoindoline-1,3-dione (A15)

A mixture of N-(2,3-epoxypropyl)phthalimide (0.471 g, 2.31 mmol) and 1,2,3,4-tetrahydro-2-naphthalenamine (0.310 g, 2.10 mmol) in ethanol (3 mL) was heated at reflux for 20 hours under a nitrogen atmosphere. The volatiles were removed in vacuo. The material was adsorbed directly onto silica gel and the product was purified by column chromatography (12 g SiO$_2$ Cartridge, 0-20% methanol in DCM) to give the desired compound as a light yellow oil.

(0.267 g, 36%). LCMS-D: RT 4.95 min; m/z 351.2 [M+H]$^+$.

(b) 1-Amino-3-((1,2,3,4-tetrahydronaphthalen-2-yl)amino)propan-2-ol (A16)

A mixture of 2-(2-hydroxy-3-((1,2,3,4-tetrahydronaphthalen-2-yl)amino)propyl)isoindoline-1,3-dione A15 (0.267 g, 0.762 mmol) and hydrazine monohydrate (0.075 mL, 1.5 mmol) in ethanol (2 mL) and DCM (1 mL) was stirred at room temperature for 20 hours under a nitrogen atmosphere. The volatiles were removed by rotary evaporation. The residue was dissolved in methanol and passed through a SCX cartridge (5 g, Agilent, Bond Elut, Mega BE-SCX) washing with 100% methanol and eluting with 100% 2 M ammonia in methanol solution to give the desired compound (0.150 g, 89%). The material was used in the next step without further purification.

(c) 4-Chloro-N-(2-hydroxy-3-((1,2,3,4-tetrahydronaphthalen-2-yl)amino)propyl)benzamide (30)

A solution of 4-chlorobenzoic acid (0.117 g, 0.749 mmol) in N,N-dimethylformamide (2 mL) containing N,N-diisopropylethylamine (0.474 mL, 2.72 mmol), N-ethyl-N'-(3-dimethylaminopropyl)carbodiimide hydrochloride (0.196 g, 1.02 mmol) and 1-hydroxybenzotriazole hydrate (wetted with not less than 20 wt. % water, 0.156 g, 1.02 mmol) was stirred at room temperature for 20 minutes under a nitrogen atmosphere. A solution of 1-amino-3-((1,2,3,4-tetrahydronaphthalen-2-yl)amino)propan-2-ol A16 (0.150 g, 0.681 mmol) in N,N-dimethylformamide (2 mL) was added and stirred at room temperature for 20 hours under a nitrogen atmosphere. Water and ethyl acetate were added. The aqueous phase was extracted with ethyl acetate (2×20 mL) and the combined organic extracts were washed with water (×3), brine, dried (sodium sulfate), filtered and concentrated in vacuo to give the product. The material was adsorbed directly onto silica gel and purified by column chromatography (12 g SiO$_2$ Cartridge, 0-20% DCM in methanol) to give the desired compound as an amorphous white solid (0.075 g, 30%) $^1$H NMR (300 MHz, d$_4$-methanol) δ 7.83 (d, J=8.55 Hz, 2H), 7.49 (d, J=8.55 Hz, 2H), 7.06 (br. s., 4H), 3.99-3.95 (m, 1H), 3.50-3.48 (m, 2H), 3.10-2.58 (m, 7H), 2.15-2.11 (m, 1H), 1.68-1.61 (m, 1H). LCMS-D: RT 3.63 min; m/z 359.3 [M+H]$^+$.

Example 16: 4-Chloro-N-(3-((7-fluoro-1,2,3,4-tetrahydronaphthalen-2-yl)amino)-2-hydroxypropyl)benzamide (31)

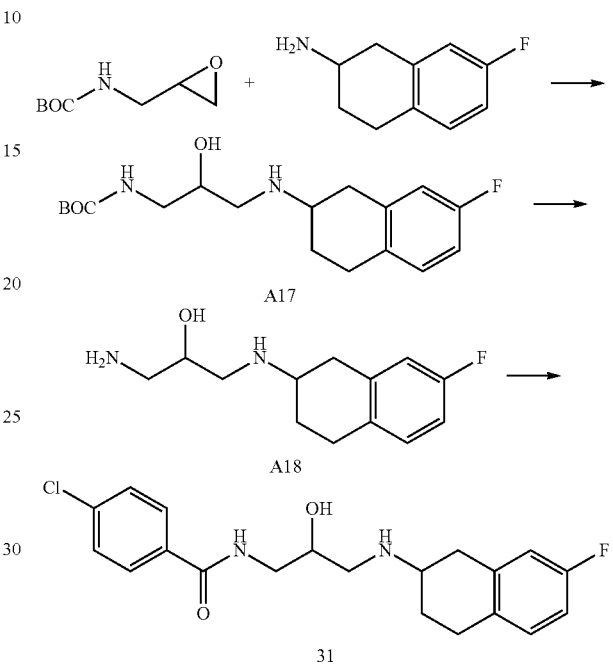

(a) tert-Butyl (3-((7-fluoro-1,2,3,4-tetrahydronaphthalen-2-yl)amino)-2-hydroxypropyl)carbamate (A17)

7-Fluoro-1,2,3,4-tetrahydro-napthalene-2-ylamine hydrochloride (120 mg) was neutralised by adding 10% w/v NaOH (aq.) (5 mL) and DCM (5 mL) to the salt. The phases were separated and the aqueous phase was extracted with DCM (3×10 mL). The combined organic phases were dried with sodium sulfate and concentrated under reduced pressure to give the free amine (76 mg) as an oil. To a solution of 7-fluoro-1,2,3,4-tetrahydro-napthalene-2-ylamine (76 mg, 0.46 mmol) in dry acetonitrile (1.5 mL) was added tert-butyl N-(oxiran-2-yl methyl) carbamate (159 mg, 0.92 mmol). The flask was sealed and the reaction was allowed to stir at 80° C. overnight. The reaction mixture was concentrated under reduced pressure and the residue was dissolved in methanol and applied to an SCX cartridge (5 g). The cartridge was washed with methanol (25 mL) and eluted with 2 M ammonia in methanol (15 mL). The volatiles were removed under vacuum to afford the desired compound (131 mg, 84%). The material was taken onto the next step without further purification.

(b) 1-Amino-3-((7-fluoro-1,2,3,4-tetrahydronaphthalen-2-yl)amino)propan-2-ol (A18)

tert-Butyl (3-((7-fluoro-1,2,3,4-tetrahydronaphthalen-2-yl)amino)-2-hydroxypropyl)carbamate A17 (131 mg, 0.39 mmol) was dissolved in DCM (7 mL) and to the solution was added TFA (0.531 mL, 7.74 mmol). The reaction was stirred at room temperature under a nitrogen atmosphere overnight and the solvent was removed under reduced pressure. The resulting oil was dissolved in methanol (7 mL) and applied to an SCX cartridge. The cartridge was washed with methanol (25 mL) and eluted with 2 M ammonia in ethanol (15 mL). The ammonia eluate was concentrated under vacuum to give the desired compound (91 mg, 99%); $^1$H NMR (300 MHz, CDCl$_3$) δ 7.01 (m, 1H), 6.82-6.72 (m, 2H), 3.68 (m, 1H), 3.02-2.50 (m, 11H), 2.01 (m, 1H), 1.59 (m, 1H).

(c) 4-Chloro-N-(3-((7-fluoro-1,2,3,4-tetrahydronaphthalen-2-yl)amino)-2-hydroxypropyl)benzamide (31)

To a solution of 4-chlorobenzoic acid (66 mg, 0.42 mmol) in DCM (7.0 mL) was added N,N-diisopropylethylamine (221 μL, 1.27 mmol), N-ethyl-N'-(3-dimethylaminopropyl)carbodiimide hydrochloride (106 mg, 0.552 mmol) and 1-hydroxybenzotriazole hydrate (84.5 mg, 0.552 mmol) under a nitrogen atmosphere. The solution was stirred for 20 minutes at room temperature and 1-amino-3-((7-fluoro-1,2,3,4-tetrahydronaphthalen-2-yl)amino)propan-2-ol A18 (91 mg, 0.38 mmol) was added. The reaction was stirred at room temperature for 24 hours. Water (25 mL) and DCM (25 mL) were added and the aqueous phase was extracted with DCM (3×20 mL). The combined organic extracts were washed with water (50 mL), brine (50 mL), dried over sodium sulfate and concentrated. The resulting oil was dissolved in methanol and applied to an SCX cartridge (5 g), the cartridge was washed with methanol (30 mL) then eluted with 2 M ammonia in ethanol (20 mL). The ammonia eluate was concentrated and the resulting residue was purified by preparative HPLC (Waters) to give the desired compound (5 mg, 3%). LCMS-D RT 5.17 min; m/z 377.3.

Example 17: 4-Chloro-N-(3-((6-fluoro-1,2,3,4-tetrahydronaphthalen-2-yl)amino)-2-hydroxypropyl)benzamide (32)

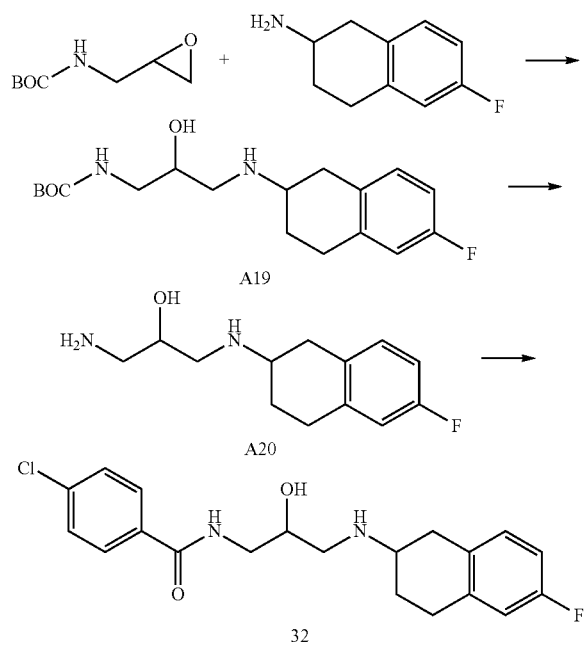

(a) tert-Butyl (3-((6-fluoro-1,2,3,4-tetrahydronaphthalen-2-yl)amino)-2-hydroxypropyl)carbamate (A19)

6-Fluoro-1,2,3,4-tetrahydro-napthalene-2-ylamine hydrochloride (100 mg) was neutralised by adding 10% NaOH (aq.) (5 mL) and DCM (10 mL) to the salt. The phases were separated and the aqueous phase was extracted with DCM (2×10 mL). The combined organic phases were dried with sodium sulfate and concentrated under reduced pressure to give the free amine as an oil (86 mg). To a solution of 6-fluoro-1,2,3,4-tetrahydro-napthalene-2-ylamine (86 mg, 0.52 mmol) in dry acetonitrile (1.5 mL) was added tert-butyl N-(oxiran-2-yl methyl) carbamate (180 mg, 1.04 mmol). The flask was sealed and the mixture stirred at 80° C. overnight. The reaction mixture was concentrated under reduced pressure and the residue was dissolved in methanol (5 mL) and applied to an SCX cartridge (5 g). The cartridge was washed with methanol (25 mL) then eluted with 2 M ammonia in methanol (15 mL). The ammonia eluate was concentrated under vacuum to give the desired compound (172 mg, 98%); $^1$H NMR (300 MHz, CDCl$_3$) 6.99 (m, 1H), 6.82-6.74 (m, 2H), 5.24 (m, 1H), 3.73 (m, 1H), 3.32 (m, 1H), 3.12 (m, 1H), 2.95-2.75 (m, 7H), 2.64 (m, 1H), 2.54 (m, 1H), 2.04 (m, 1H), 1.57 (m, 1H), 1.43 (s, 9H).

(b) 1-Amino-3-((6-fluoro-1,2,3,4-tetrahydronaphthalen-2-yl)amino)propan-2-ol (A20)

tert-Butyl (3-((6-fluoro-1,2,3,4-tetrahydronaphthalen-2-yl)amino)-2-hydroxypropyl)carbamate A19 (172 mg, 0.51 mmol) was dissolved in DCM (7 mL) and to the solution was added trifluoroacetic acid (697 μL, 10.2 mmol). The reaction was stirred at room temperature under a nitrogen atmosphere for 22 hours and the solvent was removed under reduced pressure. The resulting oil was dissolved in methanol (5 mL) and applied to an SCX cartridge. The cartridge was washed with methanol (25 mL) and eluted with 2 M ammonia in ethanol (15 mL). The ammonia eluate was concentrated under vacuum to give the desired compound (121 mg, 100%); $^1$H NMR (300 MHz, CDCl$_3$) 6.98 (m, 1H), 6.78 (m, 2H), 3.65 (m, 1H), 3.01-2.48 (m, 13H), 2.01 (m, 1H), 1.57 (m, 1H).

(c) 4-Chloro-N-(3-((6-fluoro-1,2,3,4-tetrahydronaphthalen-2-yl)amino)-2-hydroxypropyl)benzamide (32)

To a solution of 4-chlorobenzoic acid (88 mg, 0.56 mmol) in DCM (7.0 mL) was added N,N-diisopropylethylamine (294 μL, 1.69 mmol), N-ethyl-N'-(3-dimethylaminopropyl)carbodiimide hydrochloride (140.6 mg, 0.73 mmol) and 1-hydroxybenzotriazole hydrate (112 mg, 0.73 mmol) under a nitrogen atmosphere. The solution was stirred for 20 minutes at room temperature and 1-amino-3-((6-fluoro-1,2,3,4-tetrahydronaphthalen-2-yl)amino)propan-2-ol A20 (121 mg, 0.51 mmol) was added. The mixture was stirred at room temperature for 24 hours. Water (25 mL) and DCM (25 mL) were added and the aqueous phase was extracted with DCM (3×20 mL). The combined organic extracts were washed with water (50 mL), brine (50 mL), dried over sodium sulfate and concentrated. The resulting oil was dissolved in methanol (5 mL) and applied to an SCX cartridge (5 g). The cartridge was washed with methanol (30 mL) then eluted with 2 M ammonia in ethanol (20 mL). The ammonia eluate was concentrated and the resulting residue was purified by preparative HPLC (Waters) to give the desired compound (2 mg, 1%); LCMS-D RT 5.07 min; m/z 377.2.

Example 18: 4-Chloro-N-(2-hydroxy-3-(methyl(1,2,3,4-tetrahydronaphthalen-2-yl)amino)propyl) benzamide (33)

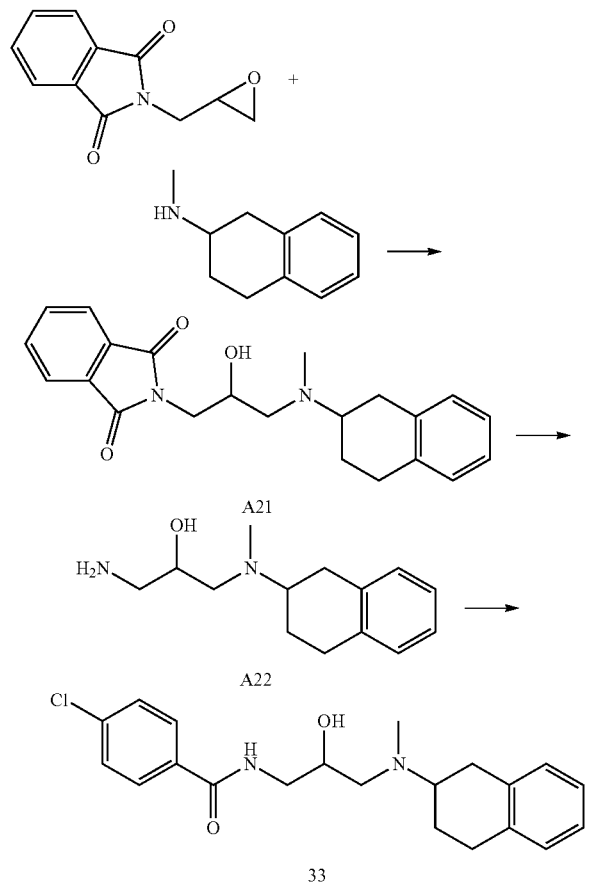

(a) 2-(2-Hydroxy-3-(methyl(1,2,3,4-tetrahydronaphthalen-2-yl)amino)propyl)isoindoline-1,3-dione (A21)

A mixture of N-(2,3-epoxypropyl)phthalimide (0.463 g, 2.27 mmol) and N-methyl-1,2,3,4-tetrahydronaphthalen-2-amine (0.368 mL, 2.17 mmol) in ethanol (3 mL) was refluxed for 4 hours under a nitrogen atmosphere. The volatiles were removed in vacuo. The material was adsorbed onto silica gel and purified by column chromatography (12 g SiO$_2$ Cartridge, 0-15% methanol in dichloromethane) to give the desired compound as a light yellow coloured oil (0.525 g, 66%). $^1$H NMR (300 MHz, CDCl$_3$) δ 7.89-7.85 (m, 2H), 7.75-7.72 (m, 2H), 7.14-7.07 (m, 4H), 4.21-4.09 (br. s., 1H), 3.90-3.73 (m, 2H), 3.04-2.72 (m, 8H), 2.49 (br. s., 3H), 2.19-2.06 (m, 1H), 1.80-1.66 (m, 1H).

(b) 1-Amino-3-(methyl(1,2,3,4-tetrahydronaphthalen-2-yl)amino)propan-2-ol (A22)

A mixture of 2-(2-hydroxy-3-(methyl(1,2,3,4-tetrahydronaphthalen-2-yl)amino)propyl)isoindoline-1,3-dione A21 (0.525 g, 1.44 mmol) and hydrazine monohydrate (0.143 mL, 2.88 mmol) in ethanol (2 mL) and dichloromethane (2 mL) was stirred at room temperature for 20 hours under a nitrogen atmosphere. The volatiles were removed by rotary evaporation. The residue was dissolved in methanol and passed through a SCX cartridge (5 g, Agilent, Bond Elut, Mega BE-SCX) washing with 100% methanol and eluting with 100% 2 M ammonia in methanol solution to give the desired compound (0.283 g, 83%). The material was used in the next step without further purification.

(c) 4-Chloro-N-(2-hydroxy-3-(methyl(1,2,3,4-tetrahydronaphthalen-2-yl)amino)propyl)benzamide (33)

A solution of 4-chlorobenzoic acid (0.208 g, 1.32 mmol) in N,N-dimethylformamide (3 mL) containing N,N-diisopropylethylamine (0.841 mL, 4.83 mmol), N-ethyl-N'-(3-dimethylaminopropyl)carbodiimide hydrochloride (0.347 g, 1.81 mmol) and 1-hydroxybenzotriazole hydrate (wetted with not less than 20 wt. % water, 0.277 g, 1.81 mmol) was stirred at room temperature for 20 minutes. After this time, a solution of 1-amino-3-(methyl(1,2,3,4-tetrahydronaphthalen-2-yl)amino)propan-2-ol A22 (0.283 g, 1.20 mmol) in N,N-dimethylformamide (3 mL) was added and stirred at room temperature for 20 hours under a nitrogen atmosphere. Water and ethyl acetate were added. The aqueous phase was extracted with ethyl acetate (2×20 mL) and the combined organic extracts were washed with water (2×20 mL), brine, dried (sodium sulfate), filtered and concentrated under reduced pressure. The material was purified by column chromatography (12 g SiO$_2$ Cartridge, 0-10% methanol in dichloromethane) to give the desired compound as a white solid (0.279 g, 61%). $^1$H NMR (300 MHz, d$_4$-methanol) δ 7.81 (dd, J=8.52, 1.41 Hz, 2H), 7.48 (dd, J=8.58, 0.99 Hz, 2H), 7.05-7.04 (m, 4H), 3.99-3.93 (m, 1H), 3.54 (dd, J=13.53, 4.89 Hz, 1H), 3.44-3.35 (m, 1H), 2.92-2.80 (m, 5H), 2.68-2.63 (m, 2H), 2.43 (s, 3H), 2.10-2.02 (m, 1H), 1.70-1.59 (m, 1H). LCMS-D: RT 5.12 min; m/z 373.3 [M+H]$^+$.

Example 19: N-(3-(Bicyclo[4.2.0]octa-1(6),2,4-trien-7-ylamino)-2-hydroxypropyl)-4-chlorobenzamide (34)

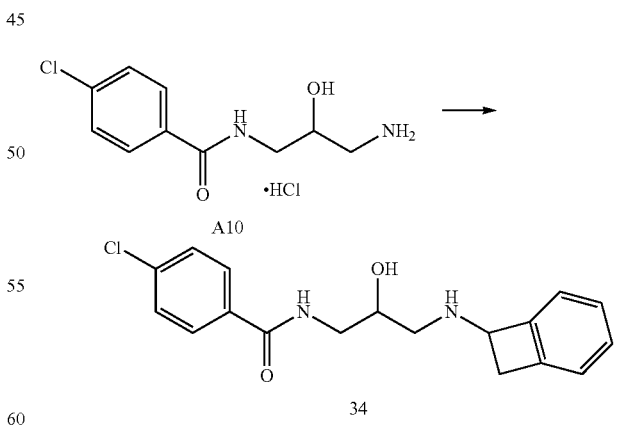

A mixture of N-(3-amino-2-hydroxypropyl)-4-chlorobenzamide hydrochloride A10 (0.080 g, 0.30 mmol), N,N-diisopropylethylamine (0.053 mL, 0.30 mmol), benzocyclobuten-1(2H)-one (0.039 mL, 0.33 mmol) and titanium (IV) isopropoxide (0.119 mL, 0.392 mmol) in absolute ethanol (2 mL) was stirred at 30° C. for 16 hours under a nitrogen atmosphere. Sodium borohydride (0.023 g, 0.60 mmol) was added and the mixture was stirred for 6 hours under a nitrogen atmosphere. The reaction mixture was quenched with a saturated aqueous sodium hydrogen carbonate solution and ethyl acetate. The precipitated inorganic solid was separated by filtration and the aqueous layer was extracted with ethyl acetate (2×15 mL). The combined organic extracts were washed with water, brine, dried (sodium sulfate), filtered and concentrated under reduced pressure. The material was purified by column chromatography (12 g SiO$_2$ cartridge, 0-15% methanol in DCM) to give the desired compound as a white solid (0.028 g, 28%). $^1$H NMR (300 MHz, d$_4$-methanol) δ 7.80 (d, J=8.61 Hz, 2H), 7.46 (d, J=8.61 Hz, 2H), 7.30 (t, J=3.85 Hz, 1H), 7.22-7.11 (m, 3H), 4.05-3.94 (m, 1H), 3.91-3.77 (m, 2H), 3.51-3.43 (m, 1H), 2.88-2.65 (m, 2H), 2.37 (s, 2H). LCMS-D: RT 4.77 min; m/z 331.2 [M+H]$^+$.

Example 20: 2-((1-Acetylpiperidin-4-yl)amino)-N-(3-((2,3-dihydro-1H-inden-2-yl)amino)-2-hydroxypropyl)isonicotinamide (35)

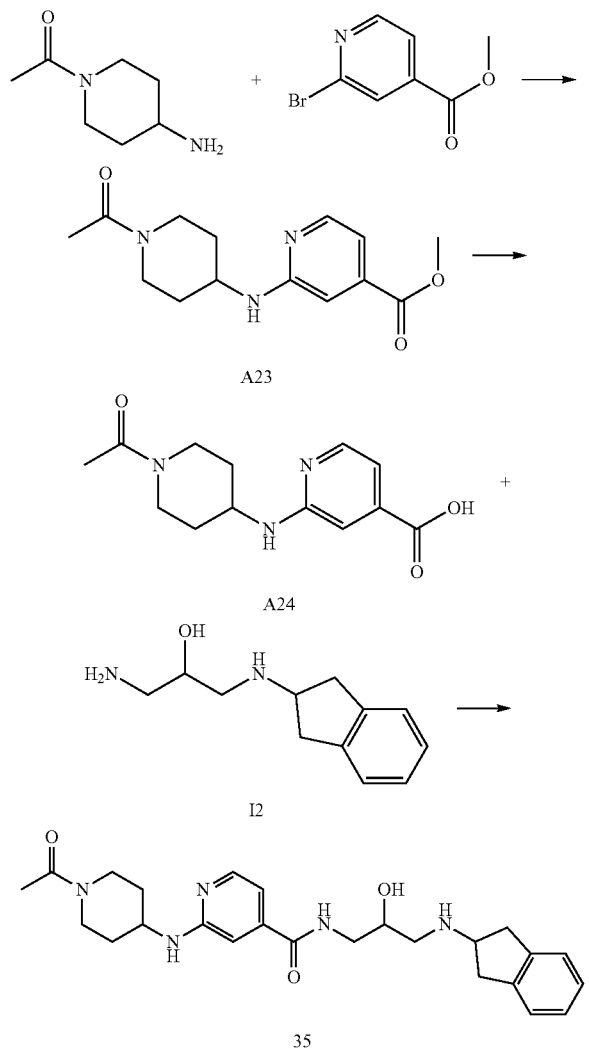

(a) Methyl 2-((1-acetylpiperidin-4-yl)amino)isonicotinate (A23)

A mixture of 1-(4-aminopiperidin-1-yl)ethan-1-one hydrochloride (0.500 g, 2.80 mmol), methyl 2-bromoisonicotinate (0.423 g, 1.96 mmol), Cs$_2$CO$_3$ (2.55 g, 7.84 mmol), xantphos (0.057 g, 0.098 mmol) and Pd$_2$(dba)$_3$ (0.090 g, 0.098 mmol) in 1,4-dioxane (15 mL) was bubbled with nitrogen for 10 minutes. The mixture was stirred under an atmosphere of nitrogen at 80° C. for 16 hours. Another portion of Cs$_2$CO$_3$ (2.55 g, 7.84 mmol), xantphos (0.057 g, 0.098 mmol) and Pd$_2$(dba)$_3$ (0.090 g, 0.098 mmol) was added. The mixture was stirred under an atmosphere of nitrogen at 80° C. for 4 hours. The reaction mixture was cooled to room temperature and diluted with EtOAc (~50 mL). Solid impurities were removed by filtration and the filtrate was removed in vacuo. The resultant solid was purified by column chromatography (40 g SiO$_2$ cartridge, 0-100% EtOAc in petroleum benzine 40-60° C., then 0-20% MeOH in EtOAc) to give the desired compound as a yellow oil (0.268 g, 49%). LCMS-B: RT 3.08 min; m/z 278.2 [M+H]$^+$.

(b) 2-((1-Acetylpiperidin-4-yl)amino)isonicotinic acid (A24)

A mixture of methyl 2-((1-acetylpiperidin-4-yl)amino)isonicotinate A23 (0.268 g, 0.966 mmol), LiOH.H$_2$O (0.811 g, 19.3 mmol), THF (7 mL), MeOH (7 mL) and H$_2$O (1.5 mL) was stirred at 40° C. for 2 hours. The mixture was cooled to room temperature and the volatiles were removed. Water (~20 mL) was added and the pH was adjusted to ~6 with aqueous HCl (2 M). A yellow precipitate formed which was isolated by vacuum filtration and air dried to give the desired compound as a yellow solid (0.058 g, 23%). The aqueous filtrate was passed through an Oasis HLB 35 cc LP extraction cartridge (6 g) which was washed with 3 column volumes of water. The lipophilic component was eluted with 3 column volumes of MeOH and concentration in vacuo gave the desired compound as a yellow solid (0.122 g, 48%). Overall yield: 0.180 g, 71%. $^1$H NMR (400 MHz, d$_6$-DMSO) δ 8.08 (d, J=5.2 Hz, 1H), 7.01-6.95 (m, 1H), 6.85 (dd, J=5.2, 1.4 Hz, 1H), 6.81 (d, J=7.5 Hz, 1H), 4.27-4.15 (m, 1H), 4.02-3.91 (m, 1H), 3.82-3.71 (m, 1H), 3.22-3.11 (m, 1H), 2.86-2.74 (m, 1H), 2.00 (s, 3H), 1.97-1.83 (m, 2H), 1.41-1.14 (m, 2H); LCMS-B: RT 1.26 min; m/z 264.2 [M+H]$^+$ (c) 2-((1-Acetylpiperidin-4-yl)amino)-N-(3-((2,3-dihydro-1H-inden-2-yl)amino)-2-hydroxypropyl) isonicotinamide (35)

A mixture of 2-((1-acetylpiperidin-4-yl)amino)isonicotinic acid A24 (0.122 g, 0.463 mmol), triethylamine (258 μL, 1.85 mmol), and DCM (10 mL) was cooled to 0° C. under a nitrogen atmosphere and isobutyl chloroformate (61 μL, 0.46 mmol) was added. The mixture was stirred for 30 minutes at 0° C. before being transferred via syringe to a solution of 1-amino-3-((2,3-dihydro-1H-inden-2-yl)amino) propan-2-ol I2 (0.096 g, 0.46 mmol) in DCM (10 mL) at 0° C. After 2.5 hours, the mixture was diluted with DCM (10 mL), water (10 mL) and aqueous sodium hydroxide (2 M, 10 mL). The separated aqueous phase was extracted with DCM (2×15 mL). The combined organic extracts were washed with brine (25 mL), dried (MgSO$_4$) and concentrated in vacuo. The residue was purified by column chromatography (12 g SiO$_2$ cartridge, 0-35% MeOH in CHCl$_3$) to give the desired compound as a yellow oil (0.012 g, 6%). $^1$H NMR (400 MHz, $d_6$-DMSO) δ 8.76 (t, J=5.9, 5.9 Hz, 1H), 8.05 (d, J=5.2 Hz, 1H), 7.26-7.22 (m, 2H), 7.20-7.16 (m, 2H), 6.94-6.87 (m, 2H), 6.76 (d, J=7.6 Hz, 1H), 5.78 (s, 1H), 4.26-4.17 (m, 1H), 4.03-3.91 (m, 3H), 3.82-3.72 (m, 1H), 3.32-3.20 (m, 4H), 3.17-3.06 (m, 5H), 2.91-2.83 (m, 1H), 2.83-2.74 (m, 1H), 2.00 (s, 3H), 1.95-1.82 (m, 2H), 1.41-1.21 (m, 2H); LCMS-A: RT 4.06 min; m/z 452.2 [M+H]$^+$.

Example 21: (S)-4-((3-((2,3-Dihydro-1H-inden-2-yl)amino)-2-hydroxypropyl)carbamoyl)benzoic acid (36)

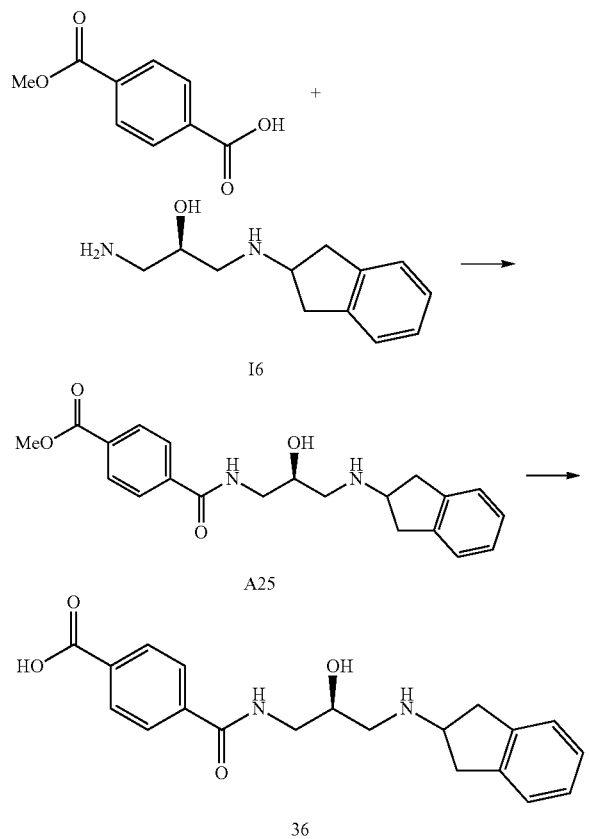

(a) Methyl (S)-4-((3-((2,3-dihydro-1H-inden-2-yl)amino)-2-hydroxypropyl)carbamoyl)benzoate (A25)

To a solution of 4-(methoxycarbonyl)benzoic acid (0.96 g, 5.3 mmol) in DCM (30 mL) at 0° C. was added HATU (2.77 g, 7.28 mmol). A solution of (R)-1-amino-3-((2,3-dihydro-1H-inden-2-yl)amino)propan-2-ol (1.0 g, 4.9 mmol) in DCM (20 mL) and DIPEA (1.87 mL, 14.6 mmol) were added and the mixture stirred at room temperature overnight. Water (25 mL) and DCM (25 mL) were added and the organic layer separated. The aqueous layer was further extracted with DCM (2×25 mL) and the combined organic layers dried (Na$_2$SO$_4$), filtered and concentrated in vacuo. The residue obtained was purified by column chromatography (ethyl acetate: petroleum ether=1:50, then DCM, then DCM: methanol 10:1) to give the desired compound as a white solid (958 mg, 53%). LCMS-E: RT 1.86 min; m/z 369.2 [M+H]$^+$.

(b) (S)-4-((3-((2,3-Dihydro-1H-inden-2-yl)amino)-2-hydroxypropyl)carbamoyl)benzoic acid (36)

To a solution of (S)-methyl 4-((3-((2,3-dihydro-1H-inden-2-yl)amino)-2-hydroxypropyl) carbamoyl) benzoate A25 (935 mg, 2.54 mmol) in a mixture of THF (15 mL), methanol (8 mL) and water (4 mL) was added LiOH.H$_2$O (533 mg, 12.7 mmol). The reaction mixture was stirred at room temperature overnight. The mixture was concentrated and the remaining aqueous solution acidified to pH=5-6 with 2 M HCl. The solid precipitate that formed was collected by filtration, washed with water and dried to give the desired compound as a white solid (610 mg, 67%). LCMS-E: RT 0.69 min; m/z 355.2 [M+H]$^+$.

Example 22: N—((S)-3-((2,3-Dihydro-1H-inden-2-yl)amino)-2-hydroxypropyl)-4-((R)-3-methylmorpholine-4-carbonyl)benzamide (37)

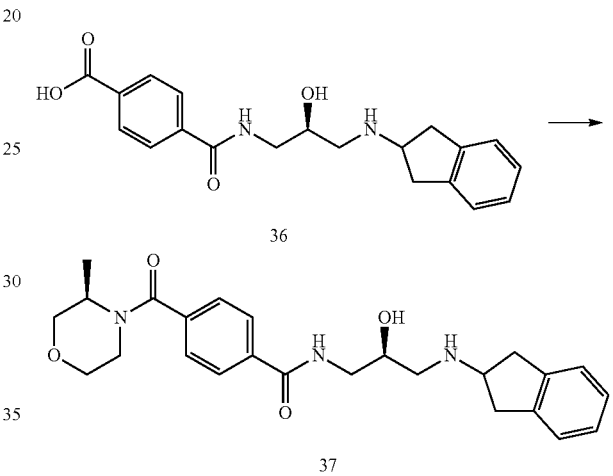

To a solution of (S)-4-((3-((2,3-dihydro-1H-inden-2-yl) amino)-2-hydroxypropyl)carbamoyl) benzoic acid 36 (50 mg, 0.14 mmol) in DMF (2 mL) were added HATU (80 mg, 0.21 mmol), triethylamine (52 mg, 0.52 mmol) and (R)-3-methylmorpholine (17 mg, 0.17 mmol). The resultant mixture was stirred at room temperature overnight. The mixture was diluted with water (20 mL) and extracted with DCM (20 mL×3). The combined organic layers were washed with water (30 mL×2) and brine (30 mL×4), dried (Na$_2$SO$_4$), filtered and concentrated under reduced pressure. The residue obtained was purified by Preparative TLC (DCM: MeOH=10:1) to give the desired product as a yellow solid (14 mg, 23%). LCMS-C: RT 0.78 min; m/z 438.3 [M+H]$^+$.

Example 23: N—((S)-3-((2,3-Dihydro-1H-inden-2-yl)amino)-2-hydroxypropyl)-4-((S)-3-methylmorpholine-4-carbonyl)benzamide (38)

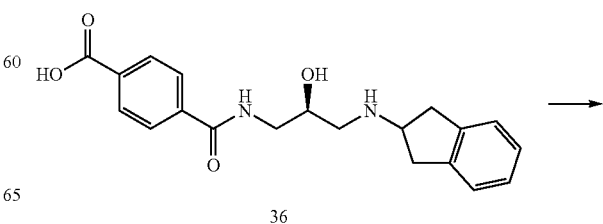

-continued

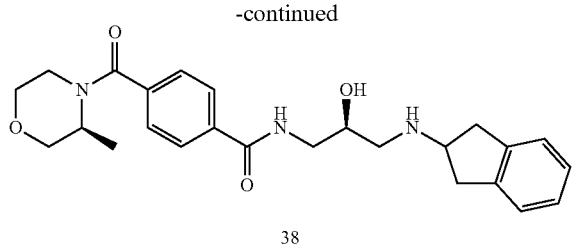

38

To a solution of (S)-4-((3-((2,3-dihydro-1H-inden-2-yl)amino)-2-hydroxypropyl)carbamoyl) benzoic acid 36 (50 mg, 0.14 mmol) in DMF (2 mL) were added HATU (80 mg, 0.21 mmol), triethylamine (52 mg, 0.52 mmol) and (S)-3-methylmorpholine (17 mg, 0.17 mmol). The resultant mixture was stirred at room temperature overnight. The mixture was diluted with water (20 mL) and extracted with DCM (20 mL×3). The combined organic layers were washed with brine (30 mL×3), dried ($Na_2SO_4$), filtered and concentrated under reduced pressure. The residue was purified by Preparative TLC (DCM:MeOH=10:1) to give the desired compound as a white solid (6 mg, 10%); LCMS-C: RT 0.91 min; m/z 438.3 $[M+H]^+$.

Example 24: 4-(8-Oxa-3-azabicyclo[3.2.1]octane-3-carbonyl)-N-(3-((2,3-dihydro-1H-inden-2-yl)amino)-2-hydroxypropyl)benzamide (39)

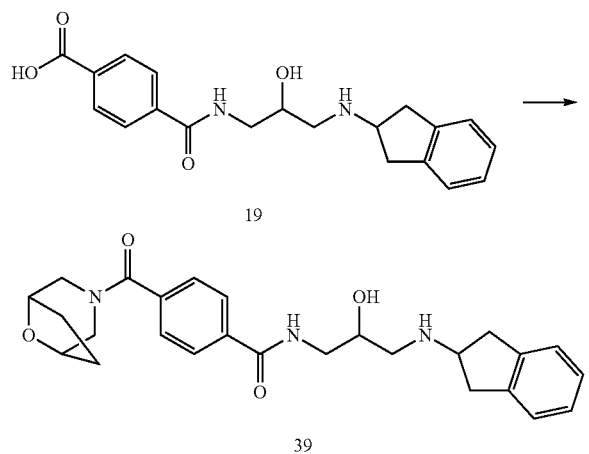

To a solution of 4-((3-((2,3-dihydro-1H-inden-2-yl)amino)-2-hydroxypropyl)carbamoyl) benzoic acid 19 (50 mg, 0.14 mmol) in a mixture of DCM (15 mL) and DMF (5 mL) were added HATU (76 mg, 0.20 mmol) and DIPEA (82 mg, 0.63 mmol). The mixture was stirred at room temperature for 30 minutes, then 8-oxa-3-azabicyclo[3.2.1]octane hydrochloride (25.4 mg, 0.17 mmol) was added. The resulting mixture was stirred at room temperature overnight. The mixture was diluted with water (20 mL) and extracted with DCM (30 mL×4). The combined organic layers were washed with brine (30 mL), dried ($Na_2SO_4$), filtered and concentrated under reduced pressure. The residue was purified by Preparative-TLC (DCM:MeOH=10:1) to give the desired product as an off-white solid (20 mg, 32%). LCMS-C: RT 0.83 min; m/z 450.2 $[M+H]^+$.

Example 25: 4-(3-Oxa-8-azabicyclo[3.2.1]octane-8-carbonyl)-N-(3-((2,3-dihydro-1H-inden-2-yl)amino)-2-hydroxypropyl)benzamide (40)

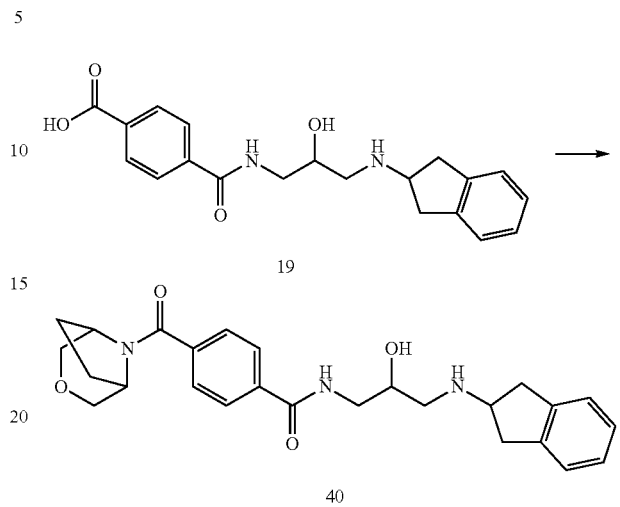

To a solution of 4-((3-((2,3-dihydro-1H-inden-2-yl)amino)-2-hydroxypropyl)carbamoyl) benzoic acid 19 (50 mg, 0.14 mmol) in DCM (4 mL) were added HATU (80 mg, 0.21 mmol) and DIPEA (73 mg, 0.56 mmol). The mixture was stirred at room temperature for 30 minutes. 3-Oxa-8-azabicyclo[3.2.1]octane hydrochloride (25 mg, 0.17 mmol) was added and the resulting mixture was stirred at room temperature overnight. The mixture was diluted with water (20 mL) and extracted with DCM (10 mL×5). The combined organic layers were washed with brine (10 mL×3), dried ($Na_2SO_4$), filtered and concentrated under reduced pressure. The residue was purified by Preparative TLC (DCM:MeOH=15:1) to give the desired compound as an off-white solid (35 mg, 56%). LCMS-C: RT 1.03 min; m/z 450.3 $[M+H]^+$.

Example 26: N-(3-((2,3-Dihydro-1H-inden-2-yl)amino)-2-hydroxypropyl)-4-(2,2-dimethylmorpholine-4-carbonyl)benzamide (41)

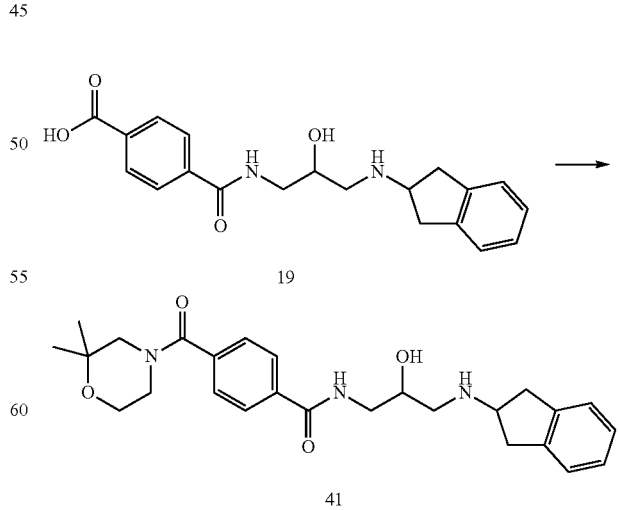

To a solution of 4-((3-((2,3-dihydro-1H-inden-2-yl)amino)-2-hydroxypropyl)carbamoyl) benzoic acid 19 (50 mg, 0.14 mmol) in a mixture of DCM (15 mL) and DMF (5 mL) were added HATU (76 mg, 0.20 mmol) and DIPEA (82 mg, 0.63 mmol). The mixture was stirred at room temperature for 30 minutes, then 2,2-dimethylmorpholine (19.6 mg, 0.17 mmol) was added and the resulting mixture stirred at room temperature overnight. The mixture was diluted with water (20 mL) and extracted with DCM (30 mL×4). The combined organic layers were washed with water (30 mL×3) and brine (30 mL), dried (Na$_2$SO$_4$), filtered and concentrated under reduced pressure. The residue was purified by Preparative TLC (DCM:MeOH=10:1) to give the desired compound as an off-white solid (15 mg, 24%). LCMS-C: RT 1.24 min; m/z 452.3 [M+H]$^+$.

Example 27: (S)-3-((1-Acetylpiperidin-4-yl)amino)-N-(3-((2,3-dihydro-1H-inden-2-yl)amino)-2-hydroxypropyl)benzamide (42)

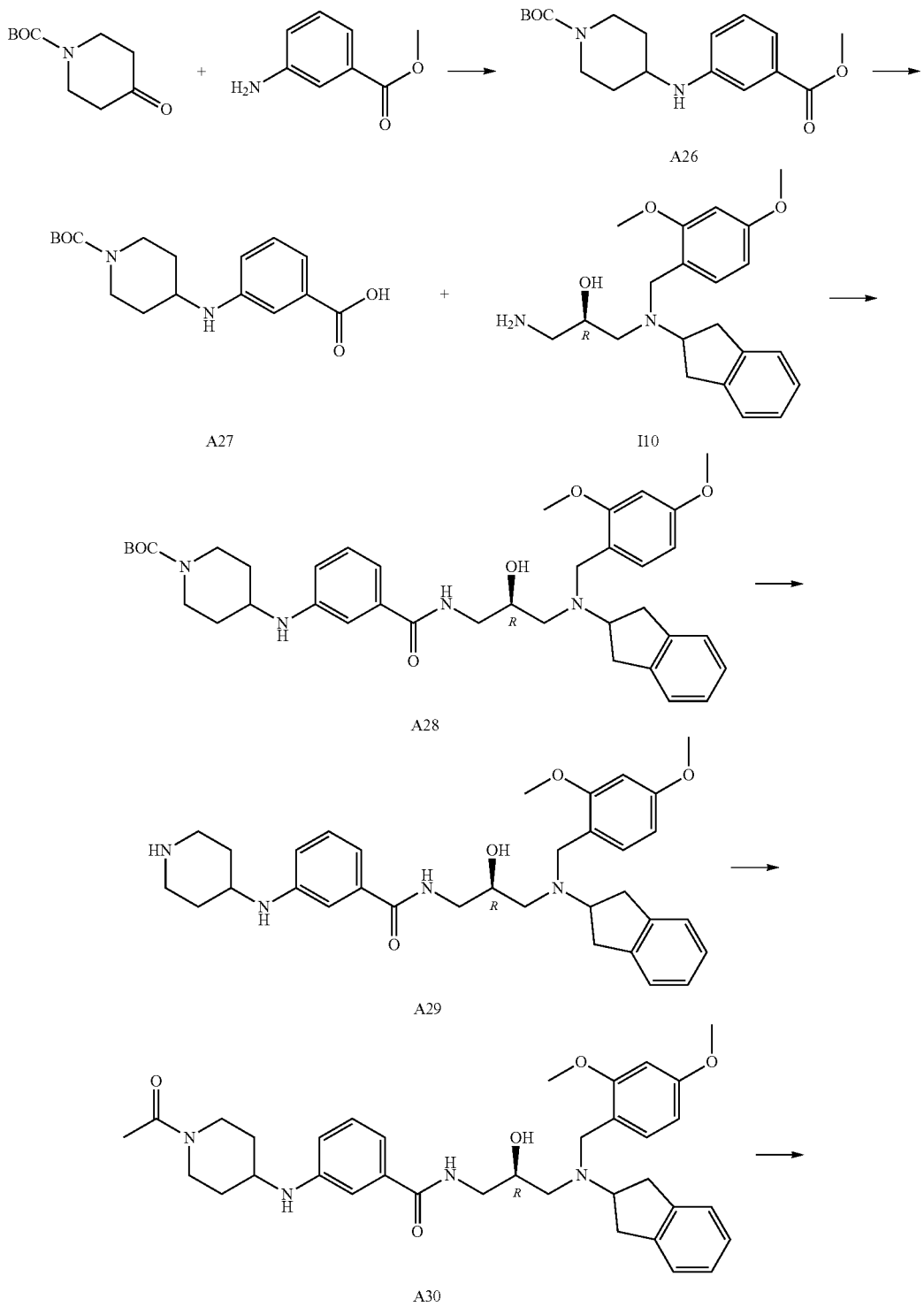

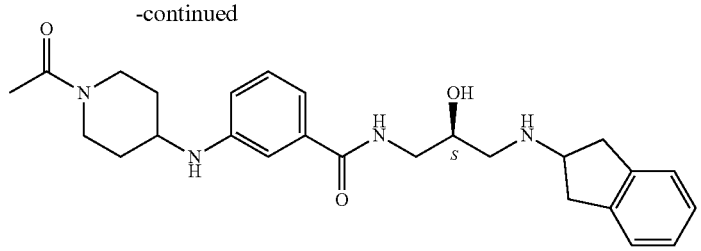

42

(a) tert-Butyl 4-((3-(methoxycarbonyl)phenyl)amino)piperidine-1-carboxylate A26

A mixture of 1-Boc-4-piperidone (0.725 g, 3.64 mmol), methyl 3-aminobenzoate (0.500 g, 3.31 mmol) and acetic acid (0.38 mL, 6.6 mmol) in DCE (25 mL) was stirred at room temperature for 15 minutes before sodium triacetoxyborohydride (1.05 g, 4.96 mmol) was added. The mixture was stirred for a further 16 hours at room temperature and then quenched by the addition of H$_2$O (20 mL). The mixture was concentrated in vacuo, saturated aqueous NaHCO$_3$ (50 mL) was added and the aqueous was extracted with EtOAc (3×75 mL). The organic layers were combined, washed with brine, dried (MgSO$_4$) and the solvent removed in vacuo. The solid residue was purified by column chromatography (Biotage Isolera, 40 g SiO$_2$ cartridge, 0-30% EtOAc in petroleum benzine 40-60° C.) to give the desired compound as a colourless oil (1.35 g, ~80% purity, >95% yield). $^1$H NMR (400 MHz, chloroform-d) δ 7.46-7.40 (m, 1H), 7.38-7.32 (m, 1H), 7.25-7.17 (m, 1H), 6.92-6.84 (m, 1H), 4.07-3.99 (m, 1H), 3.90-3.86 (m, 3H), 3.71 (t, J=6.2 Hz, 1H), 3.47 (tt, J=10.4, 3.9 Hz, 1H), 2.90 (t, J=12.5 Hz, 2H), 2.43 (t, J=6.2 Hz, 1H), 2.10-1.97 (m, 2H), 1.46 (s, 9H), 1.41-1.31 (m, 2H). LCMS-A: RT 6.70 min; m/z 279.1 [M-t-Bu+2H]$^+$.

(b) 3-((1-(tert-Butoxycarbonyl)piperidin-4-yl)amino)benzoic acid A27

A mixture of tert-butyl 4-((3-(methoxycarbonyl)phenyl)amino)piperidine-1-carboxylate A26 (1.35 g, ~80 purity, 3.23 mmol), LiOH.H$_2$O (1.69 g, 40.4 mmol), THF (14 mL), MeOH (14 mL) and H$_2$O (3 mL) was stirred overnight at room temperature. The reaction mixture was concentrated in vacuo, H$_2$O (50 mL) and aqueous NaOH (2 M, 30 mL) were added and the aqueous solution was washed with EtOAc (3×50 mL). The aqueous phase was acidified with an aqueous HCl solution (2 M) and extracted with EtOAc (3×50 mL). The organic layers were combined, washed with brine, dried (MgSO$_4$) and the solvent removed in vacuo to give the desired compound as a yellow oil (0.801 g, 77%). $^1$H NMR (400 MHz, DMSO-d$_6$) δ 7.20-7.14 (m, 2H), 7.12-7.08 (m, 1H), 6.84-6.77 (m, 1H), 5.78 (s, 1H), 3.92-3.80 (m, 2H), 3.49-3.39 (m, 1H), 3.02-2.82 (m, 2H), 1.89-1.82 (m, 2H), 1.40 (s, 9H), 1.28-1.19 (m, 2H). LCMS-A: RT 6.04 min; m/z 265.1 [M-t-Bu+2H]+; 319.1 [M−H]$^-$.

(c) tert-Butyl (R)-4-((3-((3-((2,3-dihydro-1H-inden-2-yl)(2,4-dimethoxybenzyl)amino)-2-hydroxypropyl)carbamoyl)phenyl)amino)piperidine-1-carboxylate A28

A solution of 3-((1-(tert-butoxycarbonyl)piperidin-4-yl)amino)benzoic acid A27 (0.099 g, 0.31 mmol) and DIPEA (98 μL, 0.56 mmol) in DCM (5 mL) was stirred with HATU (0.117 g, 0.309 mmol) for 10 minutes at room temperature. A solution of (R)-1-amino-3-((2,3-dihydro-1H-inden-2-yl)(2,4-dimethoxybenzyl)amino)propan-2-ol I10 (0.100 g, 0.281 mmol) in DCM (5 mL) was then added dropwise and the mixture was stirred at room temperature for 24 h. Water (30 mL) and aqueous NaOH (2 M, 10 mL) were then added and the aqueous was extracted with DCM (3×30 mL). The organic layers were combined, the solvent was removed in vacuo and the residue was purified by column chromatography (Biotage Isolera, 24 g SiO$_2$ cartridge, 0-100% EtOAc in petroleum benzine 40-60° C.) to give the desired compound as a colourless oil (0.105 g, 56%). $^1$H NMR (400 MHz, chloroform-d) δ 7.18-7.08 (m, 6H), 7.01 (t, J=2.0 Hz, 1H), 6.88 (d, J=7.6 Hz, 1H), 6.71-6.60 (m, 2H), 6.43 (d, J=2.4 Hz, 1H), 6.39 (dd, J=8.3, 2.4 Hz, 1H), 4.07-3.98 (m, 2H), 3.87-3.81 (m, 2H), 3.79-3.73 (m, 7H), 3.71-3.54 (m, 3H), 3.51-3.40 (m, 1H), 3.36-3.24 (m, 1H), 3.14-2.98 (m, 4H), 2.95-2.86 (m, 2H), 2.65-2.48 (m, 2H), 2.01-1.97 (m, 1H), 1.46 (s, 9H), 1.36-1.28 (m, 2H); N—H and O—H not observed. LCMS-A: RT 5.20 min; m/z 659.3 [M+H]$^+$.

(d) (R)—N-(3-((2,3-Dihydro-1H-inden-2-yl)(2,4-dimethoxybenzyl)amino)-2-hydroxypropyl)-3-(piperidin-4-ylamino)benzamide A29

A mixture of tert-butyl (R)-4-((3-((3-((2,3-dihydro-1H-inden-2-yl)(2,4-dimethoxybenzyl)amino)-2-hydroxypropyl)carbamoyl)phenyl)amino)piperidine-1-carboxylate A28 (0.105 g, 0.159 mmol) and TFA (122 μL, 1.59 mmol) in DCM (10 mL) was stirred at room temperature for 16 hours. Water (20 mL) was added and the aqueous was washed with DCM (3×10 mL). The aqueous was adjusted to a pH of ~14 with an aqueous NaOH solution (2 M) and then extracted with DCM (3×15 mL). The organic layers were combined, washed with brine, dried (MgSO$_4$) and the solvent removed in vacuo to give the desired compound as a white powder (0.024 g, 27%). $^1$H NMR (400 MHz, DMSO-d$_6$) δ 8.08 (t, J=5.4 Hz, 1H), 7.28 (d, J=8.3 Hz, 1H), 7.19-7.04 (m, 5H), 6.96 (s, 1H), 6.88 (d, J=7.6 Hz, 1H), 6.69 (dd, J=8.1, 2.3 Hz, 1H), 6.48 (d, J=2.4 Hz, 1H), 6.42 (dd, J=8.3, 2.4 Hz, 1H), 5.59 (d, J=8.1 Hz, 1H), 4.66 (d, J=4.3 Hz, 1H), 3.83-3.75 (m, 1H), 3.73-3.68 (m, 7H), 3.57 (d, J=2.8 Hz, 2H), 3.27-3.09 (m, obscured by solvent), 3.01-2.80 (m, 7H), 2.47-2.39 (m, obscured by solvent), 1.88-1.77 (m, 2H), 1.26-1.14 (m, 3H).

(e) (R)-3-((1-Acetylpiperidin-4-yl)amino)-N-(3-((2,3-dihydro-1H-inden-2-yl)(2,4-dimethoxybenzyl)amino)-2-hydroxypropyl)benzamide A30

A solution of (R)—N-(3-((2,3-dihydro-1H-inden-2-yl)(2,4-dimethoxybenzyl)amino)-2-hydroxypropyl)-3-(piperidin-4-ylamino)benzamide A29 (0.024 g, 0.043 mmol) and triethylamine (12 μL, 0.086 mmol) in DCM (4 mL) was cooled to 0° C. before acetic anhydride (4 μL, 0.05 mmol) was added. The mixture was stirred and allowed to return to room temperature over 3 hours. Water (10 mL) and an aqueous solution of NaOH (2 M, 10 mL) were added and the mixture was stirred for 20 minutes. The aqueous was extracted with DCM (3×15 mL), the organic layers were combined and the solvent removed in vacuo to give the desired compound as a white solid (0.026 g, >95%). LCMS-B: RT 3.38 min; m/z 601.3 [M+H]$^+$.

(f) (S)-3-((1-Acetylpiperidin-4-yl)amino)-N-(3-((2,3-dihydro-1H-inden-2-yl)amino)-2-hydroxypropyl)benzamide 42

A mixture of (R)-3-((1-acetylpiperidin-4-yl)amino)-N-(3-((2,3-dihydro-1H-inden-2-yl)(2,4-dimethoxybenzyl)amino)-2-hydroxypropyl)benzamide A30 (0.026 g, 0.043 mmol) and TFA (2 mL) was stirred at 70° C. for 16 hours. The mixture was returned to room temperature, water was added (20 mL) and the aqueous was washed with DCM (3×20 mL). The pH of the aqueous layer was adjusted to ~14 with an aqueous NaOH solution (2 M) and then extracted with DCM (3×20 mL). The organic layers were combined and the solvent removed in vacuo to give the desired compound as a white solid (0.017 g, 87%). $^1$H NMR (400 MHz, DMSO-d$_6$) δ 8.26 (t, J=5.7 Hz, 1H), 7.21-7.03 (m, 6H), 6.94 (d, J=7.6 Hz, 1H), 6.78-6.66 (m, 1H), 5.70 (d, J=8.2 Hz, 1H), 4.97-4.76 (m, 1H), 4.29-4.14 (m, 1H), 3.83-3.73 (m, 1H), 3.72-3.65 (m, 1H), 3.54-3.45 (m, 2H), 3.30-3.21 (m, 2H), 3.21-3.13 (m, 1H), 3.09-2.99 (m, 2H), 2.86-2.75 (m, 1H), 2.70-2.50 (m, 4H), 2.00 (s, 3H), 1.96-1.82 (m, 2H), 1.36-1.12 (m, 2H); N—H not observed. LCMS-B:RT 3.20 min; m/z 451.3 [M+H]$^+$.

Example 28: Amide Couplings

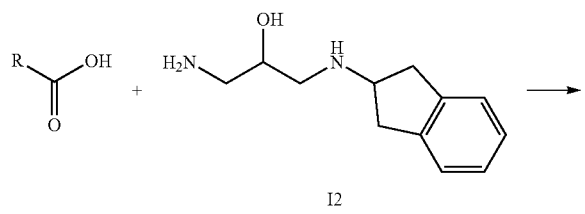

-continued

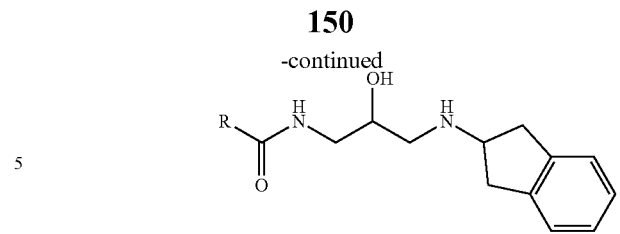

Method X1—A solution of HATU (0.080 g, 0.21 mmol, 1.5 equiv) in CH$_3$CN (1 mL) was added to the desired acid (0.14 mmol, 1 equiv.), CH$_3$CN (1 mL) and DIPEA (73 µL, 0.42 mmol, 3 equiv.) and the mixture was stirred for 10 minutes. A solution of 1-amino-3-((2,3-dihydro-1H-inden-2-yl)(2,4-dimethoxybenzyl)amino)propan-2-ol I2 (0.050 g, 0.14 mmol, 1 equiv) in DMF (1 mL) was then added and the mixture was stirred at room temperature for 16 h. DCM (1 mL) and a solution of NaOH (aqueous 2 M, 2 mL) were added and the phases were separated. The aqueous phase was extracted with DCM (2 mL) and the organic layers were combined. The organic extracts were concentrated by a stream of air and the resultant residue dissolved in MeOH and purified by solid-phase extraction (1 g SCX-2 cartridge, 4 column volumes of methanol followed by 4 column volumes of 7 N NH$_3$ in MeOH). The basic fractions were concentrated by a stream of air, taken up in TFA (0.5 mL) and stirred at 70° C. for 5 hours. Water (2 mL) was added and the aqueous solution was washed with DCM (3×2 mL). The aqueous layer was brought to ~pH 14 by the addition of an aqueous NaOH solution (2 M) and then extracted with DCM (2×2 mL). The organic layers were concentrated with a stream of air to give the desired compounds.

| Compound | Name and structure | LCMS data | Method |
|---|---|---|---|
| 43 | 2-(cyclopentyl(methyl)amino)-N-(3-((2,3-dihydro-1H-inden-2-yl)amino)-2-hydroxypropyl)isonicotinamide | LCMS-B: RT = 3.35 min, m/z = 409 [M + H]$^+$. | X1 |
| 44 | 2-(cyclopentylamino)-N-(3-((2,3-dihydro-1H-inden-2-yl)amino)-2-hydroxypropyl)isonicotinamide | LCMS-B: RT = 3.14 min, m/z = 395 [M + H]$^+$. | X1 |

| Compound | Name and structure | LCMS data | Method |
|---|---|---|---|
| 45 | N-(3-((2,3-dihydro-1H-inden-2-yl)amino)-2-hydroxypropyl)-5-(pyridin-2-yl)-1H-pyrazole-3-carboxamide | LCMS-B: RT = 3.21 min, m/z = 378 [M + H]+. | X1 |
| 46 | N-(3-((2,3-dihydro-1H-inden-2-yl)amino)-2-hydroxypropyl)-1-(pyridin-3-yl)-1H-pyrazole-4-carboxamide | LCMS-B: RT = 3.18 min, m/z = 378 [M + H]+. | X1 |
| 47 | N-(3-((2,3-dihydro-1H-inden-2-yl)amino)-2-hydroxypropyl)-2-morpholinoisonicotinamide | LCMS-B: RT = 3.14 min, m/z = 397 [M + H]+. | X1 |
| 48 | N-(3-((2,3-dihydro-1H-inden-2-yl)amino)-2-hydroxypropyl)-2-(pyrrolidin-1-yl)isonicotinamide | LCMS-B: RT = 3.13 min, m/z = 381 [M + H]+. | X1 |
| 49 | N-(3-((2,3-dihydro-1H-inden-2-yl)amino)-2-hydroxypropyl)-2-(1H-pyrazol-1-yl)isonicotinamide | LCMS-B: RT = 3.35 min, m/z = 378 [M + H]+. | X1 |

Example 29: 2-((1-Acetylpiperidin-4-yl)oxy)-N-(3-((2,3-dihydro-1H-inden-2-yl)amino)-2-hydroxypropyl)isonicotinamide 50
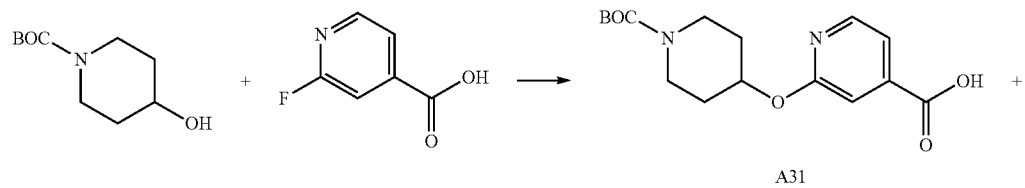
A31
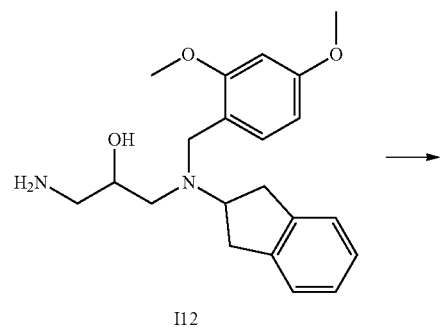
I12
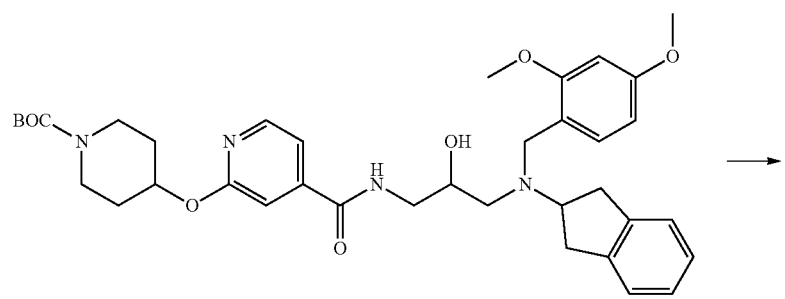
A32
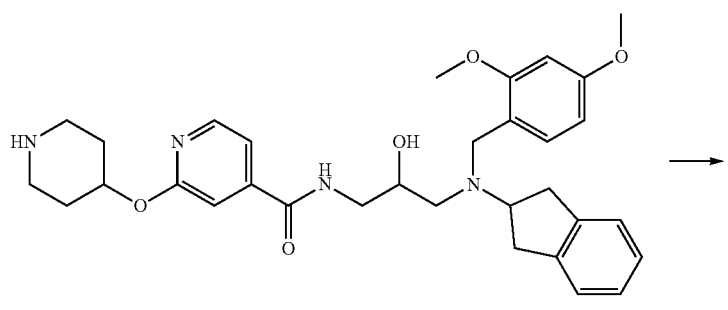
A33
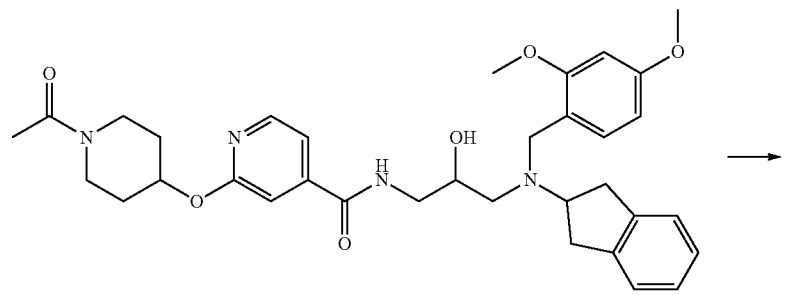
A34

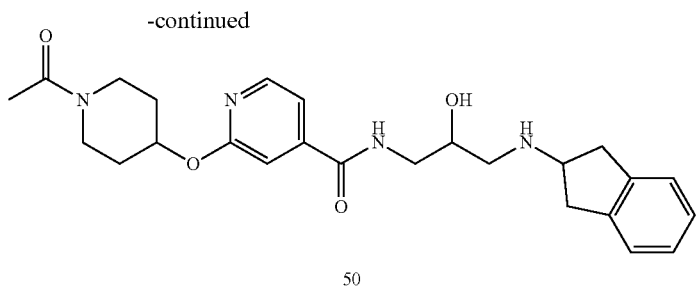

(a) 2-((1-(tert-Butoxycarbonyl)piperidin-4-yl)oxy)isonicotinic acid A31

A solution of tert-butyl 4-hydroxypiperidine-1-carboxylate (0.500 g, 2.48 mmol) in anhydrous DMF (5 mL) was added to a stirring suspension of sodium hydride (60% dispersion in mineral oil; 0.238 g, 9.94 mmol) in anhydrous DMF (5 mL) under an atmosphere of nitrogen. The mixture was stirred at room temperature for 10 minutes before a solution of 2-fluoroisonicotinic acid (0.319 g, 2.26 mmol) in DMF (5 mL) was added. The mixture was stirred for a further 16 hours at room temperature and 4 hours at 60° C. After returning to room temperature, $H_2O$ (20 mL) was carefully added and the pH of the aqueous mixture was adjusted to ~2 with an aqueous HCl solution (2 M). The aqueous solution was extracted with EtOAc (3×30 mL), the organic layers were combined, washed with brine, dried ($MgSO_4$) and the solvent removed in vacuo. The resultant residue was purified by column chromatography (Biotage Isolera, 40 g $SiO_2$ cartridge, 0-100% EtOAc in petroleum benzine 40-60° C.) to give a white solid that was an approximate 1:1 mixture of the desired product and the isonicotinic acid starting material. This material was dissolved in DMF (5 mL) and added to a mixture of tert-butyl 4-hydroxypiperidine-1-carboxylate (0.500 g, 2.48 mmol) in anhydrous DMF (5 mL) that had been added to a stirring suspension of sodium hydride (60% dispersion in mineral oil; 0.238 g, 9.94 mmol) in anhydrous DMF (5 mL) under an atmosphere of nitrogen. The mixture was stirred for 16 hours before $H_2O$ (20 mL) was carefully added and the pH of the aqueous mixture was adjusted to ~2 with an aqueous HCl solution (2 M). The aqueous solution was extracted with DCM (3×30 mL), the organic layers were combined, dried ($MgSO_4$) and the solvent removed in vacuo. The resultant residue was purified by column chromatography (Biotage Isolera, 40 g $SiO_2$ cartridge, 0-100% EtOAc in petroleum benzine 40-60° C.) to give the desired compound as a white solid (0.419 g, 58%). $^1$H NMR (400 MHz, DMSO-$d_6$) δ 8.34-8.27 (m, 1H), 7.39-7.34 (m, 1H), 7.17-7.13 (m, 1H), 5.27-5.15 (m, 1H), 3.74-3.62 (m, 2H), 3.23-3.11 (m, 2H), 2.00-1.88 (m, 2H), 1.63-1.49 (m, 2H), 1.40 (s, 9H); COOH not observed. LCMS-B: RT 3.65 min; m/z 321.2 [M−H]$^-$.

(b) tert-Butyl 4-((4-((3-((2,3-dihydro-1H-inden-2-yl)(2,4-dimethoxybenzyl)amino)-2-hydroxypropyl)carbamoyl)pyridin-2-yl)oxy)piperidine-1-carboxylate A32

A mixture of 2-((1-(tert-butoxycarbonyl)piperidin-4-yl)oxy)isonicotinic acid A31 (0.100 g, 0.310 mmol), DIPEA (108 μL, 0.620 mmol) and HATU (0.118 g, 0.310 mmol) in DCM (5 mL) was stirred for 15 minutes at room temperature under an atmosphere of nitrogen. A solution of 1-amino-3-((2,3-dihydro-1H-inden-2-yl)(2,4-dimethoxybenzyl)amino)propan-2-ol I12 (0.111 g, 0.310 mmol) in DCM (5 mL) was then added and the mixture was stirred for 16 hours at room temperature. An aqueous NaOH solution (2 M, 20 mL) was added and the aqueous was extracted with DCM (3×30 mL). The organic layers were combined, dried ($MgSO_4$), filtered, and the volatiles removed in vacuo. The residue was purified by column chromatography (Biotage Isolera, 24 g $SiO_2$ cartridge, 0-10% MeOH in DCM) to give the desired compound as a brown oil (0.204 g, >95%). $^1$H NMR (400 MHz, DMSO-$d_6$) δ 8.53 (t, J=5.6 Hz, 1H), 8.24 (d, J=5.2 Hz, 1H), 7.31-7.24 (m, 2H), 7.19-7.04 (m, 5H), 6.48 (d, J=2.4 Hz, 1H), 6.42 (dd, J=8.3, 2.4 Hz, 1H), 5.26-5.14 (m, 1H), 4.67 (d, J=4.3 Hz, 1H), 3.85-3.76 (m, 1H), 3.76-3.63 (m, 10H), 3.57 (s, 2H), 3.25-3.09 (m, 3H), 3.01-2.78 (m, 4H), 2.45 (d, J=6.0 Hz, 2H), 2.00-1.89 (m, 2H), 1.62-1.51 (m, 2H), 1.41 (s, 9H). LCMS-A: RT 2.10 min; m/z 661.3 [M+H]$^+$.

(c) N-(3-((2,3-Dihydro-1H-inden-2-yl)(2,4-dimethoxybenzyl)amino)-2-hydroxypropyl)-2-(piperidin-4-yloxy)isonicotinamide A33

A mixture of tert-butyl 4-((4-((3-((2,3-dihydro-1H-inden-2-yl)(2,4-dimethoxybenzyl)amino)-2-hydroxypropyl)carbamoyl)pyridin-2-yl)oxy)piperidine-1-carboxylate A32 (0.184 g, 0.278 mmol), TFA (0.32 mL, 4.2 mmol) and DCM (10 mL) was stirred at room temperature for 1 hour. Another aliquot of TFA (0.11 mL, 1.4 mmol) was added and the mixture was stirred at room temperature for 2.5 hours. Water (10 mL) and aqueous NaOH (2 M, 10 mL) were added and the aqueous was extracted with DCM (3×15 mL). The organic layers were combined and the solvent removed in vacuo to give a yellow oil that was dissolved in a minimum amount of MeOH and loaded onto an SCX cartridge (SiliCycle SCX-2 cartridge, 5 g). The cartridge was washed with 5 column volumes of MeOH before the desired component was eluted with 5 column volumes of $NH_3$ in MeOH (3.5 M). The fractions containing the suspected product were combined and the solvent removed in vacuo to give a colourless oil. The oil was taken up in a minimum amount of DCM and cyclohexane was added to form a white precipitate. The volatiles were removed in vacuo to give the desired compound as a white solid (0.115 g, 74%). $^1$H NMR (400 MHz, chloroform-d) δ 8.18 (d, J=5.3 Hz, 1H), 7.19-7.06 (m, 5H), 7.04 (dd, J=5.2, 1.5 Hz, 1H), 7.01-6.95 (m, 1H), 6.70 (t, J=5.5 Hz, 1H), 6.44 (d, J=2.4 Hz, 1H), 6.38 (dd, J=8.2, 2.4 Hz, 1H), 5.31-5.05 (m, 1H), 3.84-3.76 (m, 8H), 3.62-3.51 (m, 2H), 3.47 (s, 2H), 3.33-3.24 (m, 1H), 3.22-3.14 (m, 2H), 3.12-3.03 (m, 1H), 3.01-2.83 (m, 5H), 2.53 (dd, J=13.2, 4.1 Hz, 1H), 2.49-2.41 (m, 1H), 2.15-2.05 (m, 2H), 1.80-1.70 (m, 2H); N—H not observed. LCMS-A: RT 4.42 min; m/z 561.3 [M+H]$^+$.

(d) 2-((1-Acetylpiperidin-4-yl)oxy)-N-(3-((2,3-dihydro-1H-inden-2-yl)(2,4-dimethoxybenzyl)amino)-2-hydroxypropyl)isonicotinamide A34

A solution of N-(3-((2,3-dihydro-1H-inden-2-yl)(2,4-dimethoxybenzyl)amino)-2-hydroxypropyl)-2-(piperidin-4-yloxy)isonicotinamide A33 (0.030 g, 0.054 mmol) and triethylamine (11 μL, 0.080 mmol) in DCM (2 mL) was cooled to 0° C. under an atmosphere of nitrogen. Acetic anhydride (5 μL, 0.05 mmol) was added and the mixture was returned to room temperature, with stirring, over 5 hours. Water (10 mL) and an aqueous NaOH solution (2 M, 10 mL) were added and the mixture was stirred for 20 minutes. The aqueous was extracted with DCM (3×15 mL), the organic layers were combined and the solvent removed in vacuo to give the desired compound as a yellow oil (0.032 g, >95%). LCMS-A: RT 4.79 min; m/z 603.3 [M+H]$^+$.

(e) 2-((1-Acetylpiperidin-4-yl)oxy)-N-(3-((2,3-dihydro-1H-inden-2-yl)amino)-2-hydroxypropyl)isonicotinamide 50

A solution of 2-((1-acetylpiperidin-4-yl)oxy)-N-(3-((2,3-dihydro-1H-inden-2-yl)(2,4-dimethoxybenzyl)amino)-2-hydroxypropyl)isonicotinamide A34 (0.032 g, 0.053 mmol) in TFA (2 mL) was stirred at 70° C. for 4 hours. Water (25 mL) was added and the acidic aqueous phase was washed with DCM (3×15 mL). The aqueous was adjusted to pH ~14 with aqueous NaOH (2 M) and extracted with DCM (3×20 mL). The organic layers were combined and the solvent removed in vacuo to give the desired compound as a white solid (0.004 g, 15%). $^1$H NMR (400 MHz, DMSO-d$_6$) δ 8.70 (t, J=5.7 Hz, 1H), 8.25 (d, J=5.2 Hz, 1H), 7.33-7.27 (m, 1H), 7.21-7.14 (m, 3H), 7.12-7.05 (m, 2H), 5.30-5.19 (m, 1H), 4.87 (s, 1H), 3.92-3.81 (m, 1H), 3.76-3.65 (m, 2H), 3.50 (m, 1H), 3.30-3.20 (m, peaks obscured by solvent), 3.11-2.99 (m, 2H), 2.72-2.61 (m, 3H), 2.55 (dd, J=11.8, 6.8 Hz, 1H), 2.06-1.88 (m, 5H), 1.72-1.47 (m, 2H). LCMS-B: RT 3.18 min; m/z 453.3 [M+H]$^+$.

Example 30: N-(3-((2,3-dihydro-1H-inden-2-yl)amino)-2-hydroxypropyl)-2-(piperidin-4-yloxy)isonicotinamide 51

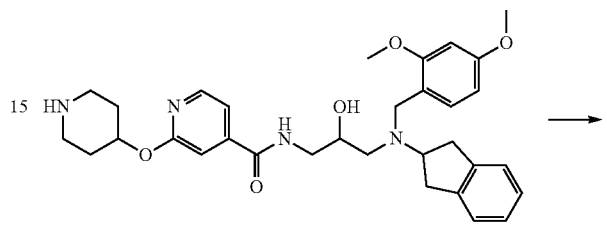

A33

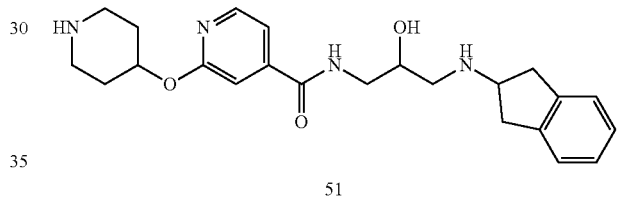

51

A solution of N-(3-((2,3-dihydro-1H-inden-2-yl)(2,4-dimethoxybenzyl)amino)-2-hydroxypropyl)-2-(piperidin-4-yloxy)isonicotinamide A33 (0.020 g, 0.036 mmol) in TFA (2 mL) was stirred at 70° C. for 16 hours. The solution was concentrated in vacuo before H$_2$O (15 mL) was added and the acidic aqueous phase was washed with DCM (3×15 mL). The aqueous phase was adjusted to pH ~14 with an aqueous NaOH solution (2 M) and extracted with DCM (3×15 mL). The organic layers were combined and the solvent removed in vacuo to give the desired compound as a yellow oil (0.005 g, 34%). $^1$H NMR (400 MHz, DMSO-d$_6$) δ 8.69 (t, J=5.8 Hz, 1H), 8.23 (d, J=5.5 Hz, 1H), 7.31-7.24 (m, 1H), 7.20-7.13 (m, 3H), 7.12-7.06 (m, 2H), 5.15-5.04 (m, 1H), 4.90 (s, 1H), 3.76-3.66 (m, 1H), 3.54-3.46 (m, peaks obscured by solvent), 3.28-3.22 (m, peaks obscured by solvent), 3.10-2.96 (m, 4H), 2.71-2.62 (m, 5H), 2.55 (dd, J=11.8, 6.8 Hz, 1H), 2.01-1.92 (m, 2H), 1.61-1.49 (m, 2H). LCMS-A: RT 1.69 min; m/z 411.2 [M+H]$^+$.

Example 31: 6-((1-Acetylpiperidin-4-yl)amino)-N-(3-((2,3-dihydro-1H-inden-2-yl)amino)-2-hydroxypropyl)pyrazine-2-carboxamide 52
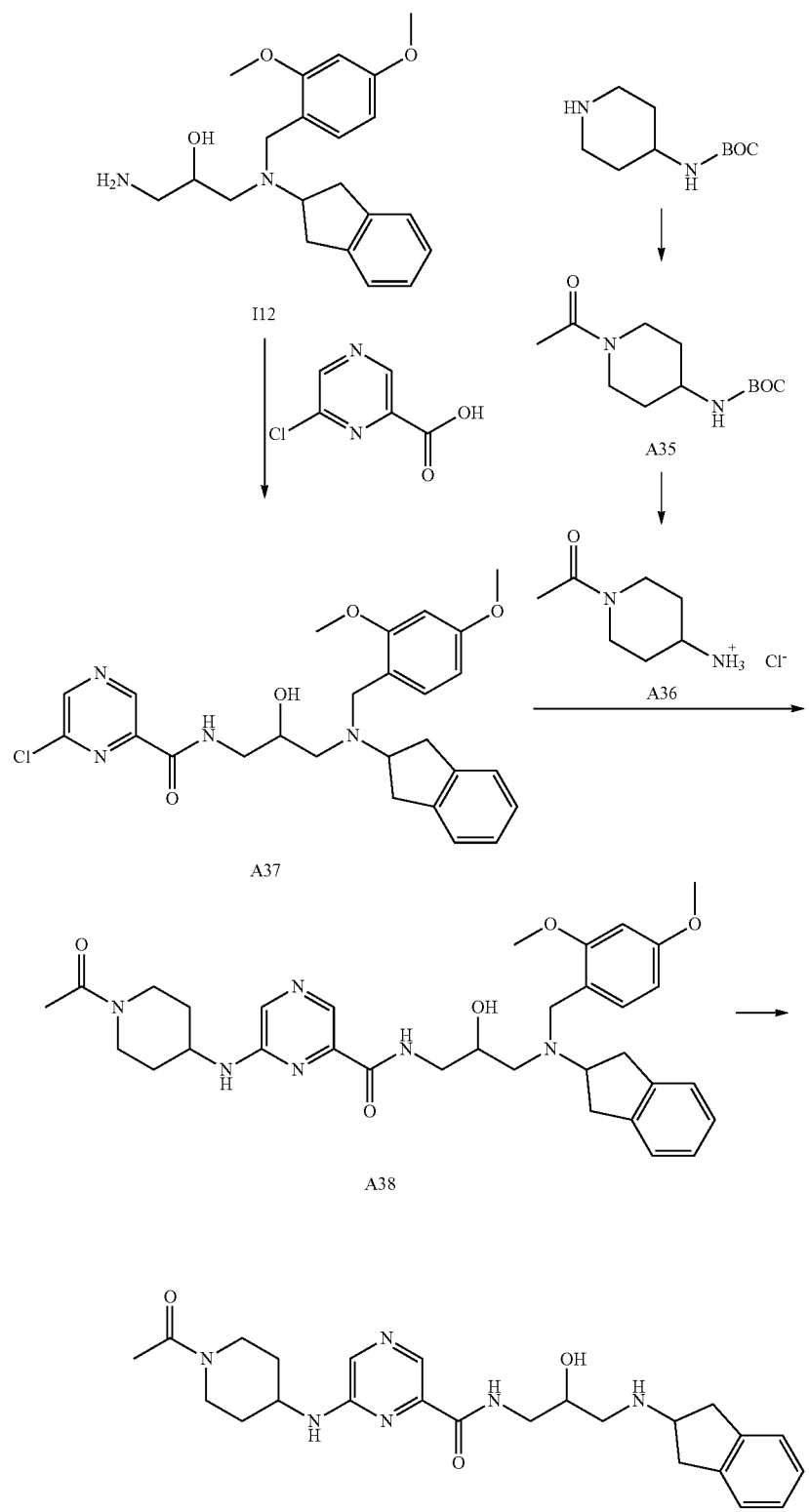

(a) tert-Butyl (1-acetylpiperidin-4-yl)carbamate A35

Acetic anhydride (4.71 mL, 49.9 mmol) was added to a solution of tert-butyl piperidin-4-ylcarbamate (10.0 g, 49.9 mmol) and triethylamine (10.4 mL, 74.9 mmol) in anhydrous DCM (100 mL) at 0° C. The reaction mixture was stirred at 0° C. for 2 hours before water (100 mL) and DCM (50 mL) were added. The organic phase was separated, washed with sat. aqueous NaHCO$_3$ (100 mL) and dried (MgSO$_4$). The solvent was removed in vacuo to give the desired compound as a white solid (10.72 g, 89%). $^1$H NMR (400 MHz, chloroform-d) δ 4.54-4.42 (m, 2H), 3.80-3.70 (m, 1H), 3.70-3.58 (m, 1H), 3.12 (m, 1H), 2.78-2.65 (m, 1H), 2.07 (s, 3H), 2.05-1.97 (m, 1H), 1.96-1.87 (m, 1H), 1.43 (s, 9H), 1.36-1.20 (m, 2H).

(b) 1-Acetylpiperidin-4-aminium chloride A36

A solution of tert-butyl (1-acetylpiperidin-4-yl)carbamate A35 (10.72 g, 44.24 mmol) in dioxane (100 mL) was cooled to 0° C. and treated with 4.0 M HCl in dioxane (12.2 mL, 48.7 mmol). The white precipitate was isolated by filtration and found to contain starting material. The precipitate was dissolved in MeOH (100 mL) and treated with 4.0 M HCl in dioxane (12.2 mL, 48.7 mmol) and the mixture was stirred at room temperature for 16 hours. Another aliquot of 4.0 M HCl in dioxane (6.10 mL, 24.4 mmol) was added and the reaction mixture was stirred for 1.5 hours at 40° C. The volatiles were removed in vacuo and the white solid was dried under high vacuum to give the desired compound (8.60 g, ~90% purity, >95% yield). $^1$H NMR (400 MHz, DMSO-d$_6$) δ 8.52-8.23 (m, 3H), 4.39-4.26 (m, 1H), 3.89-3.77 (m, 1H), 3.28-3.14 (m, 1H), 3.11-3.00 (m, 1H), 2.65-2.54 (m, 1H), 1.99 (s, 3H), 1.97-1.86 (m, 2H), 1.54-1.41 (m, 1H), 1.41-1.27 (m, 1H).

(c) 6-Chloro-N-(3-((2,3-dihydro-1H-inden-2-yl)(2,4-dimethoxybenzyl)amino)-2-hydroxypropyl)pyrazine-2-carboxamide A37

A mixture of 6-chloropyrazine-2-carboxylic acid (0.122 g, 0.771 mmol), DIPEA (0.24 mL, 1.4 mmol), HATU (0.293 g, 0.771 mmol) and DCM (10 mL) was stirred at room temperature under an atmosphere of nitrogen for 15 minutes. A solution of 1-amino-3-((2,3-dihydro-1H-inden-2-yl)(2,4-dimethoxybenzyl)amino)propan-2-ol I12 (0.250 g, 0.701 mmol) in DCM (5 mL) was then added and the mixture was stirred at room temperature overnight. The mixture was quenched by the addition of an aqueous NaOH solution (2 M, 20 mL) and H$_2$O (10 mL). DCM (10 mL) was added and the mixture was separated. The aqueous was extracted with DCM (2×30 mL), the organic layers were combined and the solvent removed in vacuo. The resultant residue was purified by column chromatography (Biotage Isolera, 24 g SiO$_2$ cartridge, 0-10% MeOH (containing 1% v/v TEA) in DCM) to give the desired compound as a yellow oil (0.208 g, 60%). $^1$H NMR (400 MHz, chloroform-d) δ 9.21 (s, 1H), 8.74 (s, 1H), 7.96 (s, 1H), 7.20-7.13 (m, 2H), 7.10-7.02 (m, 3H), 6.49-6.32 (m, 2H), 4.31-4.09 (m, 1H), 3.62-3.50 (m, 2H), 3.39-3.30 (m, 1H), 3.12-2.89 (m, 4H), 2.80 (s, 6H), 2.57-2.38 (m, 2H), 1.61 (s, 2H). LCMS-B: RT 3.66 min; m/z 497.3 [M+H]$^+$.

(d) 6-((1-Acetylpiperidin-4-yl)amino)-N-(3-((2,3-dihydro-1H-inden-2-yl)(2,4-dimethoxybenzyl)amino)-2-hydroxypropyl)pyrazine-2-carboxamide A38

A mixture of 6-chloro-N-(3-((2,3-dihydro-1H-inden-2-yl)(2,4-dimethoxybenzyl)amino)-2-hydroxypropyl)pyrazine-2-carboxamide A37 (0.108 g, 0.217 mmol), 1-acetylpiperidin-4-aminium chloride A36 (0.058 g, 0.33 mmol), Cs$_2$CO$_3$ (0.354 g, 1.09 mmol), xantphos (0.006 g, 0.01 mmol) and Pd$_2$(dba)$_3$ (0.010 g, 0.01 mmol) in 1,4-dioxane (5 mL) was bubbled with nitrogen for 10 min. The mixture was then stirred in the microwave at 120° C. for 20 minutes. The mixture was diluted with EtOAc and the solids removed by filtration. The filtrate solvent was removed in vacuo and the residue was taken up in toluene (5 mL). An extra portion of 1-acetylpiperidin-4-aminium chloride A36 (0.058 g, 0.33 mmol), rac-BINAP (0.014 g, 0.022 mmol), Pd$_2$(dba)$_3$ (0.020 g, 0.022 mmol), and t-BuOK (0.196 g, 1.75 mmol) were added and the mixture was bubbled with nitrogen for 10 minutes before heating in the microwave at 120° C. for 30 minutes. The solvent was removed in vacuo and the residue was purified by column chromatography (Biotage Isolera, 24 g SiO$_2$ cartridge, 0-100% EtOAc in petroleum benzine 40-60° C. then 0-20% MeOH in EtOAc) to give the desired compound as a yellow oil (0.032 g, 24%). LCMS-B: RT 3.32 min; m/z 603.4 [M+H]$^+$.

(e) 6-((1-Acetylpiperidin-4-yl)amino)-N-(3-((2,3-dihydro-1H-inden-2-yl)amino)-2-hydroxypropyl)pyrazine-2-carboxamide 52

A mixture of 6-((1-acetylpiperidin-4-yl)amino)-N-(3-((2,3-dihydro-1H-inden-2-yl)(2,4-dimethoxybenzyl)amino)-2-hydroxypropyl)pyrazine-2-carboxamide A38 (0.032 g, 0.053 mmol) and TFA (5 mL) was stirred at 70° C. for 16 hours. The mixture was cooled to room temperature and the volatiles were removed in vacuo. Water (30 mL) and aqueous NaOH (2 M) were added to the residue and the mixture was extracted with DCM (3×30 mL), dried (MgSO$_4$) and the solvent removed in vauco. The resultant oil was dissolved in a minimum amount of DCM and a solid was precipitated by the addition of cyclohexane. The solid was isolated by vacuum filtration and air dried to give the desired compound as a yellow solid (0.013 g, 54%, ~90% purity as assessed by $^1$H NMR). $^1$H NMR (400 MHz, DMSO-d$_6$) δ 8.37 (t, J=5.9 Hz, 1H), 8.20 (s, 1H), 8.09 (s, 1H), 7.42 (d, J=7.3 Hz, 1H), 7.19-7.13 (m, 2H), 7.12-7.06 (m, 2H), 5.05 (s, 1H), 4.25-4.16 (m, 1H), 4.12-4.03 (m, 1H), 3.85-3.71 (m, 4H), 3.28-3.16 (m, peaks obscured by solvent), 3.10-3.00 (m, 2H), 2.85 (t, J=12.1 Hz, 1H), 2.71-2.58 (m, 4H), 2.01-1.98 (m, 3H), 1.97-1.87 (m, 2H), 1.29-1.21 (m, peaks obscured by solvent). LCMS-B: RT 3.18 min; m/z 453.3 [M+H]$^+$.

Example 32: 5-((1-Acetylpiperidin-4-yl)amino)-N-(3-((2,3-dihydro-1H-inden-2-yl)amino)-2-hydroxypropyl)nicotinamide 53

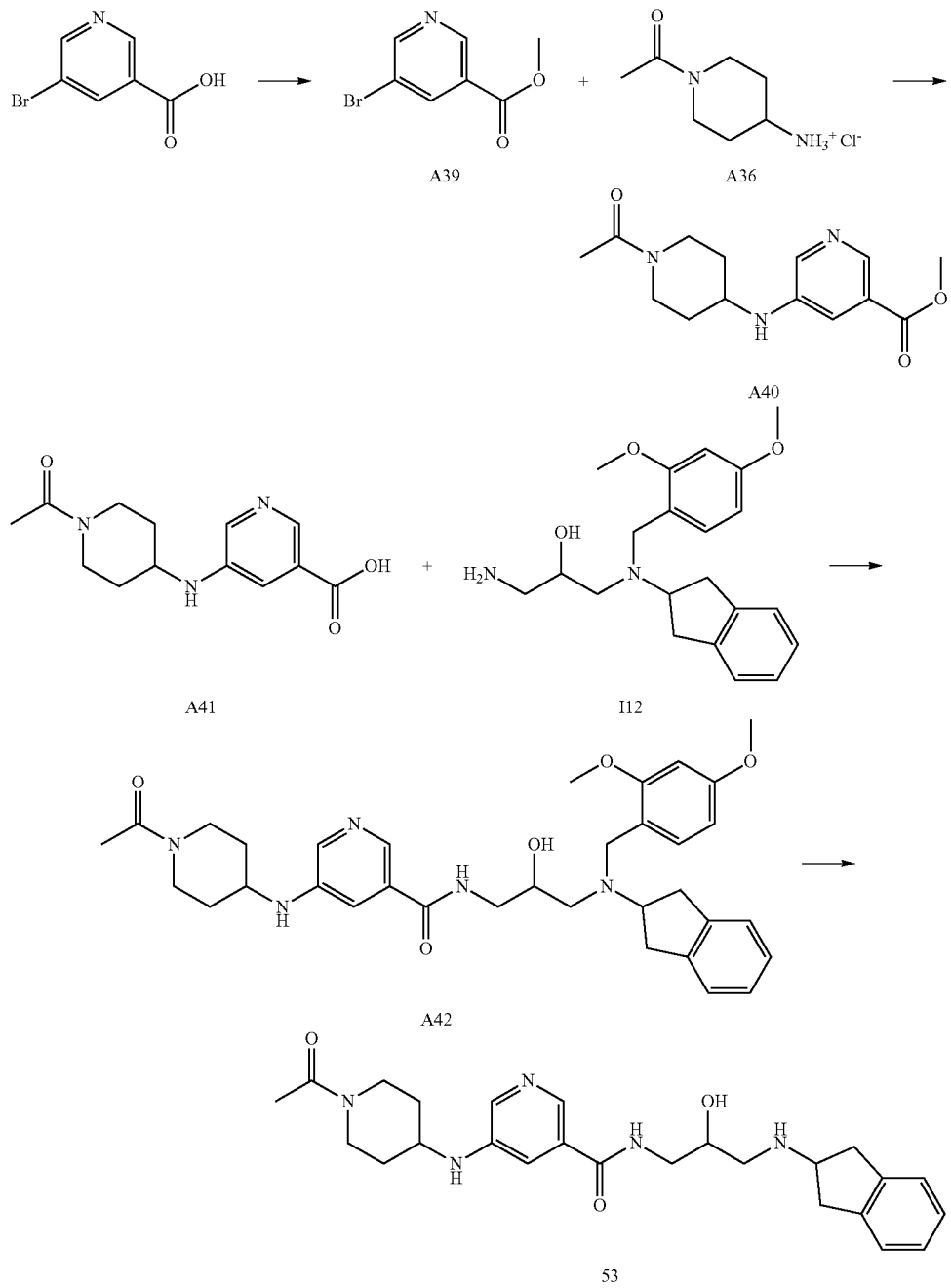

(a) Methyl 5-bromonicotinate A39

A mixture of 5-bromonicotinic acid (1.00 g, 4.95 mmol), sulfuric acid (98%, 0.5 mL) and MeOH (20 mL) was stirred at 80° C. for 16 hours. The volatiles were removed in vacuo and H$_2$O (10 mL) and aqueous NaOH (2 M, 20 mL) were added to the residue. The aqueous was extracted with DCM (40 mL) and the mixture passed through an Isolute Phase Separator. The aqueous was extracted further with DCM (2×40 mL) with the mixture passed through an Isolute Phase Separator after each extraction. The organic layers were combined and the solvent removed in vacuo to give the desired compound as a yellow solid (0.822 g, 77%). 1H NMR (400 MHz, chloroform-d) δ 9.12 (d, J=1.8 Hz, 1H), 8.84 (d, J=2.3 Hz, 1H), 8.45-8.42 (m, 1H), 3.97 (s, 3H). LCMS-B: RT 3.56 min; m/z 216/218 [M+H]$^+$.

(b) Methyl 5-((1-acetylpiperidin-4-yl)amino)nicotinate A40

A mixture of methyl 5-bromonicotinate A39 (0.500 g, 2.31 mmol), 1-acetylpiperidin-4-aminium chloride A36 (0.620 g, 3.47 mmol), Cs$_2$CO$_3$ (3.77 g, 11.6 mmol), xantphos (0.067 g, 0.12 mmol) and Pd$_2$(dba)$_3$ (0.106 g, 0.116 mmol) in 1,4-dioxane (25 mL) was bubbled with nitrogen for 10 min. The mixture was stirred under an atmosphere of nitrogen at 80° C. for 16 hours. Starting material was still present after this time, so another portion of $Cs_2CO_3$ (3.77 g, 11.6 mmol), xantphos (0.067 g, 0.12 mmol) and $Pd_2(dba)_3$ (0.106 g, 0.116 mmol) were added. The mixture was stirred under an atmosphere of nitrogen at 80° C. for 5 days. The mixture was returned to room temperature and diluted with EtOAc (50 mL), filtered and the filtrate was concentrated in vacuo. The crude solid was purified by column chromatography (Biotage Isolera, 40 g $SiO_2$ cartridge, 0-100% EtOAc in petroleum benzine 40-60° C., then 0-20% MeOH in EtOAc) to give the desired compound as a yellow solid (0.273 g, 43%). $^1$H NMR (400 MHz, DMSO-$d_6$) δ 8.26 (d, J=1.8 Hz, 1H), 8.20 (d, J=2.8 Hz, 1H), 7.41-7.39 (m, 1H), 6.18 (d, J=8.1 Hz, 1H), 4.24-4.17 (m, 1H), 3.84 (s, 3H), 3.81-3.73 (m, 1H), 3.64-3.54 (m, 1H), 3.25-3.15 (m, 1H), 2.88-2.79 (m, 1H), 2.01 (s, 3H), 1.96-1.83 (m, 2H), 1.36-1.19 (m, 2H). LCMS-B: RT 3.06 min; m/z 278.2 $[M+H]^+$.

(c) 5-((1-Acetylpiperidin-4-yl)amino)nicotinic acid A41

A mixture of methyl 5-((1-acetylpiperidin-4-yl)amino) nicotinate A40 (0.273 g, 0.984 mmol), LiOH.$H_2$O (0.413 g, 9.84 mmol), THF (7 mL), MeOH (7 mL) and $H_2O$ (1.5 mL) was stirred at 40° C. for 3 hours. The mixture was returned to room temperature and the volatiles were removed in vacuo. Water (20 mL) was added and the pH was adjusted to ~6 with aqueous HCl (2 M). A yellow precipitate was removed by filtration and the aqueous filtrate was passed through an Oasis HLB 35 cc LP extraction cartridge (6 g). The cartridge was washed with 3 column volumes of water before the lipophilic component was eluted with 3 column volumes of MeOH. Evaporation of the MeOH in vacuo gave the desired compound as a yellow oil (0.144 g, 56%). $^1$H NMR (400 MHz, DMSO-$d_6$) δ 8.27-8.22 (m, 2H), 8.15 (d, J=2.8 Hz, 1H), 7.40-7.36 (m, 1H), 6.07 (d, J=8.0 Hz, 1H), 4.26-4.16 (m, 1H), 3.80-3.74 (m, 1H), 3.60-3.53 (m, peaks obscured by solvent), 3.24-3.16 (m, peaks obscured by solvent), 2.87-2.77 (m, 1H), 2.00 (s, 3H), 1.96-1.84 (m, 2H), 1.36-1.16 (m, 2H). LCMS-B: RT 1.80 min; m/z 264.2 $[M+H]^+$.

(d) 5-((1-Acetylpiperidin-4-yl)amino)-N-(3-((2,3-dihydro-1H-inden-2-yl)(2,4-dimethoxybenzyl) amino)-2-hydroxypropyl)nicotinamide A42

A mixture of 5-((1-acetylpiperidin-4-yl)amino)nicotinic acid A41 (0.050 g, 0.19 mmol), DIPEA (60 μL, 0.35 mmol) and HATU (0.072 g, 0.19 mmol) in DCM (5 mL) was stirred for 15 minutes at room temperature under an atmosphere of nitrogen. A solution of 1-amino-3-((2,3-dihydro-1H-inden-2-yl)(2,4-dimethoxybenzyl)amino)propan-2-ol I12 (0.062 g, 0.17 mmol) in DCM (5 mL) was then added and the mixture was stirred for 4 hours at room temperature. Aqueous NaOH (2 M, 20 mL) was added and the aqueous was extracted with DCM (3×30 mL). The organic layers were combined, filtered through a Biotage phase separator and the volatiles removed in vacuo. The residue was purified by column chromatography (Biotage Isolera, 24 g $SiO_2$ cartridge, 0-20% MeOH in DCM) to give the desired compound as a colourless oil (0.066 g, 64%). LCMS-B: RT 3.51 min; m/z 602.4 $[M+H]^+$.

(e) 5-((1-Acetylpiperidin-4-yl)amino)-N-(3-((2,3-dihydro-1H-inden-2-yl)amino)-2-hydroxypropyl) nicotinamide 53

A mixture of 5-((1-acetylpiperidin-4-yl)amino)-N-(3-((2, 3-dihydro-1H-inden-2-yl)(2,4-dimethoxybenzyl)amino)-2-hydroxypropyl)nicotinamide A42 (0.066 g, 0.11 mmol) and TFA (5 mL) was stirred at 70° C. for 4 hours. The mixture was cooled to room temperature and the volatiles were removed in vacuo. Water (30 mL) was added to the residue and the aqueous was washed with DCM (3×20 mL). The aqueous layer was made basic by the addition of aqueous NaOH (2 M) and the mixture was extracted with DCM (3×30 mL). The organic extract was filtered through a Biotage phase separator cartridge and the solvent was removed in vacuo. The colourless oil was dissolved in a minimum amount of DCM and a solid was precipitated by the addition of cyclohexane. The solid was isolated by vacuum filtration and air dried to give the desired compound as a white solid (0.040 g, 81%). $^1$H NMR (400 MHz, DMSO-$d_6$) δ 8.50 (t, J=5.7 Hz, 1H), 8.17 (d, J=1.7 Hz, 1H), 8.08 (d, J=2.8 Hz, 1H), 7.32-7.26 (m, 1H), 7.19-7.14 (m, 2H), 7.12-7.07 (m, 2H), 6.02 (d, J=8.0 Hz, 1H), 4.96-4.84 (m, 1H), 4.27-4.17 (m, 1H), 3.82-3.75 (m, 1H), 3.73-3.67 (m, 1H), 3.60-3.53 (m, 1H), 3.52-3.46 (m, 1H), 3.29-3.14 (m, peaks obscured by solvent), 3.09-3.00 (m, 2H), 2.85-2.77 (m, 1H), 2.69-2.61 (m, 3H), 2.57-2.52 (m, peaks obscured by solvent), 2.00 (s, 3H), 1.93-1.84 (m, 2H), 1.37-1.15 (m, 2H). LCMS-B: RT 3.10 min; m/z 452.3 $[M+H]^+$.

Example 33: 2-((1-Acetylpiperidin-4-yl)amino)-N-(3-((2,3-dihydro-1H-inden-2-yl)amino)-2-hydroxypropyl)pyrimidine-4-carboxamide 54

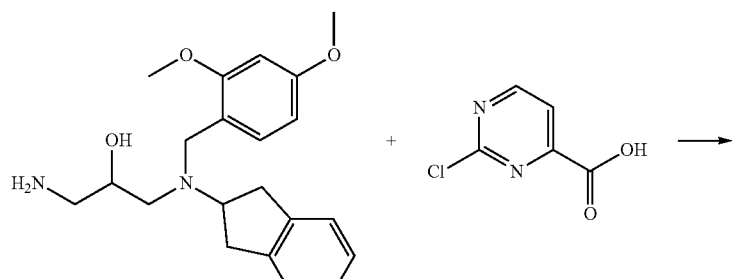

I12

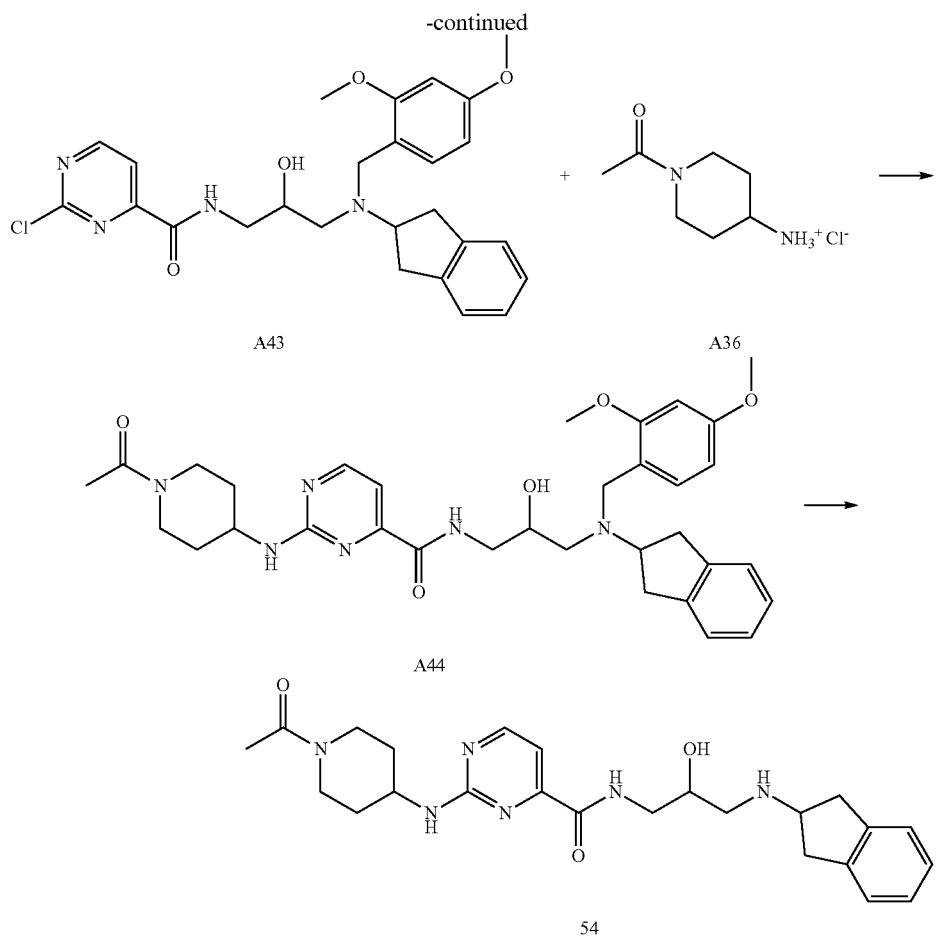

(a) 2-Chloro-N-(3-((2,3-dihydro-1H-inden-2-yl)(2,4-dimethoxybenzyl)amino)-2-hydroxypropyl)pyrimidine-4-carboxamide A43

A mixture of 2-chloropyrimidine-4-carboxylic acid (0.122 g, 0.771 mmol), DIPEA (0.24 mL, 1.4 mmol), HATU (0.293 g, 0.771 mmol) and DCM (10 mL) was stirred at room temperature under an atmosphere of nitrogen for 15 minutes. A solution of 1-amino-3-((2,3-dihydro-1H-inden-2-yl)(2,4-dimethoxybenzyl)amino)propan-2-ol I12 (0.250 g, 0.701 mmol) in DCM (5 mL) was then added and the mixture was stirred at room temperature overnight. The mixture was quenched by the addition of an aqueous NaOH solution (2 M, 20 mL) and H$_2$O (10 mL). DCM (10 mL) was added and the mixture was separated. The aqueous was extracted with DCM (2×30 mL), the organic phases were combined and the solvent removed in vacuo. The resultant residue was purified by column chromatography (Biotage Isolera, 24 g SiO$_2$ cartridge, 0-10% MeOH (containing 1% v/v TEA) in DCM) to give the desired compound as a yellow oil (0.253 g, 73%). LCMS-B: RT 3.67 min; m/z 497.3 [M+H]$^+$.

(b) 2-((1-Acetylpiperidin-4-yl)amino)-N-(3-((2,3-dihydro-1H-inden-2-yl)(2,4-dimethoxybenzyl)amino)-2-hydroxypropyl)pyrimidine-4-carboxamide A44

A mixture of 2-chloro-N-(3-((2,3-dihydro-1H-inden-2-yl)(2,4-dimethoxybenzyl)amino)-2-hydroxypropyl)pyrimidine-4-carboxamide A43 (0.100 g, 0.201 mmol), 1-acetylpiperidin-4-aminium chloride A36 (0.108 g, 0.604 mmol), triethylamine (0.28 mL, 2.0 mmol) and i-PrOH (5 mL) was heated in the microwave at the following temperatures for the amount of time indicated, with a TLC of the reaction mixture conducted after each heating period: 110° C. for 10 minutes; 110° C. for 15 minutes; 120° C. for 15 minutes; 120° C. for 15 minutes; 130° C. for 10 minutes; 150° C. for 10 minutes. The solvent was removed in vacuo and the residue was purified by column chromatography (Biotage Isolera, 24 g SiO$_2$ cartridge, 0-10% MeOH (containing 1% v/v TEA) in DCM) to give the desired compound as a yellow oil (0.022 g, 18%). LCMS-B: RT 3.33 min; m/z 603.5 [M+H]$^+$.

(c) 2-((1-Acetylpiperidin-4-yl)amino)-N-(3-((2,3-dihydro-1H-inden-2-yl)amino)-2-hydroxypropyl)pyrimidine-4-carboxamide 54

A solution of 2-((1-acetylpiperidin-4-yl)amino)-N-(3-((2,3-dihydro-1H-inden-2-yl)(2,4-dimethoxybenzyl)amino)-2-hydroxypropyl)pyrimidine-4-carboxamide A44 (0.022 g, 0.037 mmol) in TFA (5 mL) was stirred at 70° C. for 16 hours. The volatiles were removed in vacuo before the residue was diluted with H$_2$O (10 mL). The aqueous phase was washed with DCM (3×30 mL) and then made basic by the addition of an aqueous NaOH solution (2 M). The aqueous was extracted with DCM (3×20 mL), the organic layers were combined, washed with brine, dried (MgSO$_4$)

and the solvent removed in vacuo. The crude residue was dissolved in a minimum amount of DCM and a precipitate formed by the addition of cyclohexane. The precipitate was isolated by vacuum filtration and air dried to give the desired compound as a white solid (0.006 g, 36%). $^1$H NMR (400 MHz, DMSO-$d_6$) δ 8.60-8.24 (m, 2H), 7.46 (s, 1H), 7.20-7.14 (m, 2H), 7.12-7.04 (m, 3H), 5.04 (s, 1H), 4.27 (d, J=13.3 Hz, 1H), 4.04 (s, 1H), 3.86-3.63 (m, 2H), 3.57-3.41 (m, peaks obscured by solvent), 3.19-2.99 (m, 3H), 2.80-2.57 (m, 6H), 2.00 (s, 3H), 1.95-1.81 (m, 2H), 1.45-1.24 (m, peaks obscured by solvent). LCMS-A: RT 4.41 min; m/z 453.3 [M+H]$^+$.

Example 35: (R)-2-((1-Acetylpiperidin-4-yl)amino)-N-(3-((2,3-dihydro-1H-inden-2-yl)amino)-2-hydroxypropyl)isonicotinamide 55

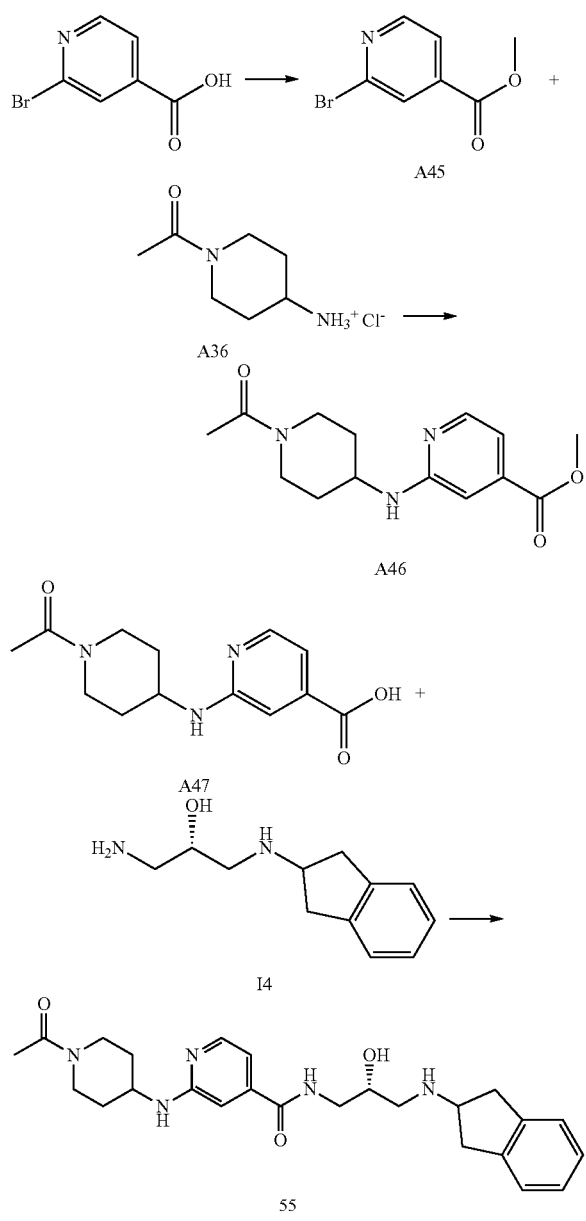

(a) Methyl 2-bromoisonicotinate A45

A solution of 2-bromoisonicotinic acid (5.00 g, 24.8 mmol) in MeOH (50 mL) was treated with sulfuric acid (98%, 0.50 mL, 9.4 mmol) and the reaction mixture was stirred at 80° C. for 1 hour. The mixture was returned to room temperature and stirred for a further 96 hours before heating to 80° C. and stirring for 24 hours. The reaction mixture was cooled to room temperature, and the volatiles were removed in vacuo. Aqueous NaOH (2 M, 50 mL) was added to the residue and the aqueous was extracted with EtOAc (3×50 mL). The organic layers were combined, washed with brine, dried (MgSO$_4$) and the solvent removed in vacuo to give the desired compound as a yellow oil (4.14 g, 77%). $^1$H NMR (400 MHz, chloroform-d) δ 8.52 (dd, J=5.0, 0.8 Hz, 1H), 8.04 (t, J=1.2 Hz, 1H), 7.80 (dd, J=5.0, 1.4 Hz, 1H), 3.96 (s, 3H). LCMS-B: RT 3.55 min; m/z 216/218 [M+H]$^+$.

(b) Methyl 2-((1-acetylpiperidin-4-yl)amino)isonicotinate A46

A mixture of 1-acetylpiperidin-4-aminium chloride A36 (2.25 g, 12.6 mmol), methyl 2-bromoisonicotinate A45 (1.81 g, 8.38 mmol), Cs$_2$CO$_3$ (10.92 g, 33.51 mmol), xantphos (0.242 g, 0.419 mmol) and Pd$_2$(dba)$_3$ (0.384 g, 0.419 mmol) in 1,4-dioxane (40 mL) was bubbled with nitrogen for 10 min. The mixture was then stirred under an atmosphere of nitrogen at 80° C. for 24 hours. Another portion of Cs$_2$CO$_3$ (5.46 g, 16.8 mmol), xantphos (0.121 g, 0.209 mmol) and Pd$_2$(dba)$_3$ (0.192 g, 0.210 mmol) were added and the mixture was stirred under an atmosphere of nitrogen at 80° C. for 5 days. The reaction mixture was returned to room temperature and diluted with EtOAc (150 mL). Solid impurities were removed by filtration and the filtrate solvent was removed in vacuo. The resultant solid was purified by column chromatography (Biotage Isolera, 40 g SiO$_2$ cartridge, 0-100% EtOAc in petroleum benzine 40-60° C., then 0-20% MeOH (containing 1% v/v TEA) in EtOAc) to give the desired compound as a yellow solid (0.558 g, 24%). LCMS-B: RT 3.05 min; m/z 278.2 [M+H]$^+$.

(c) 2-((1-Acetylpiperidin-4-yl)amino)isonicotinic acid A47

A mixture of methyl 2-((1-acetylpiperidin-4-yl)amino)isonicotinate A46 (0.558 g, 2.01 mmol), LiOH.H$_2$O (1.69 g, 40.2 mmol), THF (7 mL), MeOH (7 mL) and H$_2$O (1.5 mL) was stirred at 40° C. for 2 hours. The mixture was returned to room temperature and the volatiles were removed in vacuo. Water (30 mL) was added and the pH was adjusted to ~6 with aqueous HCl (2 M). The aqueous was passed through an Oasis HLB 35 cc LP extraction cartridge (6 g) which was washed with 4 column volumes of water. The lipophilic component was then eluted with 4 column volumes of MeOH. Evaporation of the MeOH in vacuo gave the desired compound as a yellow solid (0.197 g, 37%). The aqueous phase from the first iteration of cartridge purification was passed through another Oasis HLB 35 cc LP extraction cartridge (6 g). The column was washed with 4 column volumes of water and the product was eluted with 4 column volumes of MeOH. Evaporation of the MeOH in vacuo gave the desired compound as a white solid (0.128 g, 24%; overall yield: 0.325 g, 61%). $^1$H NMR (400 MHz, DMSO-$d_6$) δ 8.08 (d, J=5.2 Hz, 1H), 6.98 (s, 1H), 6.86-6.79 (m, 2H), 4.26-4.16 (m, 1H), 4.03-3.90 (m, 1H), 3.81-3.72 (m, 1H), 3.21-3.12 (m, 1H), 2.85-2.74 (m, 1H), 2.00 (s, 3H), 1.97-1.83 (m, 2H), 1.41-1.16 (m, 2H); —OH not observed. LCMS-B: RT 1.17 min; m/z 262.1 [M–H]⁻.

(d) (R)-2-((1-Acetylpiperidin-4-yl)amino)-N-(3-((2,3-dihydro-1H-inden-2-yl)amino)-2-hydroxypropyl)isonicotinamide 55

A mixture of 2-((1-acetylpiperidin-4-yl)amino)isonicotinic acid A47 (0.067 g, 0.26 mmol), DIPEA (63 µL, 0.36 mmol), HATU (0.097 g, 0.26 mmol) and DCM (5 mL) was stirred at room temperature for 15 minutes. A solution of (S)-1-amino-3-((2,3-dihydro-1H-inden-2-yl)amino)propan-2-ol I4 (0.050 g, 0.24 mmol) in DCM (5 mL) was then added and the mixture was stirred for 16 hours at room temperature. Water (20 mL) was added and the aqueous was extracted with DCM (3×30 mL). The organic layers were combined, washed with brine, dried (MgSO₄) and the solvent removed in vacuo. The resultant residue was purified by column chromatography (Biotage Isolera, 24 g SiO₂ cartridge, 0-30% MeOH (containing 1% v/v TEA) in DCM) to give a colourless oil. The oil was taken up in a minimum amount of DCM and the product was precipitated by the addition of cyclohexane. The product was isolated by vacuum filtration and air dried to give the desired compound as a white solid (0.011 g, 10%). ¹H NMR (400 MHz, DMSO-d₆) δ 8.49 (t, J=5.7 Hz, 1H), 8.02 (d, J=5.2 Hz, 1H), 7.21-7.14 (m, 2H), 7.12-7.06 (m, 2H), 6.84 (s, 1H), 6.77 (d, J=5.5 Hz, 1H), 6.72 (d, J=7.6 Hz, 1H), 4.93 (s, 1H), 4.28-4.14 (m, 1H), 4.02-3.88 (m, 1H), 3.83-3.66 (m, 2H), 3.52 (p, J=6.6, 6.6, 6.5, 6.5 Hz, 1H), 3.29-3.12 (m, 3H), 3.11-3.00 (m, 2H), 2.82-2.74 (m, 1H), 2.72-2.62 (m, 3H), 2.59-2.53 (m, 1H), 2.00 (s, 3H), 1.96-1.81 (m, 2H), 1.38-1.14 (m, 2H); N—H not observed. LCMS-B: RT 3.11 min; m/z 452.3 [M+H]⁺.

Example 36: (S)-2-((1-Acetylpiperidin-4-yl)amino)-N-(3-((2,3-dihydro-1H-inden-2-yl)amino)-2-hydroxypropyl)isonicotinamide 56

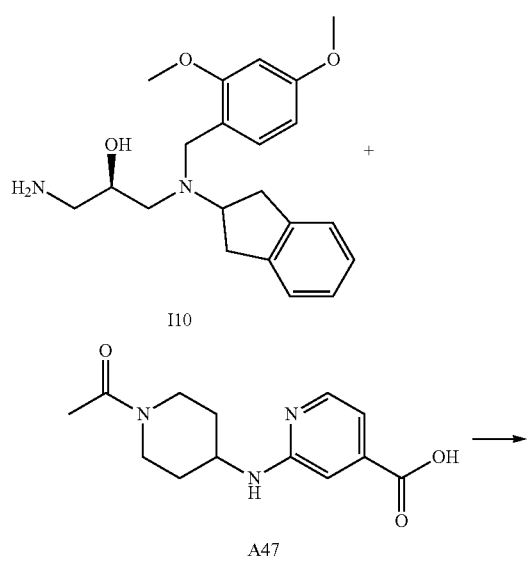

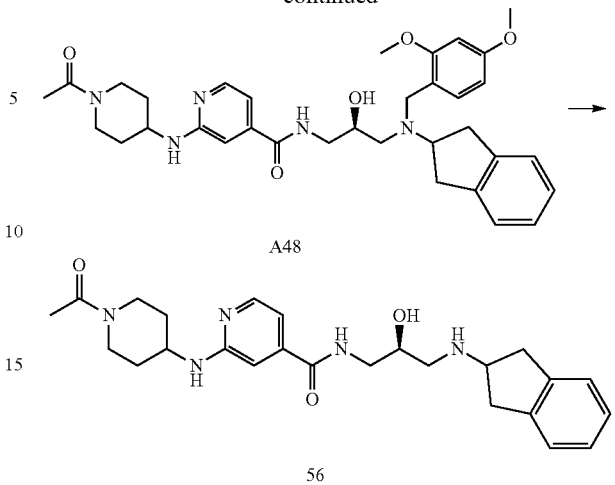

(a) (R)-2-((1-Acetylpiperidin-4-yl)amino)-N-(3-((2,3-dihydro-1H-inden-2-yl)(2,4-dimethoxybenzyl)amino)-2-hydroxypropyl)isonicotinamide A48

A mixture of 2-((1-acetylpiperidin-4-yl)amino)isonicotinic acid A47 (0.075 g, 0.29 mmol), DIPEA (68 µL, 0.39 mmol), HATU (0.108 g, 0.285 mmol) and DCM (10 mL) was stirred at room temperature for 15 minutes. A solution of (R)-1-amino-3-((2,3-dihydro-1H-inden-2-yl)(2,4-dimethoxybenzyl)amino)propan-2-ol I10 (0.092 g, 0.26 mmol) in DCM (5 mL) was then added and the mixture was stirred for 24 hours at room temperature. Water (30 mL) was added and the aqueous was extracted with DCM (3×30 mL). The organic layers were combined, washed with brine, dried (MgSO₄) and the solvent removed in vacuo. The resultant residue was purified by column chromatography (Biotage Isolera, 12 g SiO₂ cartridge, 0-20% MeOH (containing 1% v/v TEA) in DCM) to give the desired compound as a colourless oil (0.084 g, 54%). LCMS-B: RT 3.28 min; m/z 602.5 [M+H]⁺.

(b) (S)-2-((1-Acetylpiperidin-4-yl)amino)-N-(3-((2,3-dihydro-1H-inden-2-yl)amino)-2-hydroxypropyl)isonicotinamide 56

A mixture of (R)-2-((1-acetylpiperidin-4-yl)amino)-N-(3-((2,3-dihydro-1H-inden-2-yl)(2,4-dimethoxybenzyl)amino)-2-hydroxypropyl)isonicotinamide A48 (0.080 g, 0.13 mmol) and TFA (5 mL) was stirred at 70° C. for 16 hours. The volatiles were removed in vacuo before the residue was diluted with H₂O (20 mL). The aqueous phase was washed with DCM (3×30 mL) and then made basic by the addition of solid NaHCO₃. The aqueous was extracted with DCM (3×30 mL), the organic layers were combined, washed with brine, dried (MgSO₄) and the solvent removed in vacuo. The resultant residue was purified by column chromatography (Biotage Isolera, 24 g SiO₂ cartridge, 0-40% MeOH (containing 1% v/v TEA) in DCM) to give a colourless oil. The oil was dissolved in a minimum amount of DCM and the product was precipitated by the addition of cyclohexane. The solid was isolated by vacuum filtration and air dried to give the desired compound as a white solid (0.030 g, 50%). ¹H NMR (400 MHz, DMSO-d₆) δ 8.48 (t, J=5.7 Hz, 1H), 8.02 (d, J=5.3 Hz, 1H), 7.21-7.14 (m, 2H), 7.13-7.06 (m, 2H), 6.84 (s, 1H), 6.77 (d, J=5.3 Hz, 1H), 6.72

(d, J=7.6 Hz, 1H), 4.92 (s, 1H), 4.27-4.15 (m, 1H), 4.04-3.89 (m, 1H), 3.83-3.66 (m, 2H), 3.58-3.47 (m, 1H), 3.30-3.22 (m, peaks obscured by solvent), 3.20-3.12 (m, 1H), 3.10-3.00 (m, 2H), 2.84-2.74 (m, 1H), 2.72-2.62 (m, 3H), 2.60-2.52 (m, 1H), 2.00 (s, 3H), 1.97-1.82 (m, 2H), 1.38-1.15 (m, 2H). LCMS-B: RT 3.09 min; m/z 452.3 [M+H]$^+$.

Example 37: 6-((1-Acetylpiperidin-4-yl)amino)-N-(3-((2,3-dihydro-1H-inden-2-yl)amino)-2-hydroxypropyl)picolinamide 57

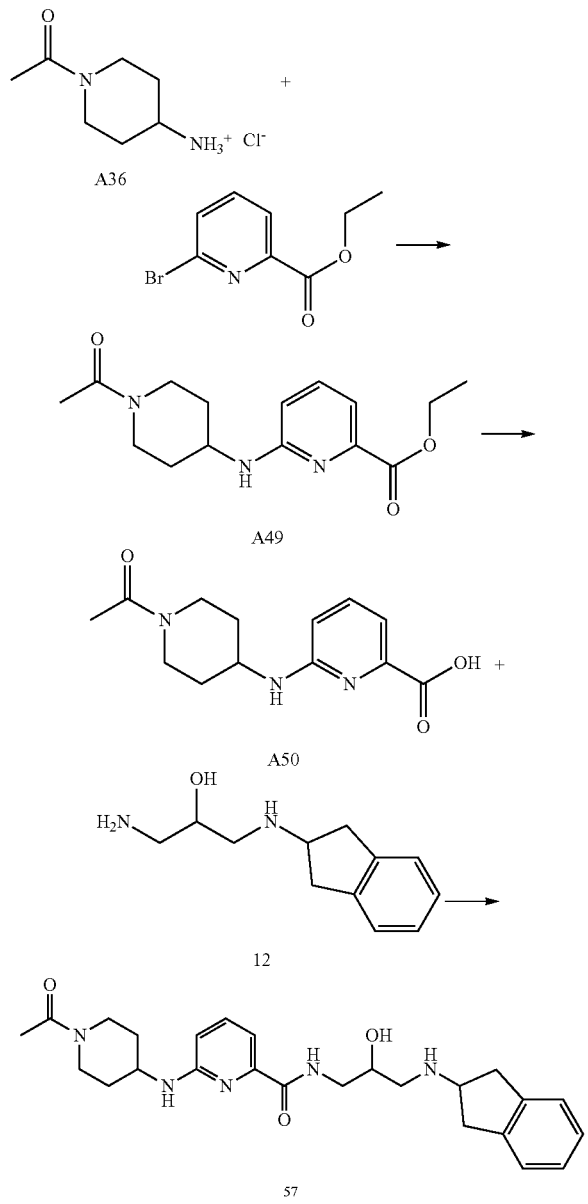

(a) Ethyl 6-((1-acetylpiperidin-4-yl)amino)picolinate A49

A mixture of 1-acetylpiperidin-4-aminium chloride A36 (0.231 g, 1.29 mmol), 6-bromopyridine-2-carboxylic acid ethyl ester (0.198 g, 0.862 mmol), Cs$_2$CO$_3$ (1.40 g, 4.31 mmol), xantphos (0.025 g, 0.043 mmol) and Pd$_2$(dba)$_3$ (0.039 g, 0.043 mmol) in 1,4-dioxane (10 mL) was bubbled with nitrogen for 10 min. The mixture was then stirred under an atmosphere of nitrogen at 80° C. for 16 hours. The reaction mixture was returned to room temperature and diluted with MeOH (20 mL). Solid impurities were removed by filtration and the filtrate solvent was removed in vacuo. The resultant solid was purified by column chromatography (Biotage Isolera, 24 g SiO$_2$ cartridge, 0-100% EtOAc in petroleum benzine 40-60° C., then 0-10% MeOH in EtOAc) to give the desired compound as a yellow oil (0.121 g, 48%). LCMS-A: RT 4.65 min; m/z 292.2 [M+H]$^+$.

(b) 6-((1-Acetylpiperidin-4-yl)amino)picolinic acid A50

A mixture of ethyl 6-((1-acetylpiperidin-4-yl)amino)picolinate A49 (0.121 g, 0.415 mmol), LiOH.H$_2$O (0.349 g, 8.31 mmol), MeOH (7 mL), THF (7 mL) and H$_2$O (1.5 mL) was stirred at room temperature for 16 hours. The volatiles were removed in vacuo and the resultant solid was taken up in H$_2$O (10 mL) and the aqueous adjusted to pH ~6 with aqueous HCl (2 M). The mixture was loaded onto an Oasis HLB 35 cc LP extraction cartridge (6 g) which was washed with 3 column volumes of water. The lipophilic component was then eluted with 3 column volumes of MeOH. Evaporation of the MeOH in vacuo gave the desired compound as a yellow solid (0.097 g, 89%). $^1$H NMR (400 MHz, chloroform-d) δ 7.91-7.82 (m, 1H), 7.46 (d, J=7.2 Hz, 1H), 6.93 (d, J=8.4 Hz, 1H), 4.25 (s, 1H), 3.99-3.88 (m, 1H), 3.80 (s, 1H), 3.41-3.31 (m, 1H), 3.29-3.14 (m, 1H), 2.13 (s, 3H), 2.09-1.94 (m, 2H), 1.83 (s, 1H), 1.74-1.60 (m, 1H). LCMS-A: RT 1.75 min; m/z 264.2 [M+H]$^+$.

(c) 6-((1-Acetylpiperidin-4-yl)amino)-N-(3-((2,3-dihydro-1H-inden-2-yl)amino)-2-hydroxypropyl) picolinamide 57

A mixture of 6-((1-acetylpiperidin-4-yl)amino)picolinic acid A50 (0.097 g, 0.37 mmol), triethylamine (0.20 mL, 1.5 mmol), and DCM (5 mL) was cooled to 0° C. under a nitrogen atmosphere before isobutyl chloroformate (48 µL, 0.37 mmol) was added. The mixture was stirred for 20 min at 0° C. before being transferred via syringe to a solution of 1-amino-3-((2,3-dihydro-1H-inden-2-yl)amino)propan-2-ol I2 (0.076 g, 0.37 mmol) in DCM (5 mL) at 0° C. After 2 h the mixture was diluted with DCM (10 mL), water (10 mL) and aqueous sodium hydroxide (2 M, 10 mL). The separated aqueous phase was extracted with DCM (2×15 mL), the pooled DCM extracts washed with brine (25 mL), dried (MgSO$_4$) and the solvent evaporated in vacuo. The residue was purified by column chromatography (Biotage Isolera, 12 g SiO$_2$ cartridge, 0-20% MeOH (containing 1% v/v 2 M NH$_3$ in MeOH) in DCM) to give the desired compound as a white solid (0.049 g, 29%). $^1$H NMR (400 MHz, DMSO-d$_6$) δ 8.66-8.55 (m, 1H), 7.57-7.47 (m, 1H), 7.28-7.21 (m, 2H), 7.20-7.14 (m, 3H), 6.82 (d, J=7.7 Hz, 1H), 6.67 (d, J=8.3 Hz, 1H), 5.92-5.81 (m, 1H), 4.27-4.14 (m, 2H), 4.09-3.96 (m, 2H), 3.82-3.67 (m, 1H), 3.52-3.38 (m, 2H), 3.30-3.21 (m, 3H), 3.18-3.03 (m, 3H), 2.96-2.84 (m, 2H), 2.03-1.96 (m, 3H), 1.96-1.83 (m, 2H), 1.38-1.20 (m, 2H); N—H not observed. LCMS-A: RT 4.46 min; m/z 452.3 [M+H]$^+$.

Example 38: 6-((1-Acetylazetidin-3-yl)amino)-N-(3-((2,3-dihydro-1H-inden-2-yl)amino)-2-hydroxypropyl)pyrimidine-4-carboxamide 2,2,2-trifluoroacetic acid salt 58

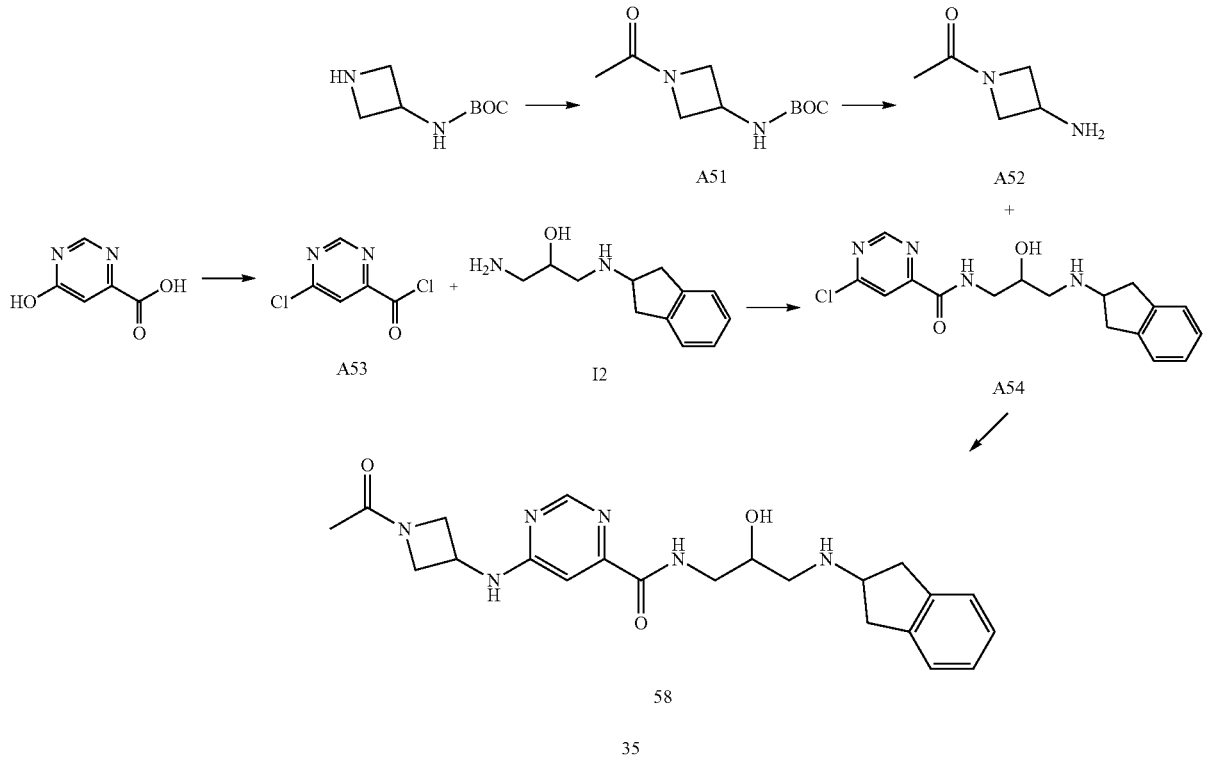

(a) tert-Butyl (1-acetylazetidin-3-yl)carbamate A51

Acetic anhydride (0.81 mL, 8.6 mmol) was added to a solution of tert-butyl azetidin-3-ylcarbamate (0.990 g, 5.75 mmol) and TEA (1.20 mL, 8.62 mmol) in DCM (20 mL) at 0° C. The mixture was stirred for 2 hours at 0° C. before water (50 mL) was added. The organic phase was separated and the aqueous was extracted with DCM (2×25 mL). The organic layers were combined, washed with brine and dried (MgSO$_4$). The solvent was removed in vacuo to give the desired compound as a colourless oil (0.915 g, 74%). $^1$H NMR (400 MHz, chloroform-d) δ 5.13-4.92 (m, 1H), 4.55-4.34 (m, 2H), 4.28 (t, J=9.2 Hz, 1H), 3.94 (dd, J=8.7, 4.8 Hz, 1H), 3.79 (dd, J=10.4, 4.9 Hz, 1H), 1.86 (s, 3H), 1.44 (s, 9H).

(b) 1-(3-Aminoazetidin-1-yl)ethan-1-one A52

A solution of tert-butyl (1-acetylazetidin-3-yl)carbamate A51 (0.879 g, 4.10 mmol) in MeOH (20 mL) was stirred with HCl (~1.25 M in MeOH, 3.61 mL, 4.51 mmol) at room temperature for 30 minutes. Another aliquot of HCl (~1.25 M in MeOH, 3.61 mL, 4.51 mmol) was added and the mixture was stirred for a further 16 hours at room temperature. TLC showed the continued presence of starting material, so another aliquot of HCl (~1.25 M in MeOH, 7.22 mL, 9.03 mmol) was added. The mixture was stirred for 2 hours at room temperature and then at 45° C. for 2 hours. The solvent was evaporated under reduced pressure and the resultant residue was taken up in DCM (10 mL) and treated with TFA (3.14 mL, 41.0 mmol). The mixture was stirred for 3 hours at room temperature before the volatiles were removed in vacuo. The residue was taken up in MeOH and loaded onto an SCX cartridge (BondElut, 10 g). The column was washed with 5 column volumes of MeOH before the desired product was eluted with 5 column volumes of 3.5 M NH$_3$ in MeOH. The basic fractions were combined and the solvent removed in vacuo to give the desired compound as a yellow oil (0.505 g, ~90% purity, >95% yield). $^1$H NMR (400 MHz, chloroform-d) δ 4.39-4.29 (m, 1H), 4.27-4.19 (m, 1H), 3.90-3.72 (m, 2H), 3.70-3.59 (m, 1H), 1.86 (s, 3H); —NH$_2$ not observed.

(c) 6-Chloropyrimidine-4-carbonyl chloride A53

Oxalyl chloride (15.3 mL, 0.178 mol) was added to a mixture of 6-hydroxypyrimidine-4-carboxylic acid (5.00 g, 35.7 mmol) in EtOAc (50 mL). The mixture was stirred at room temperature for 20 min before DMF (0.1 mL) was added and stirring continued at 80° C. for 16 hours. The volatiles were removed in vacuo and the residue was azeotroped with toluene (×3) to give the desired compound as a black solid (5.87 g, 93%). $^1$H NMR (400 MHz, DMSO-d$_6$) δ 9.23 (d, J=1.1 Hz, 1H), 8.15 (d, J=1.1 Hz, 1H).

(d) 6-Chloro-N-(3-((2,3-dihydro-1H-inden-2-yl)amino)-2-hydroxypropyl)pyrimidine-4-carboxamide A54

A solution of 6-chloropyrimidine-4-carbonyl chloride A53 (0.179 g, 1.01 mmol) in DCM (10 mL) was slowly added to a mixture of 1-amino-3-((2,3-dihydro-1H-inden-2-yl)amino)propan-2-ol I2 (0.250 g, 1.21 mmol) and TEA (1.41 mL, 10.1 mmol) in DCM (10 mL) at 0° C. under an atmosphere of nitrogen. The mixture was slowly allowed to return to room temperature and stirred for a further 16 hours under a balloon of nitrogen. Water (20 mL) and an aqueous NaOH solution (2 M, 10 mL) were added and the mixture was extracted with DCM (3×30 mL). The organic layers were combined, washed with brine and dried (MgSO$_4$). The solvent was removed in vacuo and the residue was purified by column chromatography (Biotage Isolera, 24 g SiO$_2$ cartridge, 0-10% MeOH (containing 1% v/v 2 M NH$_3$ in MeOH) in DCM) to give the desired compound as a white solid (0.111 g, 32%). $^1$H NMR (400 MHz, DMSO-d$_6$) δ 9.17 (d, J=0.6 Hz, 1H), 9.07 (t, J=5.8 Hz, 1H), 8.08 (d, J=1.1 Hz, 1H), 7.20-7.14 (m, 2H), 7.12-7.06 (m, 2H), 5.06-4.92 (m, 1H), 3.80-3.68 (m, 1H), 3.53-3.46 (m, 1H), 3.45-3.38 (m, peaks obscured by solvent), 3.10-3.00 (m, 2H), 2.70-2.57 (m, 4H). LCMS-A: RT 4.46 min; m/z 347.1 [M+H]$^+$.

(e) 6-((1-Acetylazetidin-3-yl)amino)-N-(3-((2,3-dihydro-1H-inden-2-yl)amino)-2-hydroxypropyl)pyrimidine-4-carboxamide 2,2,2-trifluoroacetic acid salt 58

A mixture of 1-(3-aminoazetidin-1-yl)ethan-1-one A52 (0.013 g, ~90% purity, 0.10 mmol), 6-chloro-N-(3-((2,3-dihydro-1H-inden-2-yl)amino)-2-hydroxypropyl)pyrimidine-4-carboxamide A54 (0.035 g, 0.10 mmol), triethylamine (0.056 mL, 0.40 mmol) and i-PrOH (5 mL) was stirred at 70° C. for 1 hour and then 75° C. for 60 hours. The mixture was returned to room temperature and the solvent was evaporated under reduced pressure. The residue was purified by column chromatography (Biotage Isolera, 4 g SiO$_2$ cartridge, 0-20% MeOH (containing 1% v/v NEt$_3$) in DCM). The resultant white solid was purified further by RP-HPLC (5-100% CH$_3$CN in water containing 0.1% TFA over 20 minutes) to give the TFA salt of the desired compound (0.020 g, 37% yield). $^1$H NMR (400 MHz, CD$_3$OD) δ 8.60-8.50 (m, 1H), 7.29-7.24 (m, 2H), 7.23-7.17 (m, 3H), 4.83-4.72 (m, 1H), 4.64-4.54 (m, 1H), 4.40-4.30 (m, 1H), 4.16-4.05 (m, 3H), 3.90 (dd, J=10.4, 5.2 Hz, 1H), 3.60-3.47 (m, 2H), 3.46-3.37 (m, 2H), 3.25 (dd, J=12.6, 3.1 Hz, 1H), 3.18-3.09 (m, 2H), 3.03 (dd, J=12.8, 9.4 Hz, 1H), 1.90 (s, 3H). LCMS-A: RT 1.67 min; m/z 459.1 [M+Cl]$^-$, 423.2 [M−H]$^-$.

Example 39: 6-((1-Acetylpiperidin-4-yl)amino)-N-(3-((2,3-dihydro-1H-inden-2-yl)amino)-2-hydroxypropyl)pyrimidine-4-carboxamide 2,2,2-trifluoroacetic acid salt 59

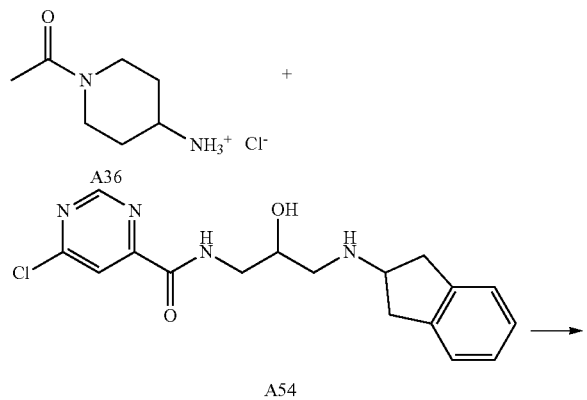

A36

A54

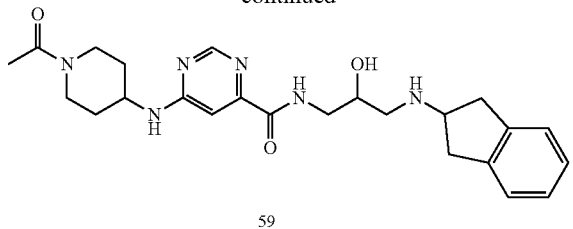

59

A mixture of 1-acetylpiperidin-4-aminium chloride A36 (0.026 g, 0.14 mmol), 6-chloro-N-(3-((2,3-dihydro-1H-inden-2-yl)amino)-2-hydroxypropyl)pyrimidine-4-carboxamide A54 (0.050 g, 0.14 mmol), triethylamine (0.080 mL, 0.58 mmol) and i-PrOH (5 mL) was stirred at 60° C. for 16 hours. Another aliquot of triethylamine (0.16 mL, 1.1 mmol) was added and the mixture was stirred at 60° C. for 3 hours and then at 70° C. for 16 hours. Another aliquot of triethylamine (0.24 mL, 1.7 mmol) was added and the mixture was stirred at 70° C. for 4.5 hours. A final addition of triethylamine (1.0 mL, 7.2 mmol) was followed by stirring of the reaction mixture for 16 hours at 75° C. The solvent was evaporated under reduced pressure and the residue purified by column chromatography (Biotage Isolera, 4 g SiO$_2$ cartridge, 0-20% MeOH (containing 1% v/v 2 M NH$_3$/MeOH) in DCM). The resultant white solid was purified further by RP-HPLC (5-100% CH$_3$CN in water containing 0.1% TFA over 20 minutes) to give the TFA salt of the desired compound (0.026 g, 32% yield). $^1$H NMR (400 MHz, CD$_3$OD) δ 8.55 (s, 1H), 7.28-7.24 (m, 2H), 7.23-7.19 (m, 2H), 7.16 (s, 1H), 4.47 (d, J=13.4 Hz, 1H), 4.34-4.18 (m, 1H), 4.16-4.06 (m, 2H), 4.01-3.91 (m, 1H), 3.59-3.47 (m, 2H), 3.46-3.37 (m, 2H), 3.28-3.22 (m, peak obscured by solvent), 3.20-3.09 (m, 2H), 3.09-2.98 (m, 1H), 2.93-2.82 (m, 1H), 2.13 (s, 3H), 2.12-1.98 (m, 2H), 1.61-1.39 (m, 2H); pyrimidine N—H, amide N—H, —OH and amine N—H not observed. LCMS-A: RT 4.28 min; m/z 487.2 [M+Cl]$^-$, 451.2 [M−H]$^-$.

Example 40: Amide Couplings

General Method X2

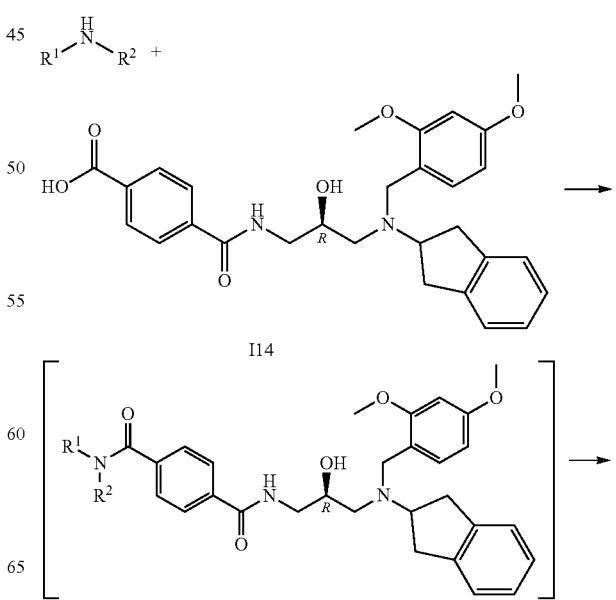

I14

-continued

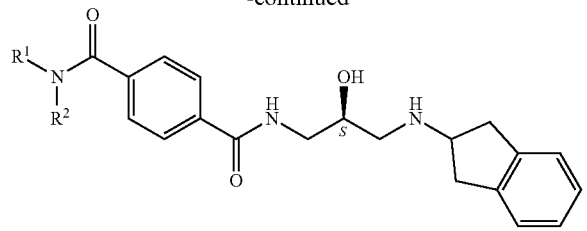

To a solution of the amine (0.20 mmol, 1 equiv) in DMF (2 mL) and MeCN (5 mL) was added 114 (100 mg, 0.198 mmol, 1 equiv), DIPEA (104 μL, 0.595 mmol, 3 equiv) and HATU (113 mg, 0.297 mmol, 1.5 equiv). The reaction was stirred at room temperature for 16 h. The mixture was quenched with a 1M aqueous solution of sodium hydroxide (10 mL) and stirred for 2 h at room temperature. Dichloromethane was added and the mixture stirred and then passed through a phase separation cartridge (3 repeats). The organic filtrates were dried in vacuo. The residue was taken up in TFA (0.5 mL) and stirred at 70° C. for 5 h. Water (2 mL) was added and the aqueous was washed with DCM (3×2 mL) and the layers separated using a phase separation cartridge. The aqueous was brought to pH ~14 by the addition of aqueous NaOH (1 M) and then extracted with DCM (2×2 mL) using a phase separation cartridge to isolate the organic fraction. The organic layers were concentrated in vacuo. The residue was taken up in MeOH and purified by solid-phase extraction (1 g SCX-2 cartridge, 3 column volumes of methanol followed by 3 column volumes of 0.2 M methanolic ammonia) to give the desired compound.

General Method X3

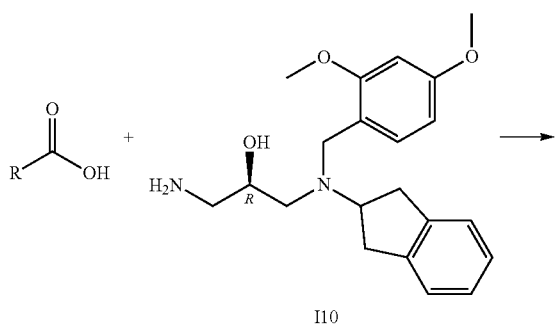

I10

-continued

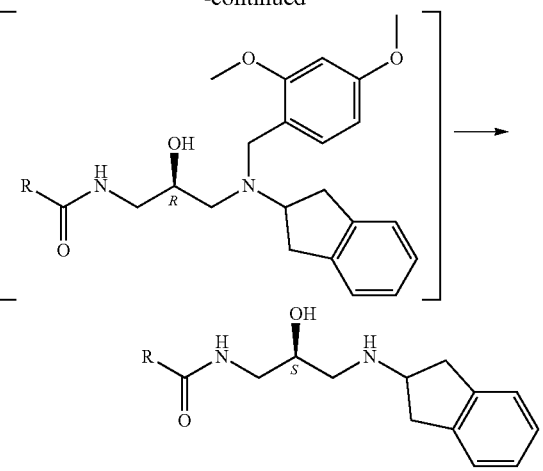

To a solution of the acid (53 mg, 0.22 mmol, 1 equiv), in MeCN (3 mL) and DMF (1 mL) was added DIPEA (117 μL, 0.670 mmol, 3 equiv) and HATU (128 mg, 0.337 mmol, 1.5 equiv). A solution of the amine 110 (80 mg, 0.22 mmol, 1 equiv) in DMF (1 mL) was added and the solution stirred at room temperature for 16 h. The reaction was quenched with a 1M aqueous solution of NaOH (15 mL) and then extracted with dichloromethane (3×8 mL—separation using a phase separation cartridge). The pooled organic filtrates were concentrated in vacuo then TFA (0.5 mL) was added and the solution stirred at 70° C. for 5 h. The reaction was quenched by the addition of DCM (2 mL) and water (2 mL). The phases were thoroughly mixed and the aqueous layer isolated using a phase separation cartridge. The aqueous layer was brought to pH ~14 by the addition of aqueous NaOH (1 M) and then extracted with DCM (2×2 mL) using a phase separation cartridge to isolate the organic fraction. The organic layers were concentrated in vacuo. The residue was taken up in MeOH and purified by solid-phase extraction (1 g SCX-2 cartridge, 3 column volumes of methanol followed by 3 column volumes of 0.2 M ammonia in methanol) to give the desired compound.

| Example | Name and Structure | LCMS data | Method |
|---|---|---|---|
| 60 | (S)-N-(3-((2,3-dihydro-1H-inden-2-yl)amino)-2-hydroxypropyl)-4-(4-hydroxypiperidine-1-carbonyl)benzamide | LCMS-B: RT = 3.13 min, m/z = 438 [M + H]+ | X2 |

| Example | Name and Structure | LCMS data | Method |
|---|---|---|---|
| 61 | 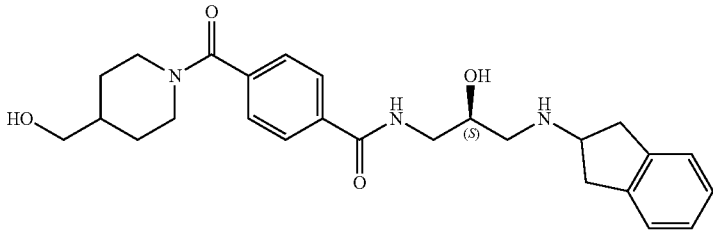

(S)-N-(3-((2,3-dihydro-1H-inden-2-yl)amino)-2-hydroxypropyl)-4-(4-(hydroxymethyl)piperidine-1-carbonyl)benzamide | LCMS-B: RT = 3.14 min, m/z = 452 [M + H]$^+$ | X2 |
| 62 | 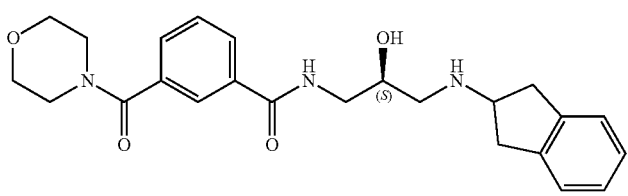

(S)-N-(3-((2,3-dihydro-1H-inden-2-yl)amino)-2-hydroxypropyl)-3-(morpholine-4-carbonyl)benzamide | LCMS-A: RT = 3.39 min, m/z = 424 | X3 |

Example 41: N-(3-((2,3-Dihydro-1H-inden-2-yl)amino)-2-hydroxypropyl)-4-(2-oxopiperidin-1-yl)benzamide 63

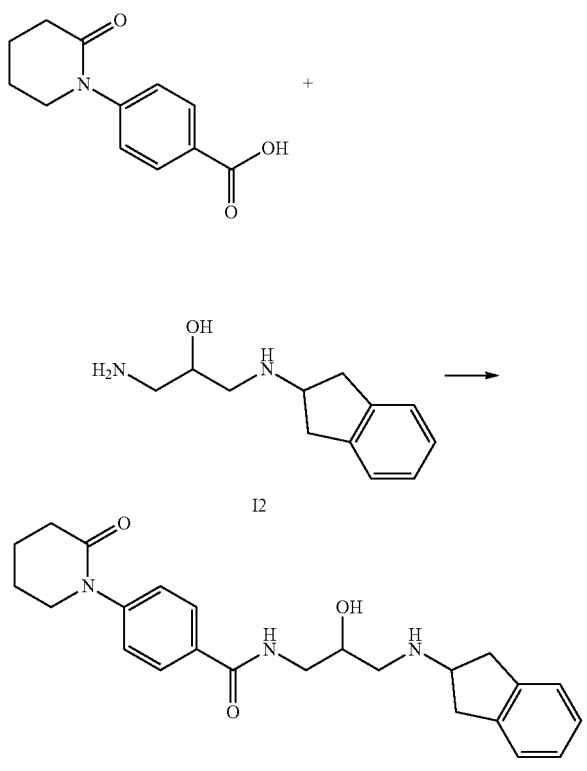

(a) N-(3-((2,3-dihydro-1H-inden-2-yl)amino)-2-hydroxypropyl)-4-(2-oxopiperidin-1-yl)benzamide 63

1-Amino-3-((2,3-dihydro-1H-inden-2-yl)amino)propan-2-ol I2 (0.084 g, 0.407 mmol), 4-(2-oxopiperidin-1-yl)benzoic acid (0.074 g, 0.339 mmol), EDCl (0.098 g, 0.509 mmol), HOBt (0.069 g, 0.509 mmol) and DIPEA (0.177 mL, 1.018 mmol) in dry DMF (5 mL) were stirred at room temperature for 45 hours under an atmosphere of nitrogen. The reaction was diluted with EtOAc (50 mL) and washed with a sat. aqueous NaHCO$_3$ (50 mL), the aqueous layer was extracted with EtOAc (50 mL) and the combined organic layers were washed with brine (50 mL), dried (Na$_2$SO$_4$), filtered and concentrated in vacuo to give a beige solid. Purification by column chromatography (Isolera Biotage, SiO$_2$ cartridge, 0-100% EtOAc in petroleum benzine 40-60° C., then 0-35% MeOH in EtOAc) gave a gum which was triturated with diethyl ether and further air-dried to yield the desired compound (0.010 g, 7% yield) as a white solid. $^1$H NMR (400 MHz, d$_6$-DMSO) δ 8.47 (t, J=5.7 Hz, 1H), 7.85-7.79 (m, 2H), 7.40-7.33 (m, 2H), 7.21-7.14 (m, 2H), 7.14-7.06 (m, 2H), 4.91-4.85 (m, 1H), 3.76-3.66 (m, 1H), 3.66-3.61 (m, 2H), 3.49 (p, J=6.6 Hz, 1H), 3.38-3.23 (m, 3H, obscured by solvent signal), 3.09-3.00 (m, 2H), 2.70-2.61 (m, 3H), 2.58-2.52 (m, 1H), 2.44-2.38 (m, 2H), 1.93-1.80 (m, 4H). LCMS-B: RT 3.227 min, m/z 408.3 [M+H]$^+$

Example 42: 4-((1-Acetylpiperidin-4-yl)amino)-N-(3-((2,3-dihydro-1H-inden-2-yl)amino)-2-hydroxypropyl) benzamide 64

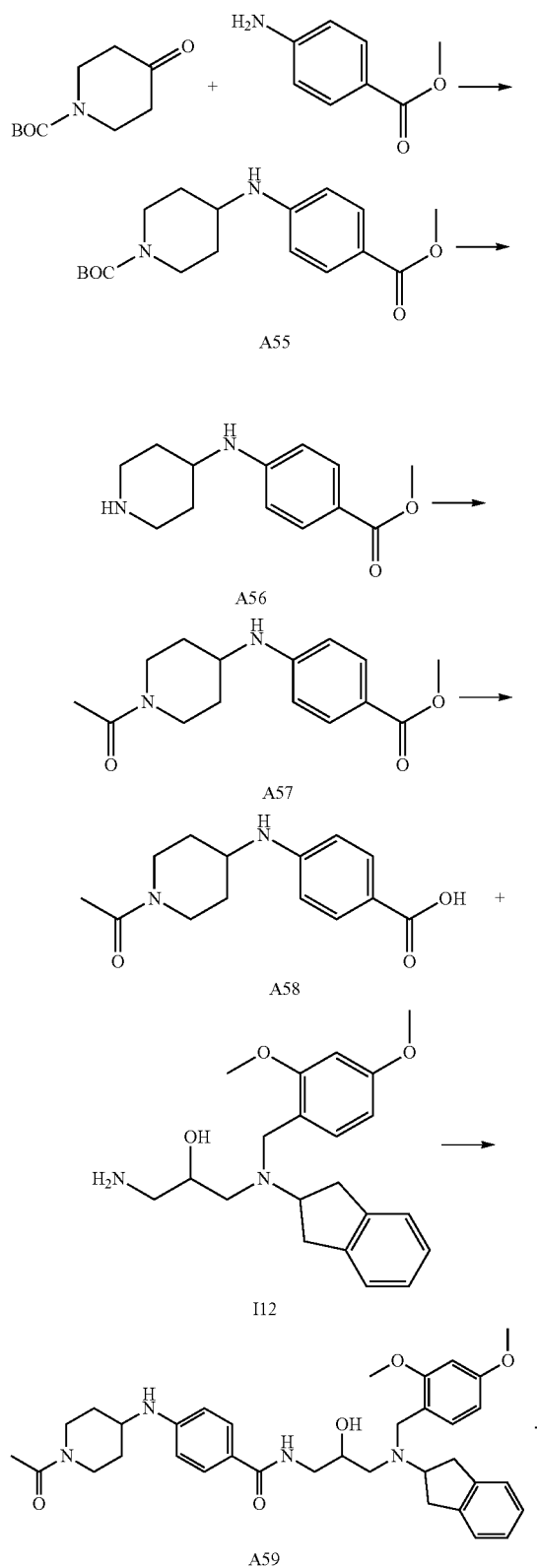

(a) tert-Butyl 4-((4-(methoxycarbonyl)phenyl)amino)piperidine-1-carboxylate A55

Methyl 4-aminobenzoate (0.250 g, 1.654 mmol) and tert-butyl 4-oxopiperidine-1-carboxylate (0.494 g, 2.481 mmol) were dissolved in dry DCE (15 mL) under an atmosphere of nitrogen and acetic acid (0.189 mL, 3.308 mmol) was added followed by sodium triacetoxyborohydride (0.701 g, 3.308 mmol). The reaction was stirred at room temperature for 45 hours, then quenched by addition of water (5 mL) and diluted with EtOAc (50 mL) and sat. aqueous NaHCO$_3$ (50 mL). The organic phase was washed with brine (50 mL), dried (Na$_2$SO$_4$), filtered and concentrated in vacuo then purified by silica gel column chromatography (Isolera Biotage: 40 g SiO$_2$ cartridge, 0-30% EtOAc in petroleum benzine 40-60° C.) to give the desired compound (0.478 g, 86% yield) as a colourless oil which partly solidified upon standing. $^1$H NMR (400 MHz, CDCl$_3$) δ 7.92-7.84 (m, 2H), 6.74-6.53 (m, 2H), 4.16-3.98 (m, 2H), 3.86 (s, 3H), 3.48 (tt, J=10.4, 3.9 Hz, 1H), 2.95-2.82 (m, 2H), 2.08-1.99 (m, 2H), 1.49-1.35 (m, 11H). NH proton not visible. LCMS-B: RT 3.826 min; m/z 279.2 [M−$^t$Bu+H]$^+$.

(b) Methyl 4-(piperidin-4-ylamino)benzoate A56 tert-Butyl 4-((4-(methoxycarbonyl)phenyl)amino)piperidine-1-carboxylate A55 (0.475 g, 1.420 mmol) was dissolved in DCM (10 mL) under an atmosphere of nitrogen and trifluoroacetic acid (3.2 mL, 42.6 mmol) was added. The reaction was then stirred at room temperature for 2 hours. The volatiles were removed in vacua and the resulting residue diluted with EtOAc (50 mL) followed by sat. aqueous Na$_2$CO$_3$ (50 mL). The layers were separated and the aqueous layer was extracted with EtOAc (50 mL), the combined organic layers were washed with water (50 mL), brine (50 mL), dried (Na$_2$SO$_4$), filtered and concentrated in vacuo to give the desired compound (0.178 g, 53% yield) as a white solid. $^1$H NMR (400 MHz, d$_6$-DMSO) δ 7.70-7.64 (m, 2H), 6.62-6.57 (m, 2H), 6.44 (d, J=7.8 Hz, 1H), 3.73 (s, 3H), 2.99 (dt, J=12.8, 3.6 Hz, 2H), 2.60 (td, J=12.1, 2.6 Hz, 2H), 1.92-1.79 (m, 2H), 1.35-1.21 (m, 2H). One of NH protons not visible, CH proton obscured by solvent peak. LCMS-B: RT 3.179 min; m/z 235.2 [M+H]$^+$.

(c) Methyl 4-((1-acetylpiperidin-4-yl)amino)benzoate A57

Methyl 4-(piperidin-4-ylamino)benzoate A56 (0.175 g, 0.747 mmol) was dissolved in DCM (7 mL) under an atmosphere of nitrogen and DIPEA (0.260 mL, 1.494 mmol) was added followed by acetic anhydride (0.070 mL, 0.747 mmol). The reaction was stirred at room temperature for 6 hours, then diluted with EtOAc (50 mL) followed by sat. aqueous Na$_2$CO$_3$ (50 mL). The layers were separated and the aqueous layer was extracted with EtOAc (50 mL), the combined organic layers were washed with brine (50 mL), dried (Na$_2$SO$_4$), filtered and concentrated in vacuo to give the desired compound (0.170 g, 82% yield) as an off-white solid. $^1$H NMR (400 MHz, d$_6$-DMSO) δ 7.71-7.66 (m, 2H), 6.67-6.60 (m, 2H), 6.46 (d, J=7.8 Hz, 1H), 4.28-4.20 (m, 1H), 3.82-3.71 (m, 4H), 3.63-3.51 (m, 1H), 3.22-3.12 (m, 1H), 2.83-2.74 (m, 1H), 2.00 (s, 3H), 1.97-1.84 (m, 2H), 1.37-1.15 (m, 2H). LCMS-B: RT 3.333 and 3.376 (two major peaks present) min; m/z 277.2 [M+H]$^+$.

(d) 4-((1-Acetylpiperidin-4-yl)amino)benzoic acid A58

Methyl 4-((1-acetylpiperidin-4-yl)amino)benzoate A57 (0.168 g, 0.608 mmol) was dissolved in THF (7 mL), MeOH (1 mL) and water (1 mL) and lithium hydroxide monohydrate (0.077 g, 1.823 mmol) was added. The reaction was then stirred at room temperature for 70 hours. Additional lithium hydroxide monohydrate (0.154 g) was added and the reaction was stirred for another 8 hours and then heated to 40° C. and stirred for an additional 45 hours. The volatiles were removed in vacuo and the resulting residue diluted with EtOAc (50 mL) followed by 2M aqueous NaOH (50 mL). The layers were separated and the organic layer was washed with 2M aqueous NaOH (50 mL), the aqueous layers were combined and acidified by addition of 2 M aqueous HCl (checked with pH paper), then extracted with EtOAc (2×70 mL). The combined organic layers were washed with brine (100 mL), dried (Na$_2$SO$_4$), filtered and concentrated in vacuo to give the desired compound (0.060 g, 38% yield) as an off-white solid. $^1$H NMR (400 MHz, d$_6$-DMSO) δ 12.04 (br s, 1H), 7.69-7.62 (m, 2H), 6.65-6.57 (m, 2H), 6.36 (d, J=7.9 Hz, 1H), 4.26-4.20 (m, 1H), 3.82-3.74 (m, 1H), 3.62-3.50 (m, 1H), 3.24-3.13 (m, 1H), 2.84-2.72 (m, 1H), 2.00 (s, 3H), 1.97-1.84 (m, 2H), 1.38-1.13 (m, 2H). LCMS-B: RT 3.134 and 3.196 (two major peaks present) min; m/z 263.2 [M+H]$^+$.

(e) 4-((1-Acetylpiperidin-4-yl)amino)-N-(3-((2,3-dihydro-1H-inden-2-yl)(2,4-dimethoxy benzyl) amino)-2-hydroxypropyl)benzamide A59

4-((1-Acetylpiperidin-4-yl)amino)benzoic acid A58 (0.056 g, 0.213 mmol) was dissolved in DCM (5 mL) and DMF (0.5 mL) and DIPEA (0.068 mL, 0.388 mmol) followed by HATU (0.081 g, 0.213 mmol) were added. The mixture was then stirred at room temperature for 10 min before 1-amino-3-((2,3-dihydro-1H-inden-2-yl)(2,4-dimethoxybenzyl)amino)propan-2-ol 112 (0.069 g, 0.194 mmol) in DCM (2 mL) was added. The reaction was then stirred at room temperature for 45 hours. The volatiles were removed in vacuo and the resulting residue diluted with EtOAc (50 mL) followed by sat. aqueous Na$_2$CO$_3$ (50 mL). The layers were separated and the aqueous layer was extracted with EtOAc (50 mL), the combined organic layers were washed with brine (50 mL), dried (Na$_2$SO$_4$), filtered and concentrated in vacuo to give the crude product which was purified by silica gel column chromatography (Isolera Biotage, 12 g SiO$_2$ Cartridge, 0-100% EtOAc in petroleum benzine 40-60° C., then 0-50% MeOH with 1% Et$_3$N in EtOAc) to give the desired compound (0.062 g, 53% yield) as an off-white foam. $^1$H NMR (400 MHz, d$_6$-DMSO) δ 7.90 (t, J=5.4 Hz, 1H), 7.61-7.52 (m, 2H), 7.28 (d, J=8.3 Hz, 1H), 7.20-7.02 (m, 4H), 6.60-6.54 (m, 2H), 6.49 (d, J=2.4 Hz, 1H), 6.42 (dd, J=8.3, 2.4 Hz, 1H), 6.07 (d, J=7.9 Hz, 1H), 4.67 (d, J=4.2 Hz, 1H), 4.27-4.18 (m, 1H), 3.81-3.66 (m, 9H), 3.60-3.46 (m, 3H), 3.30-3.24 (m, 1H), 3.23-3.08 (m, 2H), 3.00-2.74 (m, 5H), 2.48-2.39 (m, 1H), 2.00 (s, 3H), 1.97-1.82 (m, 2H), 1.36-1.19 (m, 2H). Missing one proton, possibly obscured behind solvent signal.

(f) 4-((1-Acetylpiperidin-4-yl)amino)-N-(3-((2,3-dihydro-1H-inden-2-yl)amino)-2-hydroxy propyl) benzamide 64

To 4-((1-Acetylpiperidin-4-yl)amino)-N-(3-((2,3-dihydro-1H-inden-2-yl)(2,4-dimethoxy benzyl) amino)-2-hydroxypropyl)benzamide A59 (0.060 g, 0.100 mmol) was added TFA (4.0 mL) and the reaction was then stirred at 50° C. for 70 hours. The volatiles were removed in vacuo and the resulting residue was diluted with EtOAc (50 mL) followed by 2 M aqueous NaOH (50 mL). The layers were separated and the aqueous layer was extracted with EtOAc (50 mL), the combined organic layers were washed with brine (50 mL), dried (Na$_2$SO$_4$), filtered and concentrated in vacuo to give the desired compound (0.031 g, 69% yield) as an off-white solid. $^1$H NMR (400 MHz, d$_6$-DMSO) δ 8.06 (t, J=5.6 Hz, 1H), 7.62-7.56 (m, 2H), 7.22-7.15 (m, 2H), 7.14-7.07 (m, 2H), 6.61-6.54 (m, 2H), 6.08 (d, J=8.0 Hz, 1H), 4.92 (s, 1H), 4.27-4.17 (m, 1H), 3.83-3.74 (m, 1H), 3.72-3.65 (m, 1H), 3.58-3.48 (m, 2H), 3.30-3.13 (m, 3H, obscured by solvent signal), 3.11-3.00 (m, 2H), 2.84-2.74 (m, 1H), 2.73-2.62 (m, 3H), 2.55 (dd, J=11.7, 6.8 Hz, 1H), 2.00 (s, 3H), 1.97-1.82 (m, 2H), 1.35-1.16 (m, 2H). One NH proton not visible. LCMS-A: RT 4.427 min; m/z 451.3 [M+H]$^+$.

Example 43: (S)—N-(3-((2,3-dihydro-1H-inden-2-yl)amino)-2-hydroxypropyl)-4-(1,1-dioxidothiomorpholine-4-carbonyl)benzamide 65

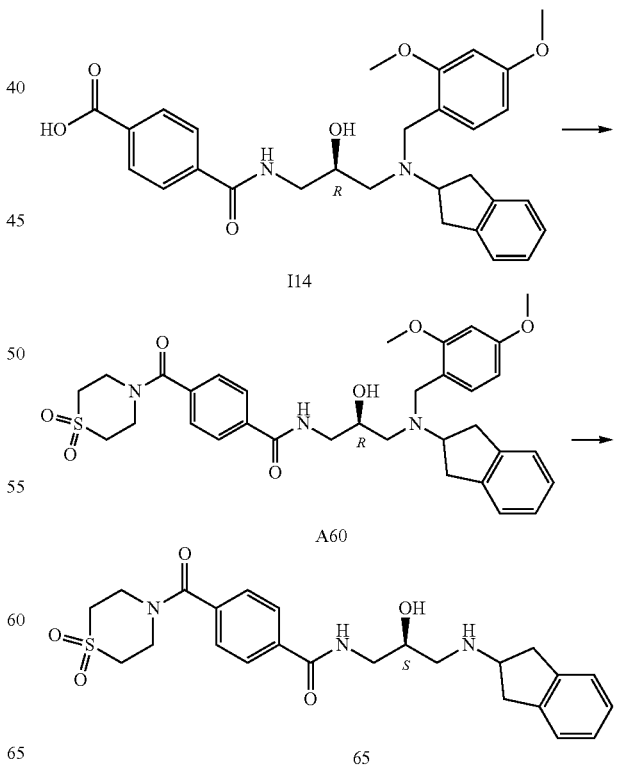

(a) (R)—N-(3-((2,3-Dihydro-1H-inden-2-yl)(2,4-dimethoxybenzyl)amino)-2-hydroxypropyl)-4-(1,1-dioxidothiomorpholine-4-carbonyl)benzamide A60

(R)-4-((3-((2,3-dihydro-1H-inden-2-yl)(2,4-dimethoxybenzyl)amino)-2-hydroxypropyl)carbamoyl)benzoic acid I14 (50 mg, 0.10 mmol), thiomorpholine dioxide (20 mg, 0.15 mmol), MeCN (1 mL), DIPEA (0.052 mL, 0.30 mmol) and HATU (41 mg, 0.11 mmol) were stirred at room temperature. After 2.5 hours methanol (1 mL) was added and the mixture concentrated in vacuo. Chromatography (4 g silica cartridge, 20-100% ethyl acetate/hexanes then 0-10% methanol/ethyl acetate) gave the desired compound as a pale yellow syrup (26 mg, 42% yield). LCMS: RT 3.38 min; m/z (positive ion): 622.4 [M+H]$^+$.

(b) (S)—N-(3-((2,3-dihydro-1H-inden-2-yl)amino)-2-hydroxypropyl)-4-(1,1-dioxidothiomorpholine-4-carbonyl)benzamide 65

(R)—N-(3-((2,3-Dihydro-1H-inden-2-yl)(2,4-dimethoxybenzyl)amino)-2-hydroxypropyl)-4-(1,1-dioxidothiomorpholine-4-carbonyl)benzamide A60 (24 mg, 0.042 mmol) and TFA (3 mL) were stirred at 70° C. After four hours the mixture was concentrated in vacuo and the residue dissolved in methanol (3 mL). The mixture was loaded onto a 2 g SCX cartridge, the cartridge washed with methanol (25 mL) and eluted with 7M ammonia in methanol (15 mL). The basic eluate was concentrated to give the desired compound as a pale yellow syrup (15 mg, 84% yield). LCMS-B: RT 3.17 min; m/z (positive ion) 472.3 [M+H]$^+$.

Example 44: Amide Couplings

General Method A

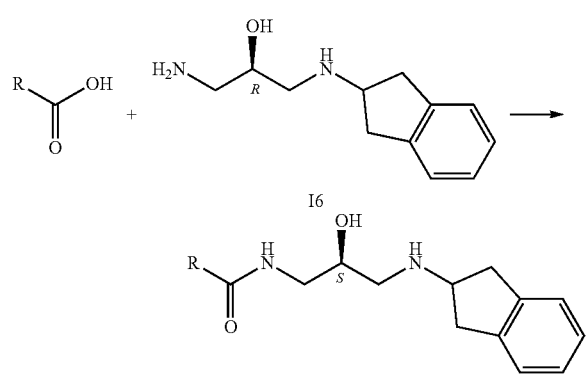

To a stirred solution of the acid (1 eq.) and NEt$_3$ (3.0 eq.) in dry DCM was added HATU (1.0 eq.). A solution of the amine 16 (1.0 eq.) in DCM was then added and the reaction stirred at room temperature overnight. The crude mixture was concentrated in vacuo and the residue obtained dissolved in DCM and washed with saturated aqueous NaHCO$_3$. The aqueous layer was further extracted with DCM (×3) and the combined organic layers were dried (Na$_2$SO$_4$) then concentrated in vacuo. The crude material was purified by silica gel chromatography (DCM:MeOH=50:1) to yield the desired product.

General Method B

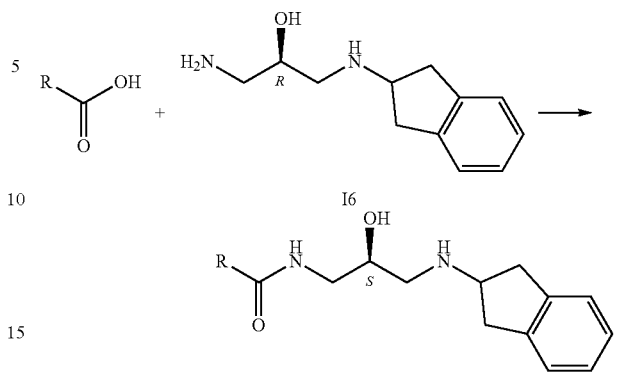

To a solution of the acid (1.0 eq.) and amine 16 (1.0 eq.) in DCM were added DIPEA (3.0 eq.), HOBt (0.1 eq.) and EDCl (2.0 eq.). The resulting mixture was stirred at room temperature overnight. Water was added to the reaction and the mixture extracted with DCM (×3). The combined organic layers were washed with brine, dried (Na$_2$SO$_4$) and concentrated to give the crude product which was purified by column chromatography (DCM:MeOH=50:1) to give the desired product.

General Method C

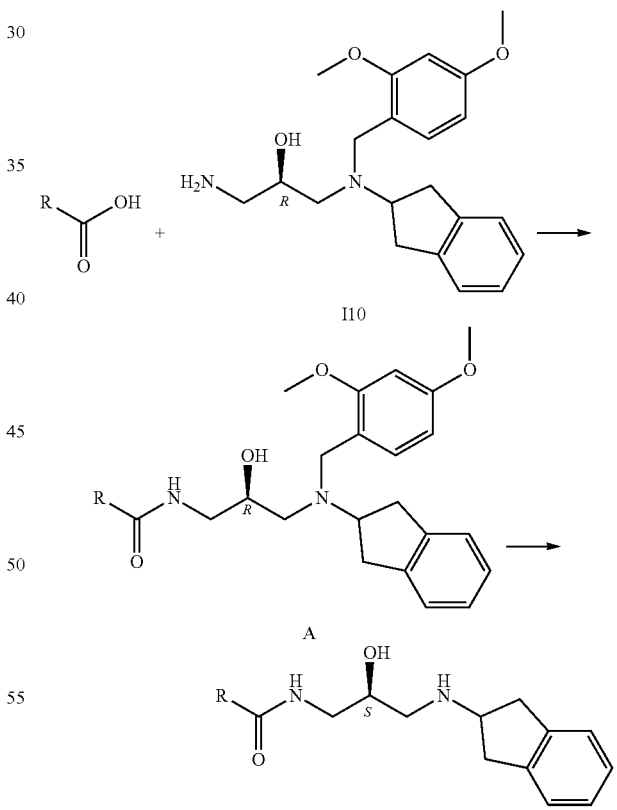

To a solution of the acid (1.0 eq.) in DCM were added DIPEA (3.0 eq.) and HATU (1.0 eq.). The amine I10 (1.0 eq.) in DCM was then added and the solution stirred at room temperature overnight. Water was added and the reaction mixture extracted with DCM×3. The combined organic layers were washed with brine, dried (Na$_2$SO$_4$) and concentrated to give the crude product which was purified by column chromatography (DCM:MeOH=50:1) to give the dimethoxybenzyl protected intermediate A.

A solution of the dimethoxybenzyl protected intermediate A (1.0 eq.) in trifluoroacetic acid was stirred at 70° C. for 4 h. The mixture was concentrated to give the crude product. A saturated aqueous solution of NaHCO₃ was then added and the resulting mixture extracted with DCM (×3). The combined organic layers were dried and concentrated to give the crude product which was purified by preparative TLC (DCM:MeOH=10:1) to give the desired product.

General Method D

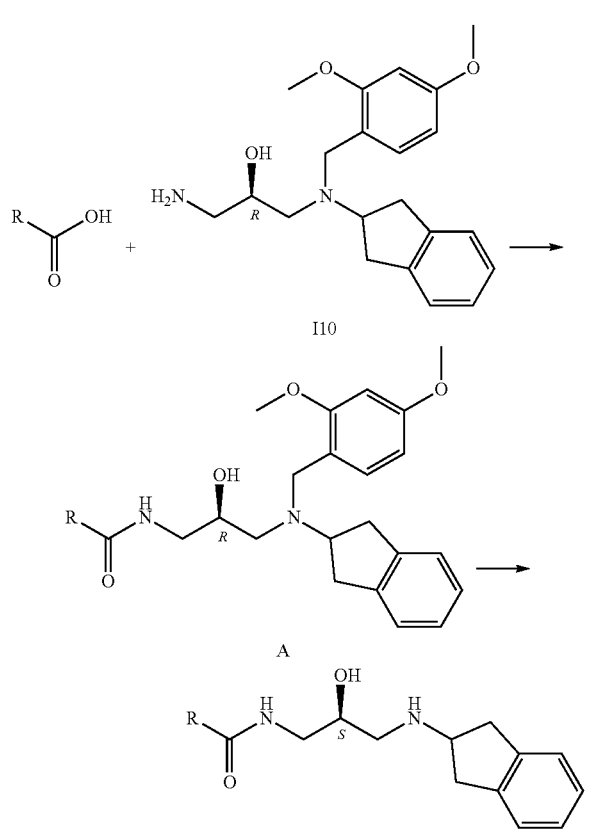

To a solution of the acid (1.0 eq.) and the amine 110 (1.0 eq.) in DCM were added DIPEA (3.0 eq.), HOBt (0.1 eq.), and EDCl (2.0 eq.). The resulting mixture was stirred at room temperature overnight. Water was added to the reaction mixture and the aqueous extracted with DCM×3. The combined organic layers were washed with brine, dried (Na₂SO₄) and concentrated to give the crude product which was purified by column chromatography (DCM:MeOH=50:1) to give the dimethoxybenzyl protected intermediate A. A solution of the dimethoxybenzyl protected intermediate A (1.0 eq.) in trifluoroacetic acid was stirred at 70° C. for 4 h. The mixture was concentrated to give the crude product which was suspended in a saturated aqueous solution of NaHCO₃. The resulting mixture was extracted with DCM (×3). The organic layers were combined, dried (Na₂SO₄) and concentrated to give the crude residue which was purified by preparative TLC (DCM:MeOH=10:1) to give the desired product.

General Method E

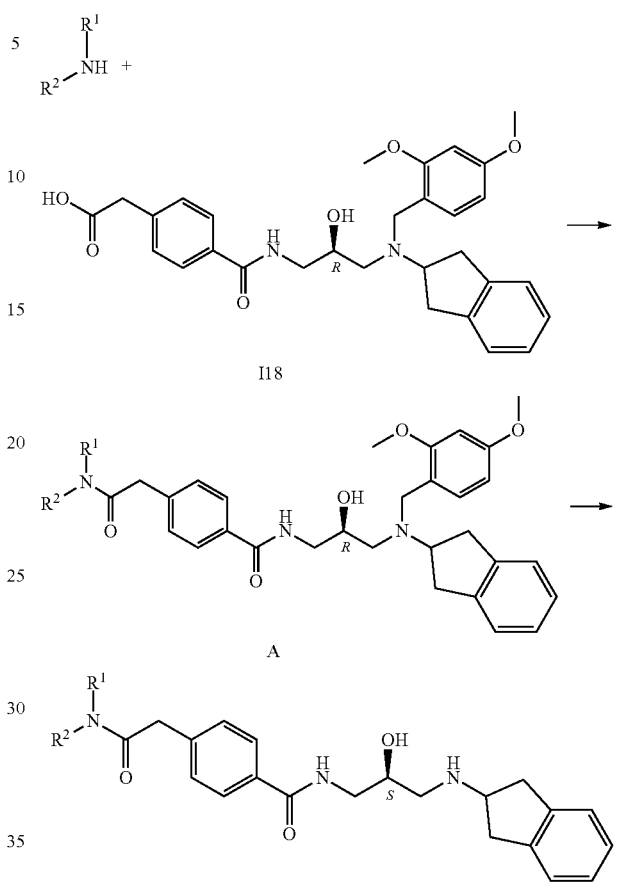

To a solution of the acid (1.0 eq.) and amine 118 (1.0 eq.) in DCM were added DIPEA (3.5 eq.), HOBt (1.4 eq.), and EDCl (1.4 eq.). The resulting mixture was stirred at room temperature overnight. Water was added to the reaction mixture and the aqueous extracted with DCM×3. The combined organic layers were washed with brine, dried (Na₂SO₄) and concentrated to give the crude product which was purified by column chromatography (DCM:MeOH=20:1) to give the dimethoxybenzyl protected intermediate A. A solution of the DMB protected intermediate A (1.0 eq.) in trifluoroacetic acid was stirred at 70° C. for 2 h. The mixture was concentrated to give the crude product which was suspended in a saturated aqueous solution of NaHCO₃. The resulting mixture was extracted with DCM (×3), the organic layers were combined, dried (Na₂SO₄) and concentrated to give the crude residue which was purified by preparative TLC (DCM:MeOH=10:1) to give the desired product.

General Method F

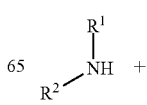

-continued

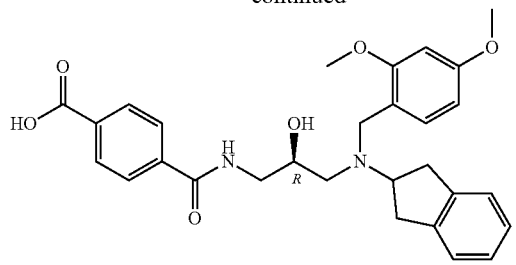

I14

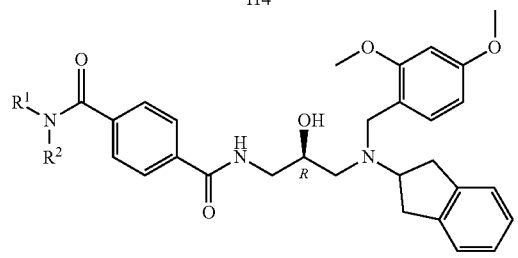

A

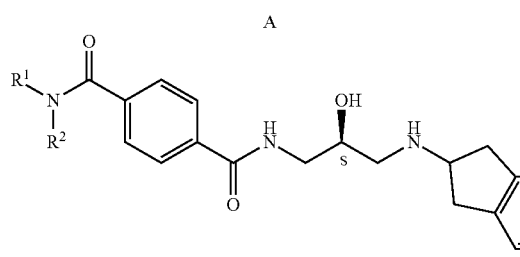

To a solution of the acid I14 (1.0 eq.) in dry DCM were added DIPEA (3.0 eq.) and HATU (1.0 eq.). The amine (1.0 eq.) in DCM was then added and the solution stirred at room temperature overnight. Water was added to the reaction mixture and the aqueous layer extracted with DCM (×3). The combined organic layers were washed with brine, dried over Na$_2$SO$_4$ and concentrated. The crude residue obtained was purified by column chromatography (DCM:MeOH=50:1) to give the desired dimethoxybenzyl intermediate A. A solution of compound A (1.0 eq.) in trifluoroacetic acid was stirred at 70° C. for 4 h. The mixture was concentrated to give the crude product which was suspended in a solution of saturated aqueous NaHCO$_3$. The aqueous layer was extracted with DCM (×3) and the combined organic layers were dried (Na$_2$SO$_4$) and concentrated. The crude product was purified by preparative TLC (DCM:MeOH=10:1) to give the desired product B General Method G

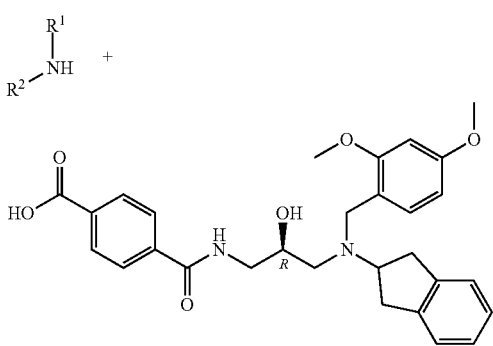

I14

-continued

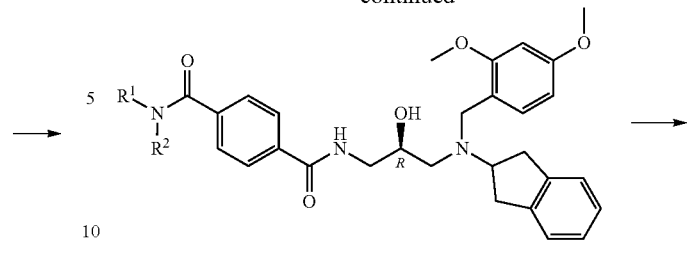

A

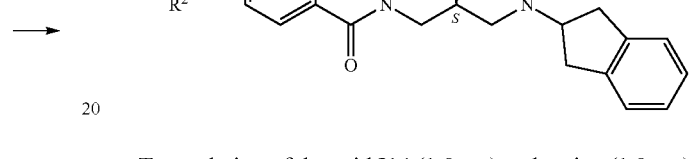

To a solution of the acid I14 (1.0 eq.) and amine (1.0 eq.) in DCM were added DIPEA (3.0 eq.), HOBt (0.1 eq.) and EDCl (2.0 eq.). The resulting mixture was stirred at room temperature overnight. Water was added and the mixture extracted with DCM (×3). The combined organic layers were washed with brine, dried (Na$_2$SO$_4$) and concentrated to give the crude product which was purified by column chromatography (DCM:MeOH=50:1) to give the desired dimethoxybenzyl intermediate A.

A solution of the dimethoxybenzyl intermediate A in trifluoroacetic acid was stirred at 70° C. for 4 h. The mixture was concentrated to give the crude product which was suspended in a solution of saturated aqueous NaHCO$_3$. The mixture was extracted with DCM (×3). The combined organic layers were dried (Na$_2$SO$_4$) and concentrated to give the crude product which was purified preparative TLC (DCM:MeOH=10:1) to give the desired product B.

General Method H

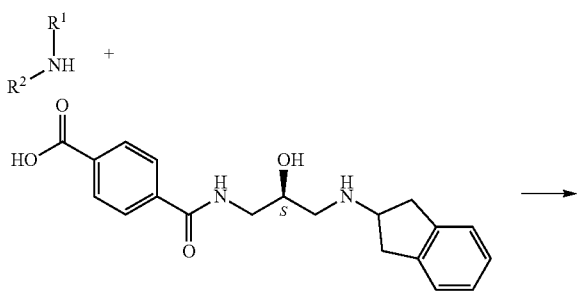

36

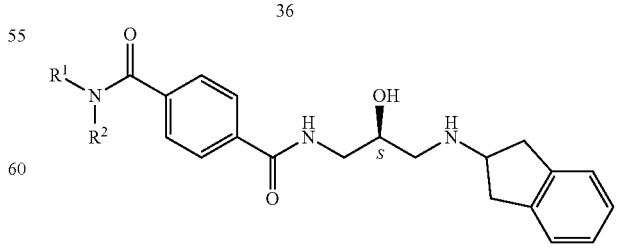

To a solution of the acid 36 (1.0 eq.) in dry DCM was added Et$_3$N (5.0 eq.) and HATU (1.2 eq.). The amine (1.2 eq.) in DCM was then added and the solution was stirred at room temperature overnight. Water was added to the reaction mixture. The mixture was extracted with DCM×3. The combined organic layers were washed with brine, dried over Na₂SO₄ and concentrated. The residue was purified by column chromatography (DCM:MeOH=50:1) to give the desired product A.

General Method I

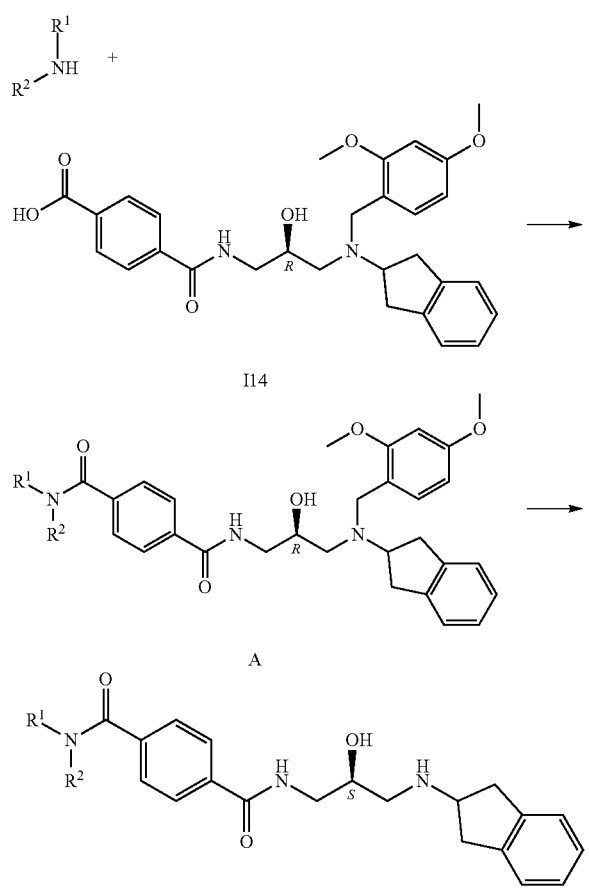

To a solution of the acid (1.0 eq.) and the amine (1.0 eq.) in DCM were added DIPEA (3.0 eq), HOBt (0.1 eq.), and EDCl (2.0 eq.). The resulting mixture was stirred at room temperature overnight. Water was added to the reaction mixture and the aqueous extracted with DCM (×3). The combined organic layers were washed with brine, dried (Na₂SO₄) and concentrated to give the crude product which was purified by column chromatography (DCM:MeOH=50:1) to give the dimethoxybenzyl protected intermediate A.

A solution of the dimethoxybenzyl protected intermediate A (1.0 eq) in trifluoroacetic acid was stirred at 70° C. for 4 h. The mixture was concentrated to give the crude product which was suspended in a saturated aqueous solution of NaHCO₃. The resulting mixture was extracted with DCM (×3). The organic layers were combined, dried (Na₂SO₄) and concentrated to give the residue which was purified by preparative TLC (DCM:MeOH=10:1) to give the desired product.

General Method J

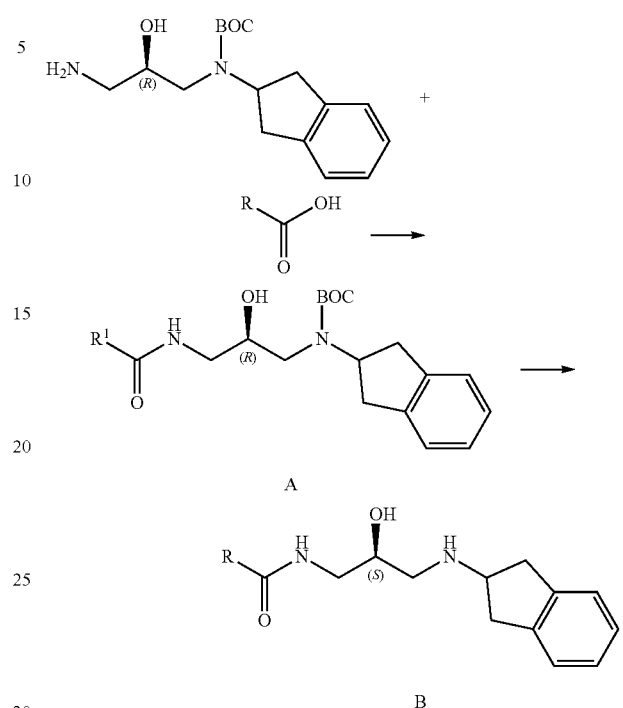

To a solution of the acid (1.0 eq) and the amine 1117 (1.0 eq) in DCM were added DIPEA (3.0 eq), HOBt (0.1 eq) and EDCl (2.0 eq). The resulting mixture was stirred at room temperature overnight. Water was added to the reaction mixture and the aqueous extracted with DCM (×3). The combined organic layers were washed with brine, dried (Na₂SO₄) and concentrated to give the crude product which was purified by preparative TLC (DCM:MeOH=20:1) to give the Boc protected intermediate A.

A solution of the Boc protected intermediate A (1.0 eq) in a saturated solution of HCl in either EtOAc or Et₂O was stirred at room temperature for 3 h. The mixture was concentrated to give the crude product. The solid was rinsed with diethyl ether to provide the desired product as a HCl salt. If the product was not pure, the HCl salt was partitioned between DCM and a saturated aqueous solution of NaHCO₃ and the aqueous extracted with DCM. The combined organic fractions were dried (Na₂SO₄) and concentrated and the crude residue obtained purified by preparative TLC (DCM:MeOH~15:1 v/v) to give the desired product.

General Method K

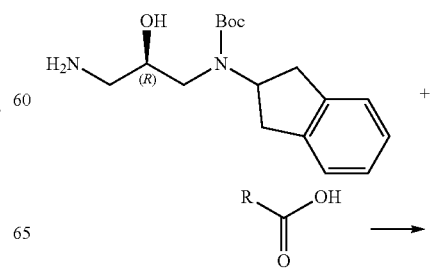

-continued

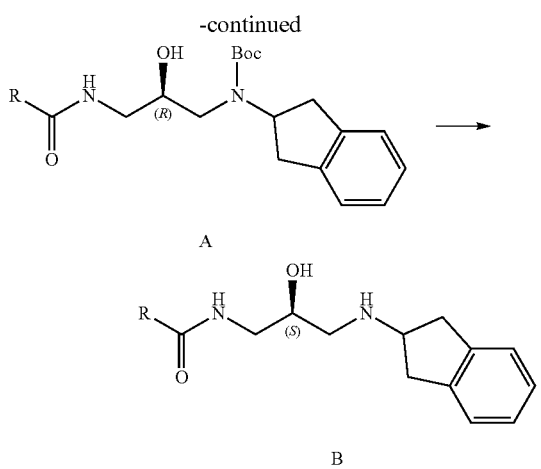

To a solution of the acid (1.0 eq) and the amine 1117 (1.0 eq) in DCM were added DIPEA (3.0 eq), HOBt (0.1 eq) and EDCl (2.0 eq). The resulting mixture was stirred at room temperature overnight. Water was added to the reaction mixture and the aqueous extracted with DCM (×3). The combined organic layers were washed with brine, dried (Na$_2$SO$_4$) and concentrated to give the crude product which was purified by preparative TLC (DCM:MeOH=20:1) to give the Boc protected intermediate A.

A solution of the Boc protected intermediate A (1.0 eq) in DCM/trifluoroacetic acid (8:1 v/v) was stirred at room temperature for 1 h. Water was added and the pH of the solution adjusted to 8-9 by addition of saturated aqueous NaHCO$_3$ solution. The resulting mixture was extracted with DCM (×3) and the combined organic fractions were dried (Na$_2$SO$_4$) and concentrated to give the desired product B.

All Examples in the following Table were prepared using starting materials with the absolute stereochemistry as indicated in the Schemes above, unless stated otherwise in the Method column.

| Compound | Name and Structure | QC data | Method |
|---|---|---|---|
| 66 | (S)-N-(3-((2,3-dihydro-1H-inden-2-yl)amino)-2-hydroxypropyl)-4-(2-oxa-6-azaspiro[3.3]heptane-6-carbonyl)benzamide | $^1$H NMR (400 MHz, MeOD) δ 7.53 (d, J = 8.4 Hz, 2H), 7.34 (d, J = 8.4 Hz, 2H), 6.86-6.77 (m, 2H), 6.77-6.69 (m, 2H), 4.15 (s, 2H), 3.96 (s, 2H), 3.66-3.51 (m, 1H), 3.18-3.04 (m, 2H), 2.97-2.90 (m, 3H), 2.89-2.78 (m, 2H), 2.54-2.30 (m, 4H). 2 Protons obscured by water. LCMS: RT 0.51 min, m/z 436.2 [M + H]$^+$ | H |
| 67 | N-(3-((2,3-dihydro-1H-inden-2-yl)amino)-2-hydroxypropyl)-6-(piperidine-1-carbonyl)nicotinamide | $^1$H NMR (400 MHz, Methanol-d$_4$) δ 9.00 (s, 1 H), 8.32-8.29 (m, 1 H), 7.64-7.62 (d, J = 8.0 Hz, 1 H), 7.19-7.10 (m, 4 H), 3.99-3.94 (m, 1 H), 3.75-3.73 (m, 2 H), 3.69-3.62 (m, 1 H), 3.55-3.45 (m, 2 H), 3.36-3.33 (m, 2 H), 3.23-3.16 (m, 2 H), 2.86-2.79 (m, 3 H), 2.76-2.69 (m, 1 H), 1.72 (m, 4 H), 1.58 (m, 2 H). LCMS: RT 1.39 min, m/z 423.2 [M + H]$^+$ | A (Using racemic amine) |
| 68 | (S)-N-(3-((2,3-dihydro-1H-inden-2-yl)amino)-2-hydroxypropyl)-6-(piperidine-1-carbonyl)nicotinamide | $^1$H NMR (400 MHz, Methanol-d$_4$) δ 9.00 (d, J = 1.6 Hz, 1 H), 8.31-8.29 (m, 1 H), 7.63-7.61 (m, 1 H), 7.18-7.16 (m, 2 H), 7.11-7.09 (m, 2 H), 3.99-3.93 (m, 1 H), 3.74-3.71 (m, 2 H), 3.65-3.58 (m, 1 H), 3.55-3.45 (m, 2 H), 3.35-3.33 (m, 2 H), 3.21-3.14 (m, 2 H), 2.83-2.76 (m, 3 H), 2.72-2.67 (m, 1 H), 1.71 (m, 4 H), 1.57 (m, 2 H). LCMS: RT 1.40 min, m/z 423.3 [M + H]$^+$ | A |

| Compound | Name and Structure | QC data | Method |
|---|---|---|---|
| 69 | 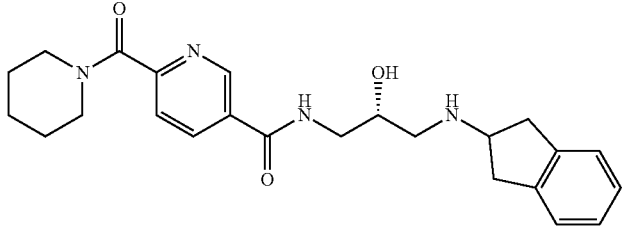 [SMILES: O=C(NC[C@H](O)CNC1Cc2ccccc2C1)c1ccc(C(=O)N2CCCCC2)nc1]<br>(R)-N-(3-((2,3-dihydro-1H-inden-2-yl)amino)-2-hydroxypropyl)-6-(piperidine-1-carbonyl)nicotinamide | $^1$H NMR (400 MHz, Methanol-d$_4$) δ 9.00 (d, J = 1.6 Hz, 1 H), 8.32-8.30 (m, 1 H), 7.65-7.63 (m, 1 H), 7.19-7.17 (m, 2H), 7.12-7.10 (m, 2H), 4.00-3.94 (m, 1H), 3.75-3.74 (m, 2H), 3.69-3.63 (m, 1H), 3.55-3.45 (m, 2 H), 3.36-3.33 (m, 2 H), 3.24-3.17 (m, 2 H), 2.87-2.79 (m, 3 H), 2.75-2.71 (m, 1 H), 1.72 (m, 4 H), 1.58 (m, 2 H).<br>LCMS: RT 1.52 min, m/z 423.2 [M + H]$^+$ | A (Using (S)-acid) |
| 70 | 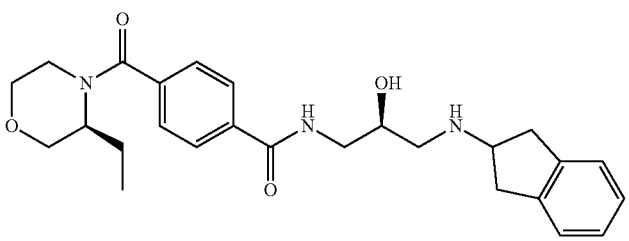 [SMILES: CC[C@H]1COCCN1C(=O)c1ccc(C(=O)NC[C@@H](O)CNC2Cc3ccccc3C2)cc1]<br>N-((S)-3-((2,3-dihydro-1H-inden-2-yl)amino)-2-hydroxypropyl)-4-((S)-3-ethylmorpholine-4-carbonyl)benzamide | $^1$H NMR (400 MHz, Methanol-d$_4$) δ 7.93-7.91 (m, 2 H), 7.51-7.49 (m, 2 H), 7.18-7.12 (m, 4 H), 3.97-3.66 (m, 6 H), 3.50-3.49 (m, 4 H), 3.24-3.17 (m, 2 H), 2.86-2.71 (m, 5 H), 1.98-1.80 (m, 2 H), 1.02-0.75 (m, 3 H).<br>LCMS: RT 3.48 min, m/z 452.3 [M + H]$^+$ | F DIPEA (3.5 eq) used |
| 71 | 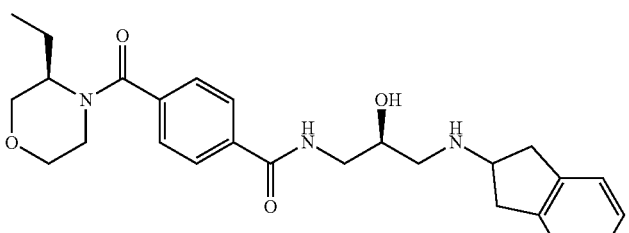<br>N-((S)-3-((2,3-dihydro-1H-inden-2-yl)amino)-2-hydroxypropyl)-4-((R)-3-ethylmorpholine-4-carbonyl)benzamide | $^1$H NMR (400 MHz, Methanol-d$_4$) δ 7.93-7.91 (m, 2 H), 7.51-7.49 (m, 2 H), 7.20-7.11 (m, 4 H), 4.49-4.28 (m, 1 H), 3.98-3.64 (m, 6 H), 3.50-3.48 (m, 4 H), 3.26-3.19 (m, 2H), 2.90-2.82 (m, 3 H), 2.77-2.72 (m, 1 H), 2.00-1.81 (m, 2 H), 1.03-0.76 (m, 3 H).<br>LCMS: RT 3.48 min, m/z 452.3 [M + H]$^+$ | F |
| 72 | 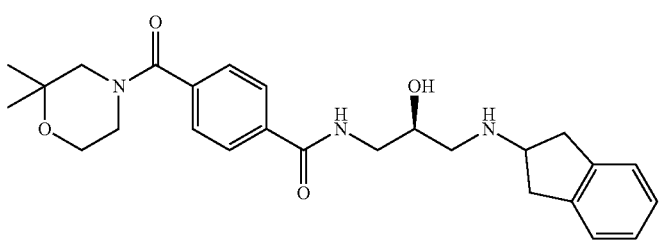 [SMILES: CC1(C)CN(C(=O)c2ccc(C(=O)NC[C@@H](O)CNC3Cc4ccccc4C3)cc2)CCO1]<br>(S)-N-(3-((2,3-dihydro-1H-inden-2-yl)amino)-2-hydroxypropyl)-4-(2,2-dimethylmorpholine-4-carbonyl)benzamide | $^1$H NMR (400 MHz, Methanol-d$_4$) δ 7.95-7.93 (m, 2 H), 7.53 (m, 2 H), 7.23-7.15 (m, 4 H), 4.05-4.04 (m, 1 H), 3.90-3.46 (m, 8 H), 3.39-3.24 (m, 3 H), 3.06-2.85 (m, 4 H), 1.29 (s, 3 H), 1.12 (s, 3 H).<br>LCMS: RT 3.43 min, m/z 452.3 [M + H]$^+$ | F |

| Compound | Name and Structure | QC data | Method |
|---|---|---|---|
| 73 | 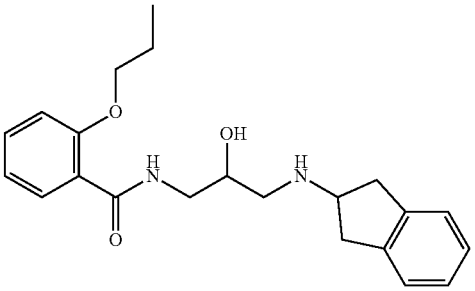 [SMILES: CCCOc1ccccc1C(=O)NCC(O)CNC1Cc2ccccc2C1]<br>N-(3-((2,3-dihydro-1H-inden-2-yl)amino)-2-hydroxypropyl)-2-propoxybenzamide | $^1$H NMR (400 MHz, Methanol-$d_4$) δ 7.96-7.94 (m, 1 H), 7.52-7.49 (m, 1 H), 7.25-7.14 (m, 5 H), 7.08-7.04 (m, 1 H), 4.17-4.03 (m, 4 H), 3.64-3.52 (m, 2 H), 3.43-3.37 (m, 2 H), 3.21-3.08 (m, 3 H), 3.05-3.00 (m, 1 H), 1.96-1.90 (m, 2 H), 1.12-1.08 (m, 3 H).<br>LCMS: RT 3.92 min, m/z 369.2 [M + H]$^+$ | D (using racemic amine) |
| 74 | 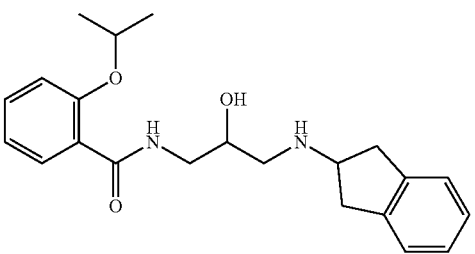 [SMILES: CC(C)Oc1ccccc1C(=O)NCC(O)CNC1Cc2ccccc2C1]<br>N-(3-((2,3-dihydro-1H-inden-2-yl)amino)-2-hydroxypropyl)-2-isopropoxybenzamide | $^1$H NMR (400 MHz, Methanol-$d_4$) δ 8.00-7.98 (m, 1 H), 7.54-7.50 (m, 1 H), 7.26-7.19 (m, 5 H), 7.09-7.06 (m, 1 H), 4.15-4.05 (m, 2 H), 3.81-3.54 (m, 3 H), 3.45-3.39 (m, 2 H), 3.22-3.01 (m, 4 H), 1.47-1.06 (m, 6 H).<br>LCMS: RT 2.18 min, m/z 369.2 [M + H]$^+$ | D (Using racemic amine) |
| 75 | 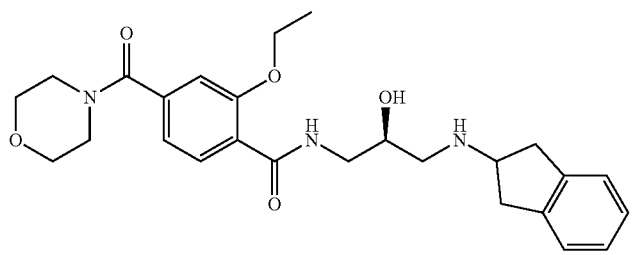<br>(S)-N-(3-((2,3-dihydro-1H-inden-2-yl)amino)-2-hydroxypropyl)-2-ethoxy-4-(morpholine-4-carbonyl)benzamide | $^1$H NMR (400 MHz, Methanol-$d_4$) δ 8.02-8.00 (m, 1 H), 7.23-7.08 (m, 6 H), 4.30-4.25 (m, 2H), 4.04-4.01 (m, 1 H), 3.89-3.76 (m, 5 H), 3.63-3.44 (m, 6 H), 3.33-3.26 (m, 2 H, overlap), 3.03-2.85 (m, 4 H), 1.54-1.51 (m, 3 H).<br>LCMS: RT 3.29 min, m/z 468.3 [M + H]$^+$ | I |
| 76 | 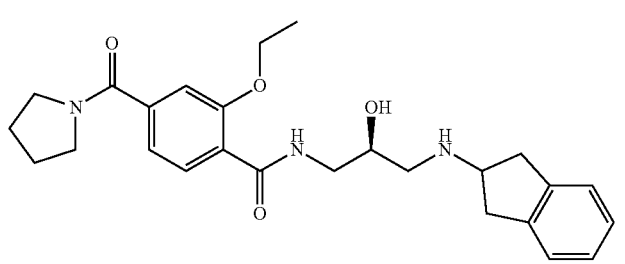 [SMILES: CCOc1cc(C(=O)N2CCCC2)ccc1C(=O)NC[C@@H](O)CNC1Cc2ccccc2C1]<br>(S)-N-(3-((2,3-dihydro-1H-inden-2-yl)amino)-2-hydroxypropyl)-2-ethoxy-4-(pyrrolidine-1-carbonyl)benzamide | $^1$H NMR (400 MHz, Methanol-$d_4$) δ 8.00-7.98 (m, 1 H), 7.25-7.19 (m, 6 H), 4.28-4.26 (m, 2 H), 4.07-3.98 (m, 2 H), 3.61-3.58 (m, 3 H), 3.55-3.50 (m, 1 H), 3.46-3.43 (m, 2H), 3.40-3.35 (m, 2 H), 3.15-2.98 (m, 4 H), 2.02-1.91 (m, 4 H), 1.54-1.50 (m, 3 H).<br>LCMS: RT 2.01 min, m/z 452.3 [M + H]$^+$ | I |

| Compound | Name and Structure | QC data | Method |
|---|---|---|---|
| 77 | 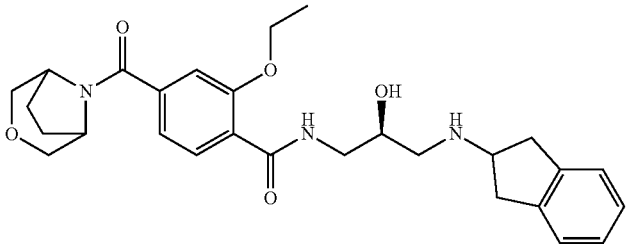 [SMILES: CCOc1cc(C(=O)N2C3CCC2COC3)ccc1C(=O)NC[C@@H](O)CNC1Cc2ccccc2C1]<br>4-(3-oxa-8-azabicyclo[3.2.1]octane-8-carbonyl)-N-((S)-3-((2,3-dihydro-1H-inden-2-yl)amino)-2-hydroxypropyl)-2-ethoxybenzamide | $^1$H NMR (400 MHz, Methanol-$d_4$) δ 8.03-8.01 (m, 1 H), 7.23 (s, 1 H), 7.18-7.15 (m, 3 H), 7.13-7.09 (m, 2 H), 4.64 (s, 1 H), 4.30-4.24 (m, 2 H), 3.97-3.92 (m, 2 H), 3.83-3.81 (m, 1 H), 3.73-3.57 (m, 5 H), 3.49-3.44 (m, 1 H), 3.23-3.16 (m, 2 H), 2.85-2.71 (m, 4 H), 2.06-2.00 (m, 4 H), 1.54-1.51 (m, 3 H).<br>LCMS: RT 1.87 min, m/z 494.3 [M + H]$^+$ | D and I |
| 78 | 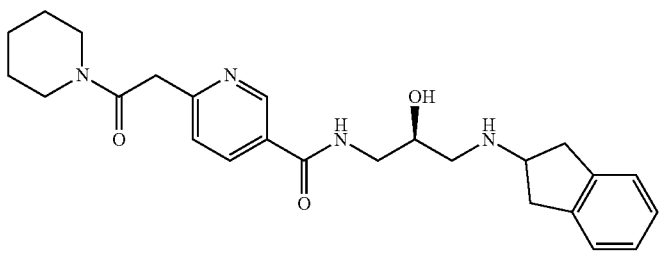 [SMILES: O=C(NC[C@@H](O)CNC1Cc2ccccc2C1)c1ccc(CC(=O)N2CCCCC2)nc1]<br>(S)-N-(3-((2,3-dihydro-1H-inden-2-yl)amino)-2-hydroxypropyl)-6-(2-oxo-2-(piperidin-1-yl)ethyl)nicotinamide | $^1$H NMR (400 MHz, Methanol-$d_4$) δ 8.98-8.95 (m, 1 H), 8.25-8.20 (m, 1 H), 7.50-7.45 (m, 1 H), 7.28-7.19 (m, 4 H), 4.60 (s, 2 H), 4.15-4.11 (m, 1 H), 3.76-3.69 (m, 2 H), 3.60-3.55 (m, 4 H), 3.48-3.40 (m, 2 H), 3.27-3.20 (m, 3 H), 3.18-3.13 (m, 1 H), 3.10-3.03 (m, 1 H), 1.70-1.63 (m, 2 H), 1.57-1.50 (m, 4 H).<br>LCMS: RT 0.26 min, m/z 437.3 [M + H]$^+$ | B<br>EDCl (1.5 eq)<br>HOBt (1.5 eq)<br>DIPEA (3.5 eq) |
| 79 | 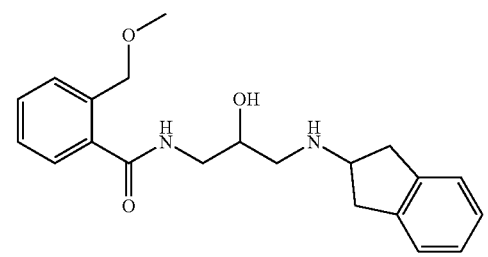 [SMILES: COCc1ccccc1C(=O)NCC(O)CNC1Cc2ccccc2C1]<br>N-(3-((2,3-dihydro-1H-inden-2-yl)amino)-2-hydroxypropyl)-2-(methoxymethyl)benzamide | $^1$H NMR (400 MHz, Methanol-$d_4$) δ 7.55-7.53 (m, 1 H), 7.48-7.41 (m, 3 H), 7.28-7.20 (m, 4 H), 4.68-4.60 (m, 2 H), 4.16-4.08 (m, 2 H), 3.53-3.41 (m, 4 H), 3.33 (s, 3 H), 3.28-3.25 (m, 1 H), 3.19-3.09 (m, 3 H).<br>LCMS: RT 3.26 min, m/z 355.2 [M + H]$^+$ | A<br>DIPEA (3.5 eq);<br>using racemic amine |
| 80 | 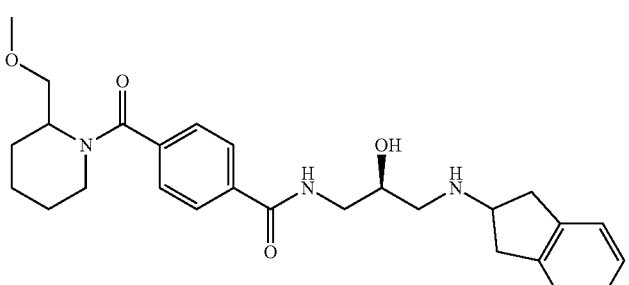<br>N-((S)-3-((2,3-dihydro-1H-inden-2-yl)amino)-2-hydroxypropyl)-4-(2-(methoxymethyl)piperidine-1-carbonyl)benzamide | $^1$H NMR (400 MHz, Methanol-$d_4$) δ 7.94-7.92 (m, 2 H), 7.52-7.50 (m, 2 H), 7.27-7.19 (m, 4 H), 4.61-4.53 (m, 1 H), 4.12-4.06 (m, 2 H), 3.81-3.76 (m, 1 H), 3.58-3.38 (m, 8 H), 3.31 (s, 3 H), 3.23-3.09 (m, 4 H), 3.05-2.99 (m, 1 H), 1.68 (m, 4 H).<br>LCMS: RT 3.43 min, m/z 466.3 [M + H]$^+$ | G |

| Compound | Name and Structure | QC data | Method |
|---|---|---|---|
| 81 | 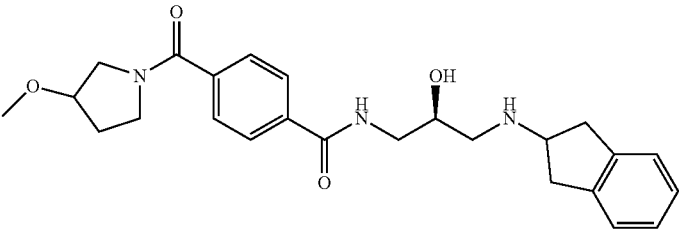 [SMILES: COC1CCN(C(=O)c2ccc(C(=O)NC[C@@H](O)CNC3Cc4ccccc4C3)cc2)C1]<br>N-((S)-3-((2,3-dihydro-1H-inden-2-yl)amino)-2-hydroxypropyl)-4-(3-methoxypyrrolidine-1-carbonyl)benzamide | $^1$H NMR (400 MHz, Methanol-$d_4$) δ 7.96-7.94 (m, 2 H), 7.64-7.62 (m, 2 H), 7.27-7.20 (m, 4 H), 4.14-4.06 (m, 3 H), 3.75-3.64 (m, 2 H), 3.62-3.54 (m, 2 H), 3.52-3.38 (m, 6 H), 3.26-3.21 (m, 2 H), 3.17-3.10 (m, 2 H), 3.06-3.01 (m, 1 H), 2.18-1.95 (m, 2 H).<br>LCMS: RT 3.05 min, m/z 438.3 [M + H]$^+$ | G |
| 82 | 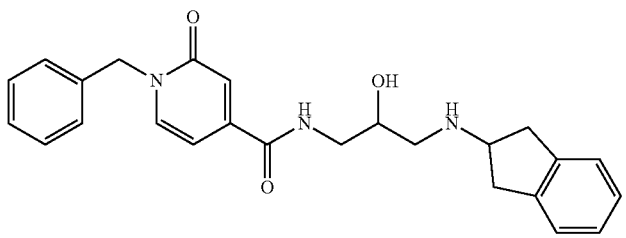 [SMILES: O=C(NCC(O)CNC1Cc2ccccc2C1)c1ccn(Cc2ccccc2)c(=O)c1]<br>1-benzyl-N-(3-((2,3-dihydro-1H-inden-2-yl)amino)-2-hydroxypropyl)-2-oxo-1,2-dihydropyridine-4-carboxamide | $^1$H NMR (400 MHz, Methanol-$d_4$) δ 7.83-7.80 (m, 1 H), 7.35-7.20 (m, 9 H), 6.95 (d, J = 1.6 Hz, 1 H), 6.70-6.68 (dd, J = 7.2, 2.0 Hz, 1 H), 5.22 (s, 2 H), 4.13-4.08 (m, 2 H), 3.46-3.39 (m, 4 H), 3.18-3.10 (m, 3H), 3.04-2.99 (m, 1 H).<br>LCMS: RT 3.28 min, m/z 418.1 [M + H]$^+$ | D (Using racemic amine) |
| 83 | 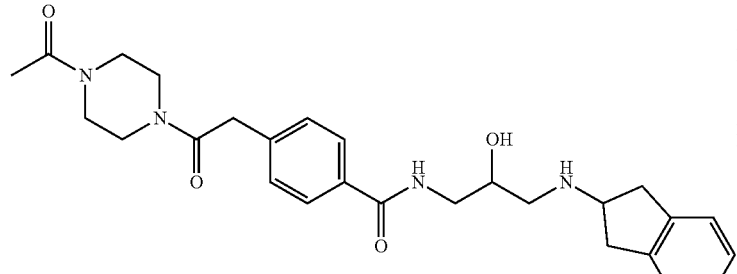<br>4-(2-(4-acetylpiperazin-1-yl)-2-oxoethyl)-N-(3-((2,3-dihydro-1H-inden-2-yl)amino)-2-hydroxypropyl)benzamide | $^1$H NMR (400 MHz, Methanol-$d_4$) δ 7.85-7.83 (m, 2 H), 7.40-7.38 (m, 2 H), 7.28-7.20 (m, 4 H), 4.14-4.10 (m, 2 H), 3.90 (s, 2 H), 3.67-3.46 (m, 12 H), 3.31-3.01 (m, 4 H), 2.11-2.09 (m, 3 H)<br>LCMS: RT 3.20 min, m/z 479.3 [M + H]$^+$ | E (Using racemic acid) |
| 84 | 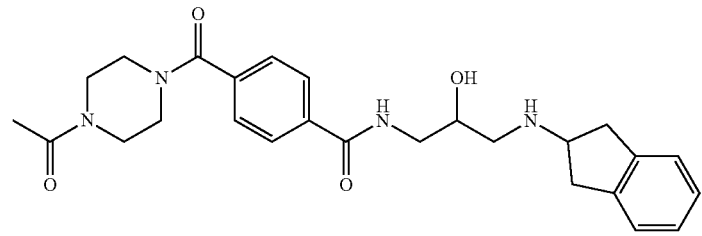 [SMILES: CC(=O)N1CCN(C(=O)c2ccc(C(=O)NCC(O)CNC3Cc4ccccc4C3)cc2)CC1]<br>4-(4-acetylpiperazine-1-carbonyl)-N-(3-((2,3-dihydro-1H-inden-2-yl)amino)-2-hydroxypropyl)benzamide | $^1$H NMR (400 MHz, Methanol-$d_4$) δ 7.97-7.95 (d, J = 8.0 Hz, 2 H), 7.57-7.55 (d, J = 8.4 Hz, 2 H), 7.25-7.17 (m, 4 H), 4.09-4.06 (m, 1 H), 3.98-3.93 (m, 1 H), 3.85-3.46 (m, 10 H), 3.39-3.34 (m, 2 H), 3.13-3.01 (m, 3 H), 2.97-2.92 (m, 1 H), 2.16 (s, 3 H).<br>LCMS: RT 0.26 min, m/z 465.3 [M + H]$^+$ | F (Using racemic acid) |

| Compound | Name and Structure | QC data | Method |
|---|---|---|---|
| 85 | 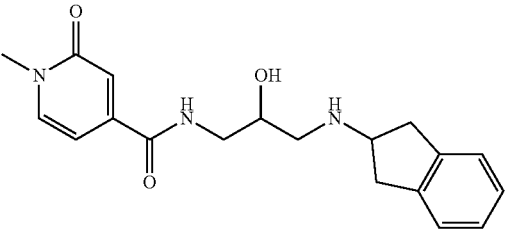 [SMILES: Cn1ccc(C(=O)NCC(O)CNC2Cc3ccccc3C2)cc1=O]<br>N-(3-((2,3-dihydro-1H-inden-2-yl)amino)-2-hydroxypropyl)-1-methyl 2-oxo-1,2-dihydropyridine-4-carboxamide | $^1$H NMR (400 MHz, Methanol-$d_4$) δ 7.76-7.74 (m, 1 H), 7.24-7.19 (m, 4 H), 6.92 (s, 1 H), 6.68-6.67 (m, 1 H), 4.04-3.96 (m, 2 H), 3.59 (s, 3 H), 3.52-3.39 (m, 4 H), 3.13-3.03 (m, 3 H), 2.95-2.90 (m, 1 H). LCMS: RT 0.62 min, m/z 342.2 [M + H]$^+$ | C (Using racemic amine) |
| 86 | 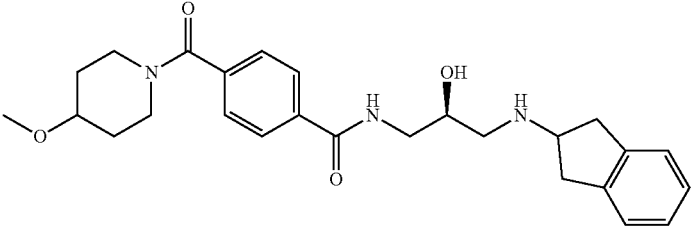 [SMILES: COC1CCN(C(=O)c2ccc(C(=O)NC[C@@H](O)CNC3Cc4ccccc4C3)cc2)CC1]<br>(S)-N-(3-((2,3-dihydro-1H-inden-2-yl)amino)-2-hydroxypropyl)-4-(4-methoxypiperidine-1-carbonyl)benzamide | $^1$H NMR (400 MHz, Methanol-$d_4$) δ 7.95-7.93 (d, J = 8.0 Hz, 2 H), 7.52-7.50 (d, J = 8.0 Hz, 2 H), 7.28-7.20 (m, 4 H), 4.16-4.09 (m, 2 H), 3.59-3.49 (m, 4 H), 3.47-3.40 (m, 3 H), 3.37 (s, 3 H), 3.27-3.12 (m, 5 H), 3.08-3.03 (m, 1 H), 2.04-1.97 (m, 2 H), 1.71-1.59 (m, 2 H). LCMS: RT 0.26 min, m/z 452.3 [M + H]$^+$ | H |
| 87 | 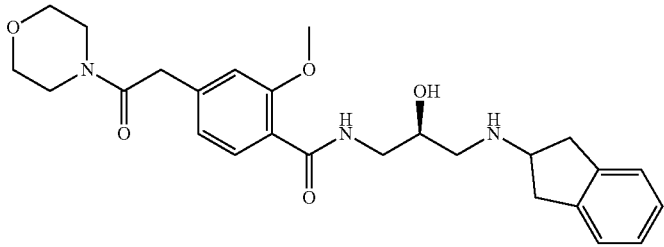 [SMILES: COc1cc(CC(=O)N2CCOCC2)ccc1C(=O)NC[C@@H](O)CNC1Cc2ccccc2C1]<br>(S)-N-(3-((2,3-dihydro-1H-inden-2-yl)amino)-2-hydroxypropyl)-2-methoxy-4-(2-morpholino-2-oxoethyl)benzamide | $^1$H NMR (400 MHz, Methanol-$d_4$) δ 7.90-7.88 (m 1 H), 7.27-7.20 (m, 4 H), 7.08 (s, 1 H), 6.98-6.96 (m, 1 H), 4.13-4.10 (m, 2 H), 3.99 (s, 3 H), 3.85 (s, 2 H), 3.63-3.54 (m, 9 H), 3.45-3.40 (m, 2 H), 3.24-2.97 (m, 5 H). LCMS: RT 1.61 min, m/z 468.3 [M + H]$^+$ | C |
| 88 | 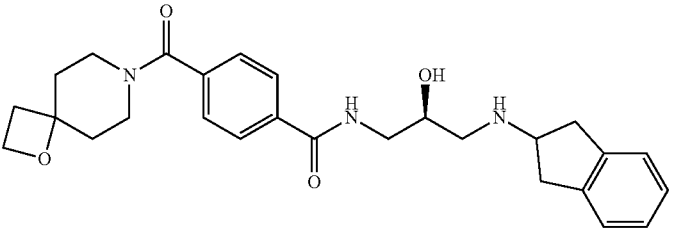 [SMILES: O=C(NC[C@@H](O)CNC1Cc2ccccc2C1)c1ccc(C(=O)N2CCC3(CCO3)CC2)cc1]<br>(S)-N-(3-((2,3-dihydro-1H-inden-2-yl)amino)-2-hydroxypropyl)-4-(1-oxa-7-azaspiro[3.5]nonane-7-carbonyl)benzamide | $^1$H NMR (400 MHz, Methanol-$d_4$) δ 7.94-7.92 (m, 2 H), 7.48-7.46 (m, 2 H), 7.22-7.13 (m, 4 H), 5.57 (br s, 1 H), 5.36 (br s, 1 H), 4.49 (br s, 1 H), 4.04 (br s, 1 H), 3.89-3.70 (m, 2 H), 3.49 (m, 2 H), 3.20-3.13 (m, 3 H), 2.93-2.87 (m, 3 H), 2.78-2.72 (m, 1 H), 2.14-2.08 (m, 4 H), 1.33 (s, 1 H), 1.23-1.22 (m, 2 H). LCMS: RT 1.11 min, m/z 464.3 [M + H]$^+$ | G |

| Compound | Name and Structure | QC data | Method |
|---|---|---|---|
| 89 | 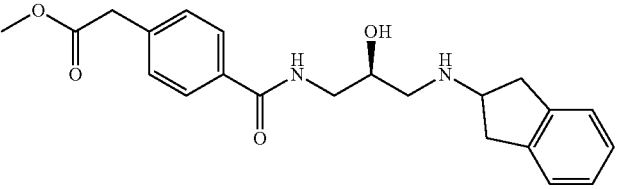 [SMILES: COC(=O)Cc1ccc(C(=O)NC[C@@H](O)CNC2Cc3ccccc3C2)cc1]<br>(S)-methyl 2-(4-((3-((2,3-dihydro-1H-inden-2-yl)amino)-2-hydroxypropyl)carbamoyl)phenyl)acetate | $^1$H NMR (400 MHz, Methanol-$d_4$) δ 7.83-7.81 (m, 2 H), 7.40-7.38 (m, 2 H), 7.27-7.19 (m, 4 H), 4.12-4.07 (m, 2 H), 3.73 (s, 2 H), 3.68 (s, 3 H), 3.53-3.49 (m, 2 H), 3.44-3.38 (m, 2 H), 3.24-3.20 (m, 1 H), 3.17-3.13 (m, 2 H), 3.05-3.00 (m, 1 H). LCMS: RT 3.28 min, m/z 383.2 [M + H]$^+$ | A With DIPEA |
| 90 | 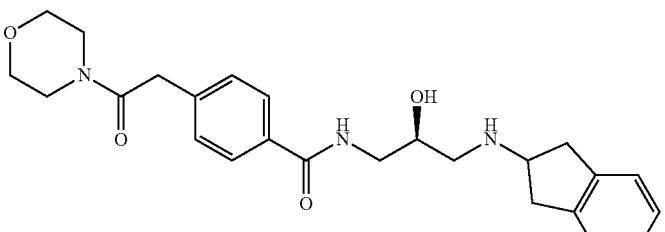<br>(S)-N-(3-((2,3-dihydro-1H-inden-2-yl)amino)-2-hydroxypropyl)-4-(2-morpholino-2-oxoethyl)benzamide | $^1$H NMR (400 MHz, Methanol-$d_4$) δ 7.86-7.84 (m, 2 H), 7.41-7.38 (m, 2 H), 7.28-7.20 (m, 4 H), 4.13-4.06 (m, 2 H), 3.88 (s, 2 H), 3.65-3.61 (m, 4 H), 3.59-3.55 (m, 4 H), 3.54-3.47 (m, 2 H), 3.45-3.38 (m, 2 H), 3.23-3.19 (m, 1 H), 3.16-3.10 (m, 2 H), 3.05-3.00 (m, 1 H). LCMS: RT 0.67 min, m/z 438.3 [M + H]$^+$ | A |
| 91 | 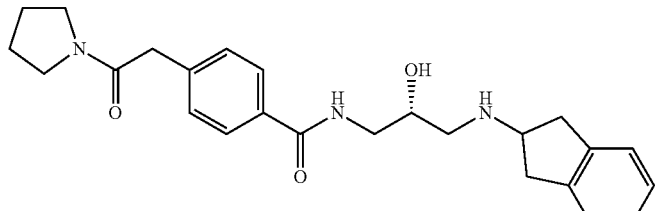<br>(R)-N-(3-((2,3-dihydro-1H-inden-2-yl)amino)-2-hydroxypropyl)-4-(2-oxo-2-(pyrrolidin-1-yl)ethyl)benzamide | $^1$H NMR (400 MHz, Methanol-$d_4$) δ 7.82-7.80 (m, 2 H), 7.39-7.37 (m, 2 H), 7.25-7.17 (m, 4 H), 4.10-4.00 (m, 2 H), 3.78 (s, 2 H), 3.56-3.34 (m, 8 H), 3.15-2.93 (m, 4 H), 1.80-2.10 (m, 4 H). LCMS: RT 3.37 min, m/z 422.3 [M + H]$^+$ | A Using (S)-amine |
| 92 | 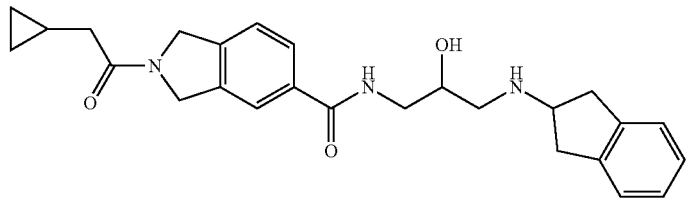 [SMILES: O=C(NCC(O)CNC1Cc2ccccc2C1)c1ccc2c(c1)CN(C(=O)CC1CC1)C2]<br>2-(2-cyclopropylacetyl)-N-(3-((2,3-dihydro-1H-inden-2-yl)amino)-2-hydroxypropyl)isoindoline-5-carboxamide | $^1$H NMR (400 MHz, Methanol-$d_4$) δ 7.83-7.80 (m, 2H), 7.47-7.43 (m, 1H), 7.25-7.18 (m, 4H), 4.92 (br s, 2H), 1H), 4.80 (br s, 2H), 4.41-4.00 (m, 2H), 3.54-3.48 (m, 2H), 3.41-3.35 (m, 2H), 3.14-3.30 (m, 5H), 2.42-40 (m, 2H), 0.59-0.57 (m, 2H), 0.24-0.23 (m, 2H). LCMS: RT 1.97 min, m/z 434.3 [M + H]$^+$ | A With DIPEA; Using racemic amine |
| 93 | 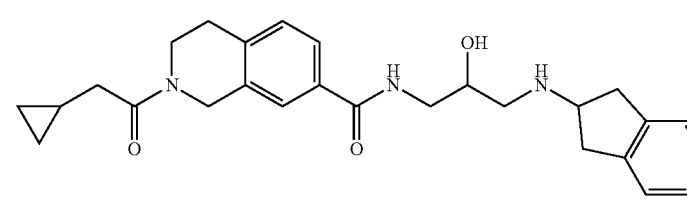<br>2-(2-cyclopropylacetyl)-N-(3-((2,3-dihydro-1H-inden-2-yl)amino)-2-hydroxypropyl)-1,2,3,4-tetrahydroisoquinoline-7-carboxamide | $^1$H NMR (400 MHz, Methanol-$d_4$) δ 7.67 (br s, 2H), 7.29-7.27 (m, 1 H), 7.18 (br s, 2 H) 7.13 (br s, 2 H), 4.76 (br s, 2 H), 3.97 (br s, 1 H), 3.83-3.69 (m, 3H), 3.48 (br s, 2H), 3.24-3.21 (m, 2H), 2.99-2.96 (m, 1H), 2.89-2.88 (m, 4H), 2.79-2.74 (m, 2H), 2.44-2.42 (m, 2H), 0.60 (br s, 2 H), 0.30 (br s, 2 H). LCMS: RT 2.07 min, m/z 448.3 [M + H]$^+$ | A With DIPEA; Using racemic amine |

| Compound | Name and Structure | QC data | Method |
|---|---|---|---|
| 94 | 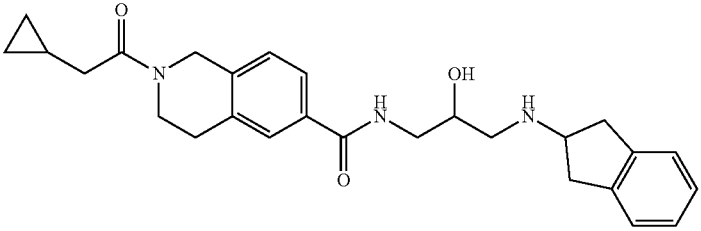 [SMILES: O=C(NCC(O)CNC1Cc2ccccc2C1)c1ccc2c(c1)CCN(C(=O)CC1CC1)C2]<br>2-(2-cyclopropylacetyl)-N-(3-((2,3-dihydro-1H-inden-2-yl)amino)-2-hydroxypropyl)-1,2,3,4-tetrahydroisoquinoline-6-carboxamide | $^1$H NMR (400 MHz, Methanol-d$_4$) δ 7.67 (br s, 2H), 7.34-7.33 (m, 1H), 7.24-7.13 (m, 4H), 4.76 (s, 2H), 4.00-3.97 (m, 1H), 3.84-3.75 (m, 3H), 3.49-3.46 (m, 2H), 3.26-3.22 (m, 2 H), 2.98-2.86 (m, 5H), 2.80-2.78 (m, 2H), 244-2.42 (m, 2H), 0.56-0.53 (m, 2H), 0.22-0.18 (m, 2H).<br>LCMS: RT 1.99 min, m/z 448.3 [M + H]$^+$ | B<br>With DIPEA;<br>Using racemic amine |
| 95 | 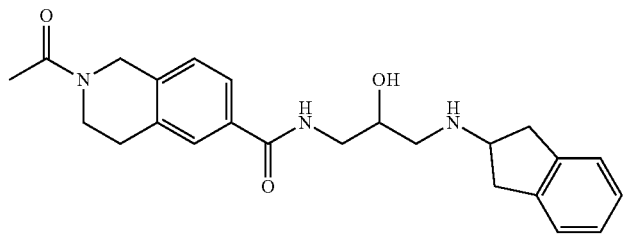 [SMILES: CC(=O)N1CCc2cc(C(=O)NCC(O)CNC3Cc4ccccc4C3)ccc2C1]<br>2-acetyl-N-(3-((2,3-dihydro-1H-inden-2-yl)amino)-2-hydroxypropyl)-1,2,3,4-tetrahydroisoquinoline-6-carboxamide | $^1$H NMR (400 MHz, Methanol-d$_4$) δ 7.69-7.66 (m, 2H), 7.30-7.26 (m, 1 H), 7.21-7.19 (m, 2H), 7.15-7.12 (m, 2H), 4.76-4.73 (m, 2H), 4.54 (br s, 1H), 4.02-3.98 (m, 1H), 3.81-3.75 (m, 3 H), 3.51-3.44 (m, 2 H) 3.25-3.23 (m, 1 H), 3.00-2.78 (m, 5H), 2.85-2.78 (m, 1H), 2.19 (s, 3H).<br>LCMS: RT 3.04 min, m/z 408.3 [M + H]$^+$ | B<br>Using racemic amine |
| 96 | 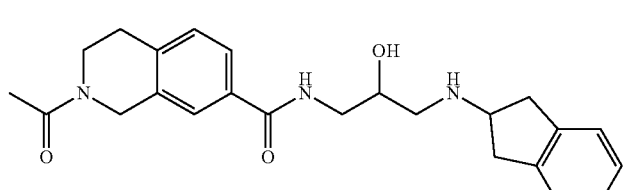<br>2-acetyl-N-(3-((2,3-dihydro-1H-inden-2-yl)amino)-2-hydroxypropyl)-1,2,3,4-tetrahydroisoquinoline-7-carboxamide | $^1$H NMR (400 MHz, Methanol-d$_4$) δ 7.68-7.66 (m, 2H), 7.31-7.29 (m, 1H), 7.21-7.20 (m, 2H), 7.16-7.14 (m, 2H), 4.75-4.74 (m, 2H), 4.02-3.99 (m, 1H), 3.81-3.75 (m, 3 H), 3.49-3.46 (m, 2H), 3.27-3.24 (m, 2 H) 2.99-2.98 (m, 3H), 2.92-2.90 (m, 2 H), 2.89-2.81 (m, 1 H), 2.19 (s, 3H).<br>LCMS: RT 3.25 min, m/z 408.3 [M + H]$^+$ | B<br>Using racemic amine |
| 97 | 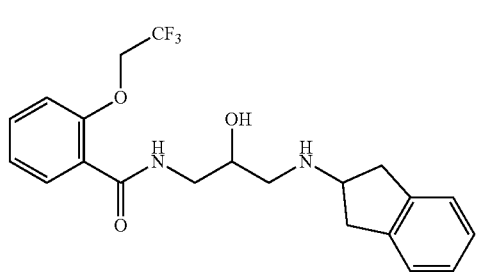 [SMILES: O=C(NCC(O)CNC1Cc2ccccc2C1)c1ccccc1OCC(F)(F)F]<br>N-(3-((2,3-dihydro-1H-inden-2-yl)amino)-2-hydroxypropyl)-2-(2,2,2-trifluoroethoxy)benzamide | $^1$H NMR (400 MHz, Methanol-d$_4$) δ 7.83-7.81 (m, 1H), 7.55-7.50 (m, 1H), 7.21-7.13 (m, 6H), 4.76-4.70 (m, 2H), 4.03-4.97 (m, 1H), 3.84-3.77 (m, 1H), 3.59-3.47 (m, 2H), 3.29-3.24 (m, 2H), 3.00-2.82 (m, 4H).<br>LCMS: RT 2.01 min, m/z 409.2 [M + H]$^+$ | B<br>with Et$_3$N (4.5 eq);<br>Using racemic amine |

| Compound | Name and Structure | QC data | Method |
|---|---|---|---|
| 98 | 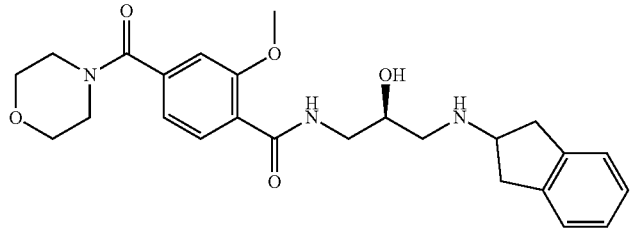 [SMILES: COc1cc(C(=O)N2CCOCC2)ccc1C(=O)NC[C@@H](O)CNC1Cc2ccccc2C1]<br>(S)-N-(3-((2,3-dihydro-1H-inden-2-yl)amino)-2-hydroxypropyl)-2-methoxy-4-(morpholine-4-carbonyl)benzamide | $^1$H NMR (400 MHz, Methanol-d$_4$) δ 7.99 (d, J = 8 Hz, 1 H), 7.29-7.21 (m, 5 H), 7.13 (d, J = 7.6 Hz, 1 H), 4.16-4.13 (m, 2 H), 4.03 (s, 3 H), 3.78-3.41 (m, 12 H), 3.28-3.05 (m, 4 H).<br>LCMS: RT 3.00 min, m/z 454.2 [M + H]$^+$ | B |
| 100 | 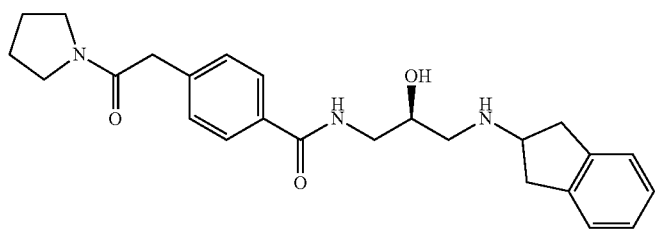 [SMILES: O=C(NC[C@@H](O)CNC1Cc2ccccc2C1)c1ccc(CC(=O)N2CCCC2)cc1]<br>(S)-N-(3-((2,3-dihydro-1H-inden-2-yl)amino)-2-hydroxypropyl)-4-(2-oxo-2-(pyrrolidin-1-yl)ethyl)benzamide | $^1$H NMR (400 MHz, Methanol-d$_4$) δ 7.83 (d, J = 8.4 Hz, 2 H), 7.39 (d, J = 8.4 Hz, 2 H), 7.27-7.19 (m, 4 H), 4.11-4.05 (m, 2 H), 3.78 (s, 2H), 3.56-3.50 (m, 4 H), 3.48-3.37 (m, 4 H), 3.23-3.10 (m, 3 H), 3.06-2.98 (m, 1 H), 2.02-1.96 (m, 2H), 1.94-1.87 (m, 2 H).<br>LCMS: RT 3.43 min, m/z 422.3 [M + H]$^+$ | A |
| 101 | 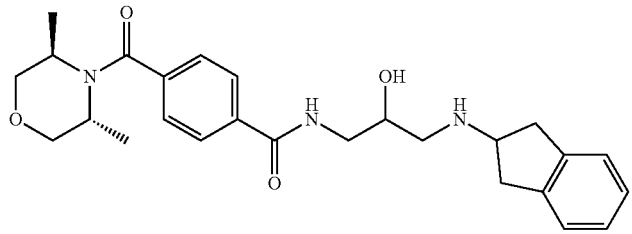 [SMILES: C[C@@H]1COC[C@@H](C)N1C(=O)c1ccc(C(=O)NCC(O)CNC2Cc3ccccc3C2)cc1]<br>N-(3-((2,3-dihydro-1H-inden-2-yl)amino)-2-hydroxypropyl)-4-((3R,5R)-3,5-dimethylmorpholine-4-carbonyl)benzamide | $^1$H NMR (400 MHz, Methanol-d$_4$) δ 7.92-7.90 (m, 2H), 7.59-7.57 (m, 2H), 7.17-7.11 (m, 4H), 3.96-3.89 (m, 5H), 3.67-3.60 (m, 1H), 3.52-3.48 (m, 4H), 3.22-3.15 (m, 2H), 2.83-2.68 (m, 4H), 1.28 (s, 3H), 1.27 (s, 3H).<br>LCMS: RT 1.81 min, m/z 452.3 [M + H]$^+$ | A<br>Using racemic amine |
| 102 | 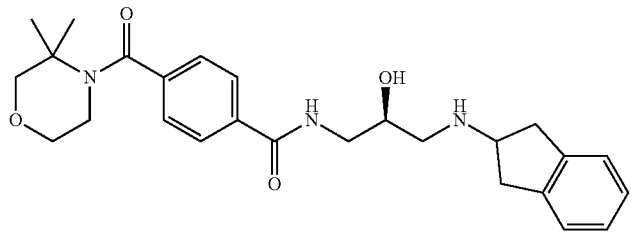 [SMILES: CC1(C)COCCN1C(=O)c1ccc(C(=O)NC[C@@H](O)CNC2Cc3ccccc3C2)cc1]<br>(S)-N-(3-((2,3-dihydro-1H-inden-2-yl)amino)-2-hydroxypropyl)-4-(3,3-dimethylmorpholine-4-carbonyl)benzamide | $^1$H NMR (400 MHz, Methanol-d$_4$) δ 7.92-7.89 (m, 2H), 7.52-7.50 (m, 2H), 7.22-7.13 (m, 4H), 4.04-3.98 (m, 1H), 3.82-3.77 (m, 1H), 3.74-3.72 (m, 2H), 3.56-3.46 (m, 4H), 3.37-3.35 (m, 2H), 3.29-3.23 (m, 2H), 2.98-2.88 (m, 3H), 2.84-2.78 (m, 1H), 1.52 (s, 6H).<br>LCMS: RT 1.87 min, m/z 452.3 [M + H]$^+$ | F |

| Compound | Name and Structure | QC data | Method |
|---|---|---|---|
| 103 | 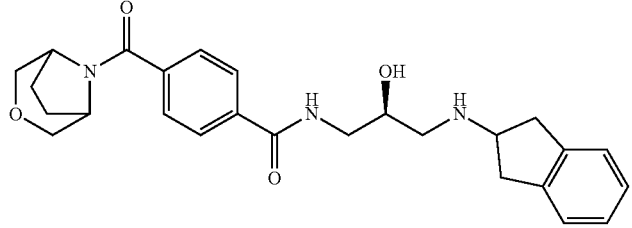 [SMILES: O=C(NC[C@@H](O)CNC1Cc2ccccc2C1)c1ccc(C(=O)N2C3CCC2COC3)cc1]<br>4-(3-oxa-8-azabicyclo[3.2.1]octane-8-carbonyl)-N-((S)-3-((2,3-dihydro-1H-inden-2-yl)amino)-2-hydroxypropyl)benzamide | $^1$H NMR (400 MHz, Methanol-$d_4$) δ 7.93-7.91 (m, 2H), 7.60-7.58 (m, 2H), 7.19-7.10 (m, 4H), 3.98-3.93 (m, 2H), 3.84-3.57 (m, 6H), 3.50-3.49 (m, 2H), 3.22-3.15 (m, 2H), 2.85-2.78 (m, 3H), 2.73-2.68 (m, 1H), 2.08-2.01 (m, 4H).<br>LCMS: RT 0.77 min, m/z 450.3 [M + H]$^+$ | G |
| 104 | 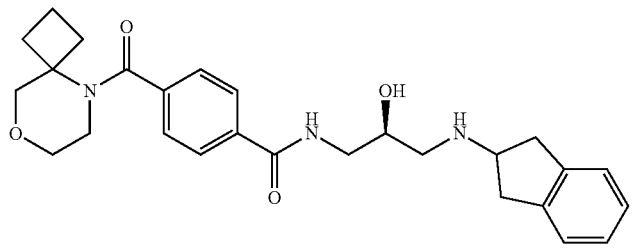 [SMILES: O=C(NC[C@@H](O)CNC1Cc2ccccc2C1)c1ccc(C(=O)N2CCOCC23CCC3)cc1]<br>(S)-N-(3-((2,3-dihydro-1H-inden-2-yl)amino)-2-hydroxypropyl)-4-(8-oxa-5-azaspiro[3.5]nonane-5-carbonyl)benzamide | $^1$H NMR (400 MHz, Methanol-$d_4$) δ 7.93-7.91 (m, 2H), 7.60-7.58 (m, 2H), 7.24-7.16 (m, 4H), 4.09-4.03 (m, 1H), 3.97-3.90 (m, 1H), 3.83 (s, 2H), 3.56-3.41 (m, 6H), 3.37-3.33 (m, 2H), 3.10-2.89 (m, 4H), 2.41-2.22 (m, 4H), 1.86-1.73 (m, 2H).<br>LCMS: RT 1.95 min, m/z 464.3 [M + H]$^+$ | F |
| 105 | 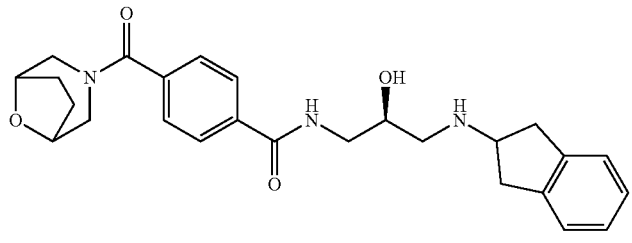 [SMILES: O=C(NC[C@@H](O)CNC1Cc2ccccc2C1)c1ccc(C(=O)N2CC3CCC(C2)O3)cc1]<br>4-(8-oxa-3-azabicyclo[3.2.1]octane-3-carbonyl)-N-((S)-3-((2,3-dihydro-1H-inden-2-yl)amino)-2-hydroxypropyl)benzamide | $^1$H NMR (400 MHz, Methanol-$d_4$) δ 7.94-7.92 (m, 2H), 7.52-7.50 (m, 2H), 7.22-7.14 (m, 4H), 4.46-4.44 (m, 1H), 4.36-4.32 (m, 1H), 4.24-4.23 (m, 1H), 4.06-4.00 (m, 1H), 3.87-3.80 (m, 1H), 3.55-3.46 (m, 3H), 3.29-3.25 (m, 2H), 3.16-3.12 (m, 1H), 3.02-2.92 (m, 3H), 2.88-2.81 (m, 2H), 1.99-1.86 (m, 3H), 1.72-1.67 (m, 1H).<br>LCMS: RT 0.75 min, m/z 450.3 [M + H]$^+$ | F |
| 113 | 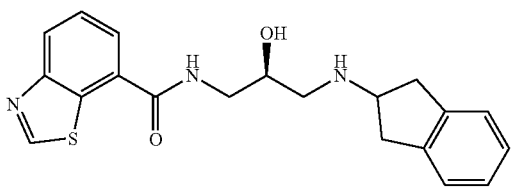 [SMILES: O=C(NC[C@@H](O)CNC1Cc2ccccc2C1)c1cccc2ncsc12]<br>(S)-N-(3-((2,3-dihydro-1H-inden-2-yl)amino)-2-hydroxypropyl)benzo[d]thiazole-7-carboxamide | $^1$H NMR (400 MHz, Methanol-$d_4$) δ 9.33 (s, 1H), 8.25 (d, J = 8.0 Hz, 1H), 8.06 (d, J = 8.0 Hz, 1H), 7.68 (t, J = 8.0 Hz, 1H), 7.22-7.13 (m, 4H), 4.10-4.04 (m, 1H), 3.90-3.81 (m, 1H), 3.62-3.49 (m, 2H), 3.28-3.26 (m, 1H), 3.06-2.86 (m, 5H)<br>LCMS: RT 1.16 min, m/z 368.2 [M + H]$^+$ | D |

| Compound | Name and Structure | QC data | Method |
|---|---|---|---|
| 114 | 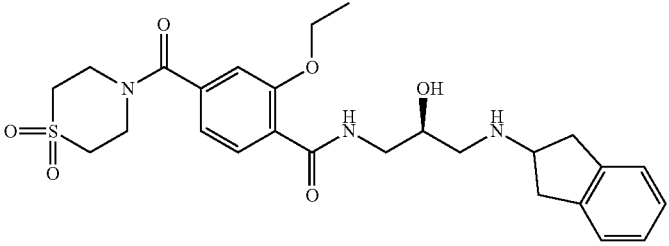 [SMILES: CCOc1cc(C(=O)N2CCS(=O)(=O)CC2)ccc1C(=O)NC[C@@H](O)CNC1Cc2ccccc2C1]<br>(S)-N-(3-((2,3-dihydro-1H-inden-2-yl)amino)-2-hydroxypropyl)-4-(1,1-dioxidothiomorpholine-4-carbonyl)-2-ethoxybenzamide | $^1$H NMR (400 MHz, Methanol-$d_4$) δ 8.02 (d, J = 7.6 Hz, 1H), 7.28 (s, 1H), 7.25-7.16 (m, 5H), 4.60 (s, 2H), 4.31-4.26 (m, 2 H), 4.20-3.86 (m, 6H), 3.64-3.50 (m, 2H), 3.38-3.34 (m, 2H), 3.18-2.93 (m, 6H), 1.53 (t, J = 6.8 Hz, 3H). LCMS: RT 3.06 min, m/z 516.3 [M + H]$^+$ | I |
| 115 | 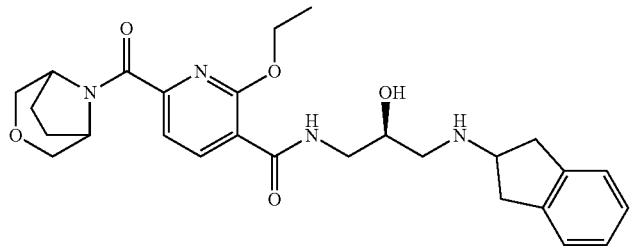 [SMILES: CCOc1nc(C(=O)N2C3CCC2COC3)ccc1C(=O)NC[C@@H](O)CNC1Cc2ccccc2C1]<br>6-(3-oxa-8-azabicyclo[3.2.1]octane-8-carbonyl)-N-((S)-3-((2,3-dihydro-1H-inden-2-yl)amino)-2-hydroxypropyl)-2-ethoxynicotinamide | $^1$H NMR (400 MHz, Methanol-$d_4$) δ 8.44 (d, J = 7.6 Hz, 1H), 7.51 (d, J = 8.0 Hz, 1 H), 7.22-7.13 (m, 4H) 4.71-4.65 (m, 2H), 4.57-4.49 (m, 2 H), 4.05-3.99 (m, 1 H), 3.91-3.89 (m, 1H), 3.84-3.68 (m, 4H), 3.64-3.59 (m, 1H), 3.53-3.47 (m, 1H), 3.28-3.24 (m, 2H), 2.99-2.83 (m, 4H), 2.10-1.98 (m, 4H), 1.50 (t, J = 6.8 Hz, 3H). LCMS: RT 4.83 min, m/z 495.0 [M + H]$^+$ | J |
| 116 | 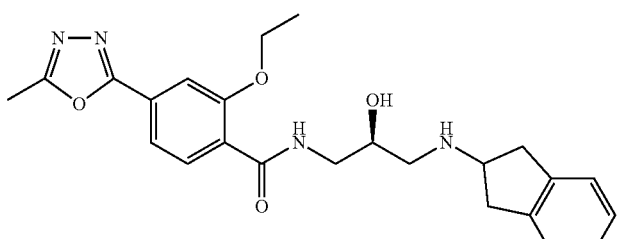<br>(S)-N-(3-((2,3-dihydro-1H-inden-2-yl)amino)-2-hydroxypropyl)-2-ethoxy-4-(5-methyl-1,3,4-oxadiazol-2-yl)benzamide | $^1$H NMR (400 MHz, Methanol-$d_4$) δ 8.09 (d, J = 8.0 Hz, 1H), 7.72 (d, J = 1.2 Hz, 1 H), 7.67 (dd, J = 8.0, 1.2 Hz, 1H), 7.18-7.16 (m, 2H), 7.11-7.09 (m, 2H), 4.33 (q, J = 6.8 Hz, 2H), 3.96-3.92 (m, 1H), 3.68-3.58 (m, 2H), 3.50-3.45 (m, 1H), 3.23-3.16 (m, 2H), 2.85-2.71 (m, 4H), 2.64 (s, 3H), 1.55 (t, J = 6.8 Hz, 3H). LCMS: RT 2.00 min, m/z 437.0 [M + H]$^+$ | K |
| 117 | 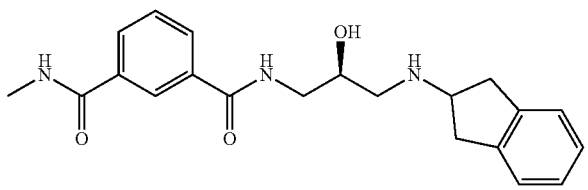 [SMILES: CNC(=O)c1cccc(C(=O)NC[C@@H](O)CNC2Cc3ccccc3C2)c1]<br>(S)-N$^1$-(3-((2,3-dihydro-1H-inden-2-yl)amino)-hydroxypropyl)-N$^3$-methylisophthalamide | $^1$H NMR (400 MHz, Methanol-$d_4$) δ 8.34 (s, 1 H), 8.01-7.96 (m, 2 H), 7.57 (t, J = 8.0 Hz, 1H), 7.25-7.17 (m, 4 H), 4.11-4.01 (m, 2 H), 3.59-3.47 (m, 2 H), 3.42-3.35 (m, 2 H) 3.21-3.17 (m, 1 H), 3.13-3.06 (m, 2 H), 3.03-2.97 (m, 1 H), 2.93 (s, 3 H). LCMS: RT 2.80 min, m/z 368.2 [M + H]$^+$ | D |

-continued

| Compound | Name and Structure | QC data | Method |
|---|---|---|---|
| 118 | (S)-N-(3-((2,3-dihydro-1H-inden-2-yl)amino)-2-hydroxypropyl)-2-(trifluoromethyl)benzamide | $^1$H NMR (400 MHz, Methanol-d$_4$) δ 7.80 (d, J = 7.6 Hz, 1 H), 7.73-7.60 (m, 3 H), 7.28-7.20 (m, 4 H), 4.16-4.08 (m, 2 H), 3.51 (d, J = 6.0 Hz, 2 H), 3.47-3.41 (m, 2 H), 3.28-3.24 (m, 1 H), 3.20-3.13 (m, 2 H), 3.10-3.04 (m, 1 H). LCMS: RT 1.90 min, m/z 379.2 [M + H]$^+$ | D |
| 119 | (S)-3-(difluoromethoxy)-N-(3-((2,3-dihydro-1H-inden-2-yl)amino)-2-hydroxypropyl)benzamide | $^1$H NMR (400 MHz, Methanol-d$_4$) δ 7.75 (d, J = 8.0 Hz, 1 H), 7.65 (s, 1 H), 7.52 (t, J = 8.0 Hz, 1 H), 7.36-7.33 (m, 1 H), 7.26-7.18 (m, 4 H), 7.09-6.72 (m, 1 H), 4.15-4.04 (m, 2 H), 3.57-3.45 (m, 2 H), 3.44-3.37 m, 2 H), 3.23-3.19 (m, 1 H), 3.16-3.09 (m, 2 H), 3.04-2.99 (m, 1 H). LCMS: RT 1.93 min, m/z 377.2 [M + H]$^+$ | D |
| 120 | (S)-N-(3-((2,3-dihydro-1H-inden-2-yl)amino)-2-hydroxypropyl)-1H-benzo[d]imidazole-4-carboxamide | $^1$H NMR (400 MHz, Methanol-d$_4$) δ 8.44 (s, 1 H), 7.98 (d, J = 7.2 Hz, 1 7.84 (d, J = 8.0 Hz, 1 H), 7.43 (t, J = 7.6 Hz, 1 H), 7.23-7.17 (m, 4 H), 4.23-4.21 (m, 1 H), 4.16-4.09 (m, 1 H), 3.74-3.64 (m, 2 H), 3.45-3.38 (m, 2 H), 3.34-3.32 (m, 1 H), 3.19-3.09 (m, 3 H). LCMS: RT 0.38 min, m/z 351.2 [M + H]$^+$ | D |
| 121 | 4-(3-oxa-8-azabicyclo[3.2.1]octane-8-carbonyl)-2-chloro-N-((S)-3-((2,3-dihydro-1H-inden-2-yl)amino)-2-hydroxypropyl)benzamide | $^1$H NMR (400 MHz, Methanol-d$_4$) δ 7.63 (d, J = 1.2 Hz, 1 H), 7.59-7.58 (m, 1 H), 7.52 (dd, J = 8.0, 1.2 Hz, 1 H), 7.24-7.16 (m, 4 H), 4.63-4.59 (m, 2 H), 4.08-4.02 (m, 1 H), 3.98-3.90 (m, 2 H), 3.83-3.80 (m, 1 H), 3.72-3.69 (m, 2 H), 3.60-3.58 (m, 1 H), 3.52 (d, J = 5.6 Hz, 2 H), 3.37-3.35 (m, 1 H), 3.14-3.10 (m, 1 H), 3.05-2.92 (m, 3 H), 2.10 (m, 4H). LCMS: RT 3.29 min, m/z 484.2 [M + H]$^+$ | D |
| 122 | (S)-N-(3-((2,3-dihydro-1H-inden-2-yl)amino)-2-hydroxypropyl)-2-ethoxy-5-methyl-4-(morpholine-4-carbonyl)benzamide | $^1$H NMR (400 MHz, Methanol-d$_4$) δ 7.83 (s, 1H), 7.27-7.19 (m, 4H), 7.01 (s, 1H), 4.26-4.21 (m, 2H), 4.13-4.06 (m, 2H), 3.79-3.76 (m, 4H), 3.66-3.57 (m, 4H), 3.45-3.39 (m, 2H), 3.27-3.26 (m, 2H), 3.22-3.02 (m, 4H), 3.27 (s, 3H), . 1.50 (t, J = 7.2 Hz, 3H). LCMS: RT 1.74 min, m/z 482.3 [M + H]$^+$ | D |

| Compound | Name and Structure | QC data | Method |
|---|---|---|---|
| 123 | N-((S)-3-((2,3-dihydro-1H-inden-2-yl)amino)-2-hydroxypropyl)-2-ethoxy-4-((R)-3-methylmorpholine-4-carbonyl)benzamide | ¹H NMR (400 MHz, Methanol-d₄) δ 8.00 (d, J = 7.6 Hz, 1H), 7.27-7.07 (m, 6H), 4.31-4.26 (m, 2H), 4.15-4.04 (m, 2H), 3.75-3.48 (m, 7H), 3.44-3.38 (m, 3H), 3.22-3.01 (m, 5H), 1.53 (t, J = 6.8 Hz, 3H), 1.38-1.37 (m, 3H) LCMS: RT 0.93 min, m/z 482.3 [M + H]⁺ | I |
| 124 | N-((S)-3-((2,3-dihydro-1H-inden-2-yl)amino)-2-hydroxypropyl)-2-ethoxy-4-((S)-3-ethylmorpholine-4-carbonyl)benzamide | ¹H NMR (400 MHz, Methanol-d₄) δ 8.01 (d, J = 7.6 Hz, 1H), 7.23-7.07 (m, 6H), 4.30-4.25 (m, 2H), 4.08-4.02 (m, 1H), 3.94-3.87 (m, 2H), 3.76 (s, 1H), 3.67-3.47 (m, 5H), 3.36-3.29 (m, 4H), 3.07-2.89 (m, 4H), 1.97-1.79 (m, 2H), 1.53 (t, J = 6.8 Hz, 3H), 1.02-0.78 (m, 3H) LCMS: RT 2.06 min, m/z 496.3 [M + H]⁺ | I |
| 125 | (S)-N-(3-((2,3-dihydro-1H-inden-2-yl)amino)-2-hydroxypropyl)benzo[d]thiazole-4-carboxamide | ¹H NMR (400 MHz, Methanol-d₄) δ 9.46 (s, 1H), 8.33-8.30 (m, 2H), 7.66-7.62 (m, 1H), 7.20-7.14 (m, 4H), 4.15-4.09 (m, 1H), 3.94-3.87 (m, 1H), 3.75-3.62 (m, 2H), 3.35-3.31 (m, 1H, overlap), 3.12-2.92 (m, 5H) LCMS: RT 1.43 min, m/z 368.2 [M + H]⁺ | D |
| 126 | 6-(3-oxa-8-azabicyclo[3.2.1]octane-8-carbonyl)-N-((S)-3-((2,3-dihydro-1H-inden-2-yl(amino-2-hydroxypropyl)-4-ethoxynicotinamide dihydrochloride | ¹H NMR (400 MHz, Methanol-d₄) δ 8.96 (s, 1H), 7.71 (s, 1H), 7.28-7.20 (m, 4H) 4.70-4.69 (m, 1H), 4.55-4.50 (m, 2H), 4.34 (s, 1H), 4.18-4.13 (m, 2H), 3.86-3.73 (m, 3H), 3.66-3.54 (m, 3H), 3.47-3.12 (m, 2H), 3.27-3.26 (m, 1H), 3.22-3.07 (m, 3H), 2.09-2.08 (m, 4H), 1.58 (t, J = 6.8 Hz, 3H). LCMS: RT 3.32 min, m/z 495.1 [M + H]⁺ for the freebase | J |

| Compound | Name and Structure | QC data | Method |
|---|---|---|---|
| 127 | 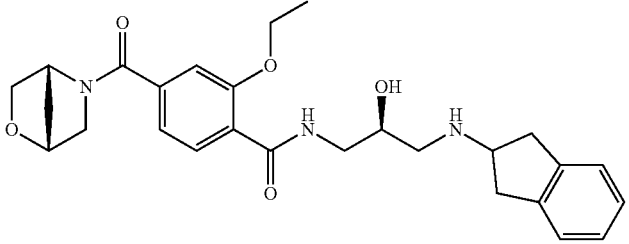 [SMILES: CCOc1cc(C(=O)N2C[C@H]3C[C@@H]2CO3)ccc1C(=O)NC[C@@H](O)CNC1Cc2ccccc2C1]<br>4-((1R,4R)-2-oxa-5-azabicyclo[2.2.1]heptane-5-carbonyl)-N-((S)-3-((2,3-dihydro-1H-inden-2-yl)amino)-2-hydroxypropyl)-2-ethoxybenzamide | $^1$H NMR (400 MHz, Methanol-$d_4$) δ 8.02-7.97 (m, 1H), 7.26-7.17 (m, 6H), 4.73-4.45 (m, 2H), 4.31-4.26 (m, 2H), 4.13-4.06 (m, 2H), 4.00-3.96 (m, 1H), 3.88-3.77 (m, 1H), 3.63-3.39 (m, 6H), 3.24-3.21 (m, 1H), 3.14-3.03 (m, 3H), 2.03-1.92 (m, 2H), 1.53 (t, J = 6.8 Hz, 3H). LCMS: RT 0.93 min, m/z 480.2 [M + H]$^+$ | I |
| 128 | 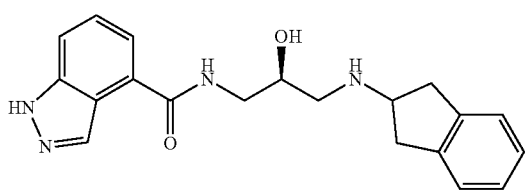 [SMILES: O=C(NC[C@@H](O)CNC1Cc2ccccc2C1)c1cccc2[nH]ncc12]<br>(S)-N-(3-((2,3-dihydro-1H-inden-2-yl)amino)-2-hydroxypropyl)-1H-indazole-4-carboxamide | $^1$H NMR (400 MHz, Methanol-$d_4$) δ 8.43 (s, 1H), 7.77-7.52 (m, 1H), 7.66-7.64 (m, 1H), 7.51-7.49 (m, 1H), 7.26-7.22 (m, 4H), 4.62 (br s, 1H), 4.19-4.13 (m, 2H), 3.61-3.55 (m, 2H), 3.47-3.41 (m, 2H), 3.20-3.07 (m, 3H) LCMS: RT 0.53 min, m/z 351.2 [M + H]$^+$ | D |
| 129 | 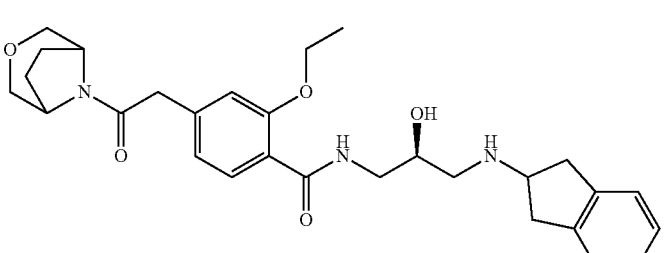<br>4-(2-(3-oxa-8-azabicyclo[3.2.1]octan-8-yl)-2-oxoethyl)-N-((S)-3-((2,3-dihydro-1H-inden-2-yl)amino)-2-hydroxypropyl)-2-ethoxybenzamide | $^1$H NMR (400 MHz, MeOH-$d_6$) δ 7.91 (d, J = 8.0 Hz, 1H), 7.29-7.18 (m, 4H), 7.12 (s, 1H), 7.01 (d, J = 7.9 Hz, 1H), 4.52 (d, J = 6.3 Hz, 1H), 4.34 (d, J = 4.9 Hz, 1H), 4.30-4.24 (m, 2H), 4.18-4.09 (m, 2H), 3.88-3.76 (m, 2H), 3.68-3.54 (m, 5H), 3.49-3.40 (m, 3H), 3.26-3.21 (m, 1H), 3.20-3.04 (m, 3H), 2.04-1.83 (m, 4H), 1.52 (t, J = 6.9 Hz, 3H). LCMS: RT 3.23 min, m/z 508.4 [M + H]$^+$ | J |
| 130 | 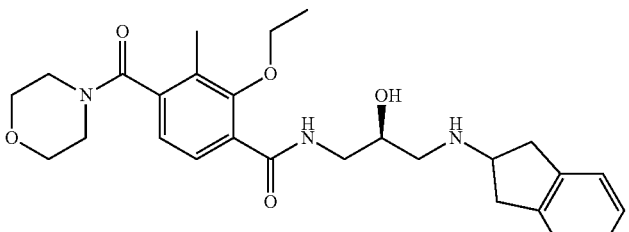<br>(S)-N-(3-((2,3-dihydro-1H-inden-2-yl)amino)-2-hydroxypropyl)-2-ethoxy-3-methyl-4-(morpholine-4-carbonyl)benzamide | $^1$H NMR (400 MHz, MeOH-$d_6$) δ 7.66 (d, J = 7.9 Hz, 1H), 7.23 (m, 4H), 7.09 (d, J = 7.9 Hz, 1H), 4.15-4.05 (m, 2H), 3.98 (m, 2H), 3.84-3.74 (m, 4H), 3.65-3.48 (m, 4H), 3.41 (m, 2H), 3.28-3.18 (m, 3H), 3.18-3.00 (m, 3H), 2.26 (s, 3H), 1.43 (t, J = 7.0 Hz, 3H). LCMS: RT 1.40 min, m/z 482.3 [M + H]$^+$ | D |

| Compound | Name and Structure | QC data | Method |
|---|---|---|---|
| 131 | 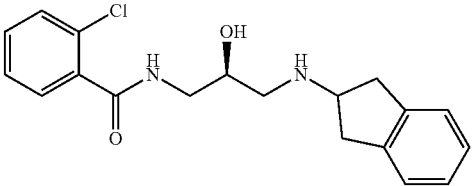<br>(S)-2-chloro-N-(3-((2,3-dihydro-1H-inden-2-yl)amino)-2-hydroxypropyl)benzamide | $^1$H NMR (400 MHz, Methanol-d$_4$) δ 7.47-7.40 (m, 4H), 7.21-7.15 (m, 4H), 3.99 (br s, 1H), 3.79 (m, 1H), 3.48 (m, 2H), 3.50 (m, 2H), 3.02-2.84 (m, 4H).<br>LCMS: RT 1.07 min, m/z 345.1; [M + H]$^+$ | D |
| 132 | 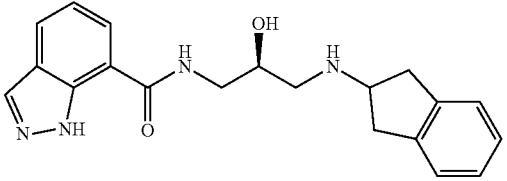 [SMILES: O=C(NC[C@@H](O)CNC1Cc2ccccc2C1)c1cccc2cn[nH]c12]<br>(S)-N-(3-((2,3-dihydro-1H-inden-2-yl)amino)-2-hydroxypropyl)-1H-indazole-7-carboxamide | $^1$H NMR (400 MHz, DMSO-d$_6$) δ 8.80 (br s, 1H), 8.17 (br s, 1H), 7.98-7.91 (m, 2H), 7.22-7.15 (m, 5H), 5.45 (br s, 1H), 3.94-3.37 (m, 2H), 3.22-3.17 (m, 4H), 2.99-2.78 (m, 4H).<br>LCMS: RT 1.12 min, m/z 351.2 [M + H]$^+$ | D |
| 133 | 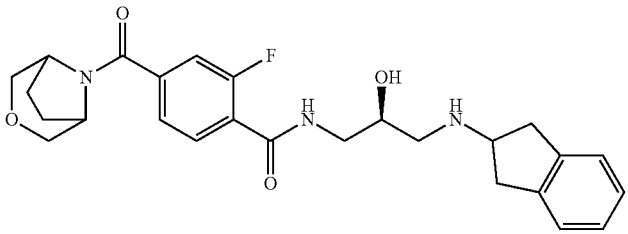 [SMILES: O=C(NC[C@@H](O)CNC1Cc2ccccc2C1)c1ccc(C(=O)N2C3CCC2COC3)cc1F]<br>4-(3-oxa-8-azabicyclo[3.2.1]octane-8-carbonyl)-N((S)-3-((2,3-dihydro-1H-inden-2-yl)amino)-2-hydroxypropyl)-2-fluorobenzamide | $^1$H NMR (400 MHz, Methanol-d$_4$) δ 7.84 (t, J = 7.2 Hz, 1H), 7.43-7.38 (m, 2H), 7.23-7.21 (m, 2H), 7.16-7.14 (m, 2H), 4.64-4.59 (m, 3H), 4.04-3.96 (m, 2H), 3.86-3.81 (m, 2H), 3.75-3.70 (m, 2H), 3.61-3.52 (m, 3H), 3.03-2.92 (m, 3H), 2.29-2.83 (m, 1H), 2.08-2.02 (m, 4H).<br>LCMS: RT 3.27 min, m/z 468.3 [M + H]$^+$ | J |
| 134 | 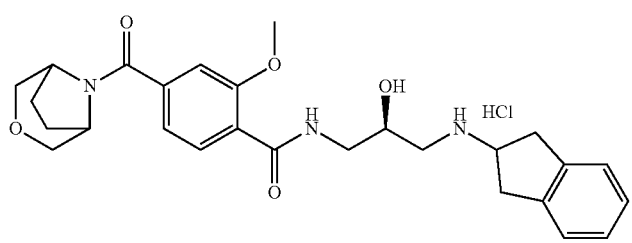 [SMILES: COc1cc(C(=O)N2C3CCC2COC3)ccc1C(=O)NC[C@@H](O)CNC1Cc2ccccc2C1 ; Cl]<br>4-(3-Oxa-8-azabicyclo[3.2.1]octane-8-carbonyl)-N-((S)-3-((2,3-dihydro-1H-inden-2-yl)amino)-2-hydroxypropyl)-2-methoxybenzamide hydrochloride | $^1$H NMR (400 MHz, Methanol-d$_4$) δ 7.98 (d, J = 7.6 Hz, 1H), 7.27-7.17 (m, 6H), 4.66 (br s, 1H), 4.15-4.13 (m, 2H), 4.03 (s, 3H), 3.98 (br s, 1H), 3.82-3.82 (m, 1H), 3.72-3.72 (m, 2H), 3.62-3.56 (m, 3H), 3.46-3.41 (m, 2H), 3.26-3.04 (m, 4H), 2.08-1.99 (m, 4H).<br>LCMS: RT 1.57 min, m/z 480.3 [M + H]$^+$ | J |

225

Example 45: N-(2-Amino-3-((2,3-dihydro-1H-inden-2-yl)amino)propyl)-4-(3-oxa-8-azabicyclo[3.2.1]octane-8-carbonyl)benzamide 106

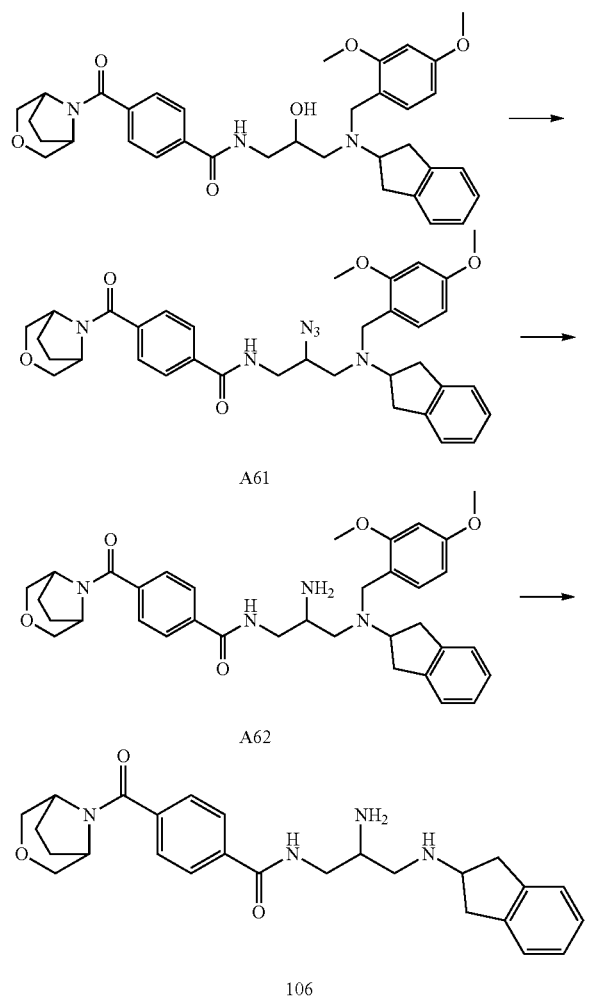

A61

A62

106

(a) N-(2-Azido-3-((2,3-dihydro-1H-inden-2-yl)(2,4-dimethoxybenzyl)amino)propyl)-4-(3-oxa-8-azabicyclo[3.2.1]octane-8-carbonyl)benzamide A62

To a solution of 4-(3-oxa-8-azabicyclo[3.2.1]octane-8-carbonyl)-N-(3-((2,3-dihydro-1H-inden-2-yl)(2,4-dimethoxybenzyl)amino)-2-hydroxypropyl)benzamide (Racemic analogue of Intermediate A in synthesis of 103, made in analogous way but with a racemic starting material) (100 mg, 0.17 mmol) in THF (5 mL) was added DPPA (95 mg, 0.34 mmol) and DBU (52 mg, 0.34 mmol). The resulting mixture was stirred at 60° C. overnight. LCMS showed the starting materials remained, further DPPA (46 mg, 0.17 mmol) and DBU (25 mg, 0.17 mmol) were added and the mixture was stirred at 60° C. overnight. The solvent was removed and the residue was purified by column chromatography (0-25% EtOAc/petroleum ether) to give the desired compound as an off-white solid (85 mg, 82%): $^1$H NMR (400 MHz, CDCl$_3$) δ 7.66-7.64 (m, 2H), 7.56-7.54 (m, 2H), 7.21-7.14 (m, 6H), 6.45-6.38 (m, 2H), 4.75 (br s, 1H), 3.95-3.83 (m, 5H), 3.79-3.76 (m, 5H), 3.74-3.69 (m, 6H),

226

3.65-3.59 (m, 2H), 3.35-3.30 (m, 1H), 3.21-3.12 (m, 4H), 2.07-2.05 (m, 4H): LCMS: RT 2.65 min, m/z 625.3 [M+H]$^+$ (b) N-(2-Amino-3-((2,3-dihydro-1H-inden-2-yl)(2,4-dimethoxybenzyl)amino)propyl)-4-(3-oxa-8-azabicyclo[3.2.1]octane-8-carbonyl)benzamide A63

To a solution of N-(2-azido-3-((2,3-dihydro-1H-inden-2-yl)(2,4-dimethoxybenzyl)amino)propyl)-4-(3-oxa-8-azabicyclo[3.2.1]octane-8-carbonyl)benzamide A62 (70 mg, 0.11 mmol) in THF (2 mL) was added PPh$_3$ (44 mg, 0.17 mmol). The resulting mixture was stirred at 50° C. for 3 h and then water (0.5 mL) was added dropwise and the mixture stirred at 30° C. overnight. The solvent was removed and the residue diluted with DCM (20 mL). The organic layer was dried (Na$_2$SO$_4$) and concentrated to give the crude product as a pale yellow solid (100 mg). The product was used directly for the next step without further purification. LCMS: RT 2.60 min, m/z 599.3 [M+H]$^+$ (c) N-(2-Amino-3-((2,3-dihydro-1H-inden-2-yl)amino)propyl)-4-(3-oxa-8-azabicyclo[3.2.1]octane-8-carbonyl)benzamide 106

A mixture of N-(2-amino-3-((2,3-dihydro-1H-inden-2-yl)(2,4-dimethoxybenzyl)amino)propyl)-4-(3-oxa-8 azabicyclo[3.2.1]octane-8-carbonyl)benzamide A63 (67 mg, 0.11 mmol) in TFA (1 mL) was stirred at 70° C. for 6 h. The solvent was removed and the residue was diluted with water (5 mL). The aqueous layer was washed with DCM (2×10 mL) and the pH adjusted to 9 by addition of solid Na$_2$CO$_3$. The aqueous layer was extracted with (10% MeOH in CH$_2$Cl$_2$) (6×10 mL). The combined organic layers were dried (Na$_2$SO$_4$) and concentrated to give the desired compound as a yellow solid (24 mg, 48%): $^1$H NMR (400 MHz, d$_4$-MeOD) δ 7.91-7.89 (m, 2H), 7.61-7.59 (m, 2H), 7.17-7.08 (m, 4H), 4.66 (br s, 1H), 3.95 (s, 1H), 3.83-3.69 (m, 4H), 3.61-3.56 (m, 2H), 3.49-3.45 (m, 1H), 3.24-3.15 (m, 2H), 2.98-2.93 (m, 1H), 2.83-2.62 (m, 4H), 2.07-2.01 (m, 4H): LCMS:RT 0.61 min, m/z 449.2 [M+H]$^+$ Example 46: N-(3-Amino-2-(((2,3-dihydro-1H-inden-2-yl)amino)methyl)-3-oxopropyl)-4-(morpholine-4-carbonyl)benzamide 107

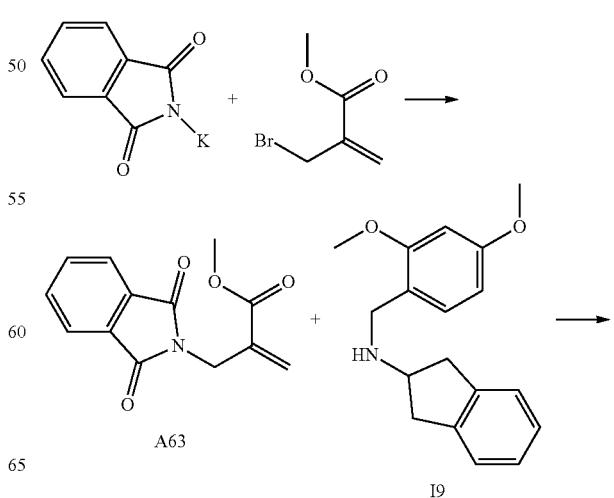

A63

I9

-continued

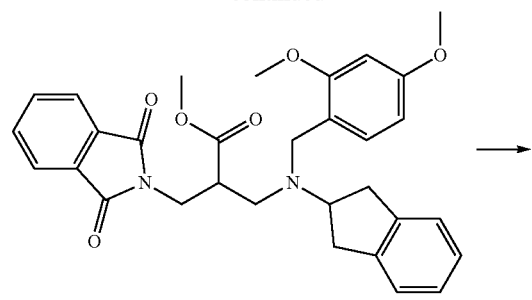

A64

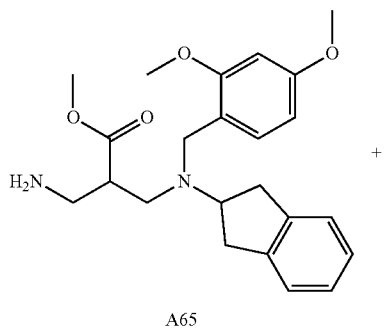

A65

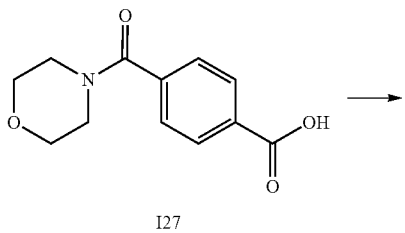

I27

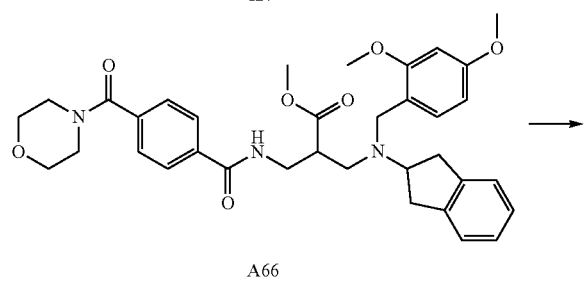

A66

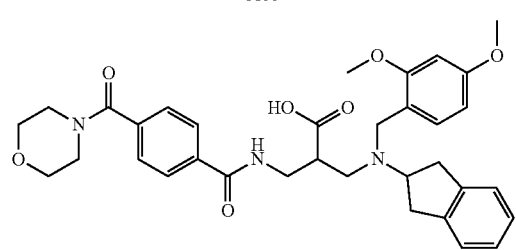

A67

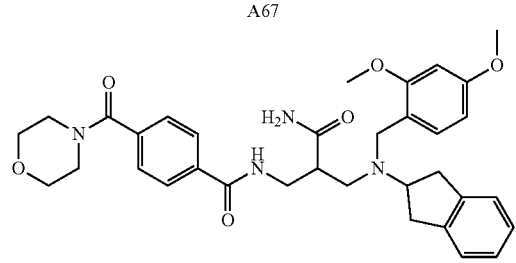

A68

-continued

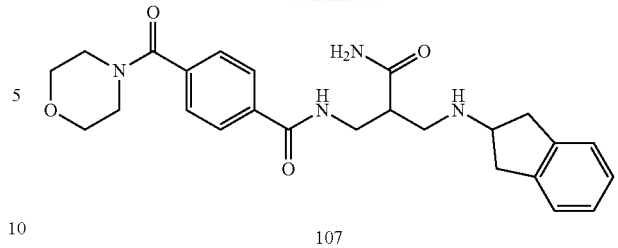

107

(a) Methyl 2-((1,3-dioxoisoindolin-2-yl)methyl)acrylate A63

To a solution of methyl 2-(bromomethyl)acrylate (2.0 g, 11.2 mmol) in toluene (50 mL) was added potassium 1,3-dioxoisoindolin-2-ide (2.0 g, 11.2 mmol) and 18-crown-6 (2.9 g, 11.2 mmol). The resulting mixture was stirred at 90° C. overnight. The reaction was partitioned with water (50 mL) and the aqueous layer further extracted with EtOAc (2×50 mL). The combined organic layers were washed with water (4×100 mL) and brine (100 mL), dried (Na$_2$SO$_4$) and concentrated to give the desired compound as a white solid (2.3 g, 85%): LCMS:RT 2.20 min, m/z 246.1 [M+H]$^+$ (b) Methyl 3-((2,3-dihydro-1H-inden-2-yl)(2,4-dimethoxybenzyl)amino)-2-((1,3-dioxoisoindolin-2-yl)methyl)propanoate A64

To a solution of methyl 2-((1,3-dioxoisoindolin-2-yl)methyl)acrylate A63 (2.0 g, 8.2 mmol) in CHCl$_3$ (15 mL) was added N-(2,4-dimethoxybenzyl)-2,3-dihydro-1H-inden-2-amine I9 (2.3 g, 8.2 mmol). The resulting mixture was heated at reflux for 3 days. The solvent was removed and the residue purified by column chromatography (0-17% Petroleum ether/EtOAc) to give the desired compound as a yellow oil (2.6 g, 60%): $^1$H NMR (400 MHz, CDCl$_3$) δ 7.84-7.82 (m, 2H), 7.72-7.70 (m, 2H), 7.29-7.27 (m, 1H), 7.16-7.15 (m, 2H), 7.11-7.08 (m, 2H), 6.47-6.44 (m, 1H), 6.42-6.40 (m, 1H), 3.93-3.92 (m, 1H), 3.84-3.81 (m, 3H), 3.78-3.77 (m, 6H), 3.76-3.73 (m, 2H), 3.62 (s, 3H), 3.16-3.13 (m, 1H), 3.00-2.93 (m, 4H), 2.69-2.64 (m, 1H): LCMS: RT 2.41 min, m/z 529.3 [M+H]$^+$ (c) Methyl 3-amino-2-(((2,3-dihydro-1H-inden-2-yl)(2,4-dimethoxybenzyl)amino)methyl)propanoate A65

To a solution of methyl-3-((2,3-dihydro-1H-inden-2-yl)(2,4-dimethoxybenzyl)amino)-2-((1,3-dioxoisoindolin-2-yl)methyl)propanoate A64 (2.6 g, 4.9 mmol) in MeOH (30 mL) was added DCM (5 mL) and hydrazine hydrate (85% aqueous solution, 270 mg, 5.4 mmol). The resultant mixture was stirred at room temperature overnight. The precipitate which formed was removed by filtration and the filtrate was concentrated in vacuo. The residue was diluted with DCM (100 mL) and a 2 M aqueous HCl solution (50 mL) was added. The pH of the aqueous layer was adjusted to 10 by addition of 6 M aqueous NaOH solution and extracted with DCM (3×100 mL). The organic layers were combined, dried (Na$_2$SO$_4$), filtered and concentrated in vacuo to give the desired compound as a yellow oil (1.0 g, 51%). The compound was used in the next step without further purification: LCMS:RT 1.38 min, m/z 399.3 [M+H]$^+$

(d) Methyl 3-((2,3-dihydro-1H-inden-2-yl)(2,4-dimethoxybenzyl)amino)-2-((4-(morpholine-4-carbonyl)benzamido)methyl)propanoate A66

To a solution of 4-(morpholine-4-carbonyl)benzoic acid I27 (420 mg, 1.80 mmol) in DCM (15 mL) was added HATU (685 mg, 1.80 mmol) and DIPEA (526 mg, 4.07 mmol) and the mixture was stirred at room temperature for 30 min. Methyl 3-amino-2-(((2,3-dihydro-1H-inden-2-yl)(2,4-dimethoxybenzyl)amino) methyl) propanoate A65 (650 mg, 1.63 mmol) was added and the mixture was stirred at room temperature overnight. The mixture was diluted with DCM (70 mL) washed with water (70 mL), saturated aqueous NaHCO$_3$ (70 mL), water (70 mL) and brine (70 mL), dried (Na$_2$SO$_4$) and concentrated. The residue was purified by column chromatography (0-30% EtOAc in DCM) to give the desired compound as a light solid (450 mg, 45%): $^1$H NMR (400 MHz, CDCl$_3$) δ 8.23 (br s, 1H), 7.68-7.66 (m, 2H), 7.34-7.33 (m, 2H), 7.19-7.17 (m, 2H), 7.12-7.10 (m, 3H), 6.43-6.41 (m, 1H), 6.34 (s, 1H), 3.99-3.84 (m, 4H), 3.82-3.70 (m, 12H), 3.56 (s, 3H), 3.52-3.38 (m, 4H), 3.04 (br s, 3H), 2.97-2.94 (m, 3H): LCMS:RT 2.21 min, m/z 616.4 [M+H]$^+$

(e) 3-((2,3-Dihydro-1H-inden-2-yl)(2,4-dimethoxybenzyl)amino)-2-((4-(morpholine-4-carbonyl)benzamido)methyl)propanoic acid A67

To a solution of methyl 3-((2,3-dihydro-1H-inden-2-yl)(2,4-dimethoxybenzyl)amino)-2-((4-(morpholine-4-carbonyl)benzamido)methyl)propanoate A66 (100 mg, 0.16 mmol) in MeOH (5 mL) was added a solution of NaOH (13 mg, 0.32 mmol) in water (0.5 mL). The resulting mixture was stirred at room temperature overnight. The solvent was removed and the residue obtained dissolved in water. The pH of the aqueous solution was adjusted to 3 by addition of a 2 M aqueous HCl solution. The aqueous layer was extracted with DCM (3×20 mL) and the combined organic layers dried (Na$_2$SO$_4$) and concentrated to give the desired compound as a yellow solid (100 mg, 100%): LCMS: RT 2.38 min, m/z 602.4 [M+H]$^+$

(f) N-(3-Amino-2-(((2,3-dihydro-1H-inden-2-yl)(2,4-dimethoxybenzyl)amino)methyl)-3-oxopropyl)-4-(morpholine-4-carbonyl)benzamide A68

To a solution of 3-((2,3-dihydro-1H-inden-2-yl)(2,4-dimethoxybenzyl)amino)-2-((4-(morpholine-4-carbonyl)benzamido)methyl)propanoic acid A67 (50 mg, 0.08 mmol) in DMF (0.5 mL) was added HATU (32 mg, 0.08 mmol) and DIPEA (32 mg, 0.24 mmol). The mixture was stirred at room temperature for 30 min, then poured into aqueous ammonia (26%, 2 mL) and stirred at room temperature for 1 h. The mixture was diluted with DCM (50 mL) and washed with water (2×50 mL) and brine (20 mL), dried (Na$_2$SO$_4$) and concentrated. The residue was purified by preparative TLC (10% methanol in DCM) to give the desired compound as a yellow solid (30 mg, 40%): LCMS: RT 2.18 min, m/z 601.3 [M+H]$^+$

(g) N-(3-Amino-2-(((2,3-dihydro-1H-inden-2-yl)amino)methyl)-3-oxopropyl)-4-(morpholine-4-carbonyl)benzamide 107

A mixture of N-(3-amino-2-(((2,3-dihydro-1H-inden-2-yl)(2,4-dimethoxybenzyl)amino)methyl)-3-oxopropyl)-4-(morpholine-4-carbonyl)benzamide A68 (30 mg, 0.05 mmol) in TFA (1 mL) was stirred at 70° C. for 6 h. The solvent was removed and the residue suspended in water. The pH was adjusted to 8 by addition of saturated aqueous NaHCO$_3$ solution. The aqueous layer was extracted with DCM (2×20 mL) and the combined organic layers washed with water (20 mL) and brine (20 mL), dried (Na$_2$SO$_4$) and concentrated. The residue obtained was purified by preparative TLC (10% methanol in DCM) to give the desired compound as a yellow solid (10 mg, 45%): $^1$H NMR (400 MHz, d$_4$-methanol) δ 7.94-7.92 (m, 2H), 7.56-7.52 (m 2H), 7.25-7.16 (m, 4H), 3.96-3.89 (m, 1H), 3.77-3.61 (m, 8H), 3.42 (brs, 2H), 3.37-3.31 (m, 2H), 3.27-3.22 (m, 1H), 3.13-3.01 (m, 4H): LCMS:RT 3.02 min, m/z 451.2 [M+H]$^+$

Example 47: N-(3-((2,3-Dihydro-1H-inden-2-yl)amino)-2-(hydroxymethyl)propyl)-4-(morpholine-4-carbonyl)benzamide 108

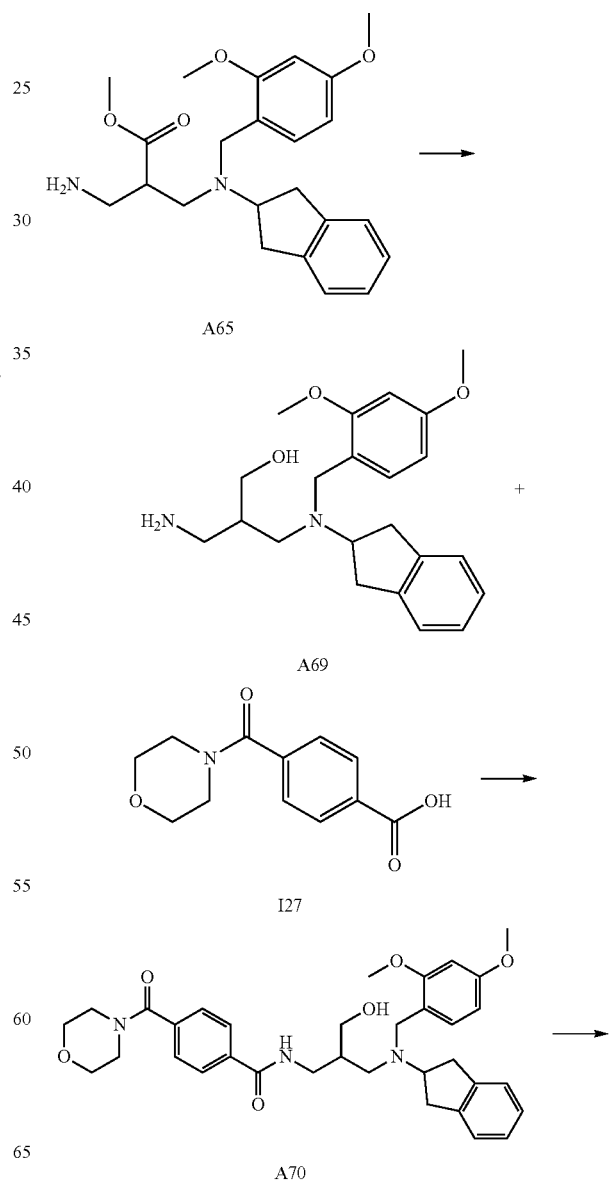

-continued

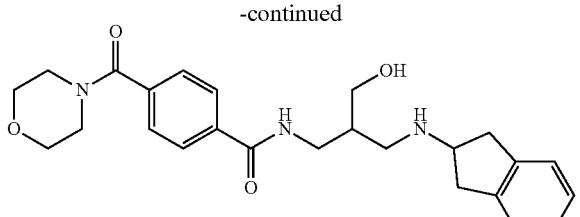

108

(a) 3-Amino-2-(((2,3-dihydro-1H-inden-2-yl)(2,4-dimethoxybenzyl)amino)methyl)propan-1-ol A69

To a solution of methyl 3-amino-2-(((2,3-dihydro-1H-inden-2-yl)(2,4-dimethoxybenzyl)amino) methyl)propanoate A65 (50 mg, 0.13 mmol) in THF (4 mL) was added LiAlH$_4$ (10 mg, 0.26 mmol). The resulting mixture was stirred at room temperature for 2 h. The mixture was quenched with water (2×0.5 mL) 10% aqueous NaOH (0.5 mL) and water (0.5 mL) and stirred at room temperature for 10 min. The solvent was removed, water was added and the mixture was extracted with DCM (3×10 mL). The combined organic layers were dried (Na$_2$SO$_4$) and concentrated to give the desired compound as yellow oil (45 mg, 98%): LCMS: RT 0.96 min, m/z 371.2 [M+H]$^+$

(b) N-(3-((2,3-Dihydro-1H-inden-2-yl)(2,4-dimethoxybenzyl)amino)-2-(hydroxymethyl)propyl)-4-(morpholine-4-carbonyl)benzamide A70

To a solution of 3-amino-2-(((2,3-dihydro-1H-inden-2-yl) (2,4-dimethoxybenzyl) amino)methyl) propan-1-ol A69 (180 mg, 0.48 mmol) in DCM (10 mL) was added 4-(morpholine-4-carbonyl)benzoic acid I27 (125 mg, 0.53 mmol), DIPEA (186 mg, 1.44 mmol), HOBt (7 mg, 0.05 mmol) and EDCl (110 mg, 0.58 mmol). The resulting mixture was stirred at room temperature for two days. The mixture was diluted with DCM (50 mL) and the organic layer washed with water (50 mL), saturated aqueous NaHCO$_3$ (50 mL), water (50 mL) and brine (50 mL), dried (Na$_2$SO$_4$) and concentrated. The residue was purified by column chromatography (0-2% MeOH in DCM) to give the desired compound as a yellow solid (80 mg, 28%): LCMS: RT 2.25 min, m/z 588.2 [M+H]$^+$

(c) N-(3-((2,3-Dihydro-1H-inden-2-yl)amino)-2-(hydroxymethyl)propyl)-4-(morpholine-4-carbonyl) benzamide 108

A mixture of N-(3-((2,3-dihydro-1H-inden-2-yl)(2,4-dimethoxybenzyl)amino)-2-(hydroxyl methyl) propyl)-4-(morpholine-4-carbonyl)benzamide A70 (80 mg, 0.14 mmol) in TFA (4 mL) was stirred at 70° C. for 6 h. The solvent was removed and the residue suspended in water. The pH was adjusted to 8 by addition of saturated aqueous NaHCO$_3$ solution. The aqueous layer was extracted with DCM (3×20 mL) and the combined organic layers washed with water (40 mL) and brine (40 mL), dried (Na$_2$SO$_4$) and concentrated. The residue obtained was purified by preparative TLC (10% methanol in DCM) to give the desired compound as a yellow solid (30 mg, 51%): $^1$H NMR (400 MHz, Methanol-d$_4$) δ 7.92-7.90 (m, 2H), 7.54-7.52 (m, 2H), 7.22-7.17 (m, 4H), 3.87-3.42 (m, 14H), 3.31 (m, 1H, overlap), 3.02-2.89 (m, 4H), 2.19-2.15 (m, 1H). LCMS: RT 3.13 min, m/z 438.2 [M+H]$^+$

Example 48: (S)—N-(3-((2,3-Dihydro-1H-inden-2-yl)amino)-2-hydroxypropyl)-2-((1-(methylsulfonyl) azetidin-3-yl)amino)isonicotinamide bis 2,2,2-trifluoroacetic acid salt 109

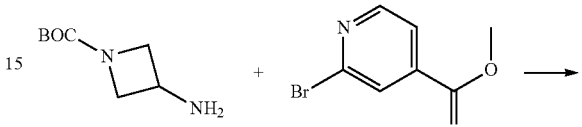

A72

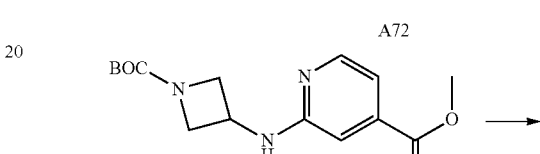

A71

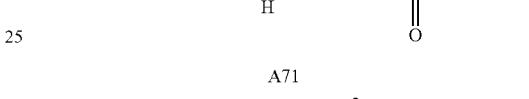

A72

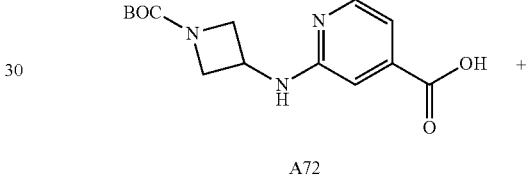

I10

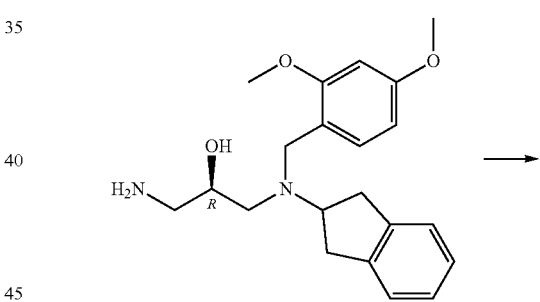

A73

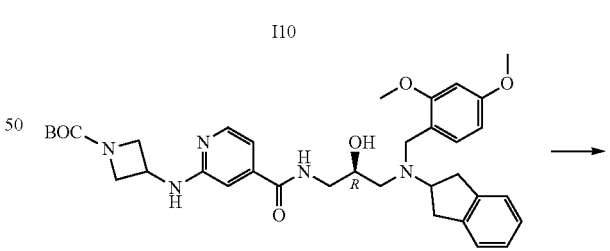

A74

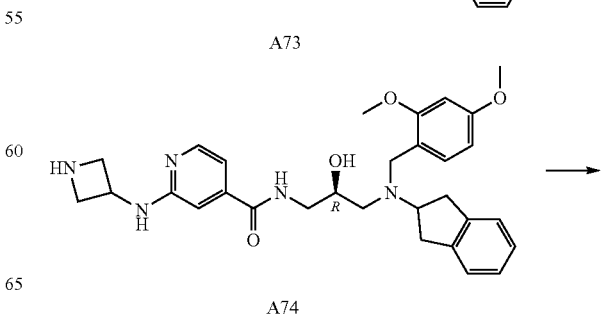

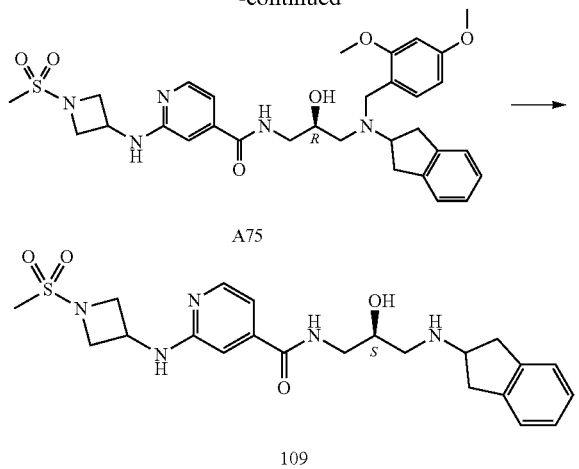

A75

109

(a) Methyl 2-((1-(tert-butoxycarbonyl)azetidin-3-yl)amino)isonicotinate A71

To a solution of methyl 2-bromoisonicotinate (3.0 g, 14.0 mmol) in dioxane (40 mL) was added tert-butyl 3-aminoazetidine-1-carboxylate (3.6 g, 21.0 mmol), cesium carbonate (9.1 g, 28.0 mmol), Xantphos (1.6 g, 2.8 mmol) and Pd$_2$(dba)$_3$ (1.3 g, 1.4 mmol) under a nitrogen atmosphere. The reaction was heated at reflux overnight, then concentrated and the residue diluted with water (40 mL). The resulting mixture was extracted with DCM (3×40 mL) and the combined organic extracts washed with saturated aqueous NaHCO$_3$ (3×30 mL) and brine (3×30 mL), dried (Na$_2$SO$_4$) and concentrated to give a crude residue which was purified by column chromatography (20% ethyl acetate/petroleum ether) to give the desired compound as a white solid (940 mg, 22%). $^1$H NMR (400 MHz, CDCl$_3$) δ 8.20-8.19 (m, 1H), 7.15-7.14 (m, 1H), 6.93 (s, 1H), 5.16-5.15 (m, 1H), 4.59-4.51 (m, 1H), 4.35-4.31 (m, 2H), 3.91 (s, 3H), 3.78-3.75 (m, 2H), 1.44 (s, 9H); LCMS RT 2.45 min; m/z 308.1 [M+H]$^+$.

(b) 2-((1-(tert-Butoxycarbonyl)azetidin-3-yl)amino)isonicotinic acid A72

To a solution of methyl 2-((1-(tert-butoxycarbonyl)azetidin-3-yl)amino)isonicotinate A71 (930 mg, 3.1 mmol) in a mixture of THF (10 mL), MeOH (5 mL) and water (4 mL) was added lithium hydroxide hydrate (1.3 g, 30.3 mmol). The resulting mixture was stirred at room temperature overnight. The mixture was concentrated under reduced pressure, then diluted with water. The pH of the aqueous solution was adjusted to 1-2 by addition of 4M aqueous HCl. Removal of the solvent provided the crude product containing lithium chloride (1.3 g). The material was carried forward without further purification. LCMS RT 1.26 min; m/z 294.1 [M+H]$^+$

(c) (R)-tert-Butyl-3-((4-((3-((2,3-dihydro-1H-inden-2-yl)(2,4-dimethoxybenzyl)amino)-2-hydroxypropyl)carbamoyl)pyridin-2-yl)amino)azetidine-1-carboxylate A73

To a suspension of 2-((1-(tert-butoxycarbonyl)azetidin-3-yl)amino)isonicotinic acid A72 (600 mg, 2.1 mmol) in DCM (10 mL) was added EDCl (786 mg, 4.1 mmol), HOBt (555 mg, 4.1 mmol) and DIEA (1.3 g, 10.3 mmol). A solution of (R)-1-amino-3-((2,3-dihydro-1H-inden-2-yl)(2,4-dimethoxybenzyl)amino)propan-2-ol I10 (875 mg, 2.5 mmol) in DCM (10 mL) was added and the resulting mixture stirred at room temperature overnight. The mixture was diluted with water (20 mL) and DCM (20 mL) and the aqueous layer extracted with DCM (3×10 mL). The combined organic extracts were washed with saturated aqueous NaHCO$_3$ (3×10 mL) and brine (3×10 mL), dried (Na$_2$SO$_4$) and concentrated. The residue obtained was purified by silica gel column chromatography (ethyl acetate: petroleum ether=2:1) to give the desired compound as an off-white solid (600 mg, 46%). LCMS RT 2.42 min; m/z 632.4 [M+H]$^+$

(d) (R)-2-(Azetidin-3-ylamino)-N-(3-((2,3-dihydro-1H-inden-2-yl)(2,4-dimethoxybenzyl)amino)-2-hydroxypropyl)isonicotinamide A74

A solution of (R)-tert-butyl 3-((4-((3-((2,3-dihydro-1H-inden-2-yl)(2,4-dimethoxybenzyl) amino)-2-hydroxypropyl)carbamoyl)pyridin-2-yl)amino)azetidine-1-carboxylate A73 (600 mg, 0.95 mmol) in a saturated solution of HCl (g) in EtOAc (30 mL) was stirred at room temperature for 2 h. The mixture was concentrated under reduced pressure and the residue obtained dissolved in DCM (30 mL) and partitioned with water. The aqueous layer neutralized by addition of saturated aqueous NaHCO$_3$ to a pH of 7-8. The organic layer was separated and the aqueous solution further extracted with DCM (3×10 mL). The combined organic extracts were washed with saturated brine (3×10 mL), dried (Na$_2$SO$_4$) and concentrated under reduced pressure to give the desired product as a yellow solid (400 mg, 79%) which was used without further purification. LCMS RT 3.13 min; m/z 532.3 [M+H]$^+$

(e) (R)—N-(3-((2,3-Dihydro-1H-inden-2-yl)(2,4-dimethoxybenzyl)amino)-2-hydroxypropyl)-2-((1-(methylsulfonyl)azetidin-3-yl)amino)isonicotinamide A75

To a solution of (R)-2-(azetidin-3-ylamino)-N-(3-((2,3-dihydro-1H-inden-2-yl)(2,4-dimethoxybenzyl)amino)-2-hydroxypropyl)isonicotinamide A74 (150 mg, 0.28 mmol) in DCM (5 mL) was added triethylamine (85 mg, 0.84 mmol). A solution of methanesulfonyl chloride (33 mg, 0.28 mmol) in DCM (1 mL) was added dropwise into the mixture and the reaction stirred at room temperature for 2 h. Water (15 mL) and DCM (10 mL) were added to the mixture and the aqueous layer extracted with DCM (3×5 mL). The combined organic extracts were washed with brine (3×10 mL), dried (Na$_2$SO$_4$) and concentrated. The residue was purified by preparative TLC (5% methanol in dichloromethane) to give the desired compound as a yellow solid (70 mg, 41%). LCMS RT 2.01 min; m/z 610.3 [M+H]$^+$

(f) (S)—N-(3-((2,3-Dihydro-1H-inden-2-yl)amino)-2-hydroxypropyl)-2-((1-(methylsulfonyl)azetidin-3-yl)amino)isonicotinamide bis 2,2,2-trifluoroacetic acid salt 109

A solution of (R)—N-(3-((2,3-dihydro-1H-inden-2-yl)(2,4-dimethoxybenzyl)amino)-2-hydroxypropyl)-2-((1-(methylsulfonyl)azetidin-3-yl)amino)isonicotinamide A75 (60 mg, 0.1 mmol) in trifluoroacetic acid (2 mL) was heated at reflux overnight. The mixture was concentrated under reduced pressure and the residue dissolved in DCM (10 mL) and partitioned with saturated aqueous NaHCO$_3$ (10 mL).

The aqueous layer was further extracted with DCM (3×5 mL) and the aqueous layer was concentrated under reduced pressure to give a crude residue. The residue was suspended in methanol/dichloromethane (1/20) (40 mL) and the salts removed by filtration. The organic solvent was removed to give the crude product which was purified by preparative HPLC to give the bis-TFA salt of the desired compound (23 mg, 51%) as an off-white solid. $^1$H NMR (400 MHz, MeOH-$d_4$) δ 8.20-8.18 (m, 1H), 7.40 (m, 1H), 7.27-7.20 (m, 5H), 4.87-4.81 (m, 1H), 4.68-4.63 (m, 1H), 4.58-4.52 (m, 1H), 4.15-4.08 (m, 2H), 3.56-3.52 (m, 1H), 3.48-3.36 (m, 5H), 3.28-3.24 (m, 1H), 3.19-3.11 (m, 2H), 3.06-3.01 (m, 1H), 2.97 (s, 3H); LCMS RT 0.26 min; m/z 460.2 [M+H]$^+$ (freebase)

Example 49: (S)-2-((1-Acetylazetidin-3-yl)amino)-N-(3-((2,3-dihydro-1H-inden-2-yl)amino)-2-hydroxypropyl)isonicotinamide bis 2,2,2-trifluoroacetic acid salt 110

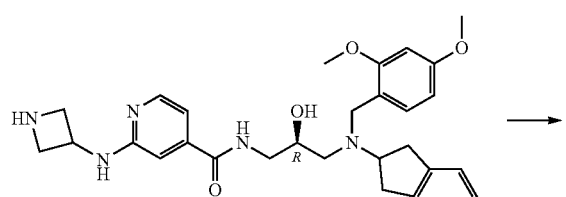

A74

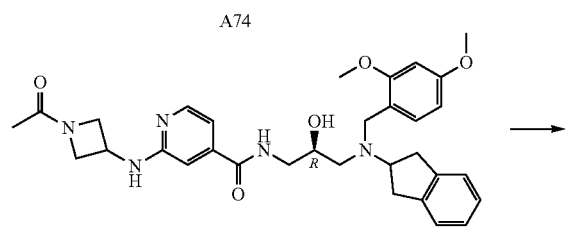

A76

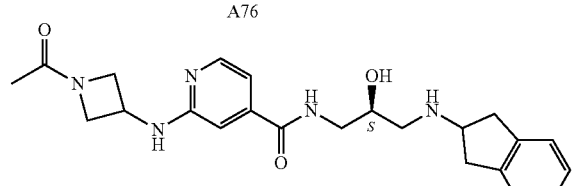

110

(a) (R)-2-((1-acetylazetidin-3-yl)amino)-N-(3-((2,3-dihydro-1H-inden-2-yl)(2,4-dimethoxybenzyl)amino)-2-hydroxypropyl)isonicotinamide A76

To a solution of (R)-2-(azetidin-3-ylamino)-N-(3-((2,3-dihydro-1H-inden-2-yl)(2,4-dimethoxybenzyl)amino)-2-hydroxypropyl)isonicotinamide A74 (220 mg, 0.41 mmol) in DCM (5 mL) was added triethylamine (212 mg, 2.10 mmol) followed by a solution of acetic anhydride (42 mg, 0.41 mmol) in DCM (1 mL) dropwise. The resulting mixture was stirred at room temperature for 2 h. The mixture was concentrated and the residue dissolved in DCM (20 mL) and partitioned with water (15 mL). The aqueous layer was extracted with DCM (3×10 mL) and the combined organic extracts washed with brine (3×10 mL), dried (Na$_2$SO$_4$) and concentrated. The residue obtained was purified by preparative TLC (5% methanol in dichloromethane) to give the desired compound as a white solid (150 mg, 64%). LCMS RT 2.04 min; m/z 574.3 [M+H]$^+$.

(b) (S)-2-((1-Acetylazetidin-3-yl)amino)-N-(3-((2,3-dihydro-1H-inden-2-yl)amino)-2-hydroxypropyl)isonicotinamide bis 2,2,2-trifluoroacetic acid salt 110

A solution of (R)-2-((1-acetylazetidin-3-yl)amino)-N-(3-((2,3-dihydro-1H-inden-2-yl)(2,4-dimethoxybenzyl)amino)-2-hydroxypropyl)isonicotinamide A76 (130 mg, 0.23 mmol) in trifluoroacetic acid (4 mL) was heated at reflux overnight. The mixture was concentrated under reduced pressure and the residue obtained dissolved in DCM (10 mL) and partitioned with saturated aqueous NaHCO$_3$ (10 mL). The aqueous layer was washed with DCM (3×5 mL) then concentrated to give a crude residue. The residue obtained was suspended in a mixture of methanol/dichloromethane (1/20) (40 mL) and the inorganic salts removed by filtration. The filtrate was concentrated and the residue was purified by preparative HPLC to give the bis-TFA salt of the desired compound (40 mg, 41%) as an off-white solid: $^1$H NMR (400 MHz, MeOD) δ 8.08-8.06 (m, 1H), 7.28-7.20 (m, 5H), 7.16-7.14 (m, 1H), 4.66-4.60 (m, 2H), 4.42-4.38 (m, 1H), 4.16-4.10 (m, 3H), 3.93-3.90 (m, 1H), 3.57-3.53 (m, 1H), 3.48-3.39 (m, 3H), 3.28-3.24 (m, 1H), 3.18-3.11 (m, 2H), 3.07-3.01 (m, 1H), 1.90 (s, 3H); LCMS: RT 2.37 min; m/z 424.3 [M+H]$^+$.

Example 50: (S)—N-(3-((2,3-Dihydro-1H-inden-2-yl)amino)-2-hydroxypropyl)-N-methyl-4-(morpholine-4-carbonyl)benzamide 111

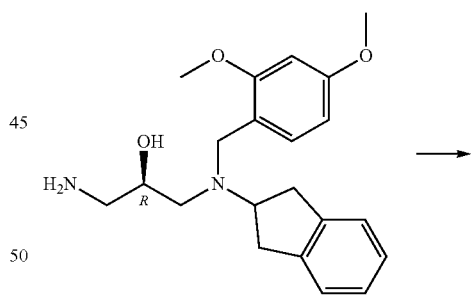

I10

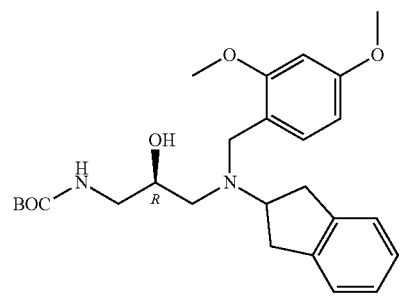

A77

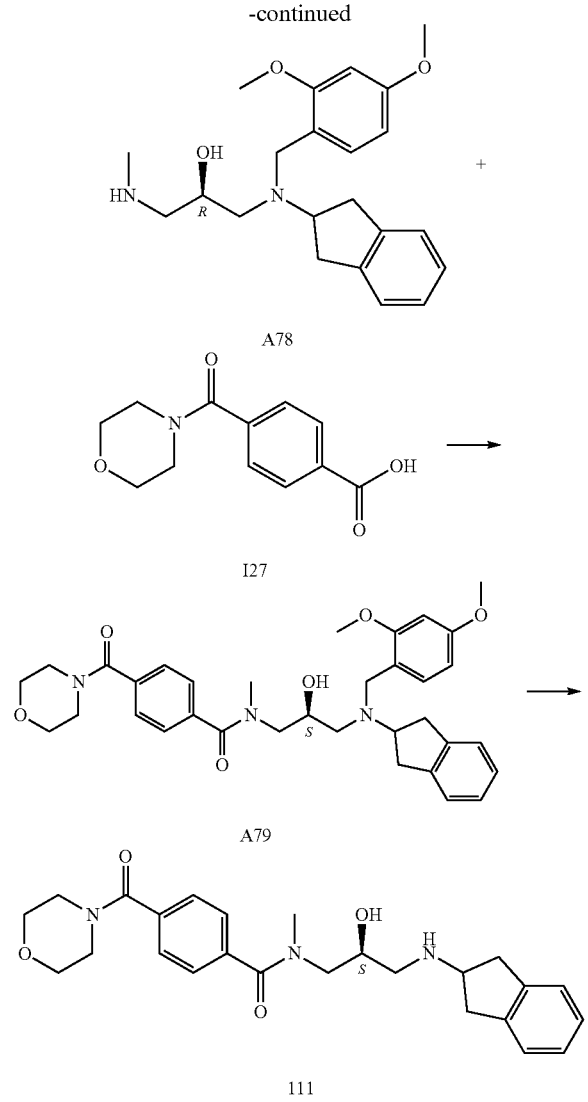

bamate A77 (670 mg, 1.47 mmol) in dry THF (10 mL) was added lithium aluminum hydride (334.3 mg, 8.82 mmol). The mixture was heated at reflux for 10 h. To the mixture was added a solution of NaOH (1.05 g, 26.4 mmol) in water (1 mL) and the precipitate that formed removed by filtration. The filter cake was rinsed with THF (200 mL×3) and the filtrate combined, dried ($Na_2SO_4$) and concentrated to give the crude product which was purified by column chromatography (Petroleum ether:ethyl acetate=1:1 to dichloromethane:methanol=20:1) to give the desired product (230 mg, 42%) as yellow oil. LCMS: RT 0.37 min; m/z 371.3 $[M+H]^+$ (c) (S)—N-(3-((2,3-Dihydro-1H-inden-2-yl)(2,4-dimethoxybenzyl)amino)-2-hydroxypropyl)-N-methyl-4-(morpholine-4-carbonyl)benzamide A79

To a solution of I27 (127.0 mg, 0.54 mmol) and (R)-1-((2,3-dihydro-1H-inden-2-yl)(2,4-dimethoxybenzyl) amino)-3-(methylamino)propan-2-ol A78 (200 mg, 0.54 mmol) in DCM (910 mL) was added DIPEA (279.0 mg, 2.16 mmol), HOBt (114.8 mg, 0.75 mmol), and EDCl (143.0 mg, 0.75 mmol). The resulting mixture was stirred at room temperature overnight. Water was added to the reaction mixture and the mixture extracted with DCM. The combined organic layers were washed with brine, dried ($Na_2SO_4$) and concentrated to give the crude product which was purified by column chromatography (DCM:MeOH=50:1) to give the desired product (170 mg, 53%) as yellow oil. LCMS: RT 2.10 min, m/z 588.3 $[M+H]^+$ (d) (S)—N-(3-((2,3-Dihydro-1H-inden-2-yl)amino)-2-hydroxypropyl)-N-methyl-4-(morpholine-4-carbonyl)benzamide 111

A mixture of (S)—N-(3-((2,3-dihydro-1H-inden-2-yl)(2, 4-dimethoxybenzyl)amino)-2-hydroxypropyl)-N-methyl-4-(morpholine-4-carbonyl)benzamide A79 (170 mg, 0.29 mmol) in TFA (5 mL) was stirred at 70° C. for 6 h. The solvent was removed and the residue suspended in water. The pH was adjusted to 8 by addition of saturated aqueous $NaHCO_3$ solution. The aqueous layer was extracted with DCM (2×20 mL) and the combined organic layers washed with water (20 mL) and brine (20 mL), dried ($Na_2SO_4$) and concentrated. The residue obtained was purified by preparative TLC (10% methanol in DCM) to give the desired compound as a white solid (40 mg, 30%): $^1$H NMR (400 MHz, Methanol-$d_4$) δ 7.57-7.55 (m, 4H), 7.26-7.21 (m, 4H), 4.27 (m, 1H), 4.08-4.04 (m, 1H), 3.76-3.76 (m, 5H), 3.64-3.57 (m, 2H), 3.58-3.56 (m, 1H) 3.55-3.35 (m, 4H), 3.22-3.05 (m, 5H) 3.00-2.86 (m, 2H), LCMS: RT 0.49 min, m/z 438.2 $[M+H]^+$ Example 51: Alternative synthesis of 4-(3-Oxa-8-azabicyclo[3.2.1]octane-8-carbonyl)-N—((S)-3-((2, 3-dihydro-1H-inden-2-yl)amino)-2-hydroxypropyl)-2-ethoxybenzamide 77

(a) (R)-Tert-butyl (3-((2,3-dihydro-1H-inden-2-yl) (2,4-dimethoxybenzyl)amino)-2-hydroxypropyl) carbamate A77

To a solution of (R)-1-amino-3-((2,3-dihydro-1H-inden-2-yl)(2,4-dimethoxybenzyl) amino)propan-2-ol I10 (500 mg, 1.4 mmol) in dichloromethane (15 mL) was added triethylamine (284.0 mg, 2.8 mmol) and $(Boc)_2O$ (305.0 mg, 1.4 mmol). The resulting mixture was stirred at room temperature overnight. Water was added to the solution and the mixture was extracted with dichloromethane (20 mL×3). The organic layer was dried ($Na_2SO_4$) and concentrated to give the crude product which was purified by column chromatography (Petroleum ether: ethyl acetate=3:1) to give the desired product (380 mg, 59%) as yellow oil. LCMS: RT 2.21 min; m/z 457.3 $[M+H]^+$ (b) (R)-1-((2,3-Dihydro-1H-inden-2-yl)(2,4-dimethoxybenzyl)amino)-3-(methylamino)propan-2-ol A78

To a solution of (R)-tert-butyl (3-((2,3-dihydro-1H-inden-2-yl)(2,4-dimethoxybenzyl)amino)-2-hydroxypropyl)car-

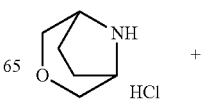

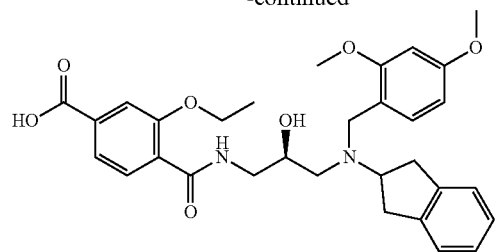

I25

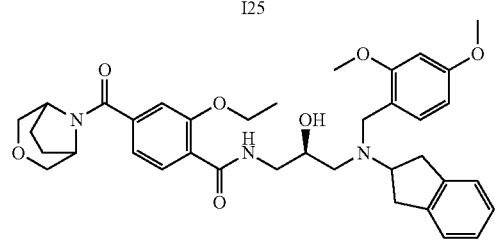

A5

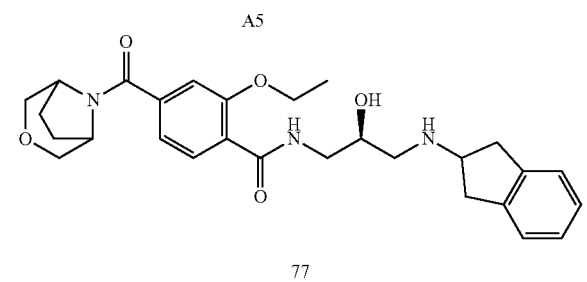

77

(a) 4-(3-Oxa-8-azabicyclo[3.2.1]octane-8-carbonyl)-N—((R)-3-((2,3-dihydro-1H-inden-2-yl)(2,4-dimethoxybenzyl)amino)-2-hydroxypropyl)-2-ethoxybenzamide A5

To a solution of (R)-4-((3-((2,3-dihydro-1H-inden-2-yl)(2,4-dimethoxybenzyl)amino)-2-hydroxypropyl)carbamoyl)-3-ethoxybenzoic acid I25 (5.2 g, 9.48 mmol) and 3-oxa-8-azabicyclo[3.2.1]octane hydrochloride (1.42 g, 9.48 mmol) in DCM (20 mL) was added DIPEA (4.8 g, 37.9 mmol), HOBt (0.29 g, 1.9 mmol), and EDCl (3.6 g, 19.0 mmol). The resulting mixture was stirred at room temperature overnight. Water (20 mL) was added to the reaction mixture and the aqueous extracted with DCM (20 mL×3). The combined organic layers were washed with brine, dried (Na$_2$SO$_4$) and concentrated to give the crude product which was purified by column chromatography (DCM:MeOH=100:1) to give the desired product (5.8 g, 95%) as yellow oil. LCMS: RT 2.22 min, m/z 644.3 [M+H]$^+$ (b) Alternate synthesis of 4-(3-Oxa-8-azabicyclo [3.2.1]octane-8-carbonyl)-N—((S)-3-((2,3-dihydro-1H-inden-2-yl)amino)-2-hydroxypropyl)-2-ethoxybenzamide 77

A solution of 4-(3-oxa-8-azabicyclo[3.2.1]octane-8-carbonyl)-N—((R)-3-((2,3-dihydro-1H-inden-2-yl)(2,4-dimethoxybenzyl)amino)-2-hydroxypropyl)-2-ethoxybenzamide A5 (5.8 g, 90.0 mmol) in trifluoroacetic acid (30 mL) was stirred at 70° C. for 4 h. The mixture was concentrated to give the crude product which was suspended in saturated aqueous NaHCO$_3$ (100 mL). The resulting mixture was extracted with DCM (×3) and the organic layers were combined, dried (Na$_2$SO$_4$) and concentrated to give a crude residue which was purified by column chromatography (DCM:MeOH=80:1→20:1) to give the desired product (2.13 g, 48%) as a white solid. LCMS: RT 1.87 min, m/z 494.3 [M+H]$^+$. $^1$H NMR (400 MHz, Methanol-d4) δ 8.03-8.01 (m, 1H), 7.24 (brs, 1H), 7.18-7.15 (m, 3H), 7.13-7.09 (m, 2H), 4.64 (s, 1H), 4.30-4.25 (m, 2H), 3.97-3.92 (m, 2H), 3.84-3.71 (m, 3H), 3.67-3.57 (m, 3H), 3.49-3.44 (m, 1H), 3.23-3.16 (m, 2H), 2.85-2.71 (m, 4H), 2.06-2.00 (m, 4H), 1.54-1.51 (m, 3H).

Example 52: (R)—N-(3-((2,3-Dihydro-1H-inden-2-yl)(methyl)amino)-2-hydroxypropyl)-4-(morpholine-4-carbonyl)benzamide 112

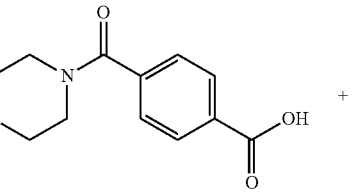

I27

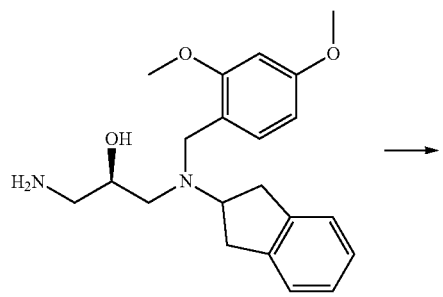

I10

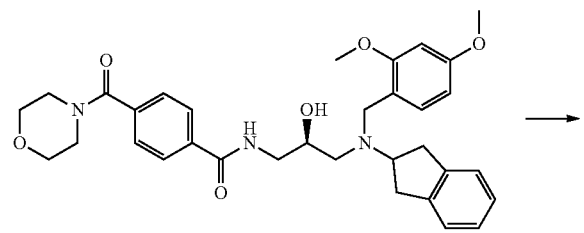

A80

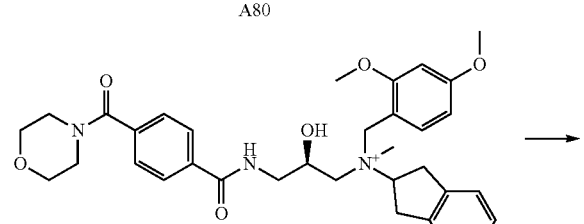

A81

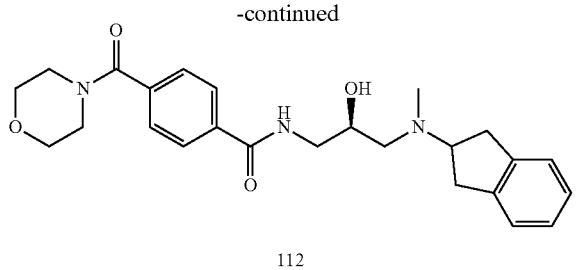

112

(a) (R)—N-(3-((2,3-dihydro-1H-inden-2-yl)(2,4-dimethoxybenzyl)amino)-2-hydroxypropyl)-4-(morpholine-4-carbonyl)benzamide A80

To a solution of 4-(morpholine-4-carbonyl)benzoic acid I27 (659 mg, 2.8 mmol) in DCM (35 mL) at 0° C. was added DIPEA (1.09 g, 8.4 mmol) and HATU (1.17 g, 3.08 mmol). The mixture was stirred at 0° C. for 30 min. To the mixture was added a solution of (R)-1-amino-3-((2,3-dihydro-1H-inden-2-yl)(2,4-dimethoxybenzyl)amino)propan-2-ol I10 (1.0 g, 2.8 mmol) in DCM (15 mL). The resulting mixture was allowed to warm to room temperature and stirred overnight. Water was added to the mixture and the solution extracted with DCM (30 mL×3). The combined organic layers were dried and concentrated to give the crude product which was purified by column chromatography (DCM:MeOH=50:1) to give the desired product (1.38 g, about 70% purity) as a yellow oil. LCMS: RT 2.00 min; m/z 574.3 [M+H]$^+$ (b) N-(2,4-dimethoxybenzyl)-N—((R)-2-hydroxy-3-(4-(morpholine-4-carbonyl)benzamido)propyl)-N-methyl-2,3-dihydro-1H-inden-2-aminium iodide A81

To a solution of (R)—N-(3-((2,3-dihydro-1H-inden-2-yl)(2,4-dimethoxybenzyl)amino)-2-hydroxypropyl)-4-(morpholine-4-carbonyl)benzamide A80 (400 mg, 0.68 mmol) in DMF (5 mL) was added K$_2$CO$_3$ (282 mg, 2.04 mmol) and iodomethane (288 mg, 2.04 mmol). The resulting mixture was stirred at 55° C. in a sealed tube overnight. Water was added to the mixture and the solution extracted with DCM (20 mL×3). The organic layer was washed with brine (20 mL×4), dried and concentrated to give the crude product which was purified by preparative TLC (DCM:MeOH=10:1) to give the desired product (90 mg, 22%) as a yellow solid. LCMS: RT2.09 min; m/z 588.1 [M+H]$^+$.

$^1$H NMR (400 MHz, DMSO-d$_6$) δ=8.80-8.71 (m, 1H), 7.96-7.85 (m, 2H), 7.54-7.45 (m, 3H), 7.31-7.12 (m, 4H), 6.66-6.61 (m, 1H), 6.56-6.47 (m, 1H). 5.93-5.92 (m, 1H), 5.81-5.75 (m, 1H), 4.84-4.80 (m, 1H), 4.67-4.45 (m, 2H), 4.30-4.26 (m, 1H), 4.25 (br s, 1H), 3.82-3.74 (m, 5H), 3.74 (s, 2H), 3.68-3.50 (m, 8H), 3.50-3.43 (m, 3H), 3.22-3.17 (m, 2H), 2.99 (s, 1H), 2.87 (s, 1H), 2.20-1.96 (m, 1H).

(c) (R)—N-(3-((2,3-dihydro-1H-inden-2-yl)(methyl)amino)-2-hydroxypropyl)-4-(morpholine-4-carbonyl)benzamide 112

A solution of N-(2,4-dimethoxybenzyl)-N—((R)-2-hydroxy-3-(4-(morpholine-4-carbonyl)benzamido) propyl)-N-methyl-2,3-dihydro-1H-inden-2-aminium iodide A81 (100 mg, 0.17 mmol) in trifluoroacetic acid was stirred at 70° C. for 4 h. The mixture was concentrated to give the crude product. Saturated aqueous NaHCO$_3$ solution was then added and the resulting mixture was extracted with DCM (×3). The organic layers were combined, dried and concentrated to give the crude product which was purified by preparative TLC (DCM:MeOH~10:1) to give the desired product (20 mg, 27%) as a yellow solid. LCMS: RT 0.46 min; m/z 438.3 [M+H]$^+$. $^1$H NMR (400 MHz, DMSO-d$_6$) δ=8.69 (s, 1H), 7.95-7.93 (m, 2H), 7.50-7.48 (m, 2H), 7.19-7.15 (m, 4H), 4.09-4.02 (m, 1H), 3.63-3.56 (m, 6H), 3.44-3.37 (m, 9H), 3.11-3.13 (m, 4H), 2.64-2.55 (m, 2H)

Example 53: 4-(3-Oxa-9-azabicyclo[3.3.1]nonane-9-carbonyl)-N—((S)-3-((2,3-dihydro-1H-inden-2-yl)amino)-2-hydroxypropyl)-2-ethoxybenzamide 135

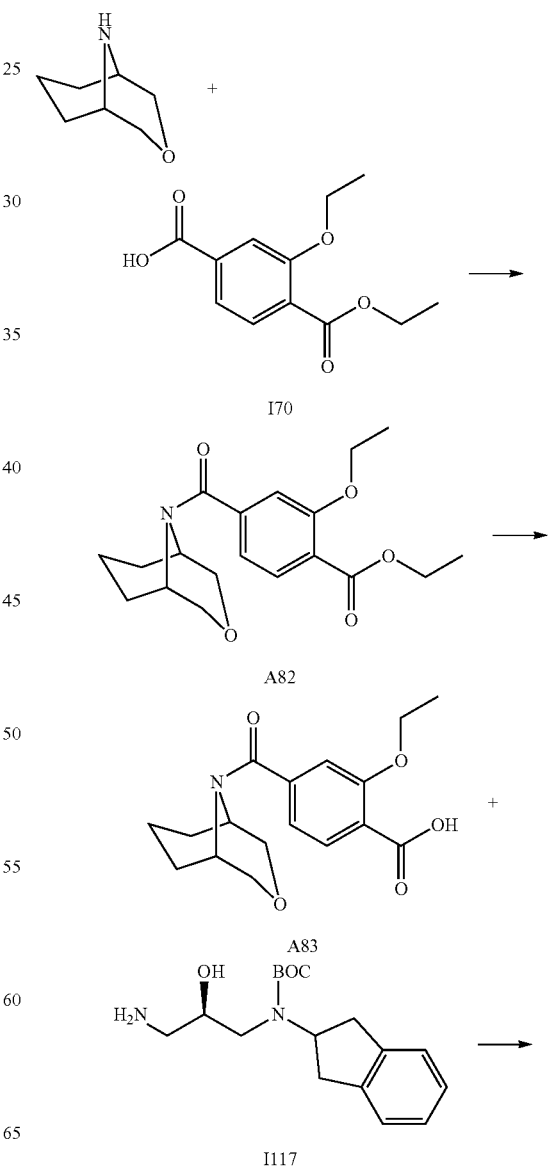

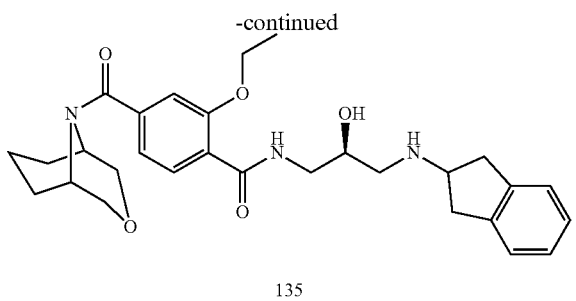

135

(a) Ethyl (3-oxa-9-azabicyclo[3.3.1]nonane-9-carbonyl)-2-ethoxybenzoate A82

To a solution of 3-ethoxy-4-(ethoxycarbonyl)benzoic acid I70 (73 mg, 0.31 mmol, 1 equiv) in DMF (2 mL) and acetonitrile (5 mL) was added DIPEA (160 µL, 0.917 mmol, 3 equiv), HATU (174 mg, 0.458 mmol, 1.5 equiv) and 3-oxa-9-azabicyclo[3.3.1]nonane hydrochloride (50 mg, 0.31 mmol, 1 equiv). The reaction was stirred overnight at room temperature. The mixture was quenched with a saturated aqueous solution of NaHCO$_3$ (5 mL) and extracted with DCM (3×5 mL). The combined organic layers were dried in vacuo and the resultant oil was purified by column chromatography (24 g SiO$_2$ cartridge, 0-65% EtOAc in petroleum benzine to give the title compound (88 mg, 83% yield) as a yellow oil. LCMS-B: RT=3.28 min, m/z=348 [M+H]$^+$.

(b) 4-(3-Oxa-9-azabicyclo[3.3.1]nonane-9-carbonyl)-2-ethoxybenzoic acid A83

To a solution of the ester A82 (88 mg, 0.25 mmol, 1 equiv) in THF:H$_2$O:MeOH (3:1:0.5 v/v, 9 mL) was added LiOH.H$_2$O (32 mg, 0.76 mmol, 3 equiv). The reaction was stirred at room temperature for 16 h before quenching by the addition of a 0.5 M aqueous solution of citric acid (10 mL) and extraction with EtOAc (3×15 mL). The combined organic layers were washed with water (30 mL), brine (30 mL), dried over MgSO$_4$ and concentrated in vacuo. The crude product mixture was purified by column chromatography (12 g SiO$_2$ cartridge, 0-100% EtOAc in petroleum benzine) to give the title compound (55 mg, 68% yield) as a colourless oil. $^1$H NMR (400 MHz, MeOD) δ 7.84 (d, J=7.8 Hz, 1H), 7.14 (d, J=1.3 Hz, 1H), 7.05 (dd, J=7.8, 1.4 Hz, 1H), 4.52 (s, 1H), 4.20 (q, J=7.0 Hz, 2H), 4.07-3.99 (m, 1H), 3.93-3.72 (m, 3H), 3.60 (s, 1H), 2.02-1.95 (m, obscured by EtOAc solvent), 1.92-1.78 (m, 2H), 1.75-1.64 (m, 1H), 1.45 (t, J=7.0 Hz, 3H), 1.40-1.27 (m, 2H). LCMS-B: RT=3.00 min, m/z=320.2 [M+H]$^+$.

(c) 4-(3-Oxa-9-azabicyclo[3.3.1]nonane-9-carbonyl)-N—((S)-3-((2,3-dihydro-1H-inden-2-yl)amino)-2-hydroxypropyl)-2-ethoxybenzamide 135

To a solution of the acid A83 (83 mg, 0.26 mmol, 1 equiv), DIPEA (136 µL, 0.780 mmol, 3 equiv) and HATU (148 mg, 0.390 mmol, 1.5 equiv) in DMF (2 mL) was added a solution of the amine I117 (80 mg, 0.26 mmol, 1 equiv) in CH$_3$CN (10 mL). The reaction was stirred at room temperature overnight, quenched with a saturated aqueous solution of NaHCO$_3$ (15 mL) and extracted with EtOAc (3×40 mL). The combined organic layers were washed with water (50 mL), brine (50 mL), dried over MgSO$_4$ and concentrated in vacuo. DCM:TFA (8 mL, 1:1 v/v) was added and the reaction stirred at room temperature overnight. The reaction mixture was concentrated in vacuo and then purified by solid-phase extraction (2×1 g SCX-2 cartridge, 3 column volumes of methanol followed by 3 column volumes of 0.2 M methanolic ammonia). The basic eluate was dried in vacuo and further purified by column chromatography (12 g SiO$_2$ cartridge, 50-100% EtOAc (modified by the addition of 1% v/v of 3.5 M methanolic ammonia) in petroleum benzine followed by 0-20% MeOH in EtOAc modified by the addition of 1% v/v of 2.0 M methanolic ammonia) to give the title compound (51 mg, 39% yield, 95% purity by $^1$H NMR) as a colourless oil. $^1$H NMR (400 MHz, MeOD) δ 8.02 (d, J=7.9 Hz, 1H), 7.23-7.15 (m, 3H), 7.13-7.03 (m, 3H), 4.52 (s, 1H), 4.27 (q, J=7.0 Hz, 2H), 4.06-3.76 (m, 5H), 3.68-3.55 (m, 3H), 3.53-3.43 (m, 1H), 3.24-3.12 (m, 2H), 2.87-2.51 (m, 5H), 2.00-1.95 (m, 2H), 1.92-1.79 (m, 2H), 1.76-1.63 (m, 1H), 1.53 (t, J=7.0 Hz, 3H). LCMS-B: RT=2.91 min, m/z=508.3 [M+H]$^+$.

Example 54: 4-((1R,5S)-3-Oxa-9-azabicyclo[3.3.1]nonane-9-carbonyl)-N—((S)-3-((2,3-dihydro-1H-inden-2-yl)amino)-2-hydroxypropyl)benzamide 136

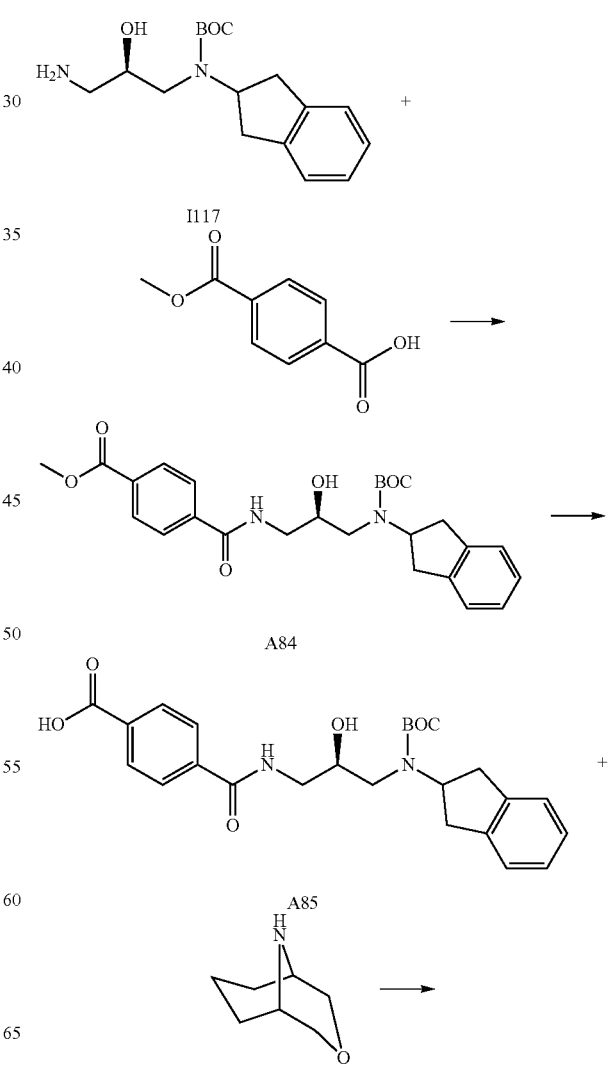

-continued

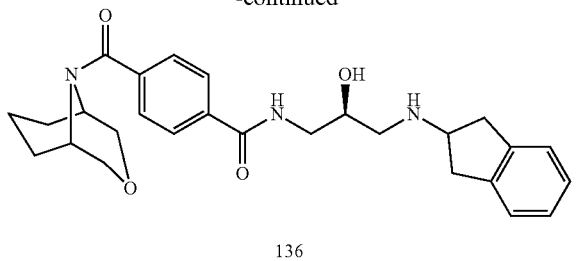

136

(a) Methyl (R)-4-((3-((tert-butoxycarbonyl)(2,3-dihydro-1H-inden-2-yl)amino)-2-hydroxypropyl)carbamoyl)benzoate A84

To a solution of 4-(methoxycarbonyl)benzoic acid (176 mg, 0.979 mmol, 1 equiv), DIPEA (512 µL, 2.94 mmol, 3 equiv) and HATU (558 mg, 1.47 mmol, 1.5 equiv) in CH$_3$CN (10 mL) was added tert-butyl (R)-(3-amino-2-hydroxypropyl)(2,3-dihydro-1H-inden-2-yl)carbamate I117 (300 mg, 0.979 mmol, 1 equiv). The reaction was stirred at room temperature overnight, quenched with a saturated aqueous solution of NaHCO$_3$ (15 mL) and extracted with EtOAc (3×40 mL). The combined organic layers were washed with water (50 mL), brine (50 mL), dried over MgSO$_4$ and concentrated in vacuo. The crude material was purified by column chromatography (12 g SiO$_2$ cartridge, 0-100% EtOAc in 40° C.-60° C. petroleum benzine) to give the title compound A84 (384 mg, 84% yield) as a pale yellow foam. $^1$H NMR (400 MHz, CDCl$_3$) δ 8.07 (d, J=8.4 Hz, 2H), 7.87 (d, J=8.4 Hz, 2H), 7.61 (s, 1H), 7.21-7.08 (m, 4H), 4.64 (p, J=8.2 Hz, 1H), 4.00-3.82 (m, 5H), 3.78-3.71 (m, 1H), 3.53-3.26 (m, 3H), 3.24-2.99 (m, 4H), 1.39 (s, 9H). LCMS-B: RT=3.43 min, m/z=467.2 [M−H]$^-$, 369.2 [M+2H−Boc]$^+$.

(b) (R)-4-((3-((tert-butoxycarbonyl)(2,3-dihydro-1H-inden-2-yl)amino)-2-hydroxypropyl)carbamoyl)benzoic acid A85

To a solution of the ester A84 (384 mg, 0.820 mmol, 1 equiv) in THF:H$_2$O:MeOH (3:1:0.5 v/v, 9 mL) was added LiOH.H$_2$O (59 mg, 2.5 mmol, 3 equiv). The reaction was stirred at room temperature overnight before the reaction was quenched by the addition of a 0.5 M aqueous solution of citric acid (10 mL). The solution was extracted with EtOAc (3×15 mL). The combined organic layers were washed with water (30 mL), brine (30 mL), dried over MgSO$_4$ and concentrated in vacuo to give the title compound A85 (358 mg, 96% yield) as a white foam. LCMS-B: RT=3.27 min, m/z=355.1 [M+2H−Boc]$^+$.

(c) 4-((1R,5S)-3-oxa-9-azabicyclo[3.3.1]nonane-9-carbonyl)-N—((S)-3-((2,3-dihydro-1H-inden-2-yl)amino)-2-hydroxypropyl)benzamide 136

To a solution of (S)-4-((3-((2,3-dihydro-1H-inden-2-yl)amino)-2-hydroxypropyl)carbamoyl)benzoic acid A85 (50 mg, 0.11 mmol, 1 equiv), DIPEA (57 µL, 0.33 mmol, 3 equiv) and HATU (63 mg, 0.17 mmol, 1.5 equiv) in DMF (2 mL) was added a solution of the amine 3-oxa-9-azabicyclo[3.3.1]nonane hydrochloride (18 mg, 0.11 mmol, 1 equiv) in CH$_3$CN (10 mL). The reaction was stirred at room temperature overnight, quenched with a 1.0 M solution of aqueous NaOH (15 mL) and extracted with EtOAc (3×40 mL). The combined organic layers were washed with water (50 mL), brine (50 mL), dried over MgSO$_4$ and concentrated in vacuo. DCM:TFA (8 mL, 1:1 v/v) was added and the reaction stirred at room temperature for 60 h. The reaction mixture was concentrated in vacuo and then purified by solid-phase extraction (2×1 g SCX-2 cartridge, 3 column volumes of methanol followed by 3 column volumes of 0.2 M methanolic ammonia). The basic eluate was dried in vacuo and further purified by column chromatography (12 g SiO$_2$ cartridge, 50-100% EtOAc (modified by the addition of 1% v/v of 3.5 M methanolic ammonia) in petroleum benzine followed by 0-30% MeOH in EtOAc modified by the addition of 1% v/v of 3.5 M methanolic ammonia) to give the title compound (34 mg, 67% yield) as a glassy solid. $^1$H NMR (400 MHz, MeOD) δ 7.92 (d, J=8.3 Hz, 2H), 7.54 (d, J=8.3 Hz, 2H), 7.22-7.15 (m, 2H), 7.15-7.06 (m, 2H), 4.54 (s, 1H), 4.16-3.76 (m, 5H), 3.67 (p, J=7.0 Hz, 1H), 3.61-3.55 (m, 1H), 3.53-3.45 (m, 1H), 3.27-3.16 (m, 2H), 2.90-2.79 (m, 3H), 2.73 (dd, J=12.2, 8.1 Hz, 1H), 2.69-2.51 (m, 1H), 2.08-1.76 (m, 5H), 1.74-1.62 (m, 1H). LCMS-B: RT=2.83 min, m/z=464.2 [M+H]$^+$. Purity ~95% by $^1$H-NMR.

Example 55

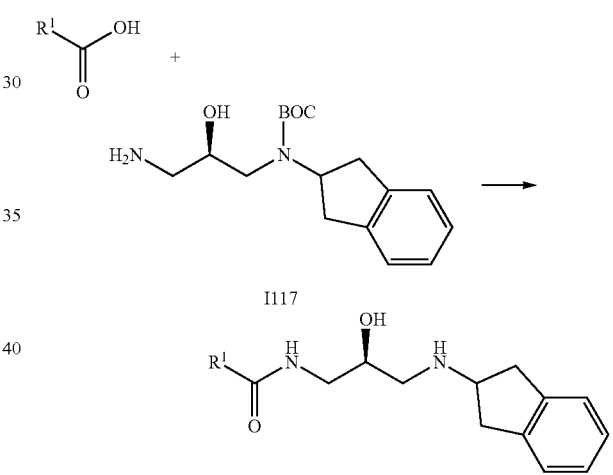

To a solution of the acid (0.17 mmol, 1 equiv), DIPEA (89 µL, 0.51 mmol, 3 equiv) and HATU (98 mg, 0.26 mmol, 1.5 equiv) was added a solution of tert-butyl (R)-(3-amino-2-hydroxypropyl)(2,3-dihydro-1H-inden-2-yl)carbamate I117 (52 mg, 0.17 mmol, 1 equiv) in DMF (2 mL). The reaction was stood at room temperature for 16 hours, quenched with a saturated aqueous solution of NaHCO$_3$ (5 mL) and extracted with DCM (×3) utilizing a phase separation cartridge. The organic filtrates were reduced under a stream of air, DCM:TFA (4 mL, 1:1 v/v) was added and the reaction stood at room temperature for the specified time. The reaction mixture was concentrated under a stream of air and then purified by solid-phase extraction (1 g SCX-2 cartridge, 3 column volumes of methanol followed by 3 column volumes of 0.2 M methanolic ammonia) to give the title compound.

| Compound | Structure & name | Analysis | Modifications to the general method |
|---|---|---|---|
| 137 | 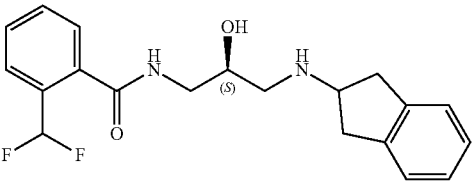<br>(S)-2-(difluoromethyl)-N-(3-((2,3-dihydro-1H-inden-2-yl)amino)-2-hydroxypropyl)benzamide | LCMS-B: RT = 2.87 min, m/z = 361.2 [M + H]$^+$. | Stir in TFA overnight |
| 138 | 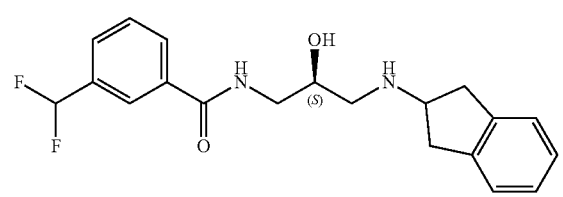<br>(S)-3-(difluoromethyl)-N-(3-((2,3-dihydro-1H-inden-2-yl)amino)-2-hydroxypropyl)benzamide | LCMS-B: RT = 2.87 min, m/z = 361.1 [M + H]$^+$. | Stir in TFA overnight |

Example 56: 3-((3-Acetyl-3-azabicyclo[3.2.1]octan-8-yl)amino)-N—((S)-3-((2,3-dihydro-1H-inden-2-yl)amino)-2-hydroxypropyl)benzamide 139

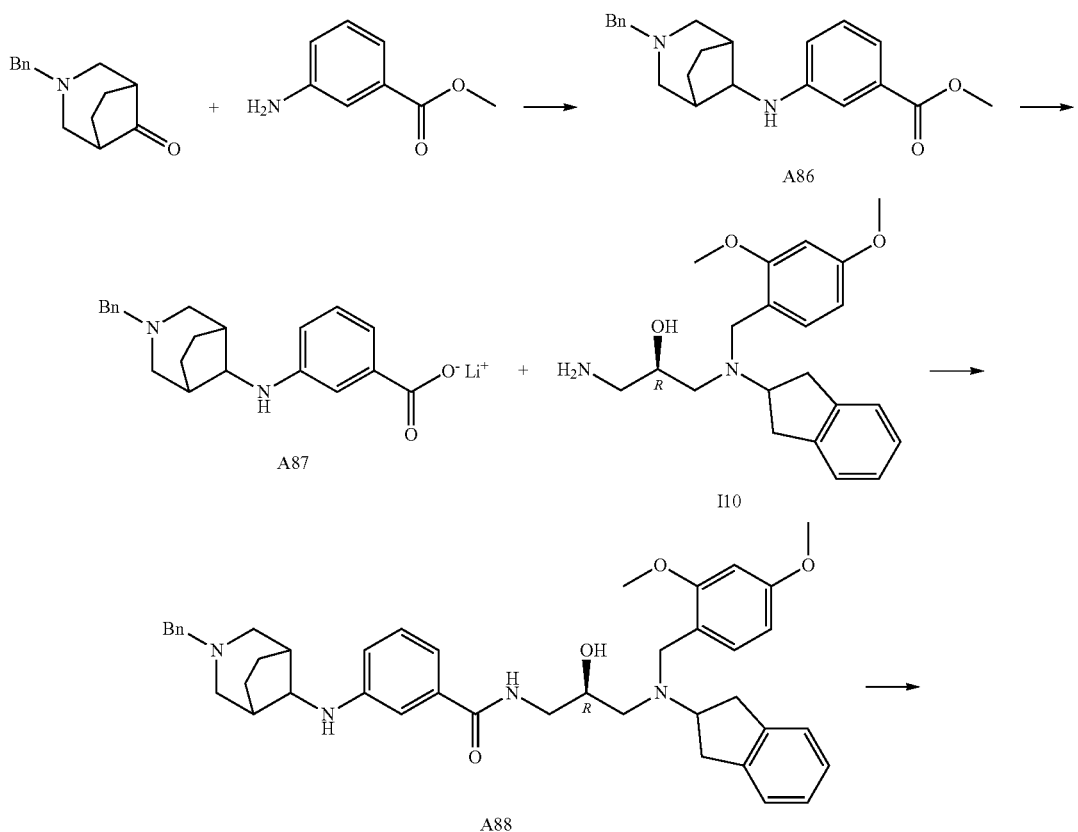

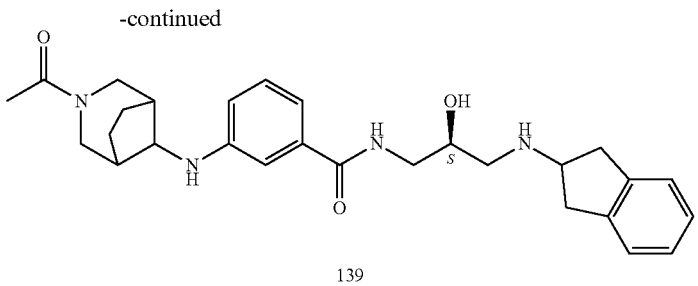

139

(a) Methyl 3-((3-benzyl-3-azabicyclo[3.2.1]octan-8-yl)amino)benzoate A86

Methyl 3-aminobenzoate (0.100 g, 0.66 mmol) and (1R,5S)-3-benzyl-3-azabicyclo[3.2.1]octan-8-one (0.214 g, 0.99 mmol) were dissolved in dry DCE (5 mL) under an atmosphere of nitrogen and acetic acid (0.076 mL, 1.32 mmol) was added followed by sodium triacetoxyborohydride (0.280 g, 1.32 mmol). The reaction was then stirred at room temperature for 20 hours. The reaction was quenched by addition of water (5 mL) and then diluted with EtOAc (50 mL) and saturated aqueous NaHCO$_3$ (50 mL). The organic phase was washed with brine (50 mL), dried (Na$_2$SO$_4$), filtered and concentrated in vacuo. The crude product was purified by column chromatography (Isolera Biotage: 12 g SiO$_2$ cartridge, 0-30% EtOAc in petroleum benzine 40-60° C.) to give the title compound (0.230 g, 99% yield) as a pale yellow gum. LCMS (LCMS-B): RT 3.406 min; m/z 351.2 [M+H]$^+$.

(b) Lithium 3-((3-benzyl-3-azabicyclo[3.2.1]octan-8-yl)amino)benzoate A87

Methyl 3-((3-benzyl-3-azabicyclo[3.2.1]octan-8-yl)amino)benzoate A86 (0.230 g, 0.656 mmol) was dissolved in THF (7 mL), MeOH (1 mL) and water (1 mL) and lithium hydroxide monohydrate (0.275 g, 6.563 mmol) was added. The reaction was then stirred at room temperature for 48 hours. The volatiles were removed in vacuo and the resulting residue diluted with EtOAc (50 mL) followed by 1M aqueous NaOH (50 mL). The layers were separated and the organic layer was concentrated in vacuo to give the title compound (0.200 g, 89% yield) as a pale yellow gum. LC-MS (LCMS-B): RT 3.298 min; m/z 337.3 [M+H]$^+$ as the free acid.

(c) 3-((3-Benzyl-3-azabicyclo[3.2.1]octan-8-yl)amino)-N—((R)-3-((2,3-dihydro-1H-inden-2-yl)(2,4-dimethoxybenzyl)amino)-2-hydroxypropyl)benzamide A88

Lithium 3-((3-benzyl-3-azabicyclo[3.2.1]octan-8-yl)amino)benzoate A87 (0.200 g, 0.584 mmol) was dissolved in DCM (5 mL) and DMF (1 mL) and DIPEA (0.278 mL, 1.593 mmol) followed by HATU (0.263 g, 0.690 mmol) were added. The mixture was then stirred at room temperature for 10 min before (R)-1-amino-3-((2,3-dihydro-1H-inden-2-yl)(2,4-dimethoxybenzyl)amino)propan-2-ol I10 (0.189 g, 0.531 mmol) in DCM (2 mL) was added. The reaction was then stirred at room temperature for 24 hours. The volatiles were removed in vacuo and the resulting residue diluted with EtOAc (50 mL) followed by saturated aqueous NaHCO$_3$ (50 mL). The layers were separated and the aqueous layer was extracted with EtOAc (50 mL), the combined organic layers were washed with brine (50 mL), dried (Na$_2$SO$_4$), filtered and concentrated in vacuo to give the crude product. Purification by column chromatography (Isolera Biotage, 24 g Si Cartridge, 0-100% EtOAc in petroleum benzine 40-60° C., then 0-20% MeOH in EtOAc) gave the title compound (0.194 g, 54% yield) as an off-white solid. LCMS (LCMS-B): RT 3.524 min, m/z 676.5 [M+H]$^+$

(d) 3-((3-Acetyl-3-azabicyclo[3.2.1]octan-8-yl)amino)-N—((S)-3-((2,3-dihydro-1H-inden-2-yl)amino)-2-hydroxypropyl)benzamide 139

3-(3-Benzyl-3-azabicyclo[3.2.1]octan-8-ylamino)-N—((R)-3-((2,3-dihydro-1H-inden-2-yl)(2,4-dimethoxybenzyl)amino)-2-hydroxypropyl)benzamide A88 (0.190 g, 0.282 mmol) was dissolved in EtOH (8 mL) under an atmosphere of nitrogen and 4 drops of concentrated HCl were added followed by 10% Pd/C (wet with water, 53%) (0.070 g) in EtOAc (4 mL). The atmosphere was changed to hydrogen and the flask was fitted with a hydrogen balloon (1 atm). The reaction was then stirred at room temperature for 24 hours then the atmosphere was changed to nitrogen and additional 10% Pd/C (wet with water, 53%) (0.070 g) in EtOAc (4 mL) was added. The atmosphere was again changed to hydrogen and the flask was fitted with a hydrogen balloon (1 atm). The reaction was then stirred at room temperature for 5 days. The reaction was filtered through Celite which was rinsed with EtOAc (~70 mL). A white precipitate was collected by filtration. Upon air-drying, the solid turned into a gum which was rinsed off the filter paper with methanol and the solution was concentrated in vacuo to give a brown foam. This residue was dissolved in DCM (3 mL) under an atmosphere of nitrogen and DIPEA (0.043 mL, 0.246 mmol) followed by acetic anhydride (0.008 mL, 0.082 mmol) were added. The reaction was stirred at room temperature for 24 hours, then diluted with DCM (20 mL) and washed with saturated aqueous NaHCO$_3$ (20 mL), brine (50 mL), dried (Na$_2$SO$_4$), filtered and concentrated in vacuo. To the resulting residue was added TFA (3 mL) and the reaction mixture was then heated to 70° C. and stirred for 20 hours. The volatiles were removed in vacuo and the resulting residue diluted with EtOAc (50 mL) followed by 2 M aqueous NaOH (50 mL). The layers were separated and the aqueous layer was extracted with EtOAc (50 mL), the combined organic layers were washed with brine (50 mL), dried (Na$_2$SO$_4$), filtered and concentrated in vacuo. Purification by column chromatography (Isolera Biotage, 4 g SiO$_2$ Cartridge, 0-100% EtOAc in petroleum benzine 40-60° C., then 0-66% MeOH (containing 1% 2M NH$_3$ v/v) in EtOAc) gave the title compound (0.006 g, 21% yield) as a brown gum. LC-MS (LCMS-B): RT 3.289 min, m/z 477.3 [M+H]$^+$

Example 57: (S)—N-(3-((2,3-Dihydro-1H-inden-2-yl)amino)-2-hydroxypropyl)-3-(methylsulfonamido)benzamide 140

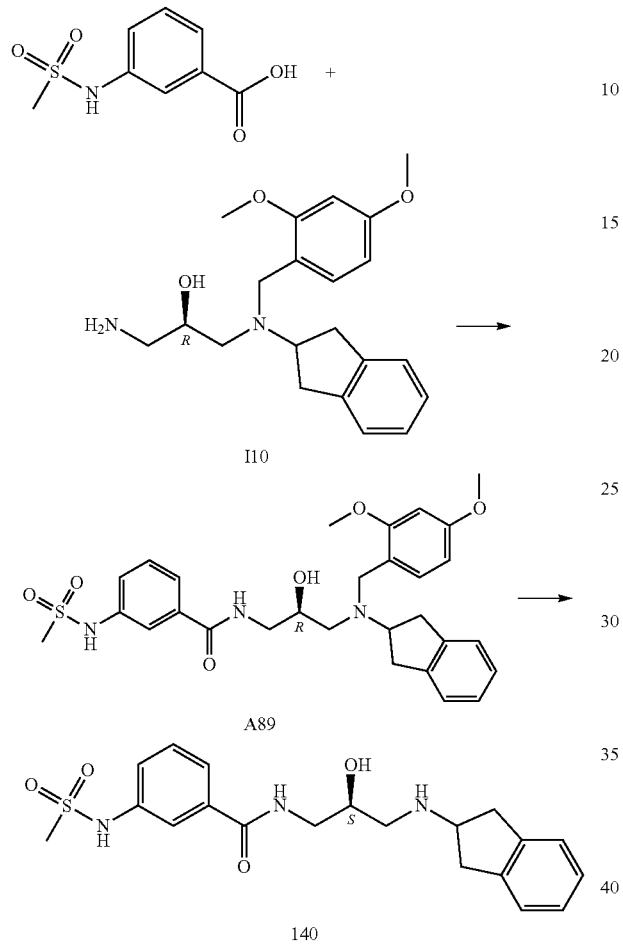

(a) (R)—N-(3-((2,3-Dihydro-1H-inden-2-yl)(2,4-dimethoxybenzyl)amino)-2-hydroxypropyl)-3-(methylsulfonamido)benzamide A89

3-(Methylsulfonamido)benzoic acid (0.109 g, 0.505 mmol) was dissolved in DCM (5 mL) and DIPEA (0.220 mL, 1.262 mmol) followed by HATU (0.208 g, 0.547 mmol) were added. The mixture was then stirred at room temperature for 10 min before (R)-1-amino-3-((2,3-dihydro-1H-inden-2-yl)(2,4-dimethoxybenzyl)amino)propan-2-ol I10 (0.150 g, 0.421 mmol) in DCM (2 mL) was added. The reaction was stirred at room temperature for 20 hours, then diluted with DCM (50 mL) and washed with saturated aqueous NaHCO₃ solution (50 mL), brine (50 mL), dried (Na₂SO₄), filtered and concentrated in vacuo to give the crude product. Purification by column chromatography (Isolera Biotage, 12 g SiO₂ Cartridge, 0-100% EtOAc in petroleum benzine 40-60° C., then 0-35% MeOH in EtOAc) gave the title compound (0.092 g, 39% yield) as a pale yellow solid. LCMS (LCMS-A): RT 4.849 min, m/z 554.3 [M+H]⁺

(b) (S)—N-(3-((2,3-Dihydro-1H-inden-2-yl)amino)-2-hydroxypropyl)-3-(methylsulfonamido)benzamide 140

To (R)—N-(3-((2,3-dihydro-1H-inden-2-yl)(2,4-dimethoxybenzyl)amino)-2-hydroxypropyl)-3-(methylsulfonamido)benzamide A89 (0.090 g, 0.163 mmol) was added TFA (3 mL) and the reaction mixture was heated to 70° C. and stirred at this temperature for 45 hours. The volatiles were partly removed in vacuo, methanol (10 mL) was added and the solution was loaded onto a SCX cartridge (2 g), the cartridge was washed with methanol (5 column volumes), then eluted with 2 M ammonia in methanol (3 column volumes). The eluate was then concentrated in vacuo to give the title compound (0.057 g, 88% yield) as a beige gum. LCMS (LCMS-B): RT 3.217 min, m/z 404.1 [M+H]⁺.

Example 58: 4-(3-oxa-8-azabicyclo[3.2.1]octane-8-carbonyl)-N—((S)-3-((2,3-dihydro-1H-inden-2-yl)amino)-2-hydroxypropyl)-2-ethoxy-5-fluorobenzamide 141

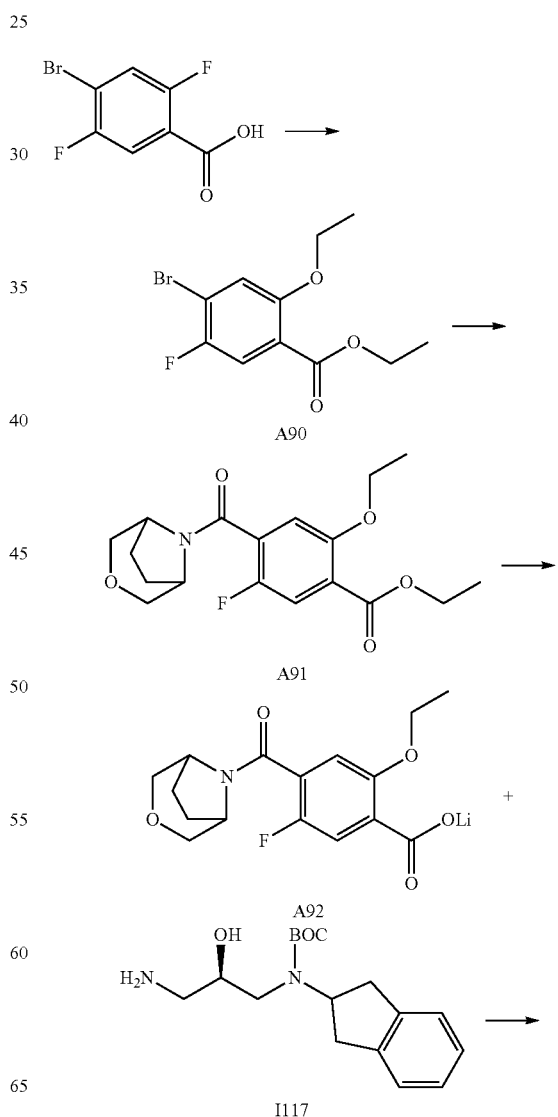

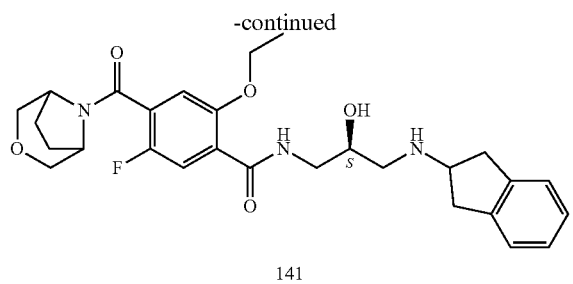

141

(a) Ethyl 4-bromo-2-ethoxy-5-fluorobenzoate A90

4-Bromo-2,5-difluorobenzoic acid (1.00 g, 4.22 mmol) was suspended in DCM (20 mL) and cooled to 0° C. Oxalyl chloride (0.543 mL, 6.33 mmol) and DMF (1 drop) were added and the mixture stirred at room temperature. After one hour the mixture was concentrated in vacuo, the residue dissolved in DCM (10 ml) and cooled to 0° C. Absolute ethanol (10 mL) was added and the mixture stirred at room temperature. After 15 minutes the mixture was concentrated in vacuo and the residue taken up in absolute ethanol. Sodium metal (146 mg, 6.33 mmol) was dissolved in absolute ethanol (30 mL) and the solution added to the solution of the ester. After two hours a thick precipitate had formed. The mixture was diluted with dry THF (50 mL) and the stir bar replaced with a larger stir bar. After 19 hours the mixture was concentrated in vacuo, the residue slurried in ethyl acetate (75 mL) and filtered. The filtrate was concentrated in vacuo and purified by chromatography (12 g silica cartridge, 0-10% ethyl acetate/petroleum benzine) to give ethyl 4-bromo-2-ethoxy-5-fluorobenzoate A90 as a white solid (216 mg, 18% yield). LCMS-B: RT 3.53 min; m/z 245.0 [M-OEt]$^+$ for $^{79}$Br; $^1$H NMR (400 MHz, CDCl$_3$) δ 7.57 (d, J=8.6 Hz, 1H), 7.13 (d, J=5.5 Hz, 1H), 4.35 (q, J=7.2 Hz, 2H), 4.07 (q, J=7.0 Hz, 2H), 1.46 (t, J=7.0 Hz, 3H), 1.37 (t, J=7.1 Hz, 3H).

(b) Ethyl 4-(3-oxa-8-azabicyclo[3.2.1]octane-8-carbonyl)-2-ethoxy-5-fluorobenzoate A91

Palladium(II) acetate (8 mg, 5 mol %), Xantphos (21 mg, 5 mol %), sodium carbonate (232 mg, 2.19 mmol), 3-oxa-8-azabicyclo[3.2.1]octane hydrochloride salt (163 mg, 1.09 mmol) and ethyl 4-bromo-2-ethoxy-5-fluorobenzoate A90 (212 mg, 0.728 mmol) were stirred in toluene (2 mL) in a schlenk tube under nitrogen. The tube was flushed with carbon monoxide, and heated to 80° C. under carbon monoxide. After 18 hours the mixture was cooled to room temperature and diluted with ethyl acetate (20 mL). The mixture was filtered through Celite and the filtrate concentrated in vacuo. Chromatography (12 g silica cartridge, 0-60% ethyl acetate/hexanes) gave ethyl 4-(3-oxa-8-azabicyclo[3.2.1]octane-8-carbonyl)-2-ethoxy-5-fluorobenzoate A91 as a pale yellow film (41 mg, 16% yield). LCMS-B RT 3.23 min; m/z (positive ion) 352.1 [M+H]; $^1$H NMR (400 MHz, CDCl$_3$) δ 7.51 (d, J=9.2 Hz, 1H), 7.01 (d, J=5.1 Hz, 1H), 4.75 (d, J=5.8 Hz, 1H), 4.36 (q, J=7.1 Hz, 2H), 4.10 (q, J=7.0 Hz, 2H), 3.84 (d, J=11.0 Hz, 1H), 3.73-3.68 (m, 2H), 3.64 (d, J=10.9 Hz, 1H), 3.56 (dd, J=11.0, 1.6 Hz, 1H), 2.13-1.90 (m, 4H), 1.45 (t, J=7.0 Hz, 3H), 1.38 (t, J=7.1 Hz, 3H).

(c) Lithium 4-(3-oxa-8-azabicyclo[3.2.1]octane-8-carbonyl)-2-ethoxy-5-fluorobenzoate A92

A solution of ethyl 4-(3-oxa-8-azabicyclo[3.2.1]octane-8-carbonyl)-2-ethoxy-5-fluorobenzoate (41 mg, 0.12 mmol) in THF (1 mL) was stirred vigorously, and a solution of lithium hydroxide monohydrate (7.3 mg, 0.18 mmol) in water (0.5 mL) was added. After 4.5 hours the mixture was concentrated in vacuo, the residue dissolved in absolute ethanol and the mixture again concentrated in vacuo to give lithium 4-(3-oxa-8-azabicyclo[3.2.1]octane-8-carbonyl)-2-ethoxy-5-fluorobenzoate. LCMS-B: RT 2.96 min; m/z (negative ion) 322.1 [M−Li]$^-$

(d) 4-(3-Oxa-8-azabicyclo[3.2.1]octane-8-carbonyl)-N—((S)-3-((2,3-dihydro-1H-inden-2-yl)amino)-2-hydroxypropyl)-2-ethoxy-5-fluorobenzamide 141

Lithium 4-(3-oxa-8-azabicyclo[3.2.1]octane-8-carbonyl)-2-ethoxy-5-fluorobenzoate A92 (used directly from previous step, ~0.059 mmol), triethylamine (0.016 mL, 0.12 mmol), tert-butyl (R)-(3-amino-2-hydroxypropyl)(2,3-dihydro-1H-inden-2-yl)carbamate I117 (18 mg, 0.059 mmol) and HATU (34 mg, 0.18 mmol) in DMF (0.5 mL) were stood at room temperature. After 18 hours the mixture was diluted with water and DCM (1.5 mL each). The organic phase was separated with a phase separation cartridge and treated with Dowex 50WX8H$^+$-form (200-400 mesh, 100 mg). The mixture was filtered and the filtrate diluted with 4.0 M HCl in dioxane (2 mL). After three hours the mixture was diluted with methanol (2 mL) and loaded onto a 1 g SCX cartridge. The cartridge was washed with methanol (15 mL) and eluted with 2 M ammonia in methanol (10 mL). The basic eluate was concentrated to afford the title compound. LCMS: RT 2.90 min; m/z (positive ion) 512.2 [M+H]

Example 59: (S)-Methyl 3-((4-((3-((2,3-dihydro-1H-inden-2-yl)amino)-2-hydroxypropyl)carbamoyl)pyridin-2-yl)amino)azetidine-1-carboxylate bis(2,2,2-trifluoroacetate) 142

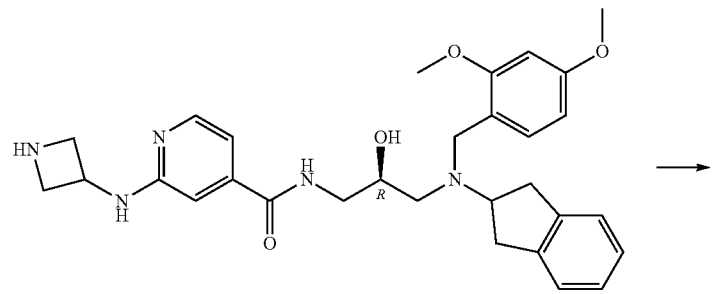

A74

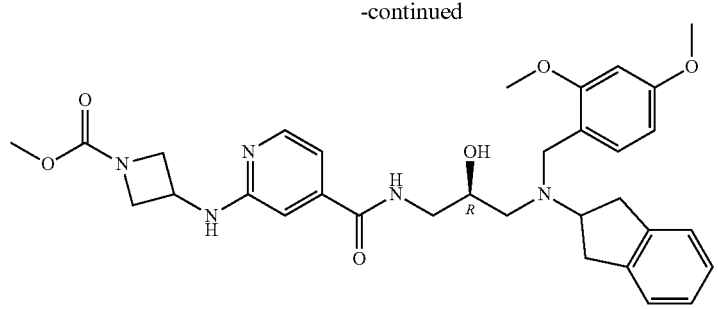

A93

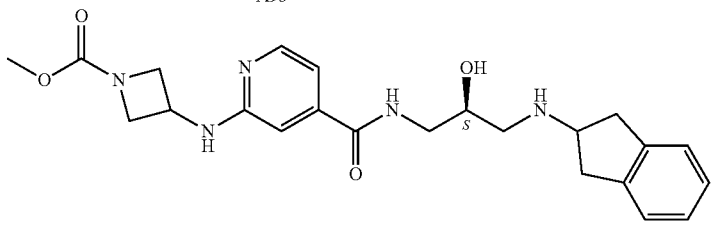

142

(a) (R)-Methyl 3-((4-((3-((2,3-dihydro-1H-inden-2-yl)(2,4-dimethoxybenzyl)amino)-2-hydroxypropyl)carbamoyl)pyridin-2-yl)amino)azetidine-1-carboxylate A93

To a solution of (R)-2-(azetidin-3-ylamino)-N-(3-((2,3-dihydro-1H-inden-2-yl)(2,4-dimethoxybenzyl)amino)-2-hydroxypropyl)isonicotinamide dihydrochloride A74 (100 mg, 0.18 mmol) in DCM (4 mL) was added triethylamine (95 mg, 0.94 mmol). A solution of methyl chloroformate (22 mg, 0.22 mmol) in DCM (1 mL) was added dropwise into the mixture. The resulting mixture was stirred at room temperature for 2 h. The mixture was concentrated under vacuum and the residue partitioned between DCM (10 mL) and water (10 mL). The aqueous layer was extracted with DCM (3×5 mL) and the combined organic extracts washed with brine (3×5 mL), dried (Na$_2$SO$_4$), filtered and concentrated. The residue was purified by preparative TLC (5% methanol in dichloromethane) to give the title compound as a white solid (53 mg, 48%). LCMS RT 2.07 min; m/z 590.3 [M+H]$^+$ (b) (S)-Methyl 3-((4-((3-((2,3-dihydro-1H-inden-2-yl)amino)-2-hydroxypropyl)carbamoyl)pyridin-2-yl)amino)azetidine-1-carboxylate bis(2,2,2-trifluoroacetate) 142

A solution of (R)-methyl 3-((4-((3-((2,3-dihydro-1H-inden-2-yl)(2,4-dimethoxybenzyl)amino)-2-hydroxypropyl)carbamoyl)pyridin-2-yl)amino)azetidine-1-carboxylate A93 (50 mg, 0.08 mmol) in trifluoroacetic acid (4 mL) was heated at reflux 6 h. The mixture was concentrated under vacuum and the residue obtained dissolved in DCM (10 mL). The reaction was quenched with saturated aqueous NaHCO$_3$ solution (15 mL). The aqueous layer was extracted with DCM (3×10 mL) and the combined organic extracts washed with saturated aqueous NaHCO$_3$ solution (3×5 mL), brine (3×5 mL), dried (Na$_2$SO$_4$), filtered and concentrated. The residue was purified by preparative HPLC to give the title compound as a yellow solid (15 mg, 40%). $^1$H NMR (400 MHz, MeOH-d$_4$) δ 8.04 (d, J=6.4 Hz, 1H), 7.33 (s, 1H), 7.27-7.19 (m, 5H), 4.66-4.60 (m, 1H), 4.45-4.40 (m, 2H), 4.14-4.08 (m, 2H), 3.98-3.95 (m, 2H), 3.68 (s, 3H), 3.57-3.53 (m, 1H), 3.49-3.38 (m, 3H), 3.29-3.25 (m, 1H), 3.19-3.11 (m, 2H), 3.07-3.02 (m, 1H). LCMS RT 2.74 min; m/z 440.2 [M+H]$^+$ for the free base.

Example 60: (S)-2-(azetidin-3-ylamino)-N-(3-((2,3-dihydro-1H-inden-2-yl)amino)-2-hydroxypropyl)isonicotinamide tris(2,2,2-trifluoroacetate) 143

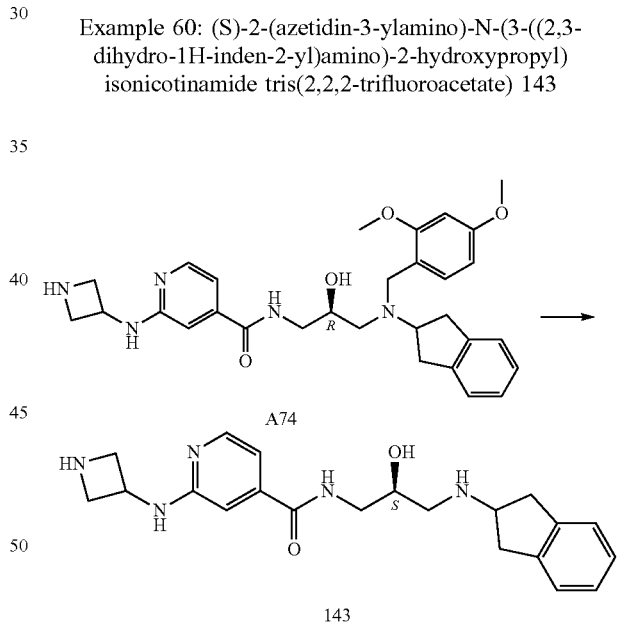

A solution of (R)-2-(azetidin-3-ylamino)-N-(3-((2,3-dihydro-1H-inden-2-yl)(2,4-dimethoxybenzyl)amino)-2-hydroxypropyl)isonicotinamide dihydrochloride A74 (70 mg, 0.13 mmol) in trifluoroacetic acid (3 mL) was heated at reflux 4 h. The mixture was concentrated under vacuum and the residue obtained dissolved in DCM (10 mL). The mixture was quenched with a saturated aqueous NaHCO$_3$ solution (10 mL). The aqueous layer was extracted with DCM (3×5 mL) and concentrated under vacuum. The residue was dissolved in a mixed solution of methanol/dichloromethane (20 mL, 1/20 v/v) and the mixture filtered. The filtrate was concentrated and the residue purified by preparative HPLC to give the title compound as an off-white solid (16 mg, 32%): ¹H NMR (400 MHz, MeOD) δ 8.25 (d, J=6.8 Hz, 1H), 7.49 (s, 1H), 7.33 (d, J=6.4 Hz, 1H), 7.27-7.20 (m, 4H), 5.02-4.96 (m, 1H), 4.79-4.74 (m, 1H), 4.68-4.63 (m, 1H), 4.15-4.08 (m, 2H), 3.57-3.53 (m, 1H), 3.49-3.35 (m, 5H), 3.29-3.25 (m, 1H), 3.19-3.11 (m, 2H), 3.07-3.02 (m, 1H); LCMS RT 0.27 min; m/z 382.2 [M+H]⁺ for the free base.

Example 61: 4-(3-Oxa-8-azabicyclo[3.2.1]octane-8-carbonyl)-N—((R)-3-((2,3-dihydro-1H-inden-2-yl)amino)-2-hydroxypropyl)-2-ethoxybenzamide hydrochloride 144

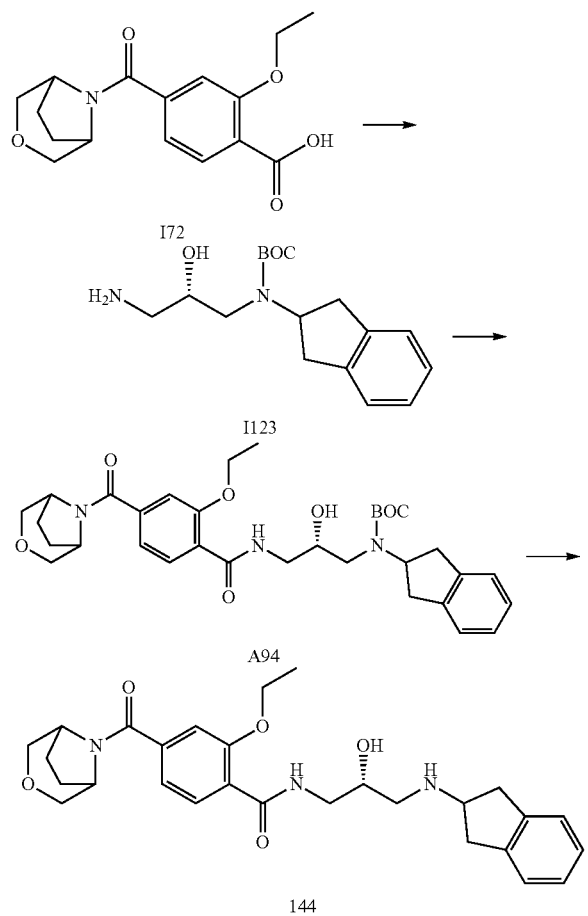

(a) tert-Butyl((R)-3-(4-(3-oxa-8-azabicyclo[3.2.1]octane-8-carbonyl)-2-ethoxybenzamido)-2-hydroxypropyl)(2,3-dihydro-1H-inden-2-yl)carbamate A94

A mixture of (S)-tert-butyl (3-amino-2-hydroxypropyl)(2,3-dihydro-1H-inden-2-yl)carbamate (1.0 g, 3.26 mmol) I123, 4-(3-oxa-8-azabicyclo[3.2.1]octane-8-carbonyl)-2-ethoxybenzoic acid I72 (1.14 g, 3.92 mmol), HOBt (0.66 g, 4.89 mmol), EDCl (0.94 g, 4.89 mmol) and triethylamine (1.32 g, 13.04 mmol) in CH₂Cl₂ (20 mL) under N₂ was stirred at room temperature overnight. The mixture was poured into water and diluted with EtOAc, the organic layer was washed with a 0.1 M aqueous HCl solution, brine, dried (Na₂SO₄), filtered, concentrated and purified by silica gel chromatography (MeOH/CH₂Cl₂=1/1, v/v) to give the title compound (1.3 g, 67%) as a white solid. LCMS: RT 3.02 min; m/z 594.4 [M+H]⁺. ¹H NMR (400 MHz, CDCl₃) δ 8.54 (br s, 1H), 8.19 (d, J=0.8 Hz, 1H), 7.16-7.07 (m, 6H), 4.72-4.68 (m, 2H), 4.23 (q, J=6.8 Hz, 2H), 3.93-3.85 (m, 3H), 3.74-3.59 (m, 4H), 3.39-3.32 (m, 3H), 3.18-3.12 (m, 2H), 3.08-2.99 (m, 2H), 2.05-1.93 (m, 4H), 1.54 (t, J=7.2 Hz, 3H), 1.41 (s, 9H).

(b) 4-(3-Oxa-8-azabicyclo[3.2.1]octane-8-carbonyl)-N—((R)-3-((2,3-dihydro-1H-inden-2-yl)amino)-2-hydroxypropyl)-2-ethoxybenzamide hydrochloride 144

To a solution of tert-butyl ((2S)-3-(4-(3-oxa-8-azabicyclo[3.2.1]octane-8-carbonyl)-2-ethoxybenzamido)-2-hydroxypropyl)(2,3-dihydro-1H-inden-2-yl)carbamate (500 mg, 0.84 mmol) in CH₂Cl₂ (5 mL) was added dropwise a solution of HCl (2.5 M, in dioxane, 5 mL) at 0° C. The mixture was stirred at room temperature overnight. The solvents were removed in vacuo and Et₂O was added, the precipitate was collected by filtration and washed with Et₂O and dried to give the title compound (435 mg, 97%) as a white solid. LCMS:RT 1.95 min, m/z 494.1 [M+H]⁺; ¹H NMR (400 MHz, DMSO-d₆) δ 9.13 (br s, 2H), 8.42 (t, J=5.6 Hz, 1H), 7.83 (d, J=8.0 Hz, 1H), 7.26-7.11 (m, 5H), 5.82 (d, J=4.2 Hz, 1H), 4.52 (br s, 1H), 4.23 (q, J=6.8 Hz, 2H), 4.05-4.02 (m, 2H), 3.86 (br s, 1H), 3.67-3.61 (m, 3H), 3.51-3.42 (m, 3H), 3.29-3.25 (m, 2H), 3.17-3.10 (m, 3H), 2.95-2.90 (m, 1H), 1.88 (br s, 4H), 1.42 (t, J=6.8 Hz, 3H).

Example 62: 6-(8-Oxa-3-azabicyclo[3.2.1]octan-3-yl)-N—((S)-3-((2,3-dihydro-1H-inden-2-yl)amino)-2-hydroxypropyl)nicotinamide 145

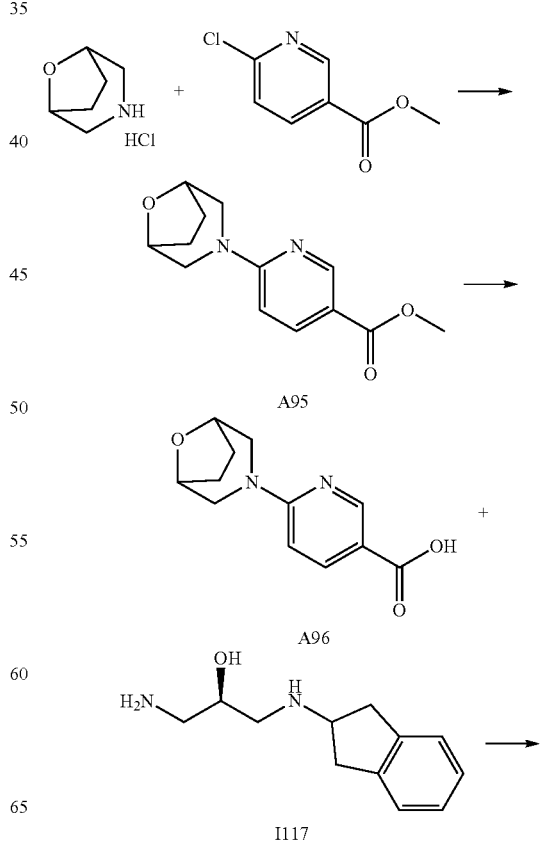

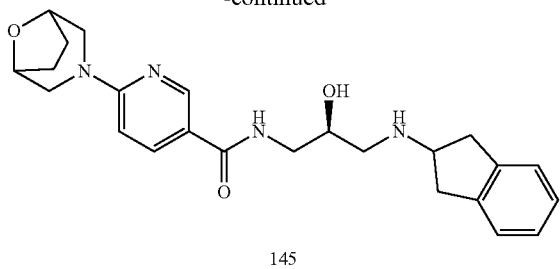

145

(a) Methyl 6-(8-oxa-3-azabicyclo[3.2.1]octan-3-yl)nicotinate A95

To a solution of methyl 6-chloronicotinate (300 mg, 1.75 mmol) in dry DMF (15 mL) was added 8-oxa-3-azabicyclo[3.2.1]octane hydrochloride (392 mg, 2.62 mmol, 1.5 equiv) and triethylamine (0.609 mL, 4.37 mmol, 2.5 equiv). The system was flushed with $N_2$ and heated at 80° C. for 20 h. The reaction was allowed to reach room temperature and was diluted with water/EtOAc. The aqueous layer was extracted with ethyl acetate (×3). The combined organic layers were washed with brine, dried over $MgSO_4$, filtered, and the solvent removed in vacuo. The crude residue was purified by column chromatography (24 g $SiO_2$ cartridge, 0-35% EtOAc in petroleum benzine 40° C.-60° C.) to give the title compound (400 mg, 92 yield) as an off-white solid. $^1$H NMR (400 MHz, $CDCl_3$) δ 8.76 (dd, J=2.3, 0.8 Hz, 1H), 8.00 (dd, J=9.0, 2.4 Hz, 1H), 6.48 (dd, J=9.1, 0.8 Hz, 1H), 4.52-4.41 (m, 2H), 3.96-3.87 (m, 2H), 3.84 (s, 3H), 3.18 (dd, J=12.6, 2.7 Hz, 2H), 1.99-1.89 (m, 2H), 1.83-1.74 (m, 2H). LCMS-B: RT 3.05 min, m/z=249.1 [M+H]$^+$.

(b) 6-(8-Oxa-3-azabicyclo[3.2.1]octan-3-yl)nicotinic acid A96

To a solution of the desired ester methyl 6-(8-oxa-3-azabicyclo[3.2.1]octan-3-yl)nicotinate A95 (400 mg, 1.61 mmol) in THF:$H_2O$:MeOH (3:1:0.5 v/v, 10 mL) was added LiOH.$H_2O$ (203 mg, 4.83 mmol, 3 equiv). The reaction was stirred at room temperature for 16 h. The reaction mixture was concentrated in vacuo. Water was added and the pH adjusted to 3 by the addition of a 0.5 M aqueous citric acid solution. The aqueous mixture was extracted with ethyl acetate (×3), washed with water, brine, dried ($Na_2SO_4$) and the solvent removed in vacuo to give the title compound (347 mg, 92% yield) as a light brown solid. $^1$H NMR (400 MHz, DMSO) δ 8.59 (d, J=2.3 Hz, 1H), 7.90 (dd, J=9.0, 2.4 Hz, 1H), 6.73 (d, J=9.0 Hz, 1H), 4.41 (dd, J=4.2, 2.1 Hz, 2H), 3.94 (d, J=12.5 Hz, 2H), 3.01 (dd, J=12.7, 2.6 Hz, 2H), 1.87-1.72 (m, 2H), 1.65 (q, J=7.1, 6.5 Hz, 2H). LCMS-A: RT 1.85 min, m/z=235.2 [M+H]$^+$.

(c) 6-(8-Oxa-3-azabicyclo[3.2.1]octan-3-yl)-N—((S)-3-((2,3-dihydro-1H-inden-2-yl)amino)-2-hydroxypropyl)nicotinamide 145

To a solution of tert-butyl (R)-(3-amino-2-hydroxypropyl)(2,3-dihydro-1H-inden-2-yl)carbamate I117 (100 mg, 0.326 mmol), DIPEA (171 µL, 0.979 mmol, 3 equiv) and HATU (186 mg, 0.490 mmol, 1.5 equiv) in DMF (2 mL) was added a solution of the 6-(8-oxa-3-azabicyclo[3.2.1]octan-3-yl)nicotinic acid A96 (76 mg, 0.33 mmol, 1 equiv) in DMF (3 mL). The reaction was stirred at room temperature overnight, quenched with a 1 M aqueous solution of NaOH (15 mL) and stirred for 4 h. The aqueous mixture was extracted with EtOAc (3×40 mL) and the combined organic layers were washed with water (50 mL), brine (50 mL), dried over $MgSO_4$ and concentrated in vacuo. DCM:TFA (8 mL, 1:1 v/v) was added and the reaction stirred at room temperature overnight. The reaction mixture was concentrated in vacuo and then purified by solid-phase extraction (5 g SCX-2 cartridge, 3 column volumes of methanol followed by 3 column volumes of 0.2 M methanolic ammonia). The basic eluate was dried in vacuo and further purified by column chromatography (12 g $SiO_2$ cartridge, 50-100% EtOAc (modified by the addition of 1% v/v of 3.5 M methanolic ammonia) in petroleum benzine followed by 0-20% MeOH in EtOAc modified by the addition of 1% v/v of 3.5 M methanolic ammonia) to give the title compound 6-(8-oxa-3-azabicyclo[3.2.1]octan-3-yl)-N—((S)-3-((2,3-dihydro-1H-inden-2-yl)amino)-2-hydroxypropyl)nicotinamide (56 mg, 41% yield) as a white solid. $^1$H NMR (400 MHz, MeOD) δ 8.60 (dd, J=2.5, 0.7 Hz, 1H), 7.95 (dd, J=9.0, 2.5 Hz, 1H), 7.25-7.16 (m, 2H), 7.16-7.06 (m, 2H), 6.74 (dd, J=9.2, 0.8 Hz, 1H), 4.51-4.42 (m, 2H), 4.01-3.90 (m, 3H), 3.73 (p, J=7.0 Hz, 1H), 3.51-3.38 (m, 2H), 3.28-3.18 (m, 2H), 3.12 (dd, J=12.7, 2.6 Hz, 2H), 2.94-2.82 (m, 3H), 2.76 (dd, J=12.3, 8.2 Hz, 1H), 2.00-1.91 (m, 2H), 1.86-1.73 (m, 2H). LCMS-B: RT 2.83 min, m/z=423.2 [M+H]$^+$.

Example 63: (S)—N-(3-((2,3-Dihydro-1H-inden-2-yl)amino)-2-hydroxypropyl)-2-ethoxy-6-morpholinonicotinamide 146

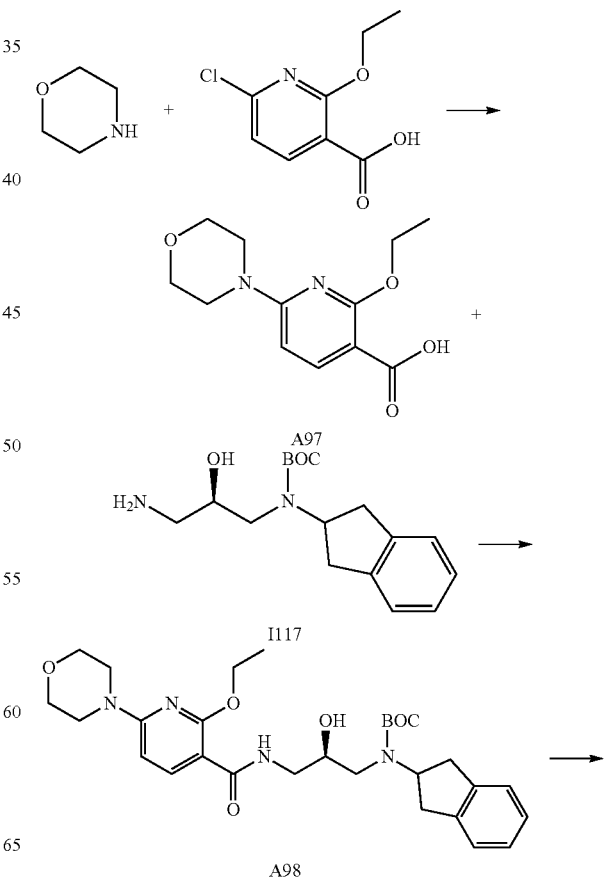

-continued

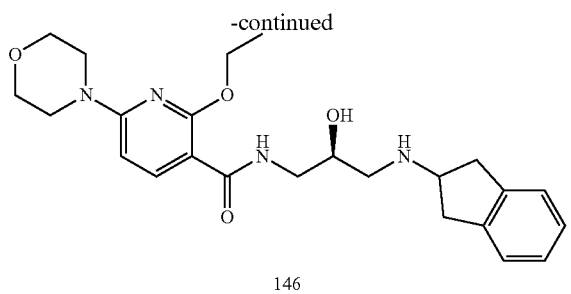

146

(a) 2-Ethoxy-6-morpholinonicotinic acid A97

6-Chloro-2-ethoxynicotinic acid (0.250 g, 1.24 mmol) was dissolved in 1,4-dioxane (2 mL) and Et₃N (0.52 mL, 3.72 mmol) and morpholine (0.16 mL, 1.86 mmol) were added and the reaction was heated in a microwave at 150° C. for 45 minutes. The solvent was evaporated and the residue was purified by chromatography (Isolera Biotage, 12 g SiO₂ cartridge, 0-100 EtOAc in petroleum benzine 40-60° C., then 0-5% MeOH in EtOAc) to give the title compound (0.174 g, 56% yield) as a pale pink solid. ¹H NMR (400 MHz, MeOD) δ 8.05 (d, J=8.7 Hz, 1H), 6.36 (d, J=8.7 Hz, 1H), 4.47 (q, J=7.1 Hz, 2H), 3.79-3.73 (m, 4H), 3.67-3.62 (m, 4H), 1.40 (t, J=7.0 Hz, 3H). LCMS-B: RT 3.098 min, m/z 253.1 [M+H]⁺

(b) tert-Butyl (R)-(2,3-dihydro-1H-inden-2-yl)(3-(2-ethoxy-6-morpholinonicotinamido)-2-hydroxypropyl)carbamate A98

2-Ethoxy-6-morpholinonicotinic acid A97 (0.050 g, 0.198 mmol) was dissolved in DMF (4 mL) and Et₃N (0.083 mL, 0.595 mmol) followed by HATU (0.113 g, 0.297 mmol) were added. The mixture was then stirred at room temperature for 10 minutes before tert-butyl (R)-(3-amino-2-hydroxypropyl)(2,3-dihydro-1H-inden-2-yl)carbamate I117 (0.061 g, 0.198 mmol) was added. The reaction was stirred at room temperature for 20 hours, then diluted with EtOAc (70 mL) and washed with saturated aqueous NaHCO₃ solution (70 mL), brine (70 mL), dried (Na₂SO₄), filtered and concentrated in vacuo to give the crude product. This was purified by column chromatography (Isolera Biotage, 12 g SiO₂ cartridge, 0-80% EtOAc in petroleum benzine 40-60° C.) to give the title compound (0.073 g, 68% yield) as a colourless gum. LCMS-B: RT 3.552 min, m/z 541.3 [M+H]⁺

(c) (S)—N-(3-((2,3-Dihydro-1H-inden-2-yl)amino)-2-hydroxypropyl)-2-ethoxy-6-morpholinonicotinamide 146 tert-Butyl (R)-(2,3-dihydro-1H-inden-2-yl)(3-(2-ethoxy-6-morpholinonicotinamido)-2-hydroxypropyl)carbamate A98 (0.073 g, 0.135 mmol) was dissolved in DCM (4 mL), TFA (0.310 mL, 4.051 mmol) was added and the reaction was stirred at room temperature for 20 hours. Volatiles were removed in vacuo and the residue was diluted with EtOAc (70 mL) and washed with 2 M aqueous NaOH solution (70 mL), brine (70 mL), dried (Na₂SO₄), filtered and concentrated in vacuo, taken up in diethyl ether and evaporated in vacuo to give the title compound (0.053 g, 89% yield) as a white foam. ¹H NMR (400 MHz, MeOD) δ 8.14 (d, 1H), 7.20-7.08 (m, 4H), 6.41 (d, J=8.7 Hz, 1H), 4.54-4.47 (m, 2H), 3.95-3.87 (m, 1H), 3.79-3.74 (m, 4H), 3.69-3.54 (m, 6H), 3.42 (dd, J=13.8, 6.4 Hz, 1H), 3.19 (ddd, J=15.7, 7.2, 5.3 Hz, 2H), 2.85-2.76 (m, 3H), 2.71 (dd, J=12.1, 8.0 Hz, 1H), 1.46 (t, J=7.1 Hz, 3H). LCMS-B: RT 2.981 min, m/z 441.2 [M+H]⁺

Assays

PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-NH₂). Full-length PRMT5 enzyme (NCBI Reference sequence NP-006100.2) was co-expressed with Hiss-MEP50 in insect cells and purified via Nickel immobilized metal affinity and gel filtration chromatography ("the enzyme").

The 6 μL assay reactions are run in Greiner brand black 384-well low volume plates. All reactions contained assay buffer (phosphate buffered saline, 0.01% (v/v) Tween-20, 0.01% (w/v) albumin from chicken egg white, 1 mM dithiothreitol, 200 nM peptide substrate, 1 μM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37° C. Reaction progress was measured using the Transcreener™ EPIGEN methyltransferase assay (Bell-Brook Labs, Madison, Wis.) as recommended by the manufacturer. To each reaction 2 μL detection mix were added, containing coupling enzymes, fluorescence polarisation tracer, and AMP antibody. Plates were incubated for 90 min before being read on a PerkinElmer EnVision™ plate reader in fluorescence polarisation mode. IC₅₀ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC₅₀ value, and D is the slope.

| Compound Number | IC₅₀ (μM) |
| --- | --- |
| 1 | 0.792 |
| 2 | 0.31 |
| 3 | 0.309 |
| 4 | 3.79 |
| 5 | 9.78 |
| 6 | 1.55 |
| 7 | 2.45 |
| 8 | 0.263 |
| 9 | 3.72 |
| 10 | 1.44 |
| 11 | 0.83 |
| 12 | 0.695 |
| 13 | 0.634 |
| 14 | 0.445 |
| 15 | 0.218 |
| 16 | 0.301 |
| 17 | 0.629 |
| 18 | 0.238 |
| 20 | 0.977 |
| 21 | 1.111 |
| 22 | 0.171 |
| 24 | 0.425 |
| 25 | 2.22 |
| 26 | 3.87 |

| Compound Number | IC$_{50}$ (µM) |
|---|---|
| 27 | 0.434 |
| 28 | 69.4 |
| 29 | 4.43 |
| 30 | 0.905 |
| 31 | 22.58 |
| 32 | 18.8 |
| 33 | 24.9 |
| 34 | 41.1 |
| 35 | 0.050 |
| 37 | 0.095 |
| 38 | 0.210 |
| 39 | 0.120 |
| 40 | 0.057 |
| 41 | 0.157 |

PRMT5 Biomarker Assay

Compounds of the invention may be tested for potency to inhibit symmetrical dimethylation of arginine in the following assay:

The cell line TE11 was seeded at a density of 12,000 cells per well in 96 well tissue culture plates in DME medium and 10% foetal bovine serum, and allowed to adhere overnight under standard culture conditions (37° C., 5% CO$_2$). Compound dilutions prepared in DMSO were added to the medium, with negative control wells reserved for treatment with DMSO only and positive controls receiving a potent PRMT5 inhibitor. The concentration of the inhibitor had been previously determined to give maximum inhibition of the methylation. After incubation for 72 h, cells were washed twice in ice-cold PBS, lysed in lysis buffer (20 mM Tris pH 7.4, 135 mM NaCl, 1.5 mM MgCl$_2$, 1 mM EGTA, 10% glycerol and 1% Triton-X100), centrifuged at 15,000×g and the supernatants collected for subsequent analysis. The methylation level was determined using the EpiQuik™ Global Di-Methyl Histone H4R3 Quantification ELISA Kit (Epigentek, Farmingdale, N.Y.) as per the manufacturer's recommendations; in parallel the total protein amount in the lysate was quantified using a Lowry protein assay. The methylation level was corrected for the total protein amount of each sample, normalised to the controls, and the data fitted against a four-parameter logistic model to determine the 50% inhibitory concentration (IC$_{50}$).

| Compound Number | IC$_{50}$ (µM) |
|---|---|
| 2 | 0.069 |
| 8 | 0.336 |
| 13 | 0.348 |
| 14 | 0.21 |
| 15 | 0.030 |
| 16 | 0.259 |
| 18 | 0.092 |
| 22 | 0.018 |
| 24 | 0.363 |
| 30 | 1.910 |
| 35 | 0.008 |
| 37 | 0.019 |
| 38 | 0.011 |
| 40 | 0.002 |
| 98 | 0.007 |

Revised PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-NH$_2$). Full-length PRMT5 enzyme (NCBI Reference sequence NP-006100.2) was co-expressed with Hiss-MEP50 in insect cells and purified via Nickel immobilized metal affinity and gel filtration chromatography ("the enzyme").

The 6 µL reactions are run in Greiner brand black 384-well low volume assay plates. All reactions contained assay buffer (phosphate buffered saline, 0.01% (v/v) Tween-20, 0.01% (w/v) albumin from chicken egg white, 1 mM Dithiothreitol, 1 µM peptide substrate, 1 µM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37 degree Celsius. Reaction progress was measured using the Transcreener™ EPIGEN methyltransferase assay (BellBrook Labs, Madison, Wis.) as recommended by the manufacturer. To each reaction 2 µL detection mix were added, containing coupling enzymes, fluorescence polarisation tracer, and AMP antibody. Plates were incubated for 90 minutes before being read on a PerkinElmer EnVision™ plate reader in fluorescence polarisation mode. IC$_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A−F((B−A)/(1+((C/[I])^D)))) where A is the lower asymptote, B is the upper asymptote, C is the IC$_{50}$ value, and D is the slope.

| Compound Number | IC$_{50}$ (µM) |
|---|---|
| 35 | 0.155 |
| 37 | 0.163 |
| 38 | 0.310 |
| 42 | 0.137 |
| 43 | 1.010 |
| 44 | 0.373 |
| 45 | 12.822 |
| 46 | 4.988 |
| 47 | 11.441 |
| 48 | 4.784 |
| 49 | 25.309 |
| 50 | 0.466 |
| 51 | 0.709 |
| 52 | 74.637 |
| 53 | 0.164 |
| 54 | 5.769 |
| 55 | 0.450 |
| 56 | 0.098 |
| 57 | 2.533 |
| 58 | 0.883 |
| 59 | 0.487 |
| 60 | 0.630 |
| 61 | 0.180 |
| 62 | 6.925 |
| 63 | 7.295 |
| 64 | 1.104 |
| 65 | 1.299 |
| 66 | 1.559 |
| 67 | 6.871 |
| 68 | 6.171 |
| 69 | 10.004 |
| 70 | 0.157 |
| 71 | 0.237 |
| 72 | 0.341 |
| 73 | 4.379 |
| 74 | 3.135 |
| 75 | 0.064 |
| 76 | 0.209 |
| 77 | 0.029 |

-continued

| Compound Number | IC$_{50}$ (µM) |
|---|---|
| 78 | 5.577 |
| 79 | 24.001 |
| 80 | 0.253 |
| 81 | 1.366 |
| 82 | 1.813 |
| 83 | 3.458 |
| 84 | 0.585 |
| 85 | 7.684 |
| 86 | 0.682 |
| 87 | 2.762 |
| 88 | 0.229 |
| 89 | 0.853 |
| 90 | 3.153 |
| 91 | 1.226 |
| 92 | 1.383 |
| 93 | 0.505 |
| 94 | 1.346 |
| 95 | 0.931 |
| 96 | 0.733 |
| 97 | 4.319 |
| 98 | 0.281 |
| 100 | 1.104 |
| 101 | 0.457 |
| 102 | 0.482 |
| 103 | 0.120 |
| 104 | 0.514 |
| 105 | 0.196 |
| 106 | 24.254 |
| 107 | 52.161 |
| 108 | 21.239 |
| 109 | 11.105 |
| 110 | 0.166 |
| 111 | 10.382 |
| 112 | 9.413 |
| 113 | 4.146 |
| 114 | 0.066 |
| 115 | 0.305 |
| 116 | 0.276 |
| 117 | 31.368 |
| 118 | 102.627 |
| 119 | 5.082 |
| 120 | 13.317 |
| 121 | 0.130 |
| 122 | 0.166 |
| 123 | 0.040 |
| 124 | 0.048 |
| 125 | 6.724 |
| 126 | 0.226 |
| 127 | 0.137 |
| 128 | 15.438 |
| 129 | 0.629 |
| 130 | 1.129 |
| 131 | 4.591 |
| 132 | 29.683 |
| 133 | 0.131 |
| 134 | 0.238 |
| 135 | 0.015 |
| 136 | 0.050 |
| 137 | 46.992 |
| 138 | 16.890 |
| 139 | 0.771 |
| 140 | 4.679 |
| 141 | 0.695 |

Revised PRMT5 Biomarker Assay

Compounds of the invention may be tested for potency to inhibit symmetrical dimethylation of arginine in the following assay:

The cell line TE11 was seeded at a density of 6,000 cells per well in 96 well optical quality tissue culture plates in DME medium and 10% foetal bovine serum, and allowed to adhere for 5 hours under standard culture conditions (37 degree Celsius, 5% $CO_2$). Compound dilutions prepared in DMSO were added to the medium, with negative control wells reserved for treatment with DMSO only and positive controls receiving a potent PRMT5 inhibitor compound at 1 µM concentration. After incubation for 72 hours, the cells were fixed with 3.7% formaldehyde in PBS for 30 minutes at room temperature, washed with phosphate buffer saline and blocked with Odyssey blocking buffer (LI-COR, Lincoln, Nebr.). Rabbit anti-Di-Methyl Histone H4 Arginine 3 specific antibody (Epigentek) in Odyssey blocking buffer was added and incubated for 14 hours at 4 degree Celsius. After washing, anti-rabbit secondary antibody labelled with Alexa647 dye (LifeTechnologies) and Hoechst 33342 (1 µg/mL, SigmaAldrich) were added for 1 hour incubation. Plates were washed and read on a PerkinElmer Envision 2103 in fluorescence intensity scanning mode (24 scans across the well area). The methylation level information was corrected for the number of cells as expressed by the Hoechst 33342 stain, converted to percent inhibition relative to controls on the same plate and the data fitted against a four-parameter logistic model to determine the 50% inhibitory concentration (IC$_{50}$ plate-reader based). Alternatively, the plates were imaged on a PerkinElmer Phenix high content imaging platform. Using a Columbus image analysis pipeline, individual nuclei were located by Hoechst 33342 stain and the methylation level was calculated from the Alexa647-related intensity in the same area. The resulting mean intensity per cell was directly converted to percent inhibition as outlined above (IC$_{50}$, imager based)).

| Compound Number | IC$_{50}$ (µM) - plate reader based |
|---|---|
| 15 | 0.025 |
| 22 | 0.106 |
| 35 | 0.040 |
| 38 | 0.053 |
| 40 | 0.021 |
| 53 | 0.662 |
| 55 | 0.122 |
| 56 | 0.007 |
| 70 | 0.015 |
| 75 | 0.004 |
| 76 | 0.008 |
| 77 | 0.0005 |
| 98 | 0.361 |
| 103 | 0.017 |
| 105 | 0.010 |
| 111 | >2 |
| 114 | 0.024 |
| 121 | 0.016 |
| 123 | 0.012 |
| 124 | 0.013 |
| 127 | 0.002 |
| 133 | 0.009 |
| 135 | 0.0003 |

The invention claimed is:

1. A compound of formula Ia, Ib or Ic:

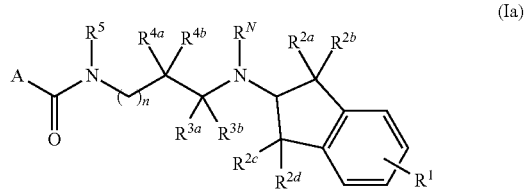

(Ia)

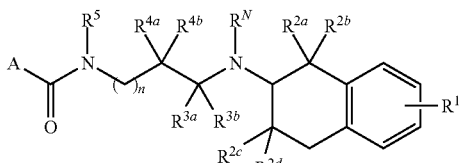
(Ib)

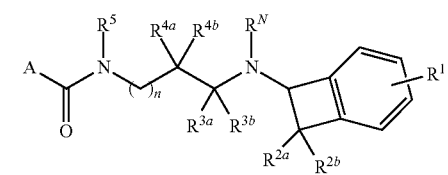
(Ic)

wherein:
n is 1 or 2;
$R^N$ is H or Me;
$R^1$ is optionally present, and when present is one or more halo or methyl groups;
$R^{2a}$ and $R^{2b}$ are independently selected from the group consisting of:
  (i) F;
  (ii) H;
  (iii) Me; and
  (iv) $CH_2OH$;
$R^{2c}$ and $R^{2d}$ (if present) are independently selected from the group consisting of:
  (i) F;
  (ii) H;
  (iii) Me; and
  (iv) $CH_2OH$;
$R^{3a}$ and $R^{3b}$ are independently selected from H and Me;
$R^{4a}$ is selected from OH, —$NH_2$, —C(=O)$NH_2$, and —$CH_2OH$;
$R^{4b}$ is either H or Me;
$R^5$ is either H or Me;
A is either
  (i) optionally substituted phenyl;
  (ii) optionally substituted naphthyl; or
  (iii) optionally substituted $C_{5-12}$ heteroaryl.

2. A compound according to claim 1, wherein $R^1$ represents one to four Me or halo groups.

3. A compound according to claim 1, wherein:
  (a) $R^{2a}$, $R^{2b}$, $R^{2c}$ and $R^{2d}$ (if present) are all H; or
  (b) of formula Ia or Ib, wherein $R^{2a}$, $R^{2b}$, $R^{2c}$ and $R^{2d}$ are comprised of three H and one Me or $CH_2OH$ group; or
  (c) of formula Ia or Ib, wherein $R^{2a}$, $R^{2b}$, $R^{2c}$ and $R^{2d}$ are comprised of two H and two Me groups; or
  (d) of formula Ic, wherein $R^{2a}$ is H and $R^{2b}$ is a Me or $CH_2OH$ group; or
  (e) of formula Ic, wherein $R^{2a}$ and $R^{2b}$ are each a Me or $CH_2OH$ group.

4. A compound according to claim 1, wherein:
  (a) $R^{3a}$ is H and $R^{3b}$ is Me; or
  (b) $R^{3a}$ and $R^{3b}$ are both H; or
  (c) $R^{3a}$ and $R^{3b}$ are both Me.

5. A compound according to claim 1 which is of formula Ia1, Ib1 or Ic1:

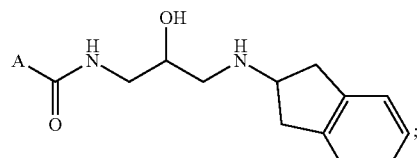
(Ia1)

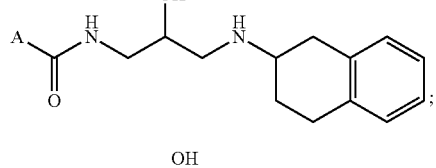
(Ib1)

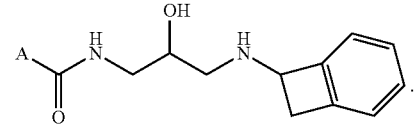
(Ic1)

6. A compound according to claim 1 which is of formula Ia2, Ib2 or Ic2:

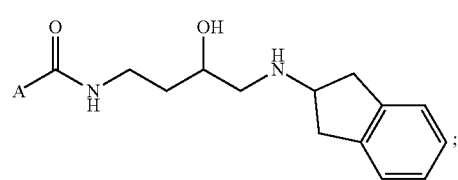
(Ia2)

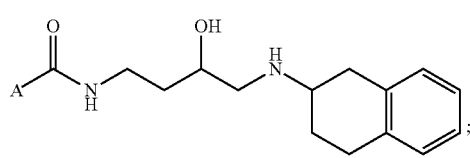
(Ib2)

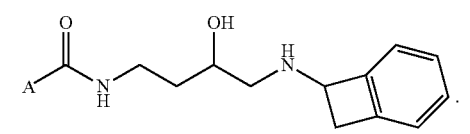
(Ic2)

7. A compound according to claim 1, wherein the compound is a racemate at the carbon atom to which $R^{4b}$ and $R^{4a}$ are attached.

8. A compound according to claim 1, wherein the compound is a single enantiomer at the carbon atom to which $R^{4b}$ and $R^{4a}$ are attached.

9. A compound according to claim 1, wherein the optional substituents on A are independently selected from the group consisting of: $C_{1-4}$ alkyl, $C_{1-4}$ fluoroalkyl, $C_{3-6}$ cycloalkyl, $C_{5-6}$ heteroaryl, $C_{5-6}$ heteroaryl methyl, $C_{4-6}$ heterocyclyl, $C_{4-6}$ heterocyclyl methyl, phenyl, benzyl, halo, amido, amidomethyl, acylamido, acylamidomethyl, $C_{1-4}$ alkyl ester, $C_{1-4}$ alkyl ester methyl, $C_{1-4}$ alkyl carbamoyl, $C_{1-4}$ alkyl carbamoyl methyl, $C_{1-4}$ alkylacyl, $C_{1-4}$ alkylacyl methyl, phenylcarbonyl, carboxy, carboxymethyl, ether, amino, aminomethyl, sulfonamido, sulfonamino, sulfone, sulfoxide, nitrile and nitrilemethyl and when A is phenyl, the optional substituent may also be a fused $C_{5-6}$ Ni-containing heterocyclic ring.

10. A compound according to claim 1, wherein A is optionally substituted phenyl, wherein the substituents are selected from: $C_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—CN, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)—pyrrolidinyl, —C(=O)-morpholino (which may be bridged or substituted with one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetrahydropyanyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$CF$_3$,-γ-lactam, —CH$_2$NHC(=O)Me, —CH$_2$NHC(=O)OMe, —CH$_2$NHC(=O)CF$_3$, morpholino, —CH$_2$NH$_2$, —C(=O)Ph, —OCH$_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

11. A compound according to claim 10, wherein:
   (a) in the ortho position of the phenyl group there is a fluoro, chloro, bromo, $C_{1-4}$ alkyl, methoxy or ethoxy substituent; or
   (b) in the meta position of the phenyl group there is a $C_{1-4}$ alkyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl or thiadiazolyl substituent; or
   (c) in the para position of the phenyl group there is a —C(=O)NH$_2$, —C(=O)NMeH, —C(=O)NMe$_2$, —C(=O)N$^i$PrH, —C(=O)-piperidinyl, —C(=O)—pyrrolidinyl, —C(=O)-morpholino (which may be bridged or substituted with one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl or —CH$_2$C(=O)-morpholino substituent; or
   (d) the phenyl group bears a fluoro, chloro, bromo or methoxy substituent in the ortho position, and a —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted with one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl or —CH$_2$C(=O)-morpholino substituent in the para position of the phenyl group; or
   (e) the phenyl group bears an ethoxy substituent in the ortho position, and a —C(=O)NH$_2$, —C(=O)NMeH, —C(=O)NMe$_2$, —C(=O)N$^i$PrH, —C(=O)— piperidinyl, —C(=O)-pyrrolidinyl, —C(=O)-morpholino (which may be bridged or substituted with one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl or —CH$_2$C(=O)-morpholino substituent in the para position of the phenyl group; or
   (f) in the meta position of the phenyl group there is an —NH-methylpyrazinyl or —NH-pyrimidinyl substituent.

12. A compound according to claim 1, wherein A is:
   (a) optionally substituted naphthyl; or
   (b) optionally substituted $C_{5-12}$ heteroaryl selected from the group consisting of: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl.

13. A compound according to claim 1, wherein A is selected from one of the following groups:

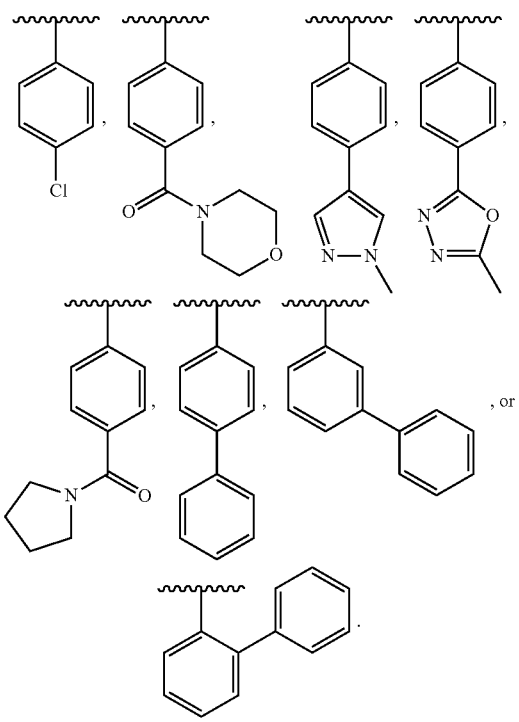

14. A compound according to claim 1, wherein A is selected from one of the following groups:

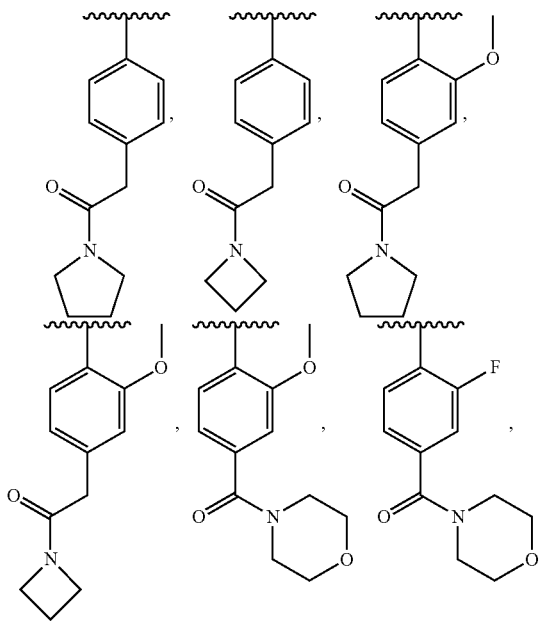

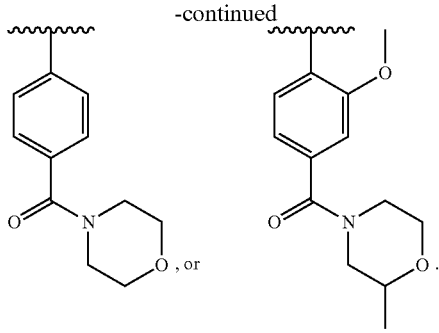

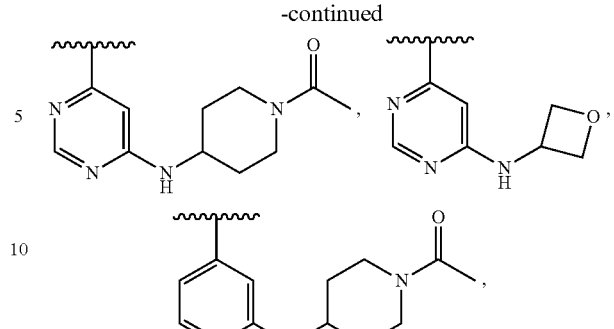

15. A compound according to claim 14, wherein A is selected from one of the following groups:

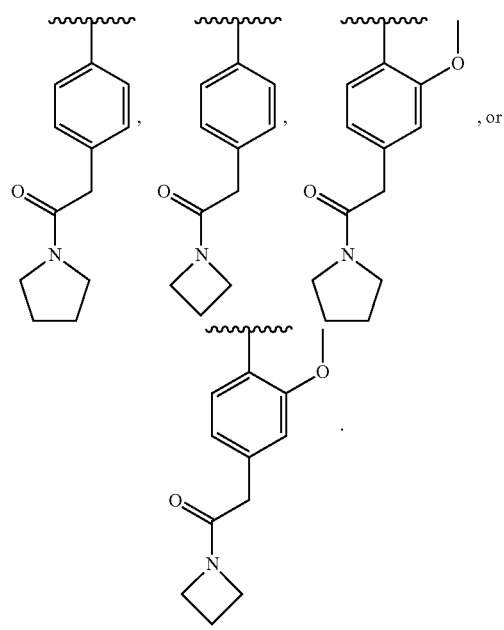

16. A compound according to claim 1, wherein A is selected from one of the following groups:

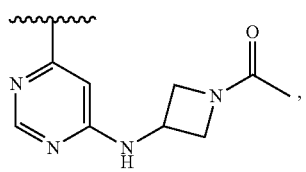

17. A compound according to claim 1, wherein A is selected from one of the following groups: phenyl, with a para-amido substituent and an optional ortho-ethoxy substituent; phenyl, with a para-ether substituent; 6-amino-3-pyridyl; 5-amino-3-pyridyl; and 2-amino-4-pyridyl.

18. A pharmaceutical composition comprising a compound according to claim 1 and a pharmaceutically acceptable excipient.

19. A method of treatment of cancer, comprising administering to a patient in need of treatment, a pharmaceutical composition according to claim 18.

20. A method of treatment of hemoglobinopathies, comprising administering to a patient in need of treatment, a pharmaceutical composition according to claim 18.

* * * * *